United States Patent
Rosen et al.

(10) Patent No.: US 6,989,383 B1
(45) Date of Patent: Jan. 24, 2006

(54) METHOD OF TREATING CANCER

(75) Inventors: Neal Rosen, Englewood, NJ (US); Laura Sepp-Lorenzino, New Haven, CT (US); Mark M. Moasser, New York, NY (US); Allen I. Oliff, Gwynedd Valley, PA (US); Jackson B. Gibbs, Chalfont, PA (US); Nancy Kohl, Wyndmoor, PA (US); Samuel L. Graham, Schwenksville, PA (US); George C. Prendergast, Bala Cynwyd, PA (US)

(73) Assignee: Sloan-Kettering Institute For Cancer Research, New York, NY (US)

( * ) Notice: Subject to any disclaimer, the term of this patent is extended or adjusted under 35 U.S.C. 154(b) by 0 days.

(21) Appl. No.: 09/445,054

(22) PCT Filed: Jun. 4, 1998

(86) PCT No.: PCT/US98/08646

§ 371 (c)(1),
(2), (4) Date: Mar. 27, 2000

(87) PCT Pub. No.: WO98/54966

PCT Pub. Date: Dec. 10, 1998

(51) Int. Cl.
| | |
|---|---|
| *A61K 31/495* | (2006.01) |
| *A61K 31/50* | (2006.01) |
| *A61K 31/335* | (2006.01) |
| *A61K 31/35* | (2006.01) |
| *A61K 31/34* | (2006.01) |

(52) U.S. Cl. .......................... 514/254.05; 514/255.01; 514/255.02; 514/449; 514/459; 514/471; 514/616

(58) Field of Classification Search ............ 514/254.05, 514/255.01, 255.02, 449, 459, 471, 616
See application file for complete search history.

(56) References Cited

U.S. PATENT DOCUMENTS

| 5,856,326 A | 1/1999 | Anthony et al. |
| 5,912,154 A | 6/1999 | Ferro-Novick et al. |

FOREIGN PATENT DOCUMENTS

| EP | 0 456 180 A1 | 11/1991 |
| EP | 0 618 221 A2 | 5/1994 |
| EP | 0 670 314 A1 | 3/1995 |
| EP | 0 856 315 A1 | 2/1997 |
| WO | WO 97/01275 | 1/1997 |
| WO | WO 97/17070 | 5/1997 |

OTHER PUBLICATIONS

Slichenmyer et al., Anti–Cancer Drugs (1991), 2(6), 519–30 abstract only.*
Moasser, et al., Farnesyl transferase inhibitors cause enchanced mitotic sensitivity to taxol and epothilones, Feb. 1998, Proc. Natl. Acad. Sci. USA, vol. 95, pp. 1369–1374Molecular Pharmacology, vol. 47, pp. 1106–1111 (1995).
Danesi, Paclitaxel (Taxol) Inhibits Protein Isoprenylation and Induces Apoptosis in PC–3 Human Prostate Cancer Cells, 1995, Molecular Pharmacology, vol. 47, pp. 1106–1111.

* cited by examiner

*Primary Examiner*—Rebecca Cook
(74) *Attorney, Agent, or Firm*—Law Offices of Albert Wai-Kit Chan, LLC

(57) ABSTRACT

The present invention relates to methods of treating cancer using a combination of a compound which is an antineoplastic agent and a compound which is a inhibitor of prenyl-protein transferase, which methods comprise administering to said mammal, either sequentially in any order or simultaneously, amounts of at lest two therapeutic agents selected from a group consisting of a compound which is an antineoplastic agent and a compound which is an inhibitor or prenyl-protein transferase. The invention also relates to methods of preparing such compositions.

14 Claims, 48 Drawing Sheets

| TAXOL DOSE | CONTROL | 1µM FTI |
|---|---|---|
| 4nM | 3.3% | 12.3% |
| 6nM | 8.8% | 16.9% |
| 8nM | 20.5% | 27.6% |
| 10nM | 30.0% | 36.0% |

FIG.5

METHOD OF TREATING CANCER

This application claims priority of International Application No. PCT/US98/08646, filed on Jun. 4, 1998, which claims priority of U.S. Ser. No. 60/048,736, filed Jun. 5, 1997, now expired, and Great Britain Patent Application No. 9801231.3, filed Jan. 21, 1998, the contents of which are incorporated herein in their entireties by reference.

BACKGROUND OF THE INVENTION

The present invention relates to methods of treating cancer using a combination of an antineoplastic agent and a compound which is an inhibitor of a prenyl-protein transferase.

Chemotherapy, the systematic administration of antineoplastic agents that travel throughout the body via the blood circulatory system, along with and often in conjunction with surgery and radiation treatment, has for years been widely utilized in the treatment of a wide variety of cancers. Unfortunately, the available chemotherapeutic drugs often fail patients because they kill many healthy cells and thus bring on serious side effects that limit the doses physicians can administer.

Prenylation of proteins by intermediates of the isoprenoid biosynthetic pathway represents a class of post-translational modification (Glomset, J. A., Gelb, M. H., and Farnsworth, C. C. (1990). Trends Biochem. Sci. 15, 139–142; Maltese, W. A. (1990). FASEB J. 4, 3319–3328). This modification typically is required for the membrane localization and function of these proteins. Prenylated proteins share characteristic C-terminal sequences including CaaX (C, Cys; a, usually aliphatic amino acid; X, another amino acid), XXCC, or XCXC. Three post-translational processing steps have been described for proteins having a C-terminal CaaX sequence: addition of either a 15 carbon (farnesyl) or 20 carbon (geranylgeranyl) isoprenoid to the Cys residue, proteolytic cleavage of the last 3 amino acids, and methylation of the new C-terminal carboxylate (Cox, A. D. and Der, C. J. (1992a). Critical Rev. Oncogenesis 3:365–400; Newman, C. M. H. and Magee, A. I. (1993). Biochim. Biophys. Acta 1155:79–96). Some proteins may also have a fourth modification: palmitoylation of one or two Cys residues N-terminal to the farnesylated Cys. While some mammalian cell proteins terminating in XCXC are carboxymethylated, it is not clear whether carboxy methylation follows prenylation of proteins terminating with a XXCC motif (Clarke, S. (1992). Annu. Rev. Biochem. 61, 355–386). For all of the prenylated proteins, addition of the isoprenoid is the first step and is required for the subsequent steps (Cox, A. D. and Der, C. J. (1992a). Critical Rev. Oncogenesis 3:365–400; Cox, A. D. and Der, C. J. (1992b) Current Opinion Cell Biol. 4:1008–1016).

Three enzymes have been described that catalyze protein prenylation: farnesyl-protein transferase (FPTase), geranylgeranyl-protein transferase type I (GGPTase-I), and geranylgeranyl-protein transferase type-II (GGPTase-II, also called Rab GGPTase). These enzymes are found in both yeast and mammalian cells (Clarke, 1992; Schafer, W. R. and Rine, J. (1992) Annu. Rev. Genet. 30:209–237). Each of these enzymes selectively uses farnesyl diphosphate (FPP) or geranyl-geranyl diphosphate as the isoprenoid donor and selectively recognizes the protein substrate. FPTase farnesylates CaaX-containing proteins that end with Ser, Met, Cys, Gln or Ala. For FPTase, CaaX tetrapeptides comprise the minimum region required for interaction of the protein substrate with the enzyme. The enzymological characterization of these three enzymes has demonstrated that it is possible to selectively inhibit one with little inhibitory effect on the others (Moores, S. L., Schaber, M. D., Mosser, S. D., Rands, E., O'Hara, M. B., Garsky, V. M., Marshall, M. S., Pompliano, D. L., and Gibbs, J. B., J. Biol. Chem., 266:17438 (1991), U.S. Pat. No. 5,470,832).

The prenylation reactions have been shown genetically to be essential for the function of a variety of proteins (Clarke, 1992; Cox and Der, 1992a; Gibbs, J. B. (1991). Cell 65: 1–; Newman and Magee, 1993; Schafer and Rine, 1992). This requirement often is demonstrated by mutating the CaaX Cys acceptors so that the proteins can no longer be prenylated. The resulting proteins are devoid of their central biological activity. These studies provide a genetic "proof of principle" indicating that inhibitors of prenylation can alter the physiological responses regulated by prenylated proteins.

The Ras protein is part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation, Ras is induced to exchange GDP for GTP and undergoes a conformational change. The GTP-bound form of Ras propagates the growth stimulatory signal until the signal is terminated by the intrinsic. GTPase activity of Ras, which returns the protein to its inactive GDP bound form (D. R. Lowy and D. M. Willumsen, Ann. Rev. Biochem. 62:851–891 (1993)). Activation of Ras leads to activation of multiple intracellular signal transduction pathways, including the MAP Kinase pathway and the Rho/Rac pathway (Joneson et al., Science 271:810–812).

Mutated ras genes are found in many human cancers, including colorectal carcinoma, exocrine pancreatic carcinoma, and myeloid leukemias. The protein products of these genes are defective in their GTPase activity and constitutively transmit a growth stimulatory signal.

The Ras protein is one of several proteins that are known to undergo post-translational prenylation. Farnesyl-protein transferase utilizes farnesyl pyrophosphate to covalently modify the Cys thiol group of the Ras CAAX box with a farnesyl group (Reiss et al., Cell, 62:81–88 (1990); Schaber et al., J. Biol. Chem., 265:14701–14704 (1990); Schafer et al., Science, 249:1133–1139 (1990); Manne et al., Proc. Natl. Acad. Sci USA, 87:7541–7545 (1990)).

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., Nature 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., Ann. Rev. Biochem. 61:355–386 (1992); W. R. Schafer and J. Rine, Ann. Rev. Genetics 30:209–237 (1992)).

Other farnesylated proteins include the Ras-related GTP-binding proteins such as RhoB, fungal mating factors, the nuclear lamins, and the gamma subunit of transducin. James, et al., J. Biol. Chem. 269, 14182 (1994) have identified a peroxisome associated protein Pxf which is also farnesylated. James, et al., have also suggested that there are farnesylated proteins of unknown structure and function in addition to those listed above.

Inhibitors of farnesyl-protein transferase have been described in two general classes. The first class includes analogs of FPP, while the second is related to protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS,* 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science,* 260:1934–1937 (1993); Graham, et al., *J. Med. Chem.,* 37, 725 (1994)).

Mammalian cells express four types of Ras proteins (H—, N-, K4A-, and K4B-Ras) among which K-Ras4B is the most frequently mutated form of Ras in human cancers. Inhibition of farnesyl-protein transferase has been shown to block the growth of H-ras-transformed cells in soft agar and to modify other aspects of their transformed phenotype. It has also been demonstrated that certain inhibitors of farnesyl-protein transferase selectively block the processing of the H-Ras oncoprotein intracellularly (N. E. Kohl et al., *Science,* 260:1934–1937 (1993) and G. L. James et al., *Science,* 260:1937–1942 (1993). Recently, it has been shown that an inhibitor of farnesyl-protein transferase blocks the growth of H-ras-dependent tumors in nude mice (N. E. Kohl et al., *Proc. Natl. Acad. Sci U.S.A.,* 91:9141–9145 (1994) and induces regression of mammary and salivary carcinomas in H-ras transgenic mice (N. E. Kohl et al., *Nature Medicine,* 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Inhibition of farnesyl pyrophosphate biosynthesis by inhibiting HMG-CoA reductase blocks Ras membrane localization in cultured cells. Because prenyl pyrophosphates are intermediates in many biosynthetic processes, direct inhibition of a prenyl-protein transferase would be more specific and attended by fewer side effects than would occur with the required dose of a general inhibitor of isoprene biosynthesis.

It is the object of the instant invention to provide a composition that comprises an antineoplastic agent and a prenyl-protein transferase inhibitor whose therapeutic effect in combination may allow use of tie antineoplastic agent at a dose which is lower than the dose of the antineoplastic agent if it was used alone and may therefore ameliorate some of the unwanted side effects normally associated with traditional chemotherapy.

A pharmaceutically effective combination of an antineoplastic agent and a prenyl-protein transferase inhibitor are used in the present invention to treat cancer, such as in tumor cells that are less susceptable to treatment by antagonist of the antineoplastic agent or prenyl-protein transferase inhibitor when administered alone.

SUMMARY OF THE INVENTION

A method of treating cancer is disclosed which is comprised of administering to a mammalian patient in need of such treatment an effective amount of a combination of an antineoplastic agent and a prenyl-protein transferase inhibitor. Preferably an antineoplastic agent and a farnesyl protein transferase inhibitor are used in such a combination.

BRIEF DESCRIPTION OF THE FIGURES

FIGS. 4 and 4A–4L: Effect of a Farnesyl-protein Transferase Inhibitor in combination with paclitaxel on the cell cycle of MCF-7 Cells: MCF-7 cells were preincubated for one day, followed by a 24 hour treatment with various concentrations of paclitaxel in the presence or absence of 1 $\mu$M Compound A. The DNA contents of the cells were then assessed according to the protocol described in "In vitro cell cycle assay." The cell population having various DNA quantities was then determined and analyzed graphically. FIG. 4 shows a composite of 12 cell DNA-content histograms representing the various treatment combinations. FIGS. 4A–4L show the individual histograms in greater detail. FIGS. 4A–4F show the histograms of the treatment in the absence of Compound A and with increasing concentrations of paclitaxel (the left column of FIG. 4). FIGS. 4G–4L show the histograms of the treatment in the presence of 1 $\mu$M of Compound A and with increasing concentrations of paclitaxel (the right column of FIG. 4). The addition of Compound A increases the molar potency with which paclitaxel causes $G_2$/M phase arrest in MCF-7 cells.

FIG. 5: Specific Effect of a Farnesyl-protein Transferase Inhibitor in combination with pactitaxel on the cell cycle of MCF-7 Cells: The cells which contained the doubled DNA content from the assay described above for FIGS. 4 and 4A–4L were analyzed to determine which particular cell cycle phase was affected by the addition of Compound A to the paclitaxel treatment. Thus, aliquots of the cell populations for the various paclitaxel/Compound A treatments were. fixed in 3% paraformaldehyde for 10 minutes, washed in PBS and stained in 24 $\mu$g/ml bis-benzimide in PBS. Mitotic cells were distinguished from interphase cells under fluorescence microscopy by characteristic chromatin condensation and mitotic indices were obtained by manual counting of 1000 cells in each experimental treatment group. The results of those counts are shown in FIG. 5. The results show that the enhancement in blockage at the $G_2$/M phase of the cell cycle is largely due to an effect on the M-phase.

DETAILED DESCRIPTION OF THE INVENTION

Figure 1:
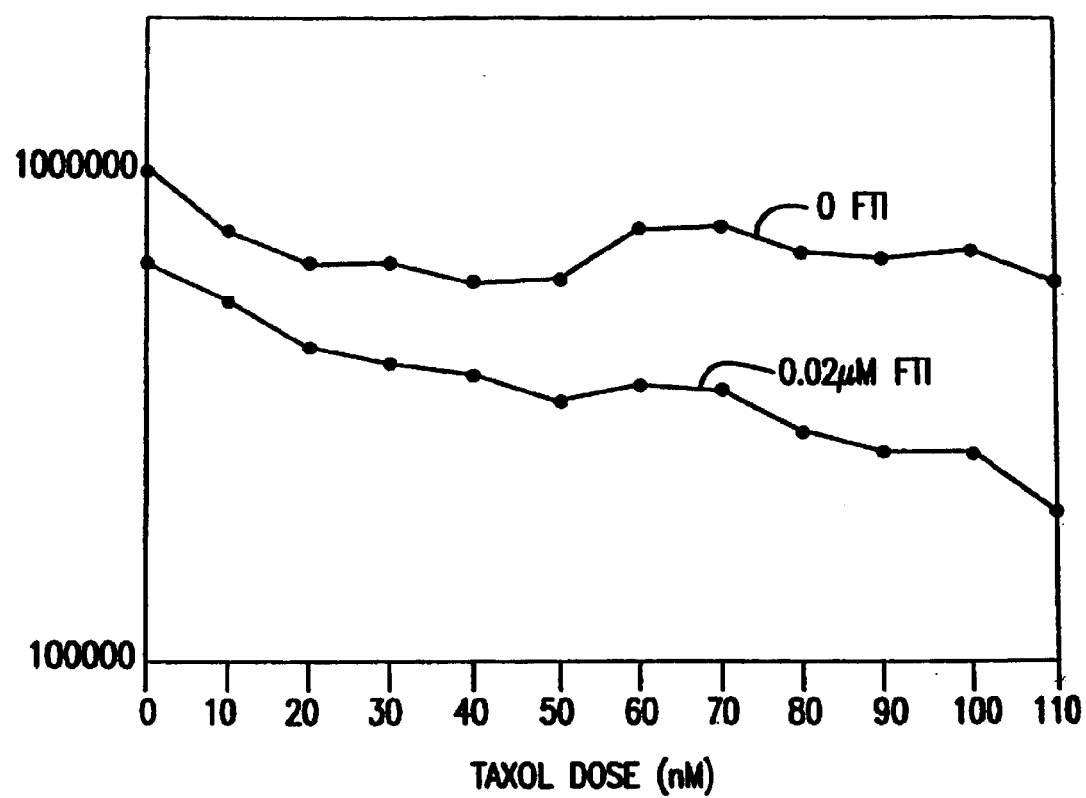
FIG. 1: Effect of a Farnesyl-protein Transferase Inhibitor in combination with paclitaxel on MCF-7 Cells: Cell proliferation of MCF-7 cells (ATCC HTB-22; *J. Nail. Cancer Inst. (Bethesda)* 51:1409–1416 (1973)) which were preincubated for one day in the presence or absence of 0.02 $\mu$M Compound A, followed by a 4 hour treatment with various concentrations of paclitaxel. After the treatment, with paclitaxel, the cell were incubated for 7 additional days in the presence or absence of 0.02 $\mu$M Compound A. See Protocol B in the "In vitro growth inhibition of human tumor cells assay."
Figure 2:
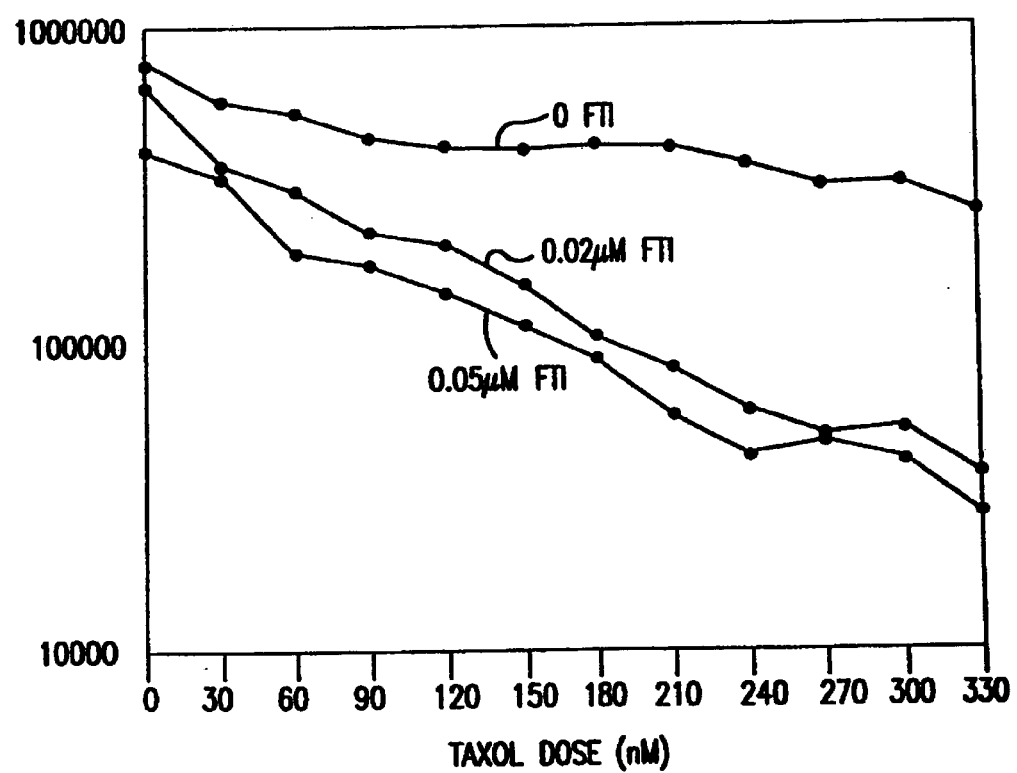
FIG. 2: Effect of a Farnesyl-protein Transferase Inhibitor in combination with paclitaxel on MDA MB-468 Cells: Cell proliferation of MDA MB-468 cells (ATCC HTB-132; *In Vitro (Rockville)* 14:911–915 (1978)) which were treated with. various concentrations of paclitaxel for 4 hours. After the treatment with paclitaxel the cell were incubated for 9 days in the absence or presence of 0.2 $\mu$M or 0.5 $\mu$M Compound A. See Protocol A in the "In vitro growth inhibition of human tumor cells assay."
Figure 2A:
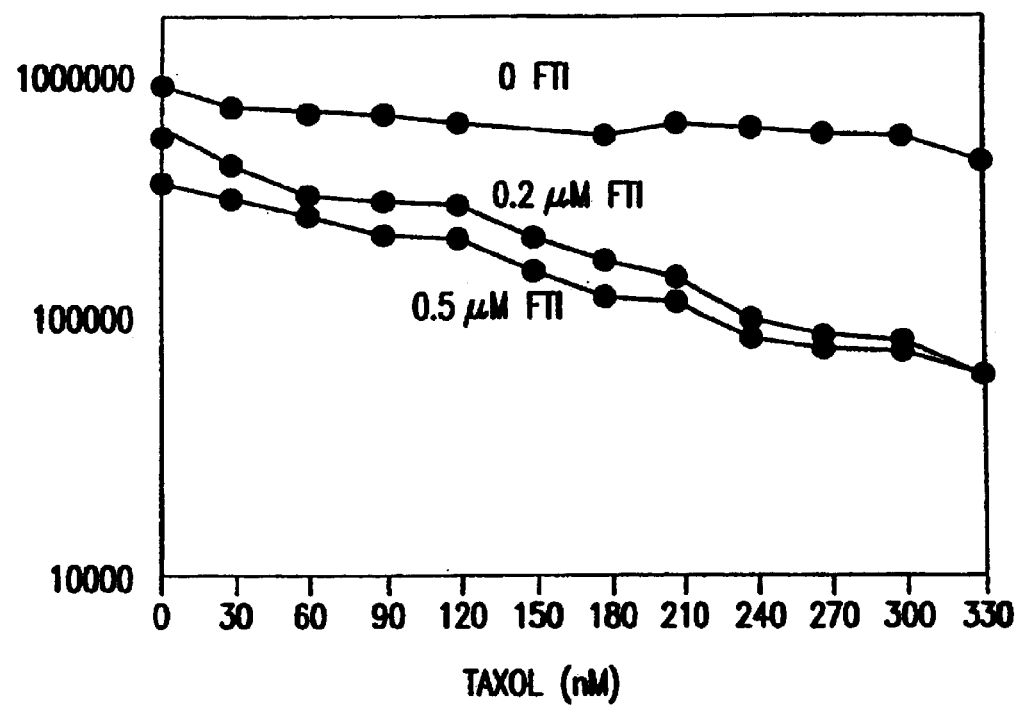
FIG. 2A: Effect of a Farnesyl-protein Transferase Inhibitor in combination with paclitaxel on MDA MB-468 Cells: Cell proliferation of MDA MB-468 cells which were pre-incubated in the absence or presence of 0.2 $\mu$M or 0.5 $\mu$M Compound A. At the end of 24 hours the cells were also exposed to various concentrations of paclitaxel for 4 hours. After the treatment with paclitaxel the cell were washed sand incubated for 8 days in the presence of the pre-incubation concentration of Compound A. See Protocol B in the "In vitro growth inhibition of human tumor cells assay."
Figure 2B:
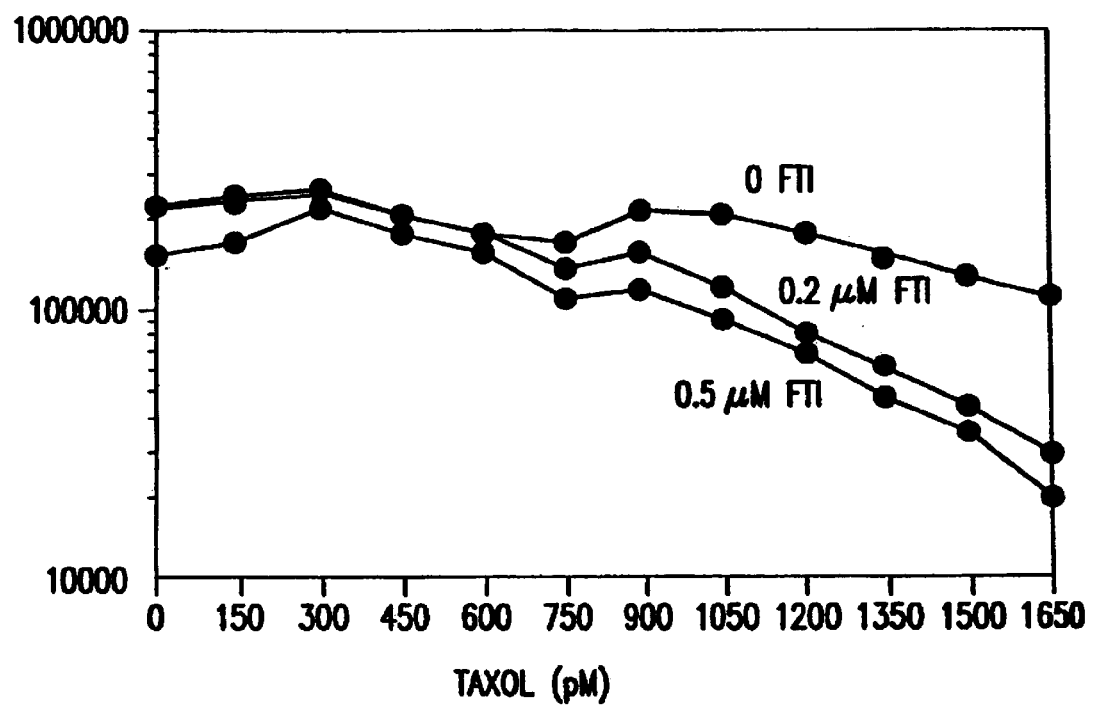
FIG. 2B: Effect of a Farnesyl-protein Transferase Inhibitor in combination with paclitaxel on MDA MB-468 Cells: Cell proliferation of MDA MB-468 cells were exposed to various concentrations of paclitaxel in the absence or presence of 0.2 $\mu$M or 0.5 $\mu$M Compound A for 6 days. See Protocol C in the "In vitro growth inhibition of human tumor cells assay."
Figure 3A:
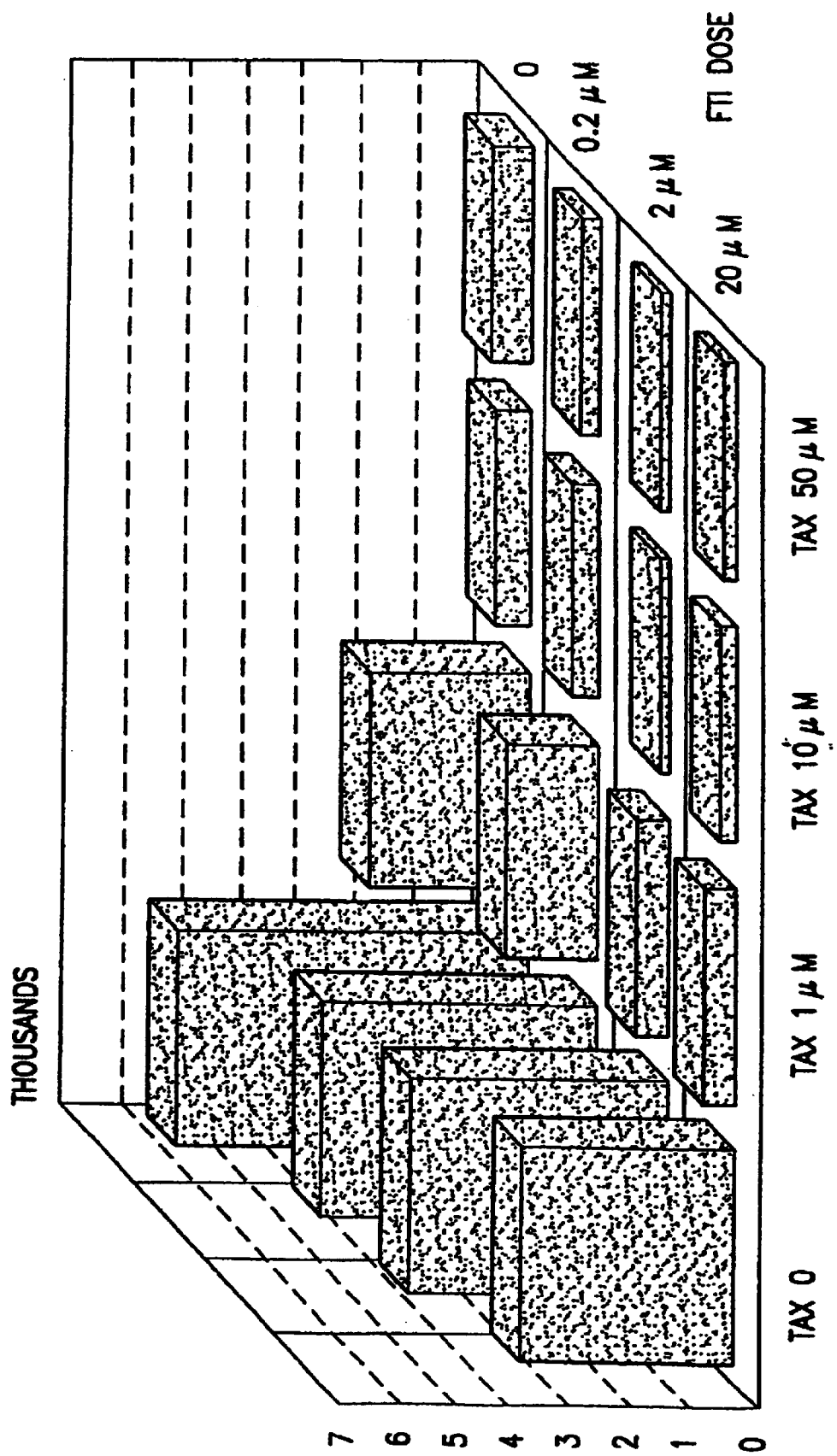
FIGS. 3A and 3B: Effect of a Farnesyl-protein Transferase Inhibitor in combination with pactitaxel on DU145 Cells: DU145 human prostate cancer cells (ATCC HTB-8 1, *Cancer Res.* 37:4049–4058 (1977), *Int. J. Cancer,* 21:274–281 (1978)), which were treated for four (4) hours with paclitaxel and then washed, were treated in anchorage-dependent and -independent growth assays in the absence or presence of 0.2 $\mu$M, 2 $\mu$M or 20 $\mu$M Compound A. For FIG. 3A, which represents the effect of a combination of paclitaxel and Compound A on anchorage-independent growth, see Protocol D-1 in the "In vitro growth inhibition of human tumor cells assay." For FIG. 3B, which represents the effect of a combination of paclitaxel and Compound A on anchorage-dependent growth, see Protocol D-2 in the "In vitro growth inhibition of human tumor cells assay."
Figure 3B:
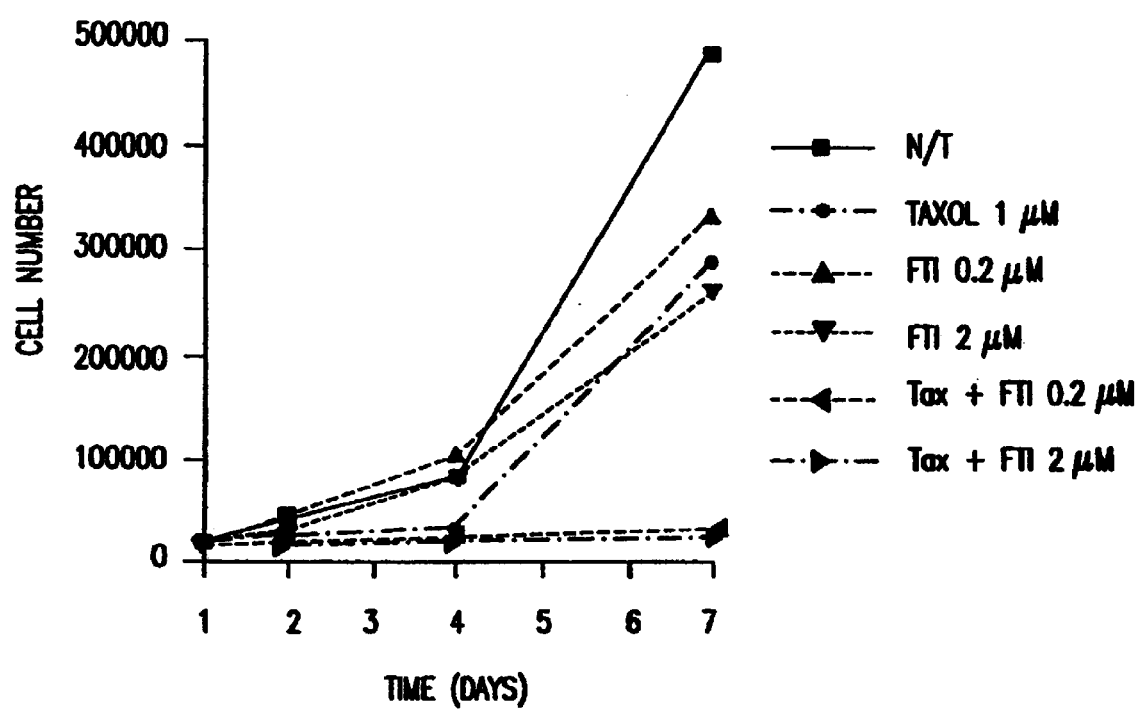
Figure 4:
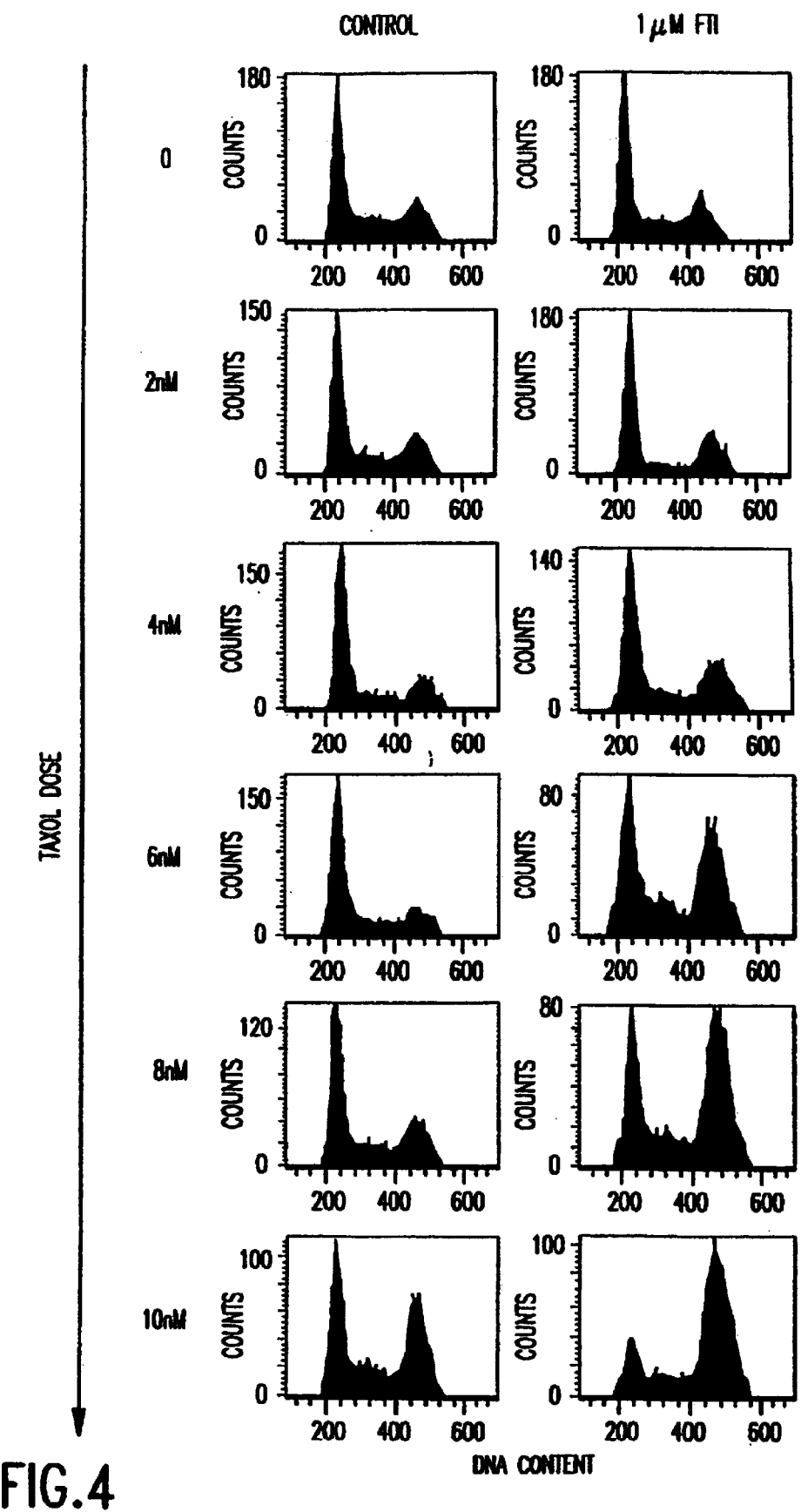
Figure 4A:
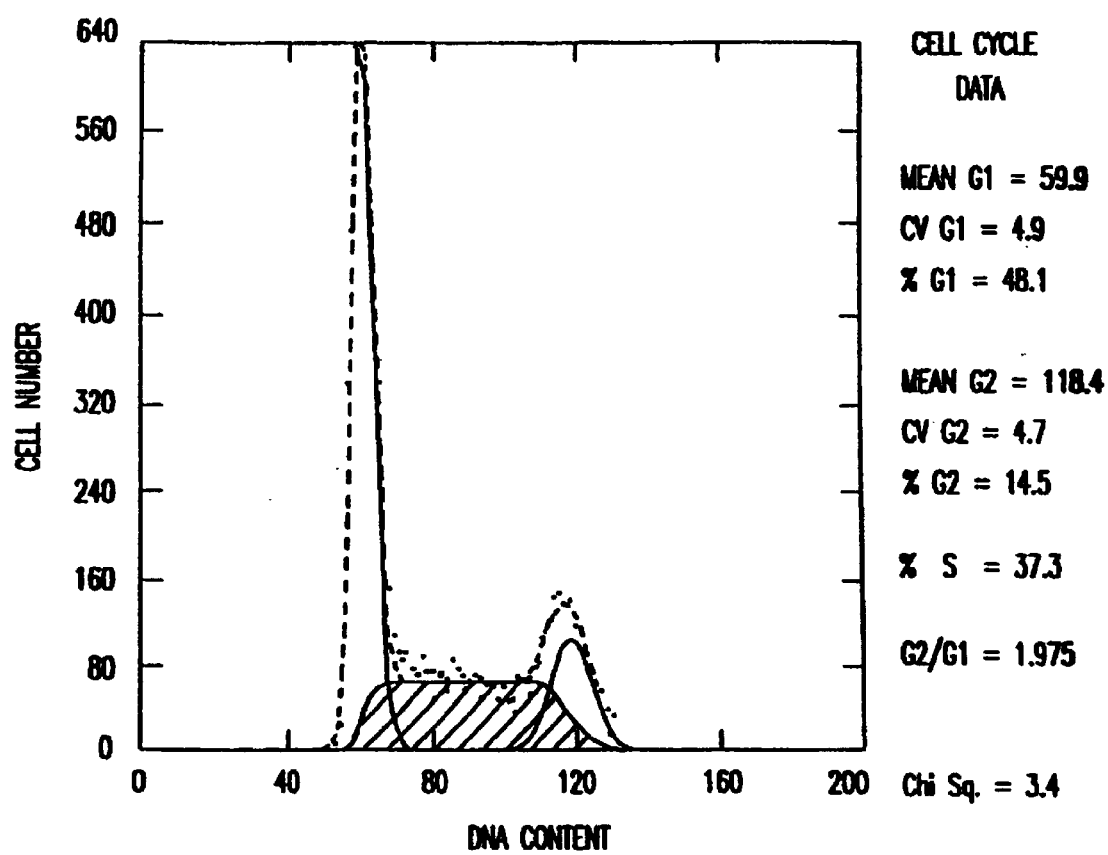
Figure 4B:
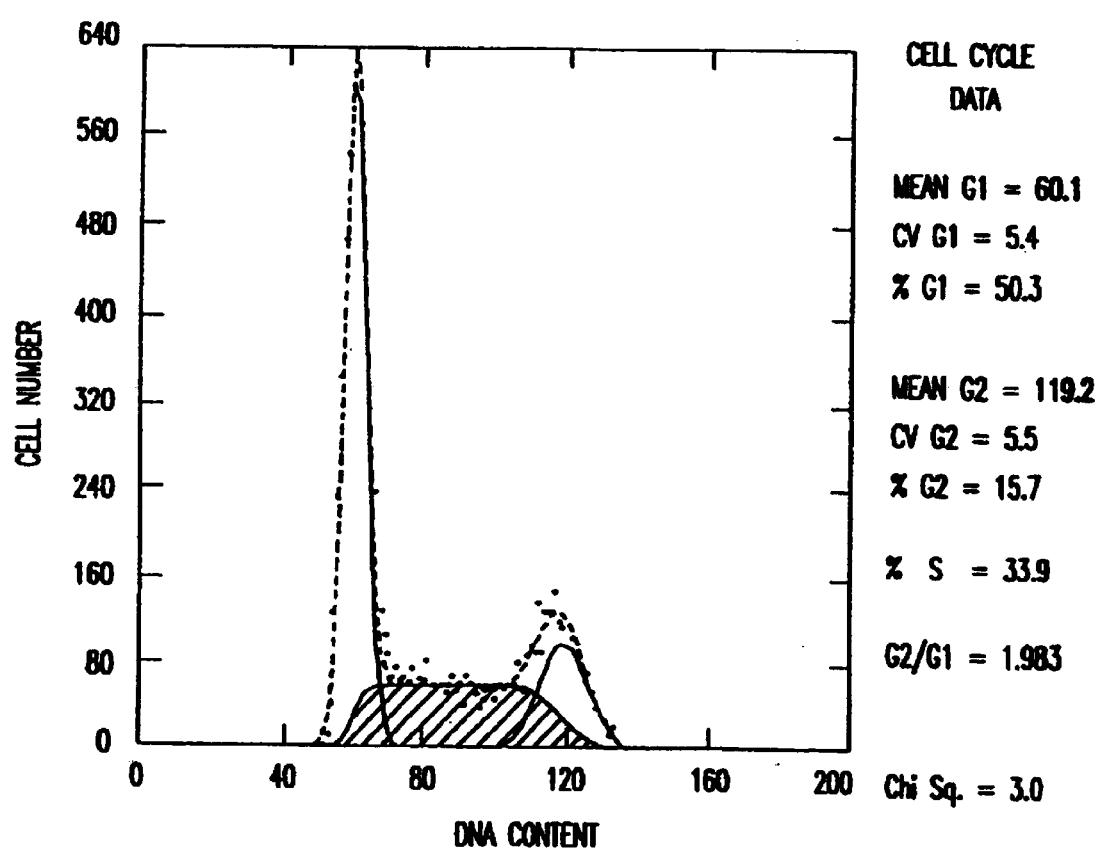
Figure 4C:
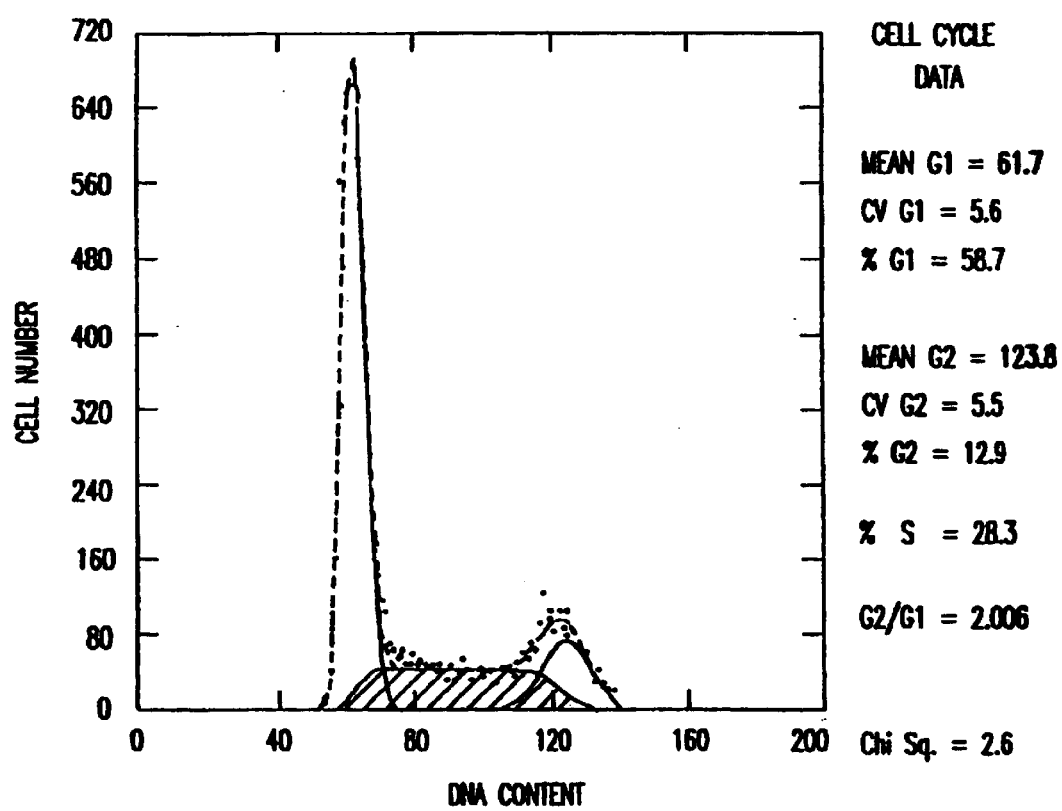
Figure 4D:
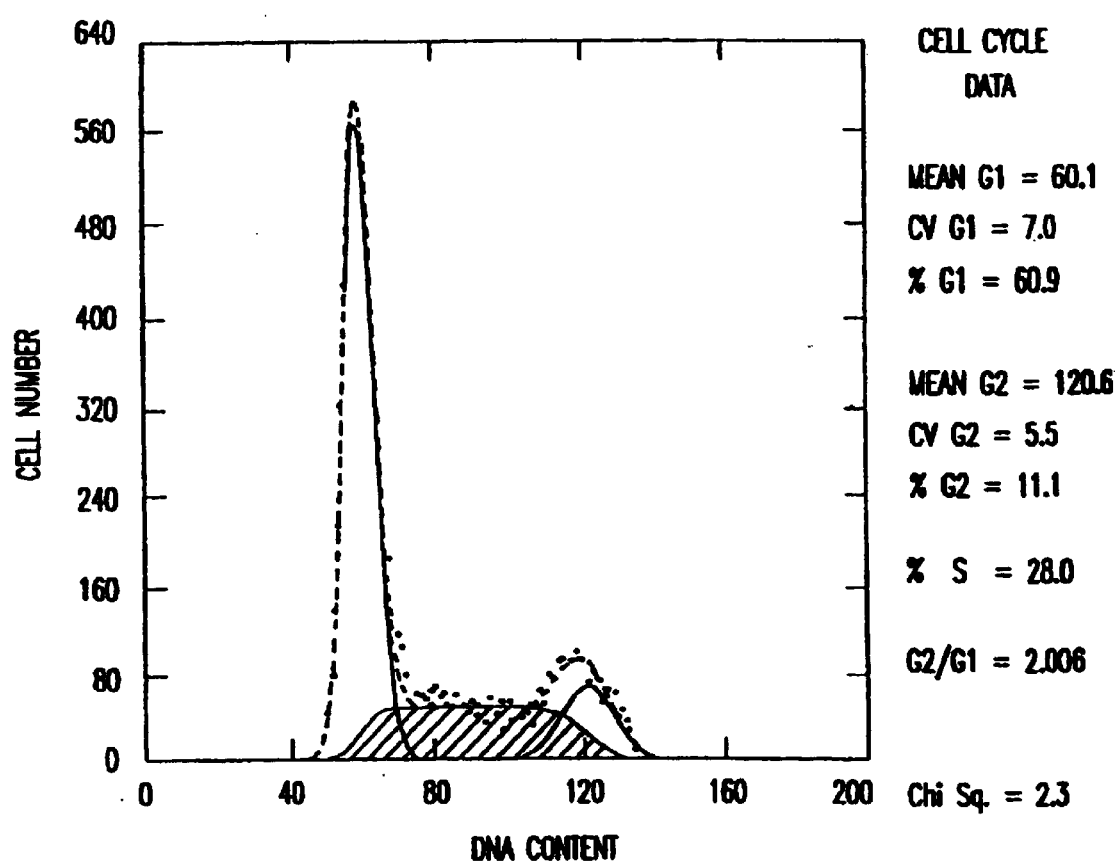
Figure 4E:
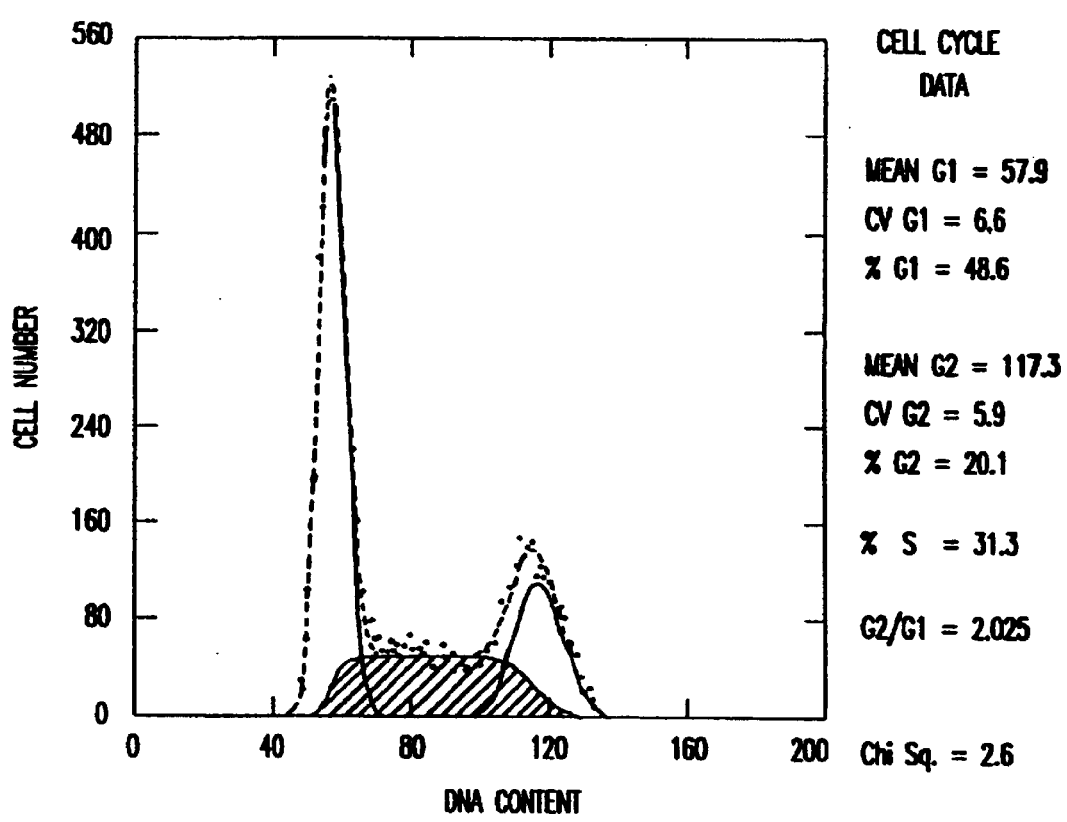
Figure 4F:
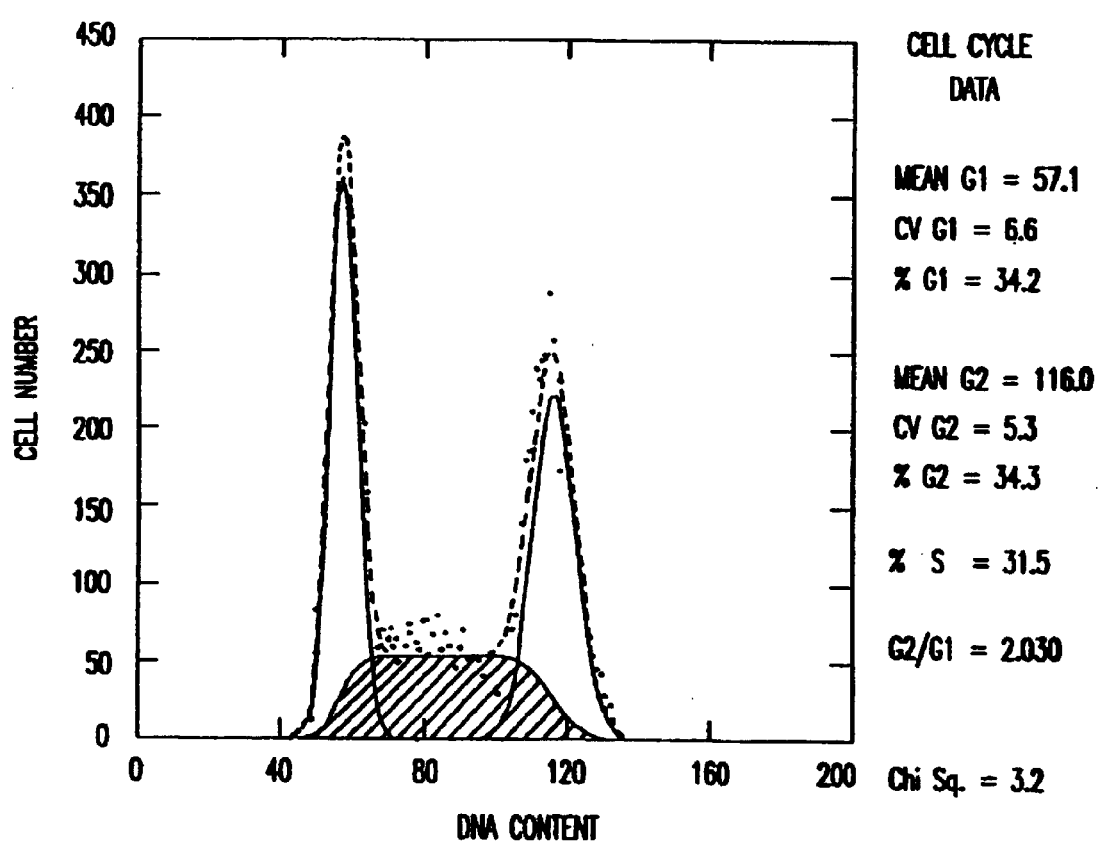
Figure 4G:
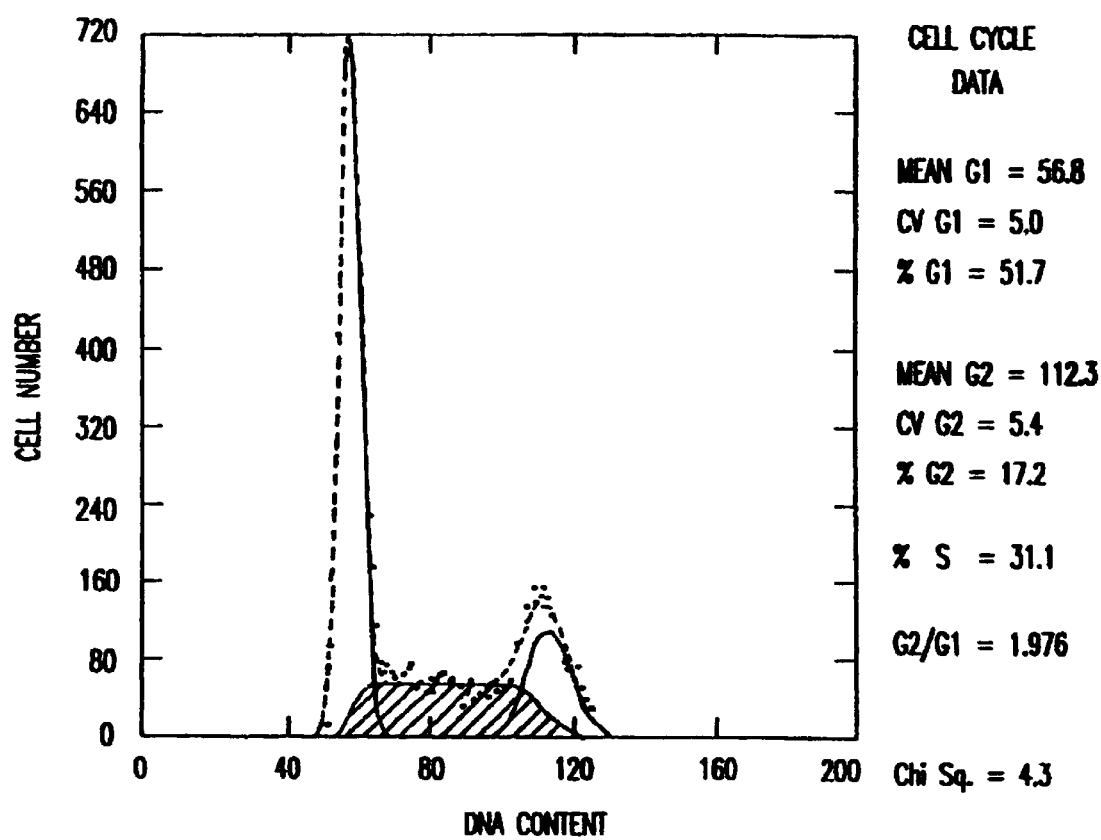
Figure 4H:
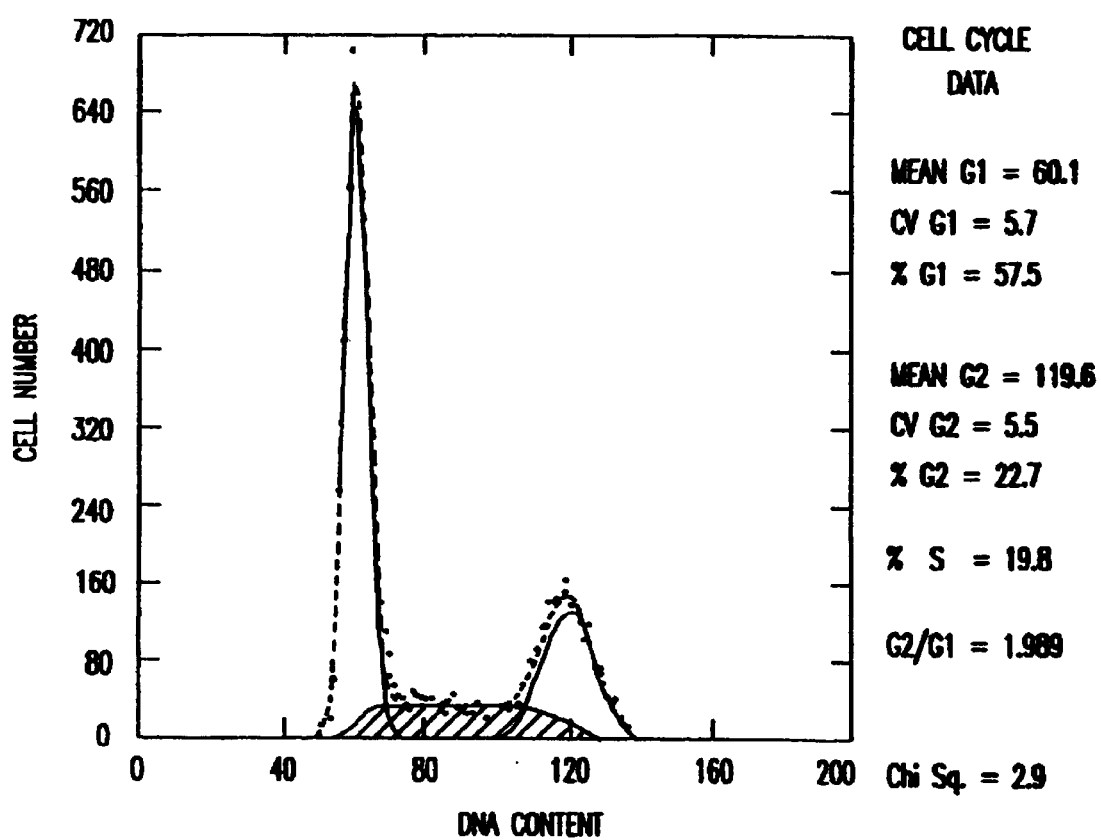
Figure 41:
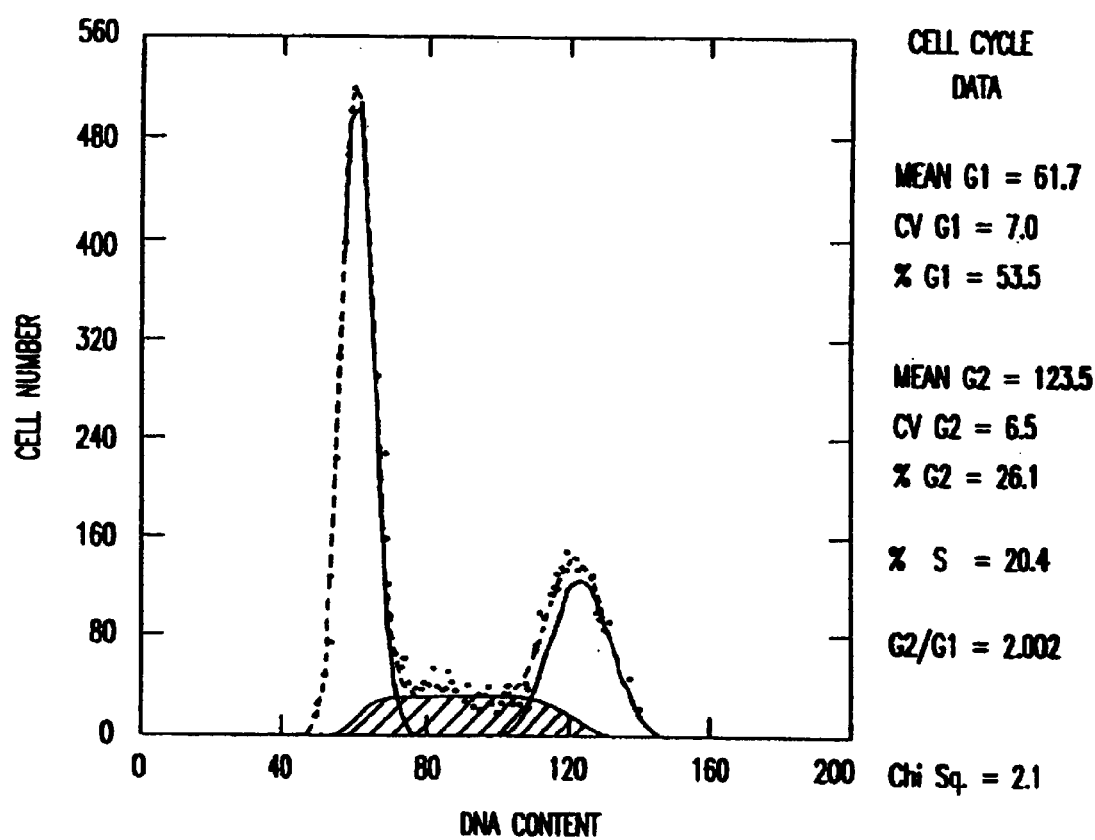
Figure 4J:
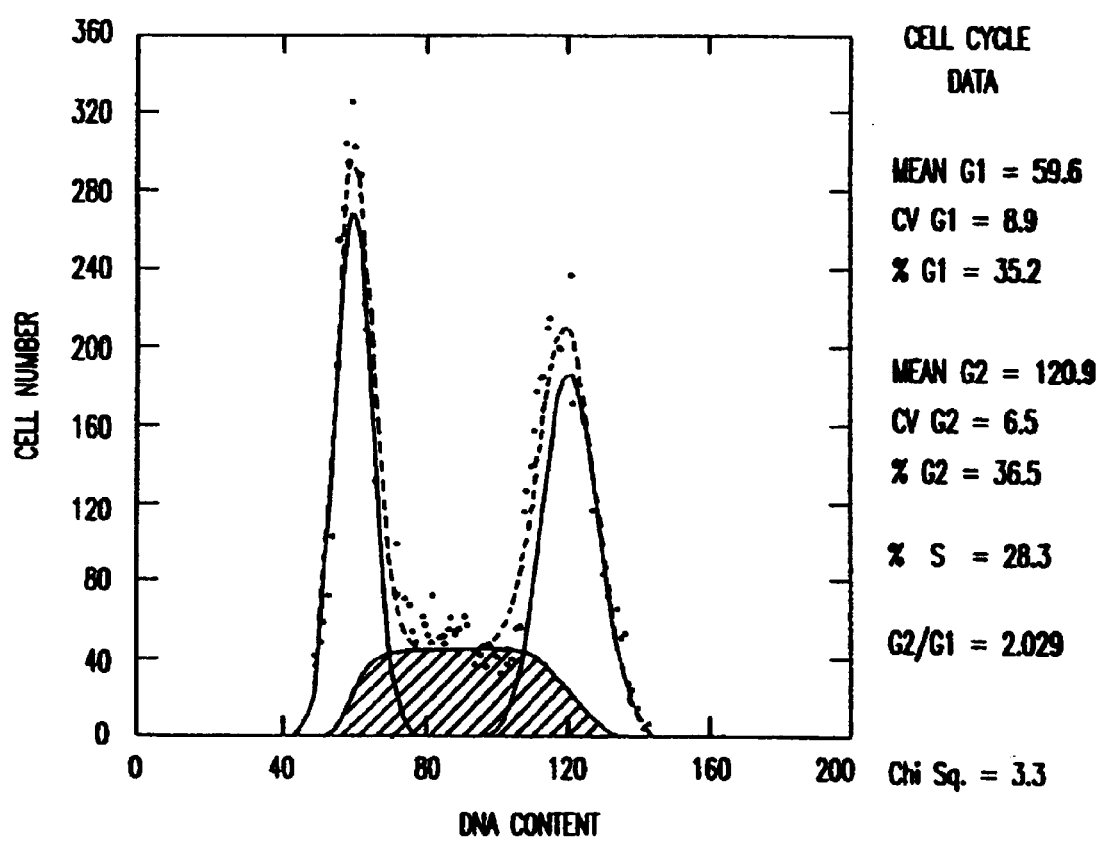
Figure 4K:
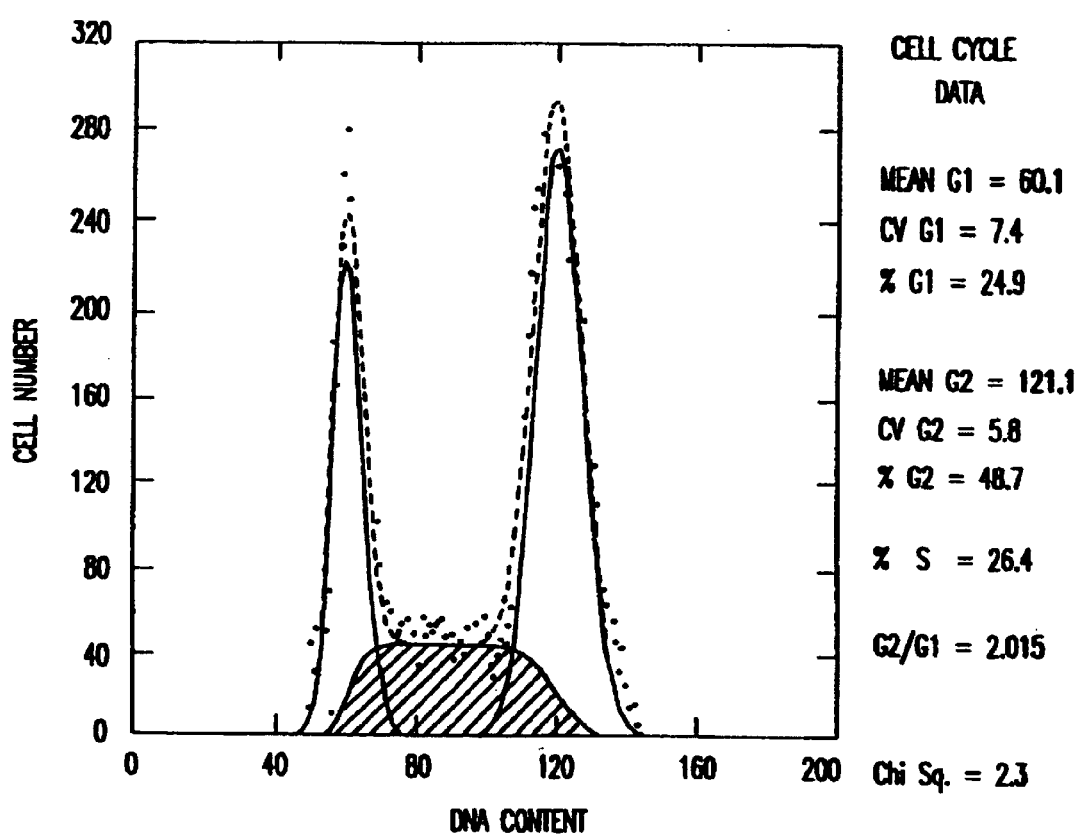
Figure 4L:
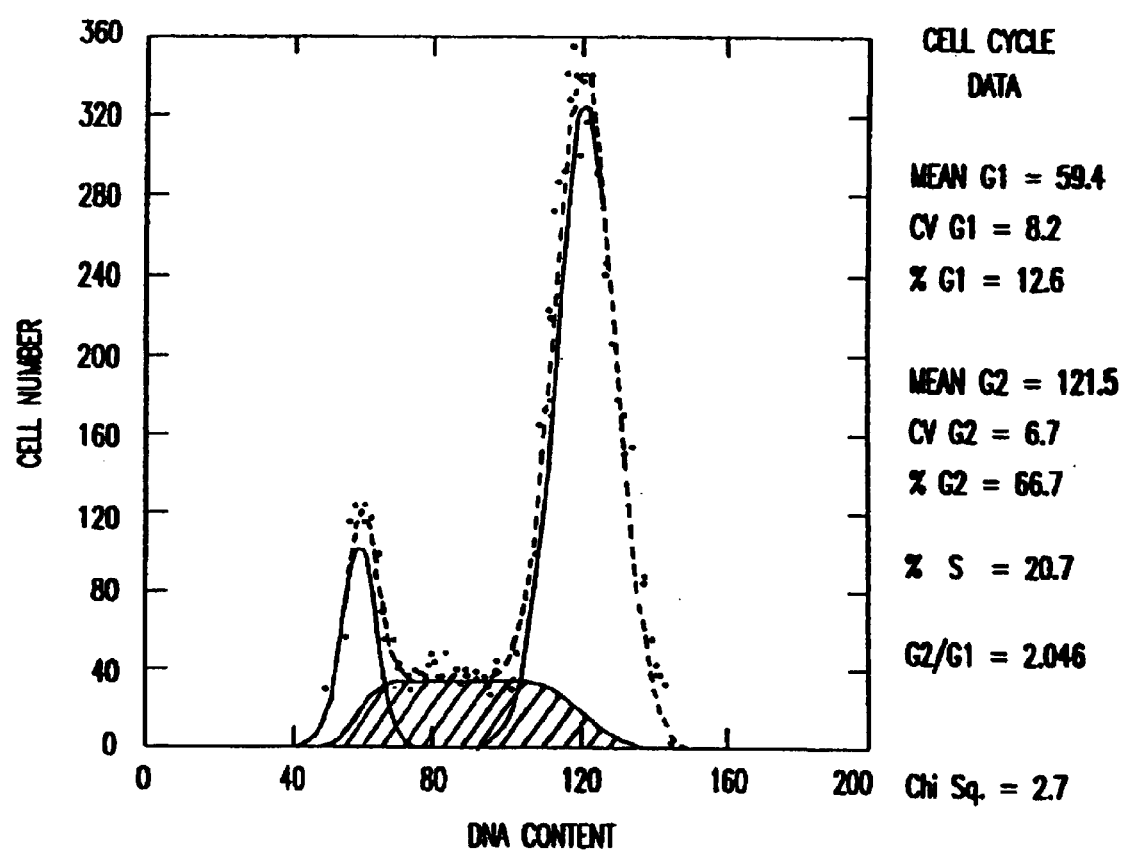
Figure 6:
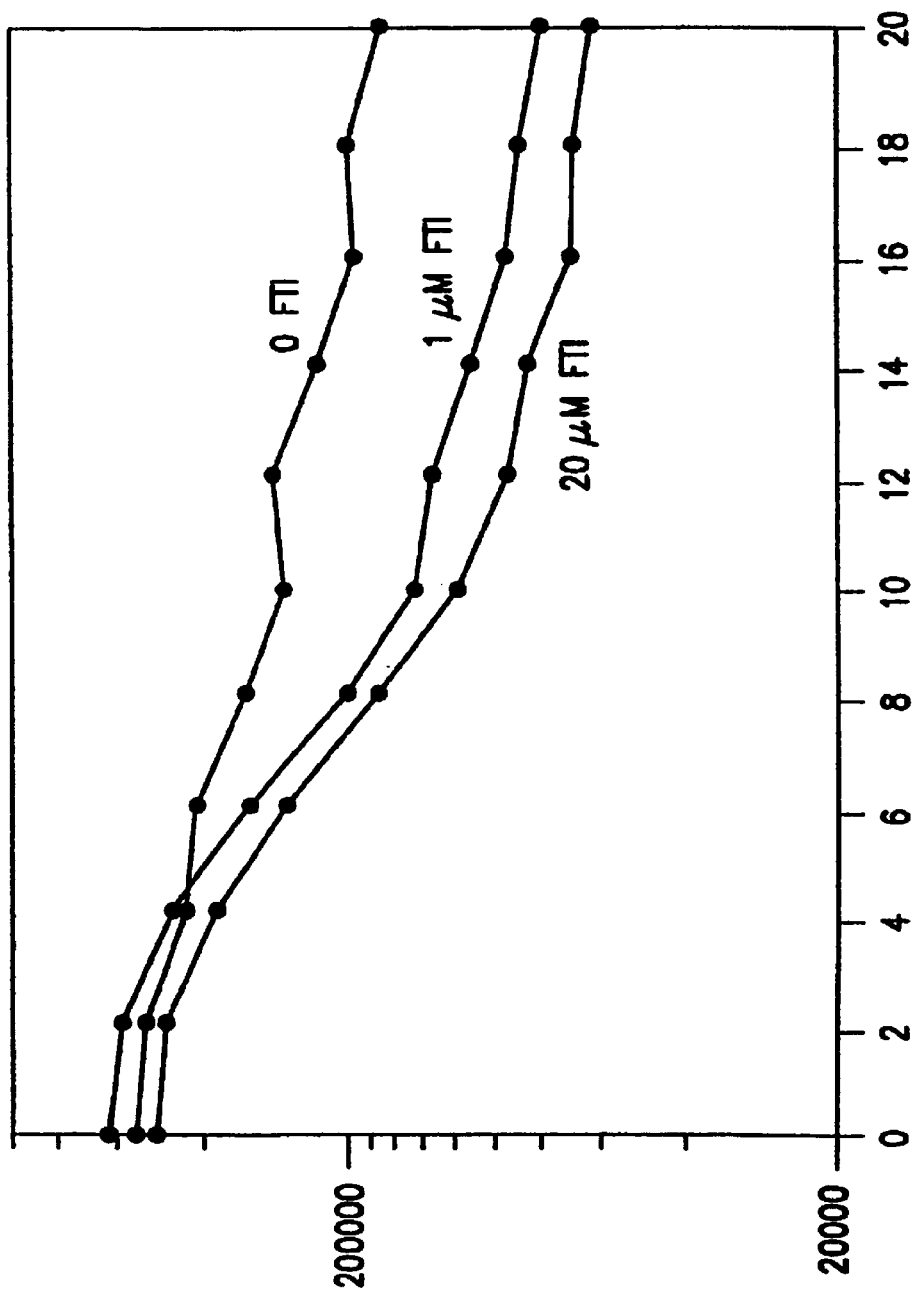
FIG. 6: Effect of a Farnesyl-protein Transferase Inhibitor in combination with paclitaxel on DU145 Cells: Cell proliferation of DU145 cells which were treated with various concentrations of paclitaxel for 4 hours. Cells were seeded 30,000/6 well plate. After the treatment with paclitaxel, the cells were incubated for 5 days in the absence or presence of various concentrations of Compound A. See Protocol A in the "In vitro growth inhibition of human tumor cells assay."
Figure 7:
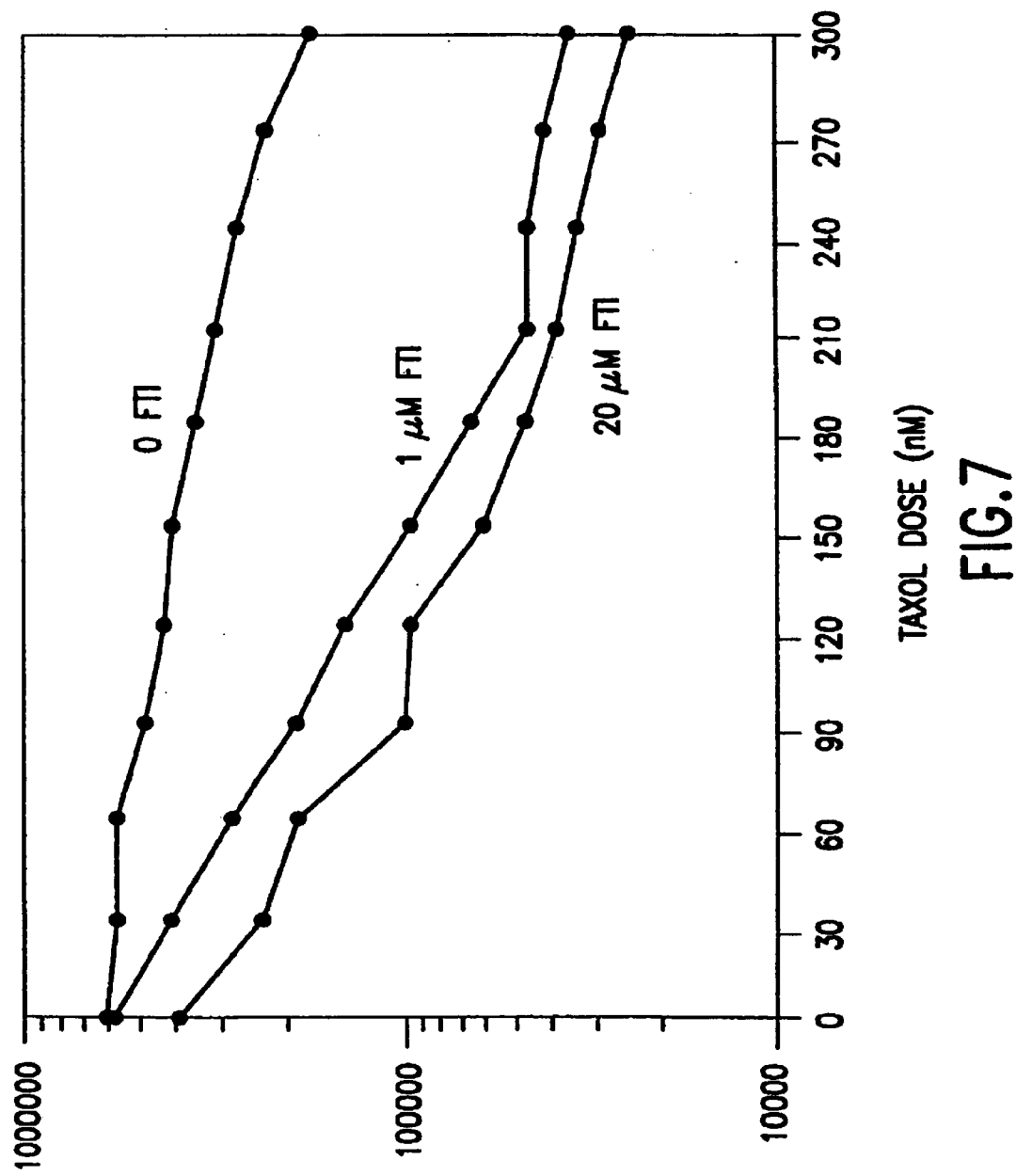
FIG. 7: Effect of a Farnesyl-protein Transferase Inhibitor in combination with paclitaxel on T47D Cells: Cell proliferation of T47D cells which were treated with various concentrations of paclitaxel for 4 hours. Cells were seeded 20,000/6 well plate. After the treatment with paclitaxel, the cells were incubated for 10 days in the absence or presence of various concentrations of Compound A. See Protocol A in the "In vitro growth inhibition of human tumor cells assay."
Figure 8:
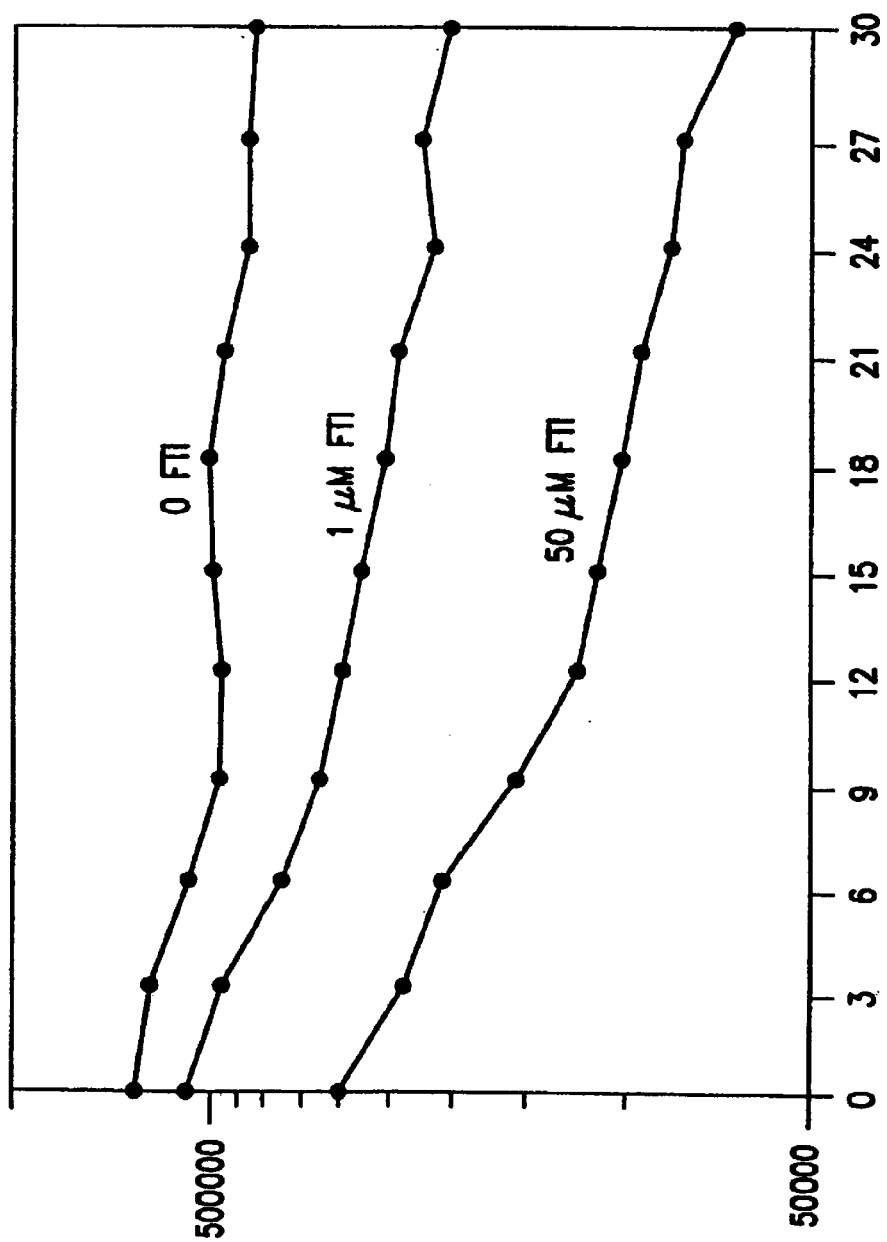
FIG. 8: Effect of a Farnesyl-protein Transferase Inhibitor in combination with paclitaxel on MDA-231 Cells: Cell proliferation of MDA-231 cells (ATCC HTB-26, *J. Natl. Cancer Inst.* (*Bethesda*) 53:661–674 (1974)) which were treated with various concentrations of paclitaxel for 4 hours. Cells were seeded 5,000/6 well plate. After the treatment with paclitaxel, the cells were incubated for 7 days in the absence or presence of various concentrations of Compound A. See Protocol A in the "In vitro growth inhibition of human tumor cells assay."
Figure 9:
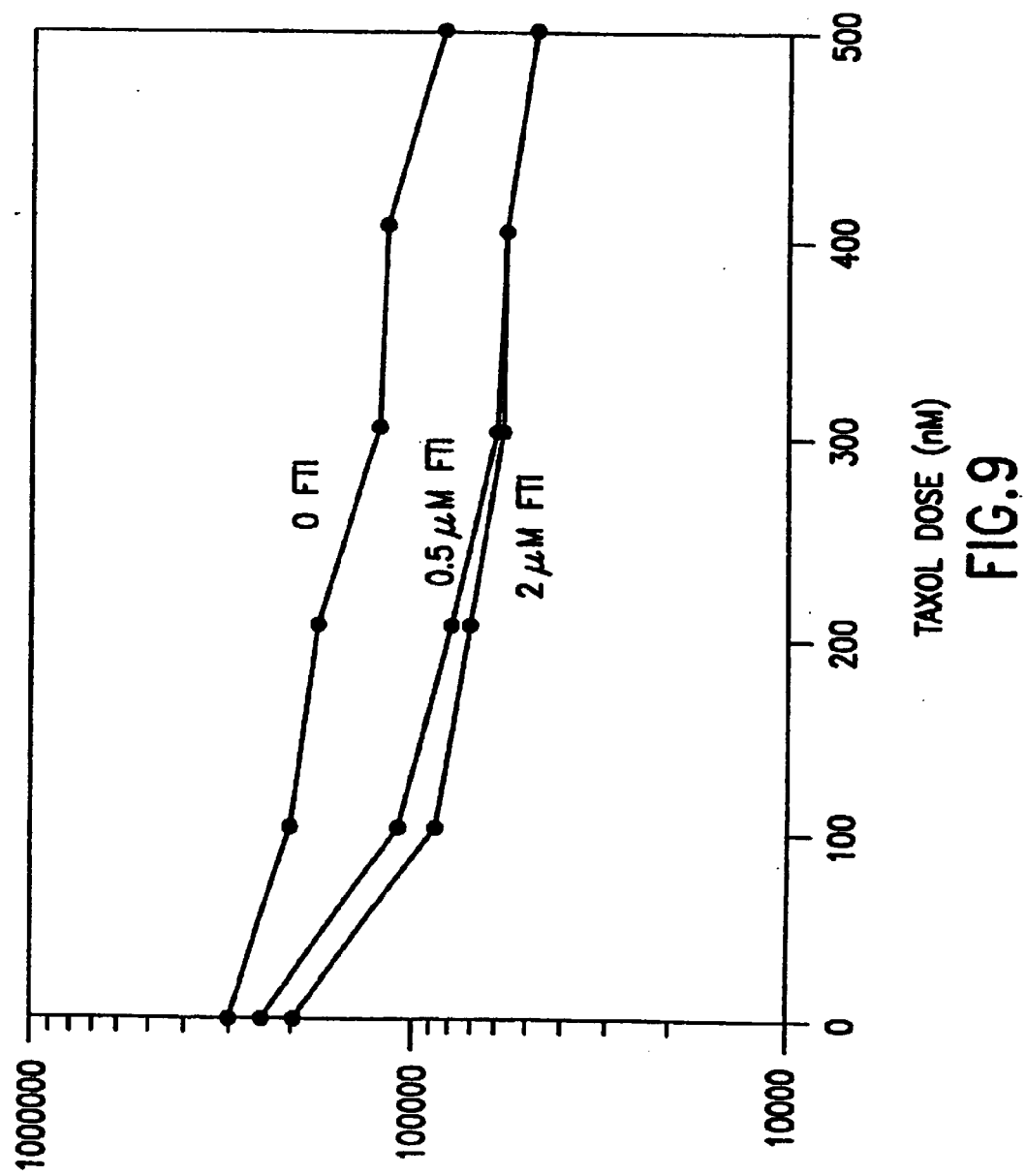
FIG. 9: Effect of a Farnesyl-protein Transferase Inhibitor in combination with paclitaxel on SK-OV-3 Cells: Cell proliferation of SK-OV-3 cells (ATCC HTB-77, *J. Natl. Cancer Inst.* (*Bethesda*) 58:209–214 (1977)) which were treated with various concentrations of paclitaxel for 4 hours. Cells were seeded 20,000/6 well plate. After the treatment with paclitaxel, the cells were incubated for 4 days in the absence or presence of various concentrations of Compound A. See Protocol A in the "In vitro growth inhibition of human tumor cells assay."
Figure 10:
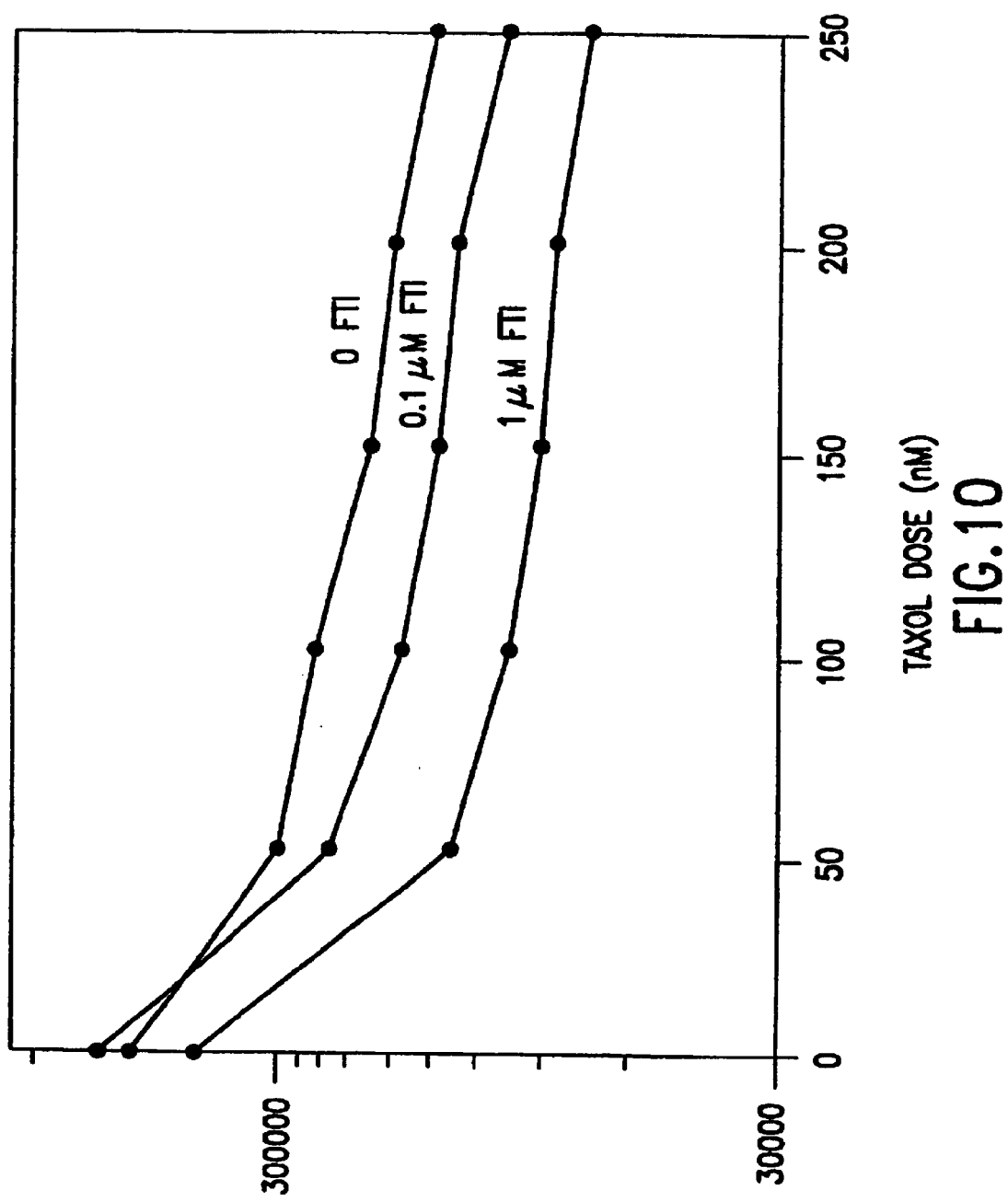
FIG. 10: Effect of a Farnesyl-protein Transferase Inhibitor in combination with paclitaxel on A549 Cells: Cell proliferation of A549 cells (ATCC CCl-185, *J. Natl. Cancer Inst.* (*Bethesda*) 51:1417–1423 (1973)) which were treated with various concentrations of paclitaxel for 4 hours. Cells were seeded 25,000/6 well plate. After the treatment with paclitaxel, the cells were incubated for 3 days in the absence or presence of various concentrations of Compound A. See Protocol A in the "In vitro growth inhibition of human tumor cells assay."
Figure 11:
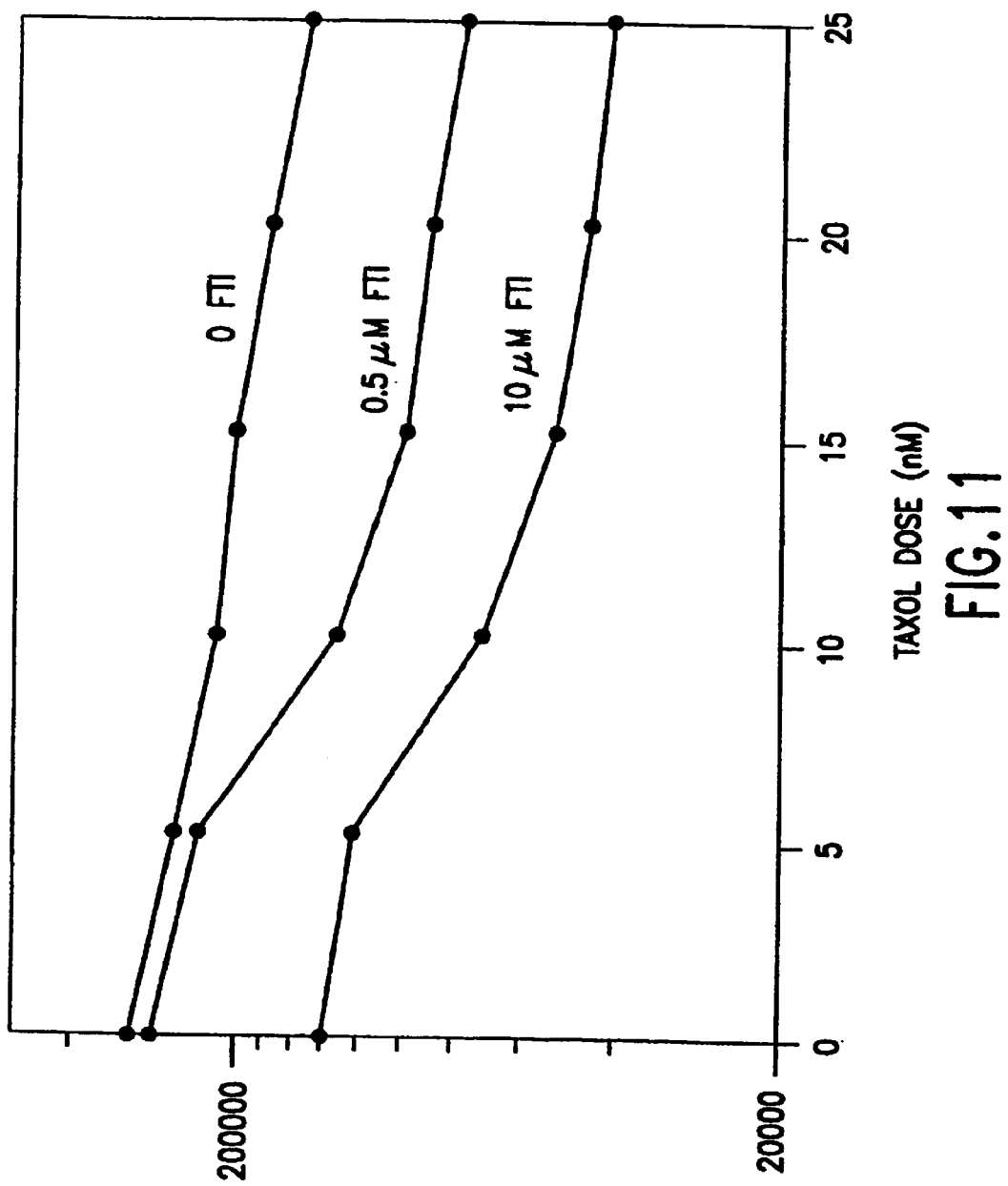
FIG. 11: Effect of a Farnesyl-protein Transferase Inhibitor in combination with paclitaxel on SkBr3 Cells: Cell proliferation of SkBr3 cells (ATCC HTB-30) which were treated with various concentrations of paclitaxel for 4 hours. Cells were seeded 40,000/6 well plate. After the treatment with paclitaxel, the cells were incubated for 6 days in the absence or presence of various concentrations of Compound A. See Protocol A in the "In vitro growth inhibition of human tumor cells assay."
Figure 12:
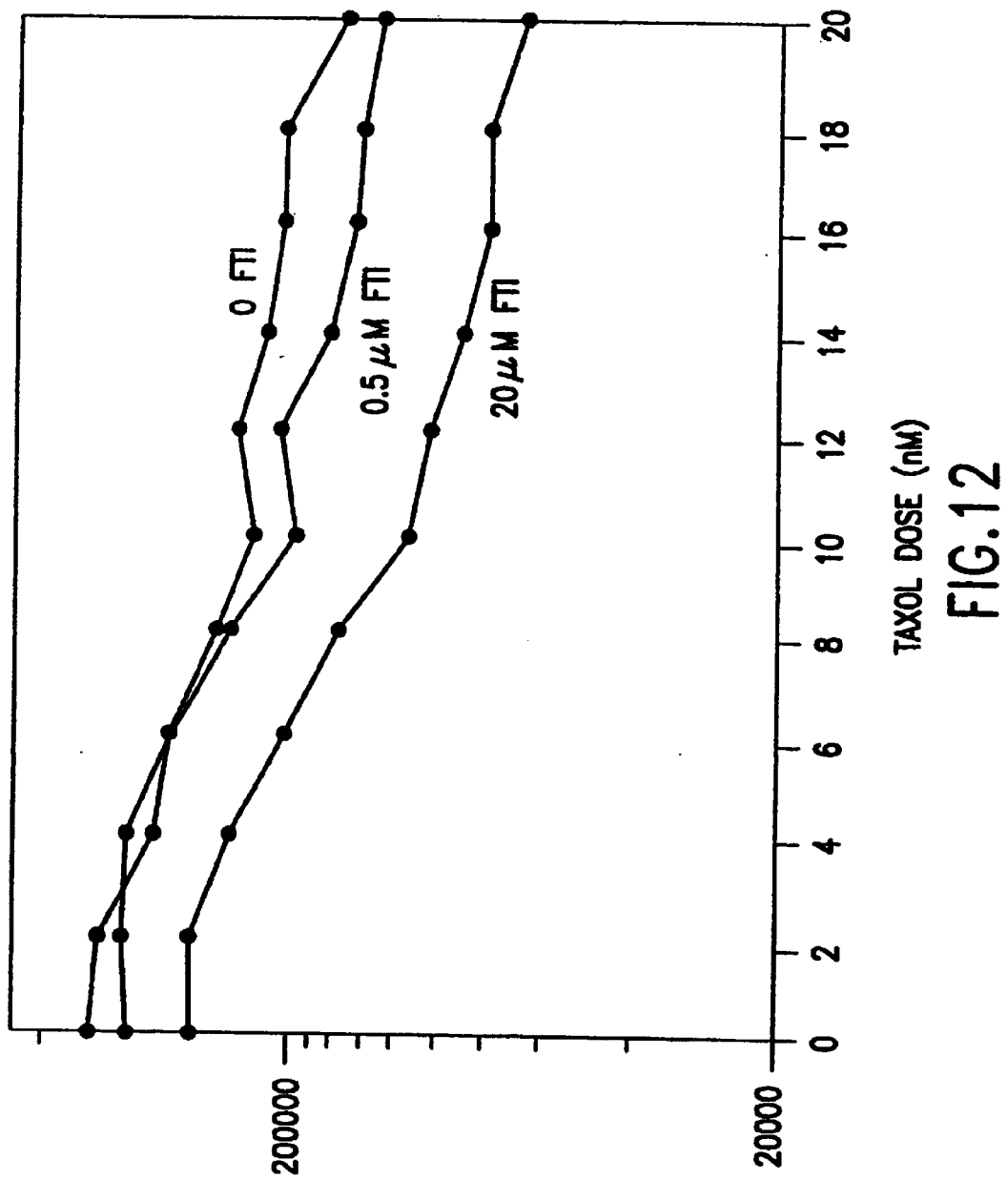
FIG. 12: Effect of a Farnesyl-protein Transferase Inhibitor in combination with paclitaxel on PC3 Cells: Cell proliferation of PC3 cells (ATCC CRL-1435; *Invest. Urol.*, 17:16–23 (1979); *Cancer Res.* 40: 524–534 (1980)) which were treated with various concentrations of paclitaxel for 4 hours. Cells were seeded 25,000/6 well plate. After the treatment with paclitaxel, the cells were incubated for 5 days in the absence or presence of various concentrations of Compound A. See Protocol A in the "In vitro growth inhibition of human tumor cells assay."
Figure 13:
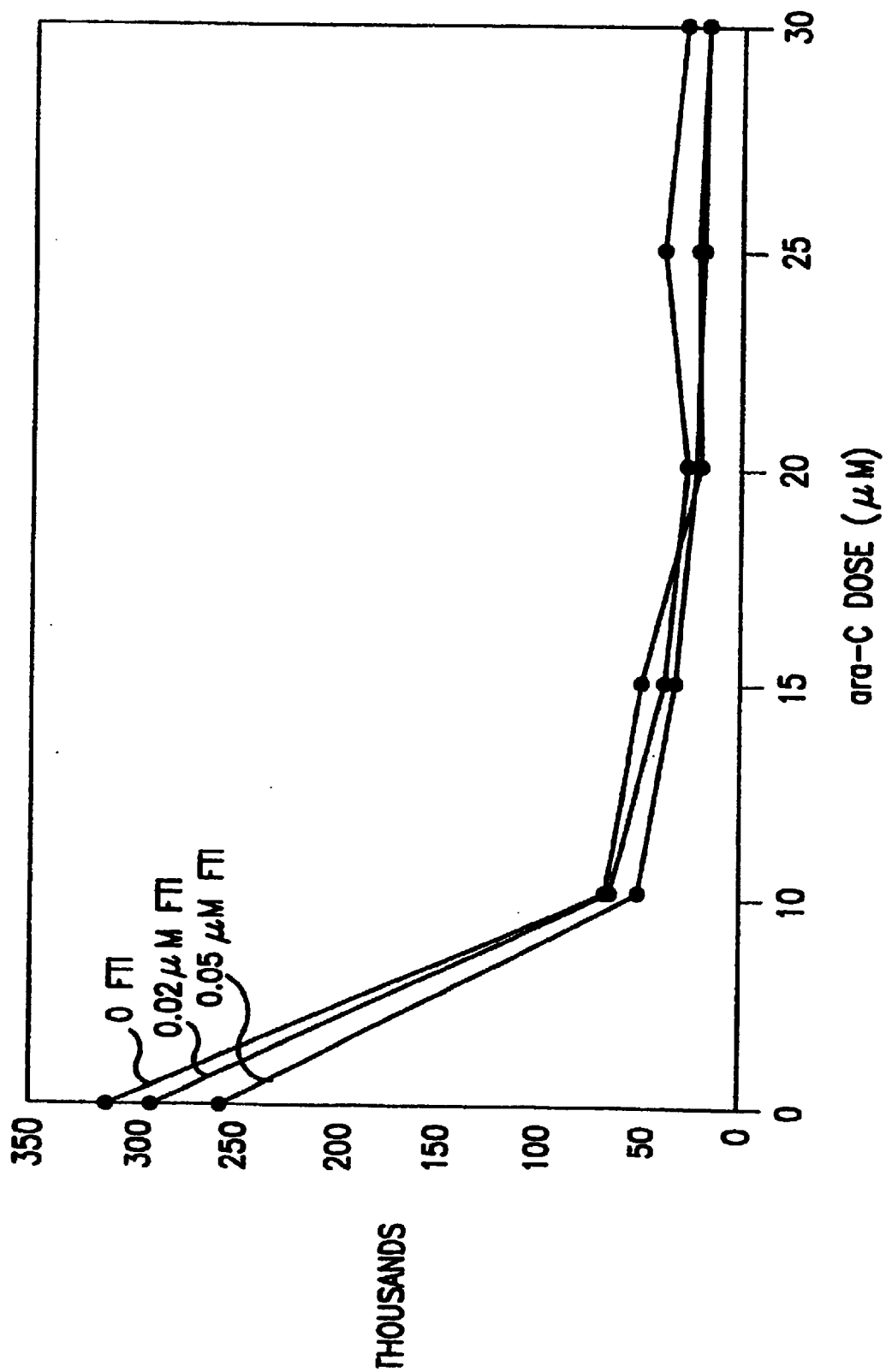
FIG. 13: Effect of a Farnesyl-protein Transferase Inhibitor in combination with ara-C on MCF-7 Cells: Cell proliferation of MCF-7 cells which were treated with various concentrations of ara-C for 4 hours. Cells were seeded 20,000/6 well plate. After the treatment with ara-C, the cells were incubated for 7 days in the absence or presence of various concentrations of Compound A. See Protocol A in the "In vitro growth inhibition of human tumor cells assay."
Figure 14:
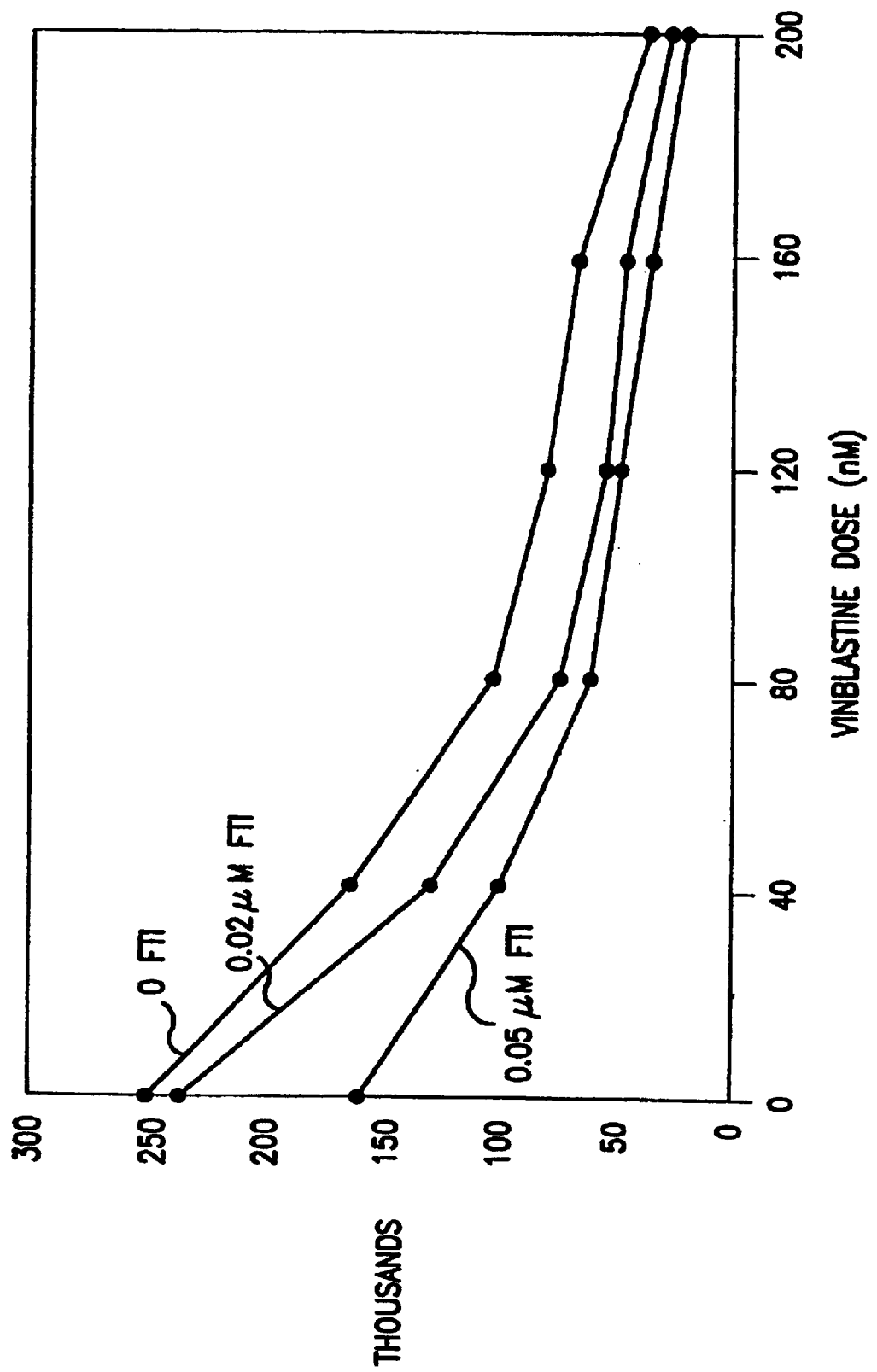
FIG. 14: Effect of a Farnesyl-protein Transferase Inhibitor in combination with vinblastine on MCF-7 Cells: Cell proliferation of MCF-7 cells which were treated with various concentrations of vinblastine for 4 hours. Cells were seeded 20,000/6 well plate. After the treatment with vinblastine the cells were incubated for 7 days in the absence or presence of various concentrations of Compound A. See Protocol A in the "In vitro growth inhibition of human tumor cells assay."
Figure 15:
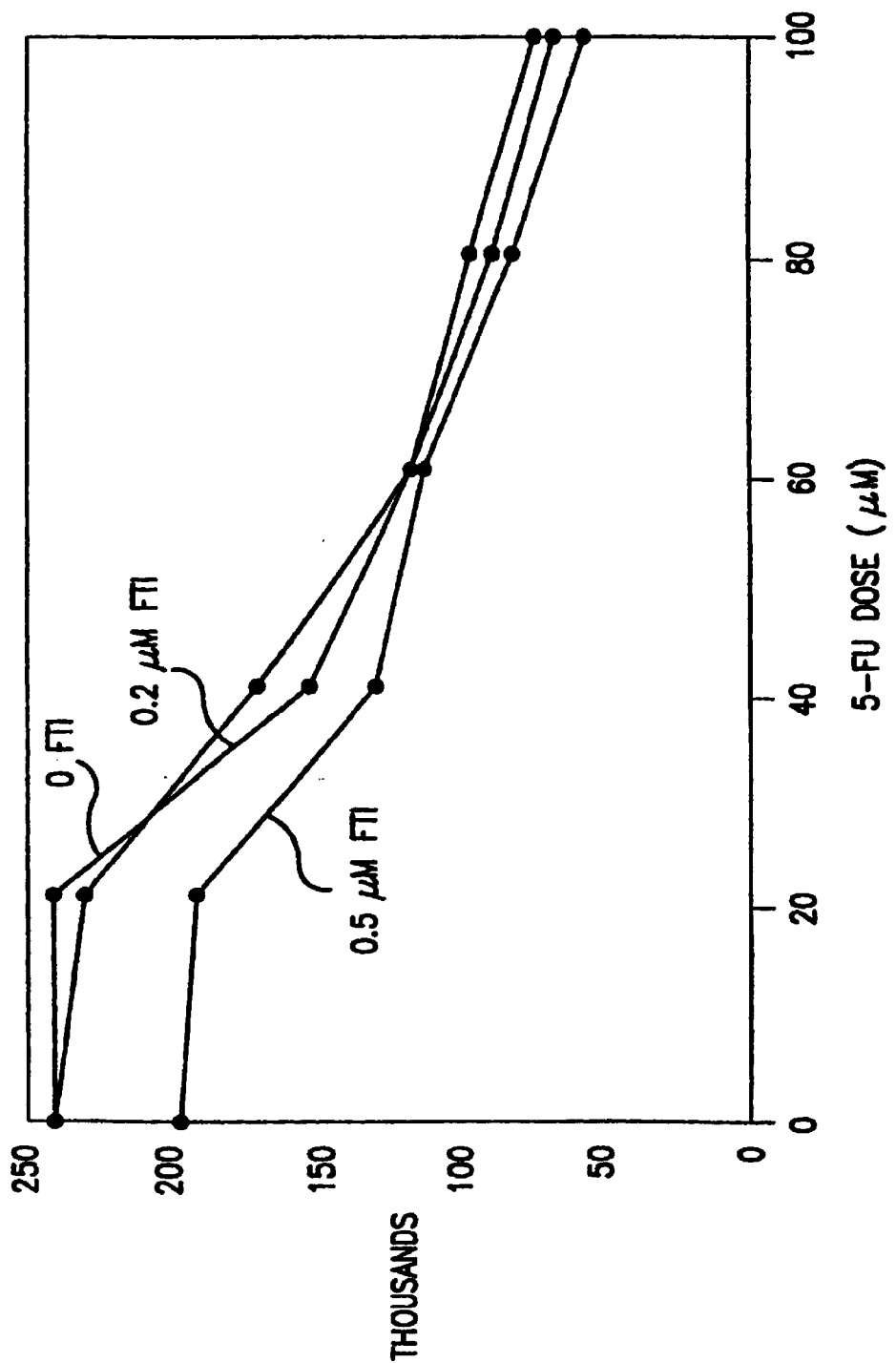
FIG. 15: Effect of a Farnesyl-protein Transferase Inhibitor in combination with 5-fluorouracil on MCF-7 Cells: Cell proliferation of MCF-7 cells which were treated with various concentrations of 5-fluorouracil for 4 hours. Cells were seeded 20,000/6 well plate. After the treatment with 5-fluorouracil, the cells were incubated for 7 days in the absence or presence of various concentrations of Compound A. See Protocol A in the "In vitro growth inhibition of human tumor cells assay."
Figure 16:
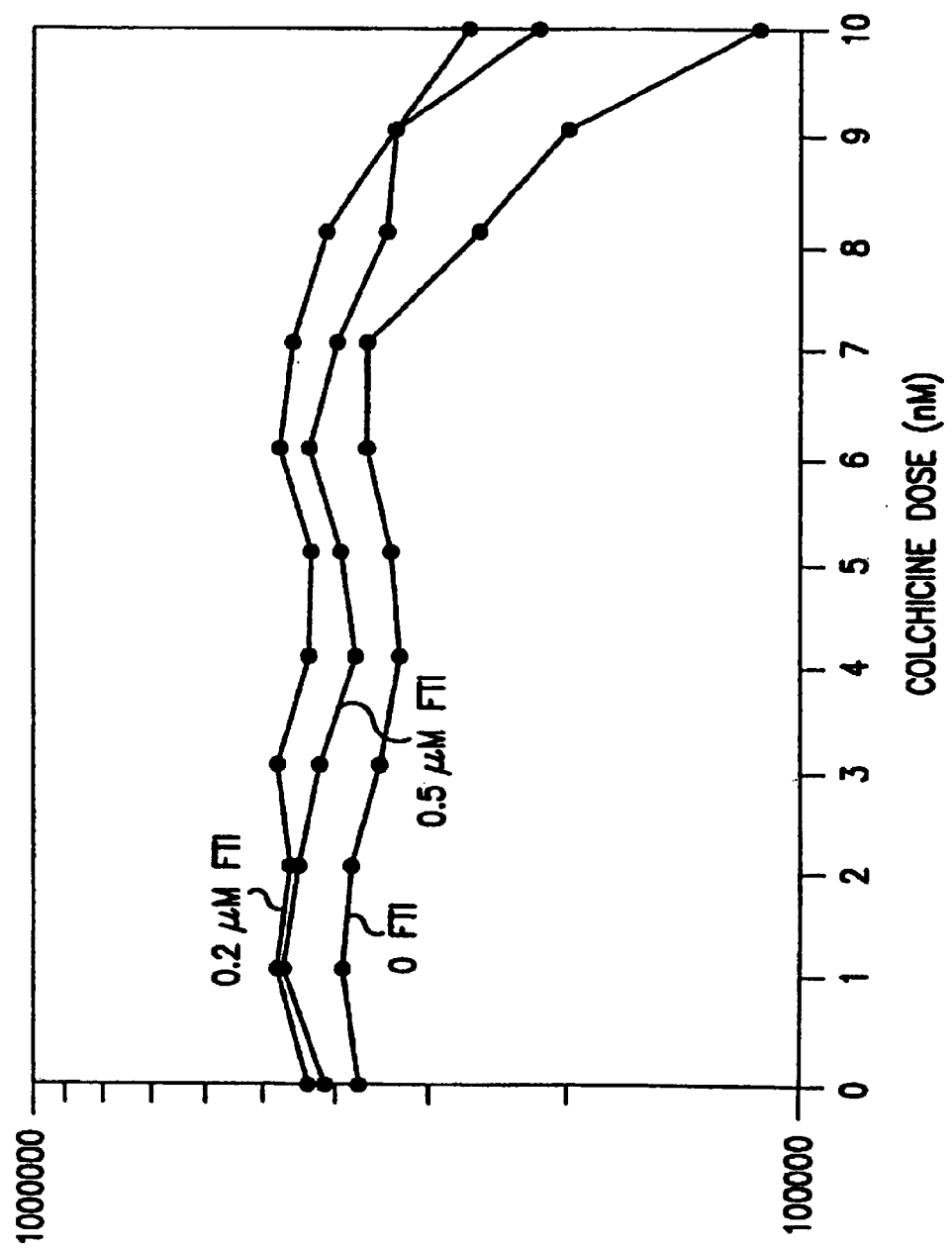
FIG. 16: Effect of a Farnesyl-protein Transferase Inhibitor in combination with colchicine on MDA-468 Cells: Cell proliferation of MDA-468 cells which were treated with various concentrations of colchicine in the absence or presence of various concentrations of Compound A for 24 hours. Cells were seeded 20,000/6 well plate. After the treatment with colchicine and Compound A, the cells were washed and then were incubated for 8 days in the absence or presence of various concentrations of Compound A. See Protocol C in the "In vitro growth inhibition of human tumor cells assay."
Figure 17:
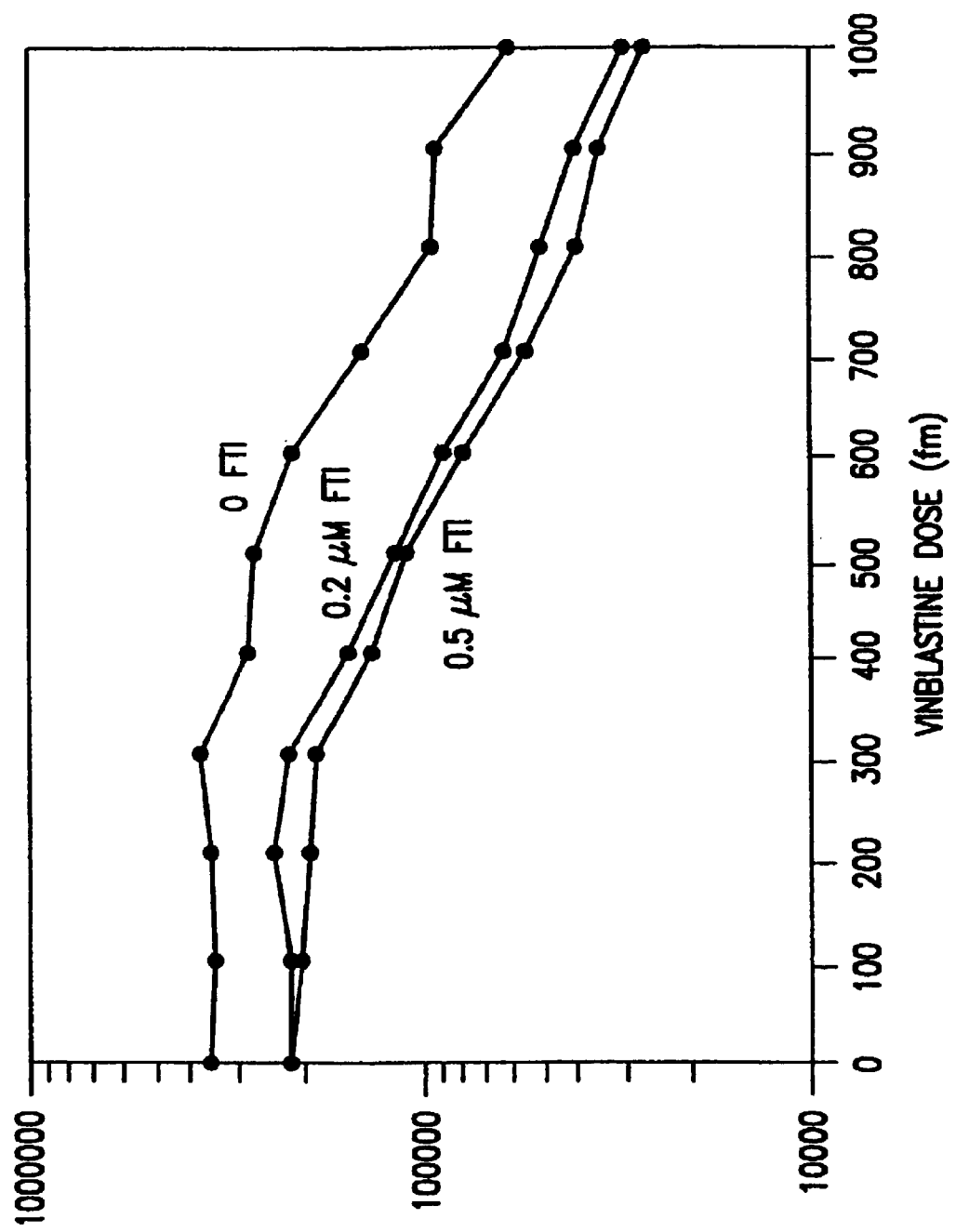
FIG. 17: Effect of a Farnesyl-protein Transferase Inhibitor in combination with vinblastine on MCF-7 Cells: Cell proliferation of MCF-7 cells which were treated with various concentrations of vinblastine for 7 days in the absence or presence of various concentrations of Compound A. Cells were seeded 10,000/6 well plate. See Protocol B in the "In vitro growth inhibition of human tumor cells assay."
Figure 18:
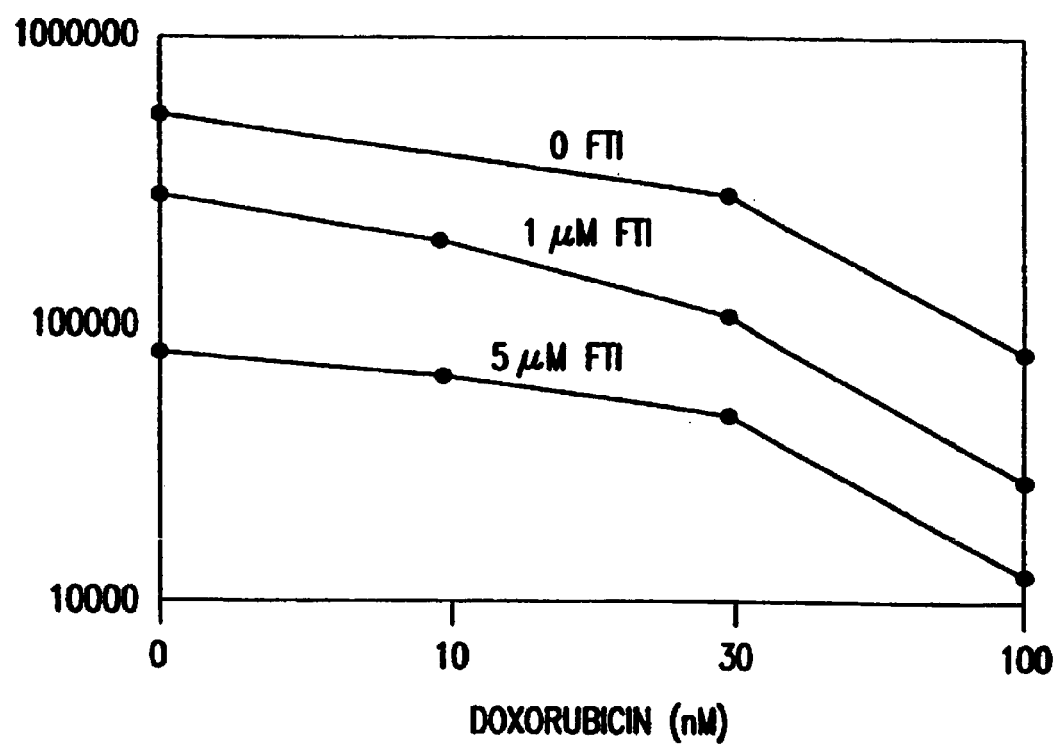
FIG. 18: Effect of a Farnesyl-protein Transferase Inhibitor in combination with doxorubicin on MDA-468 Cells: Cell proliferation of MDA-468 cells which were treated with various concentrations of doxorubicin for 4 hours. Cells were seeded 20,000/6 well cluster. After the treatment with doxorubicin, the cells were incubated for 10 days in the absence or presence of various concentrations of Compound A. See Protocol A in the "In vitro growth inhibition of human tumor cells assay."
Figure 19:
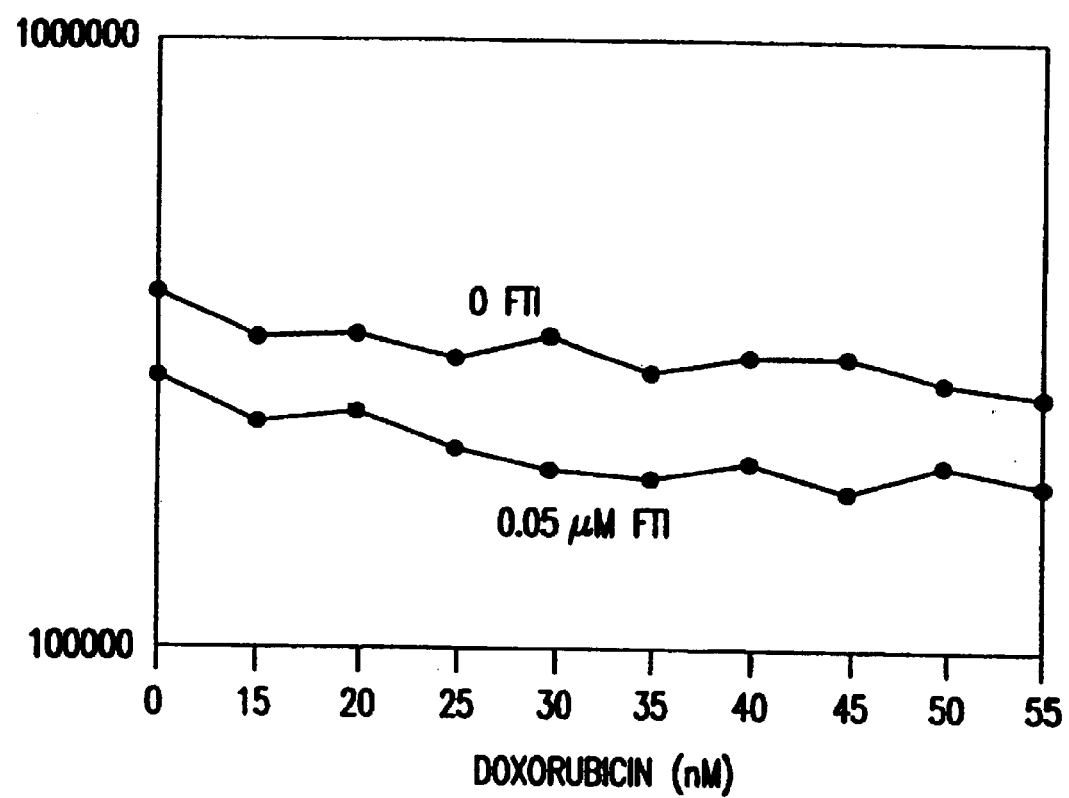
FIG. 19: Effect of a Farnesyl-protein Transferase Inhibitor in combination with doxorubicin on MCF-7 Cells: Cell proliferation of MCF-7 cells which were treated with various concentrations of doxorubicin for 4 hours. Cells were seeded 20,000/6 well cluster. After the treatment with doxorubicin, the cells were incubated for 7 days in the absence or presence of various concentrations of Compound A. See Protocol A in the "In vitro growth inhibition of human tumor cells assay."
Figure 20:
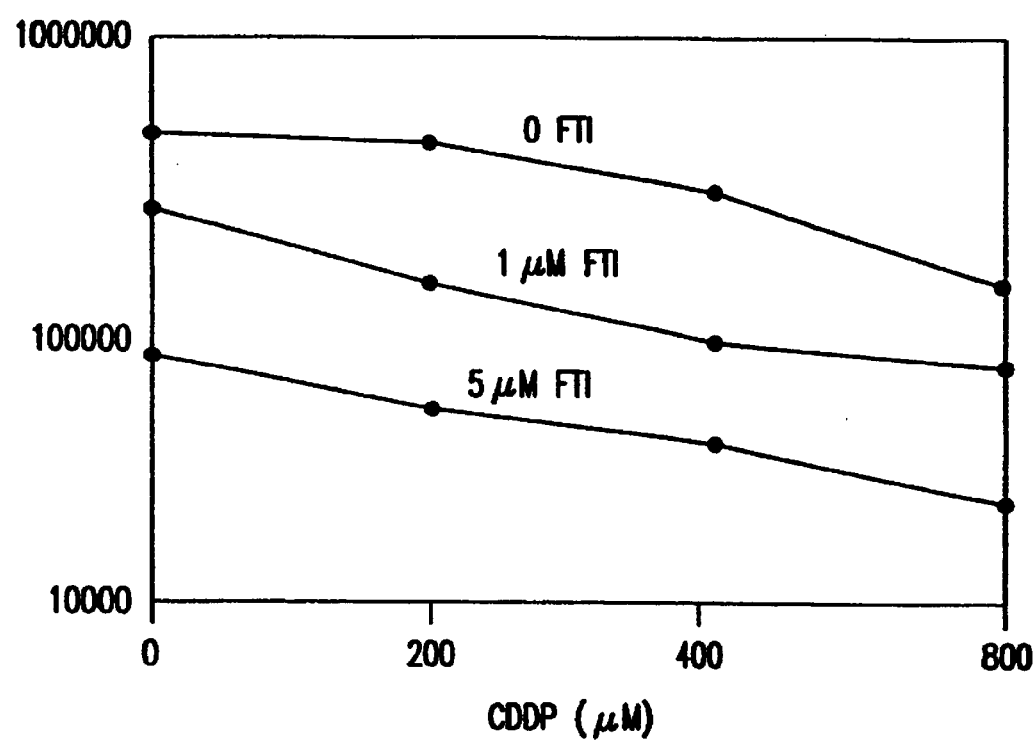
FIG. 20: Effect of a Farnesyl-protein Transferase Inhibitor in combination with cisplatinum on MDA-468 Cells: Cell proliferation of MDA-468 cells which were treated with various concentrations of cisplatinum for 4 hours. Cells were seeded 20,000/6 well cluster. After the treatment with cisplatinum, the cells were incubated for 10 days in the absence or presence of various concentrations of Compound A. See Protocol A in the "In vitro growth inhibition of human tumor cells assay."
Figure 21:
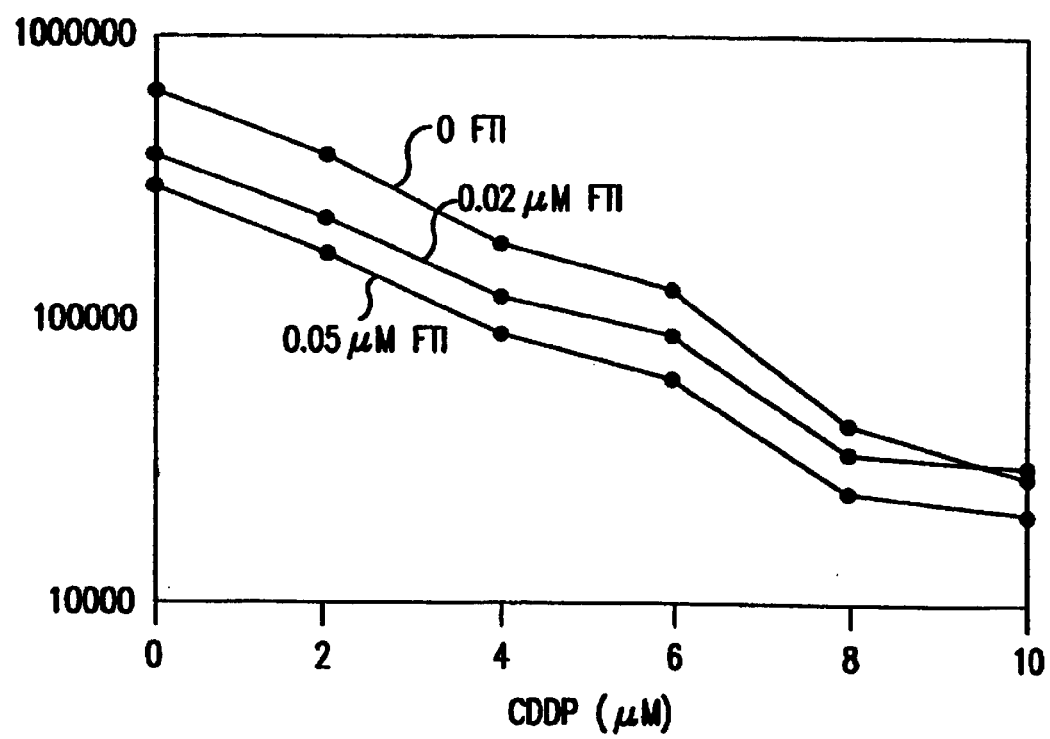
FIG. 21: Effect of a Farnesyl-protein Transferase Inhibitor in combination with cisplatinum on MCF-7 Cells: Cell proliferation of MCF-7 cells which were treated with various concentrations of cisplatinum for 4 hours. Cells were seeded 20,000/6 well cluster. After the treatment with cisplatinum, the cells were incubated for 7 days in the absence or presence of various concentrations of Compound A. See Protocol A in the "In vitro growth inhibition of human tumor cells assay."
Figure 22:
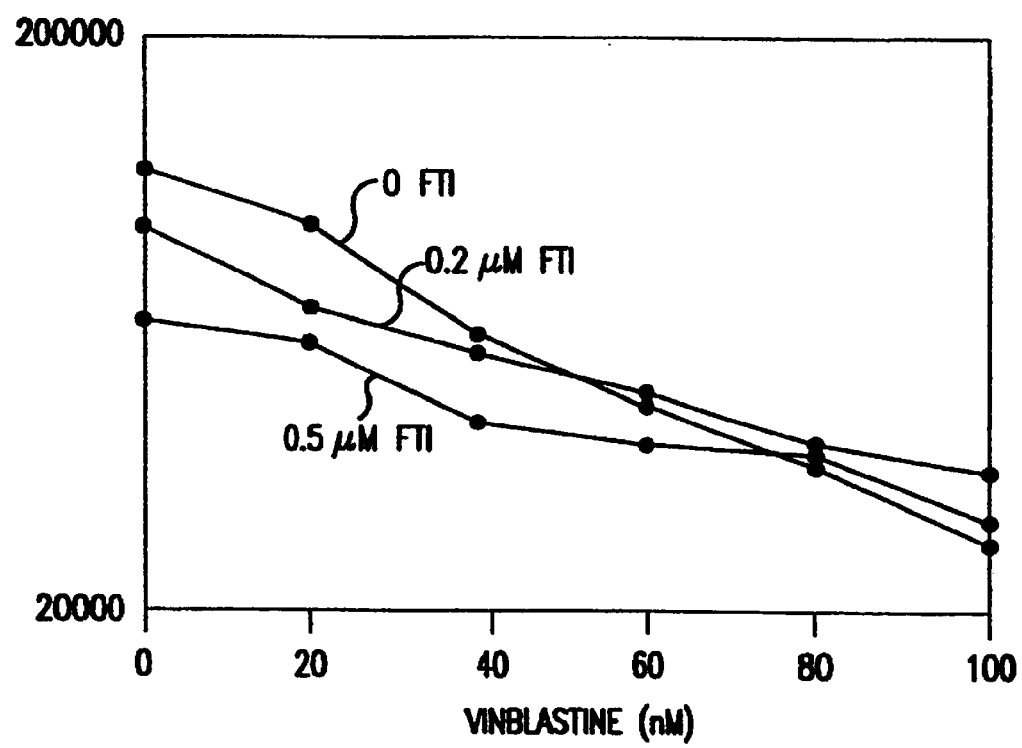
FIG. 22: Effect of a Farnesyl-protein Transferase Inhibitor in combination with vinblastine on MDA-468 Cells: Cell proliferation of MDA-468 cells which were treated with various concentrations of vinblastine for 4 hours. Cells were seeded 20,000/6 well cluster. After the treatment with vinblastine, the cells were incubated for 7 days in the absence or presence of various concentrations of Compound A. See Protocol A in the "In vitro growth inhibition of human tumor cells assay."
Figure 23:
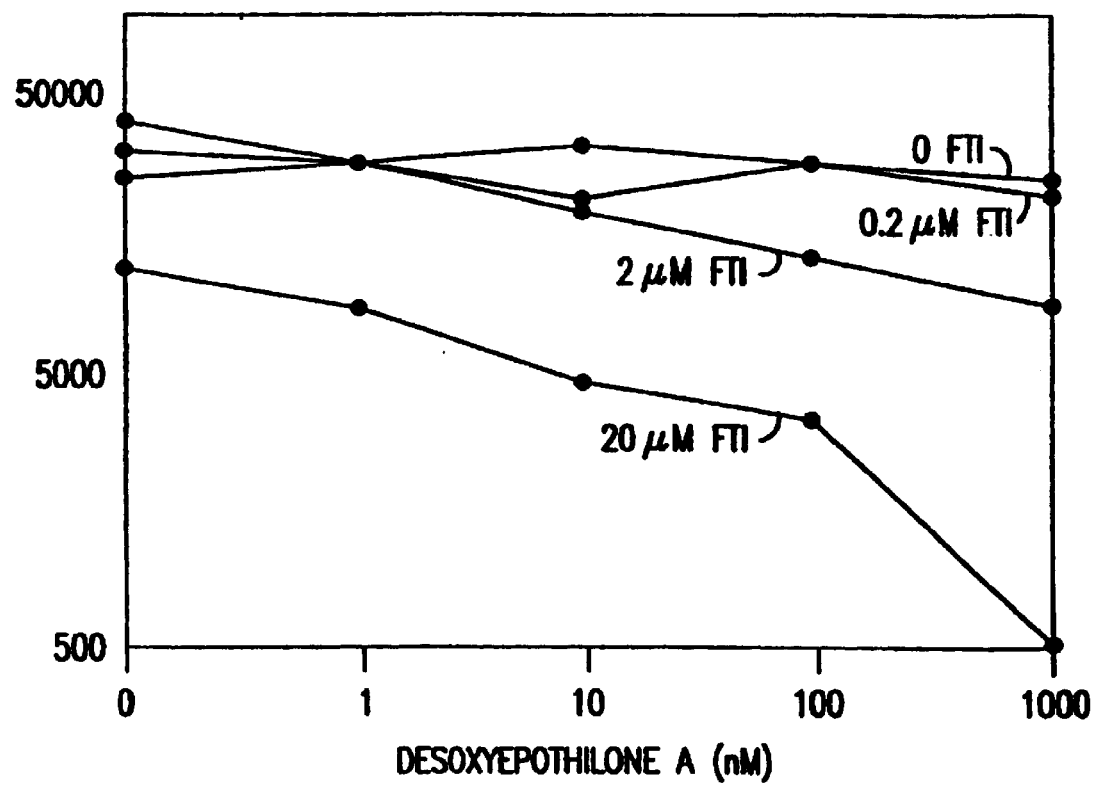
FIG. 23: Effect of a Farnesyl-protein Transferase Inhibitor in combination with desoxyepithilone A on MDA-468 Cells: Cell proliferation of MDA-468 cells which were treated with various concentrations of desoxyepithilone A for 4 hours. Cells were seeded 20,000/6 well cluster. After the treatment with desoxyepithilone A, the cells were incubated for 7 days in the absence or presence of various concentrations of Compound A. See Protocol A in the "In vitro growth inhibition of human tumor cells assay."
Figure 24:
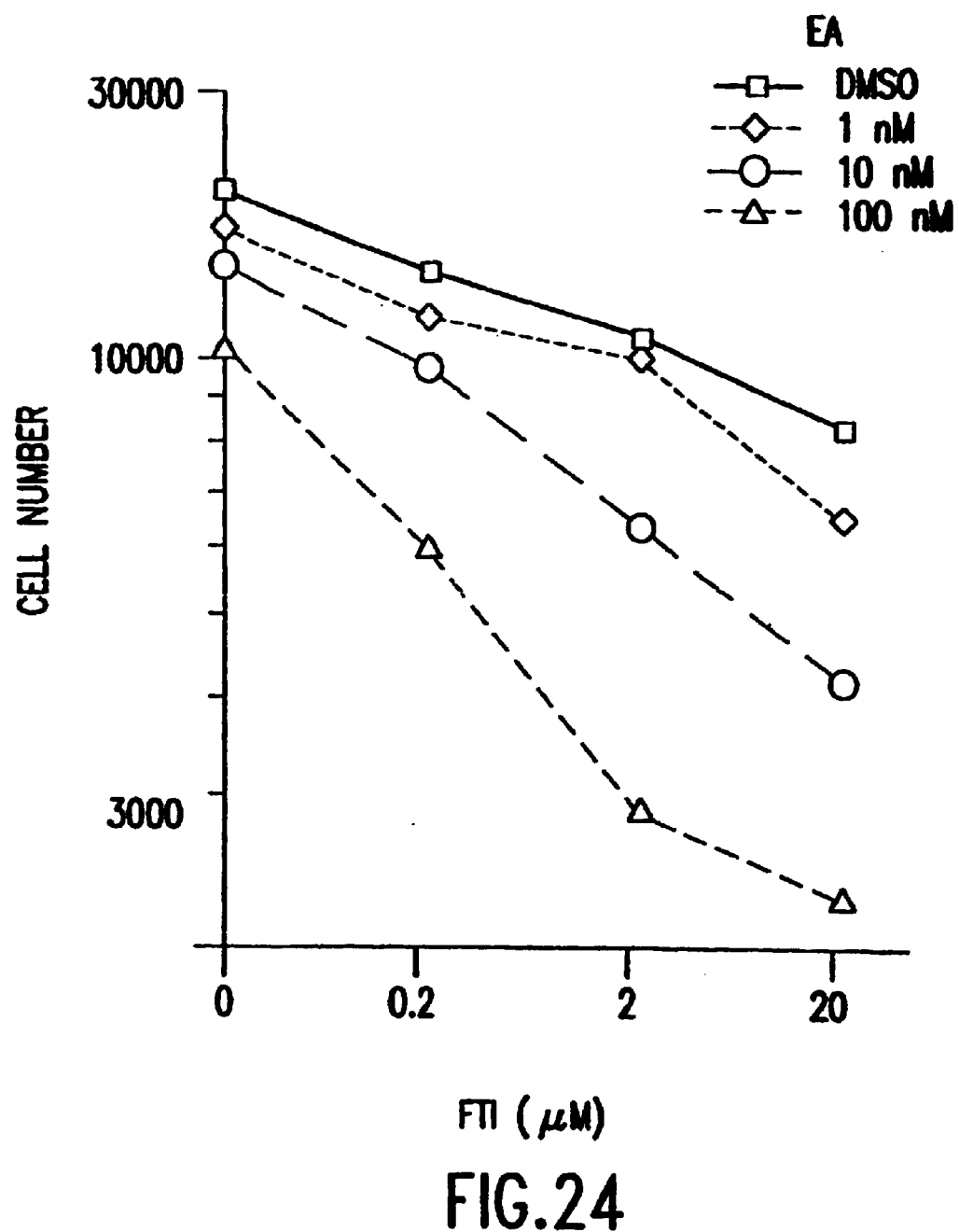
FIG. 24: Effect of a Farnesyl-protein Transferase Inhibitor in combination with epithilone A on DU 145 Cells: Cell proliferation of DU 145 cells which were treated with various concentrations of epithilone A for 4 hours. Cells were seeded 20,000/6 well cluster. After the treatment with epithilone A, the cells were incubated for 7 days in the absence or presence of various concentrations of Compound A. See Protocol A in the "In vitro growth inhibition of human tumor cells assay."
Figure 25:
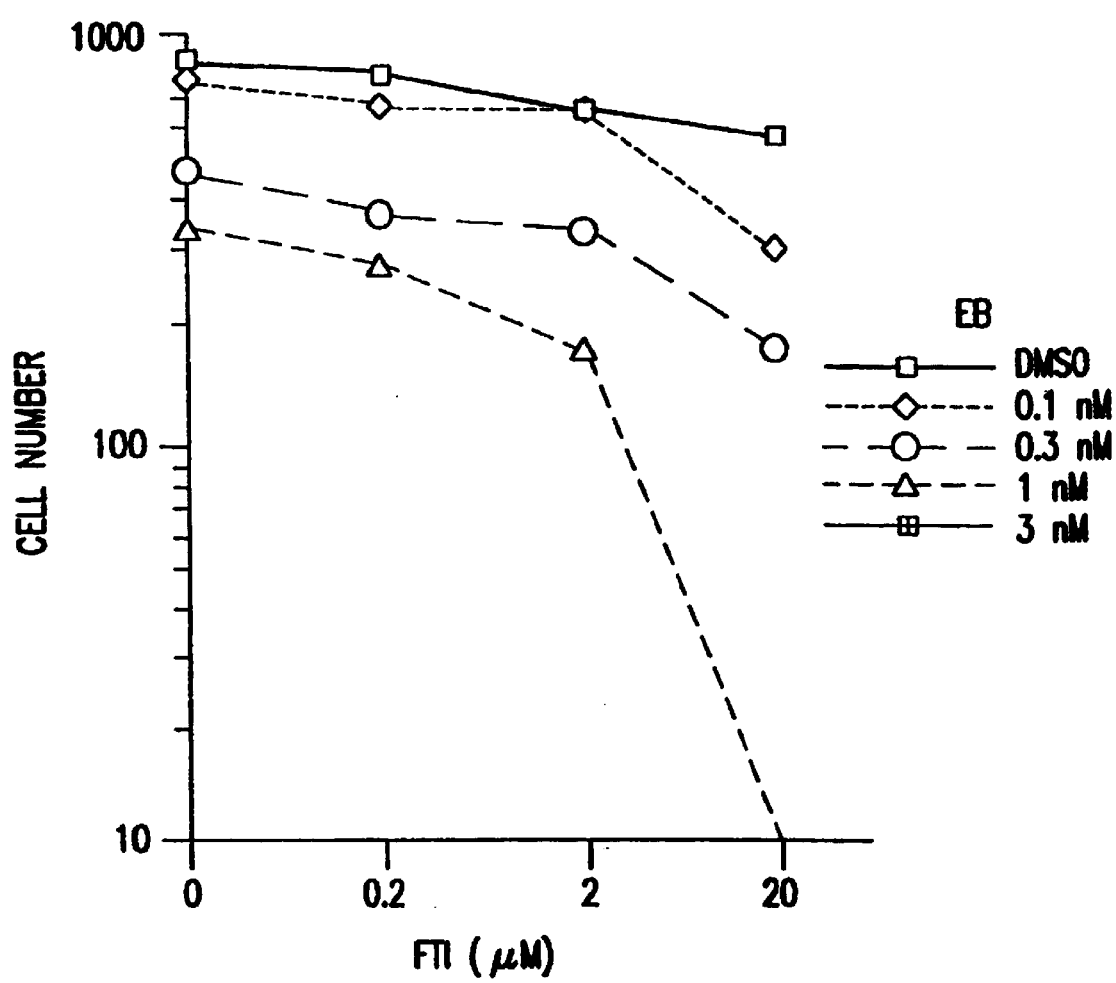
FIG. 25: Effect of a Farnesyl-protein Transferase Inhibitor in combination with epithilone B on DU 145 Cells: Cell proliferation of DU 145 cells which were treated with various concentrations of epithilone B for 4 hours. Cells were seeded 20,000/6 well cluster. After the treatment with epithilone B, the cells were incubated for 7 days in the absence or presence of various concentrations of Compound A. See Protocol A in the "In vitro growth inhibition of human tumor cells assay."
Figure 26:
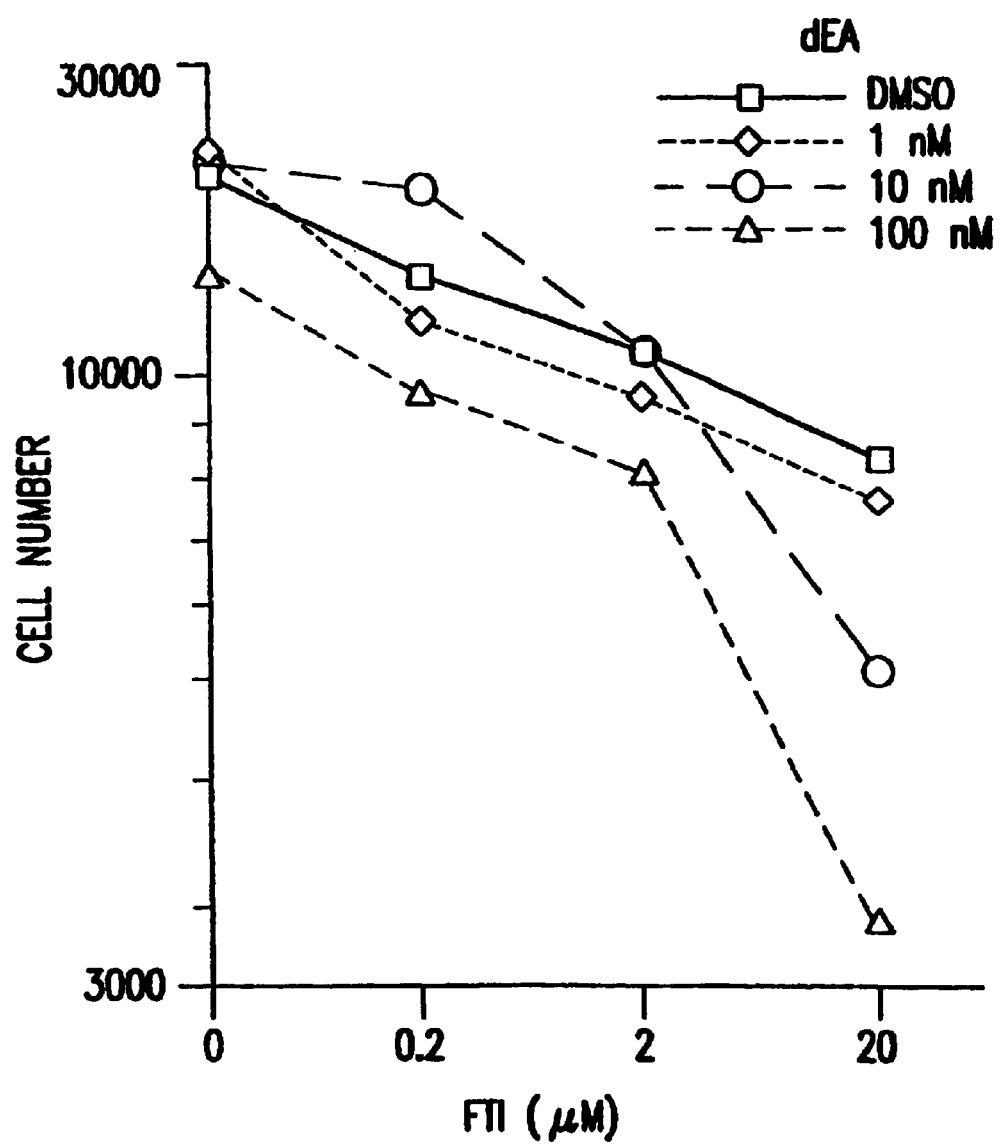
FIG. 26: Effect of a Farnesyl-protein Transferase Inhibitor in combination with desoxyepithilone A on DU 145 Cells: Cell proliferation of DU 145 cells which were treated with various concentrations of desoxyepithilone A for 4 hours. Cells were seeded 20,000/6 well cluster. After the treatment with desoxyepithilone A, the cells were incubated for 7 days in the absence or presence of various concentrations of Compound A. See Protocol A in the "In vitro growth inhibition of human tumor cells assay."
Figure 27:
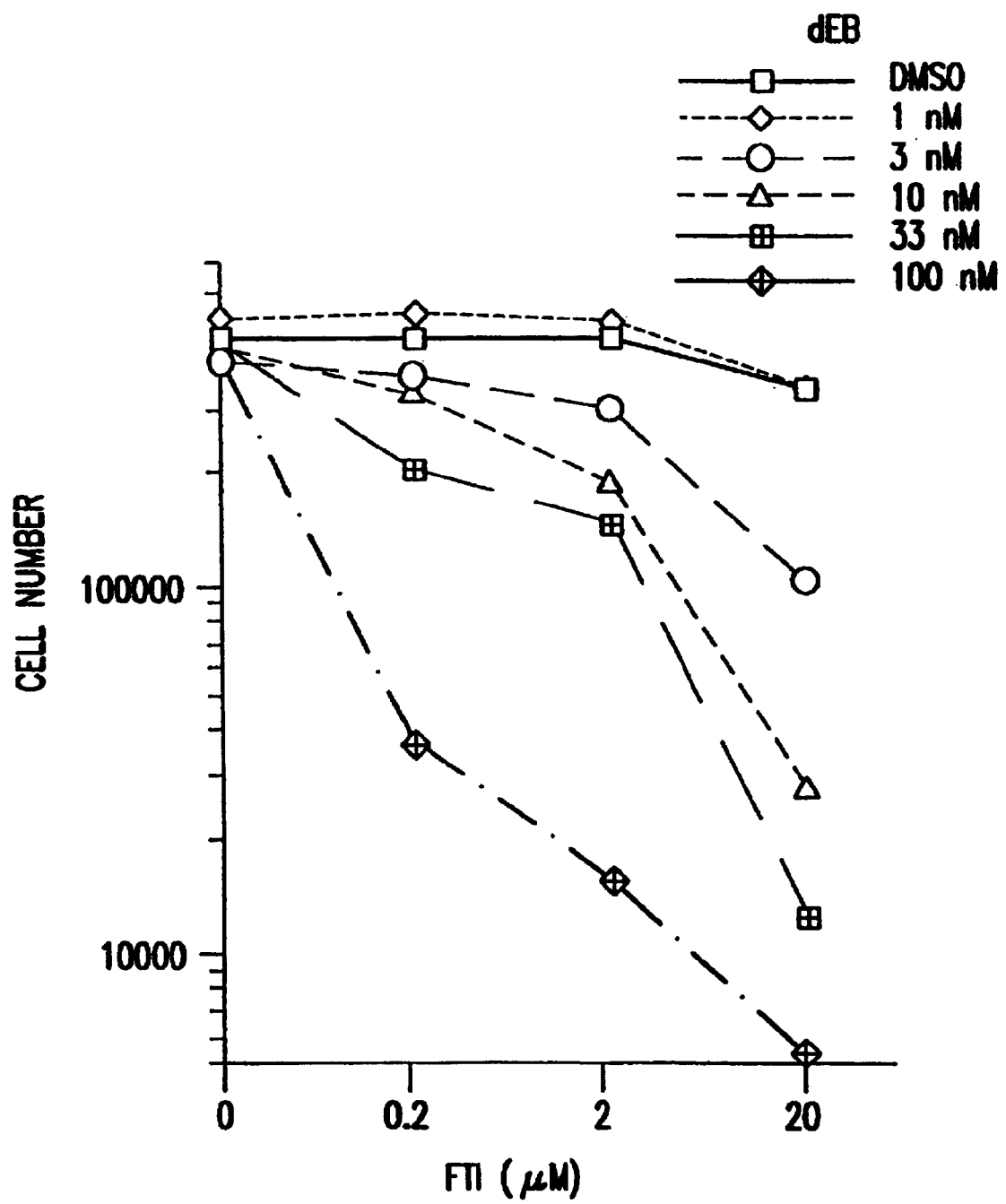
FIG. 27: Effect of a Farnesyl-protein Transferase Inhibitor in combination with desoxyepithilone B on DU 145 Cells: Cell proliferation of DU 145 cells which were treated with various concentrations of desoxyepithilone B for 4 hours. Cells were seeded 20,000/6 well cluster. After the treatment with desoxyepithilone B, the cells were incubated for 7 days in the absence or presence of various concentrations of Compound A. See Protocol A in the "In vitro growth inhibition of human tumor cells assay."
Figure 28:
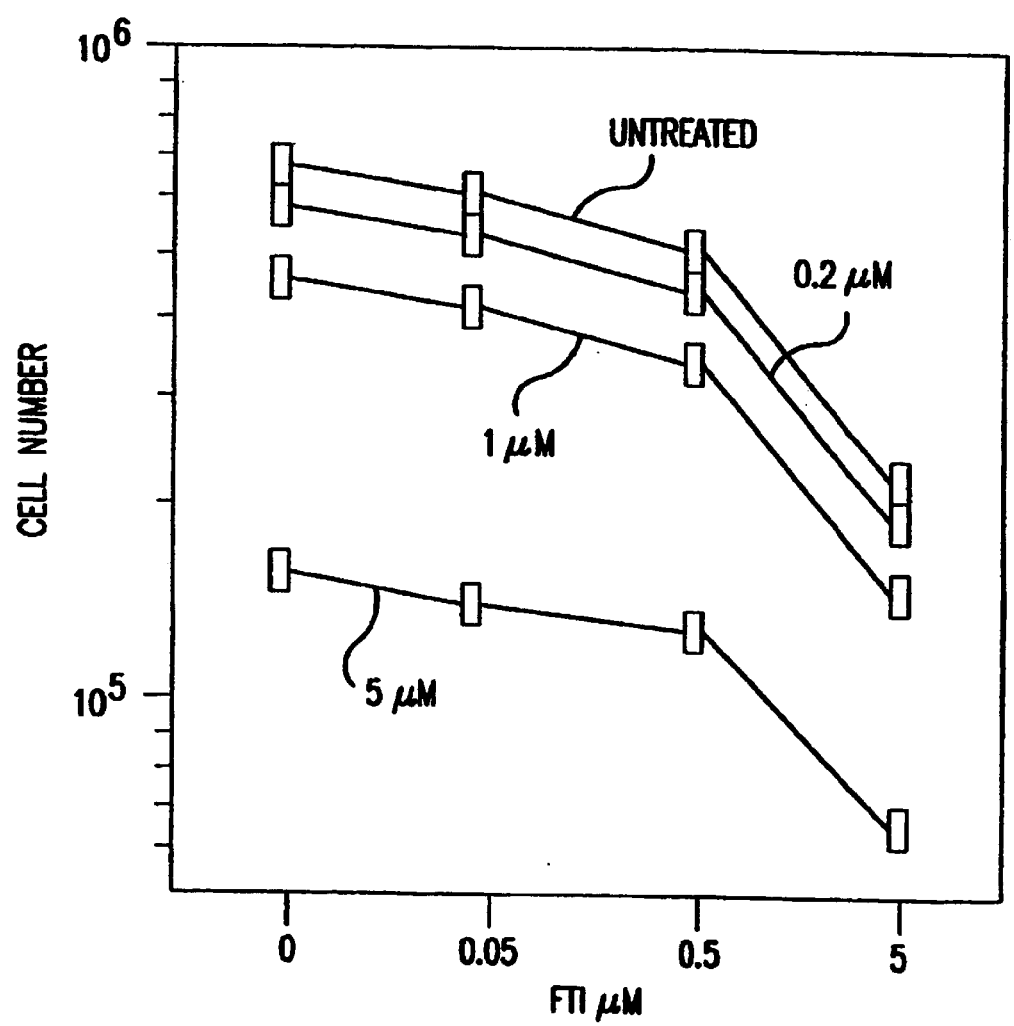
FIG. 28: Effect of a Farnesyl-protein Transferase Inhibitor in combination with etoposide on DU 145 Cells: Cell proliferation of DU 145 cells which were treated with various concentrations of etoposide for 4 hours. Cells were seeded 20,000/6 well cluster. After the treatment with etoposide, the cells were incubated for 7 days in the absence or presence of various concentrations of Compound A. See Protocol A in the "In vitro growth inhibition of human tumor cells assay."
Figure 29:
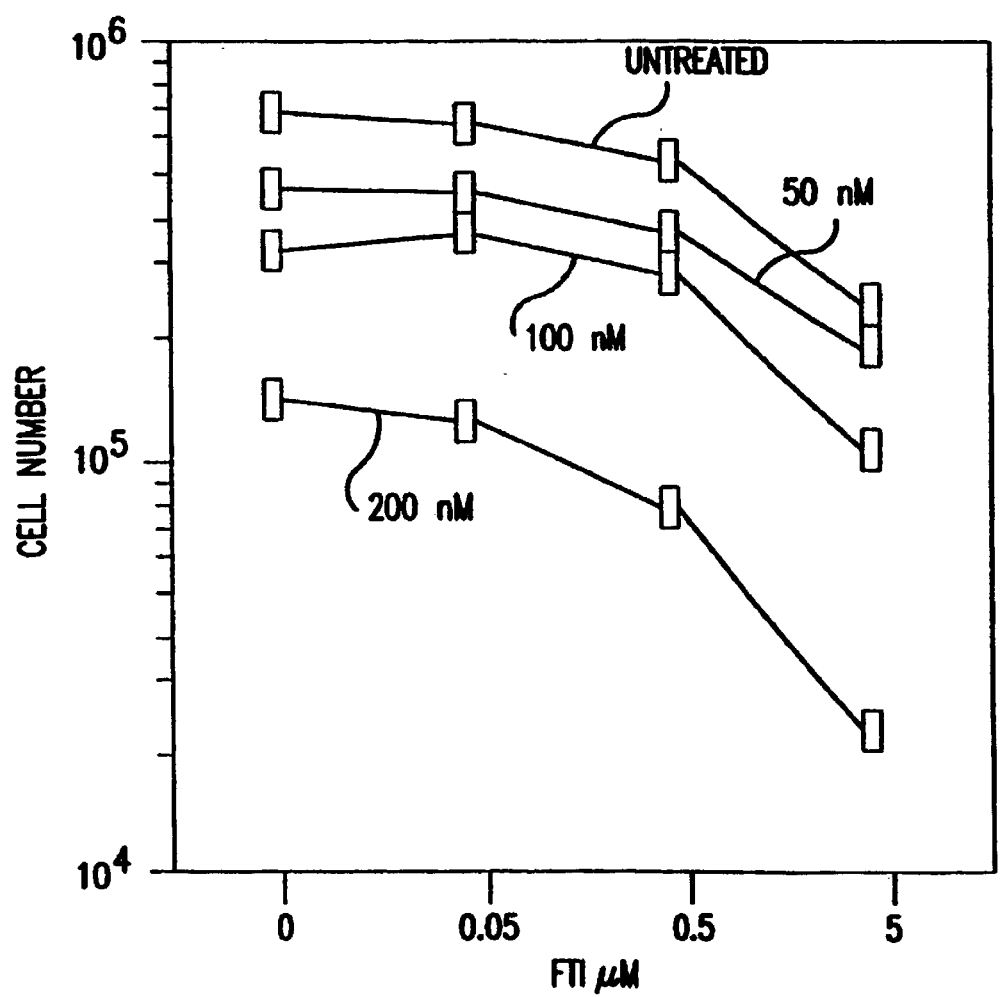
FIG. 29: Effect of a Farnesyl-protein Transferase Inhibitor in combination with doxorubicin on DU 145 Cells: Cell proliferation of DU 145 cells which were treated with various concentrations of doxorubicin for 4 hours. Cells were seeded 20,000/6 well cluster. After the treatment with doxorubicin, the cells were incubated for 7 days in the absence or presence of various concentrations of Compound A. See Protocol A in the "In vitro growth inhibition of human tumor cells assay."
Figure 30:
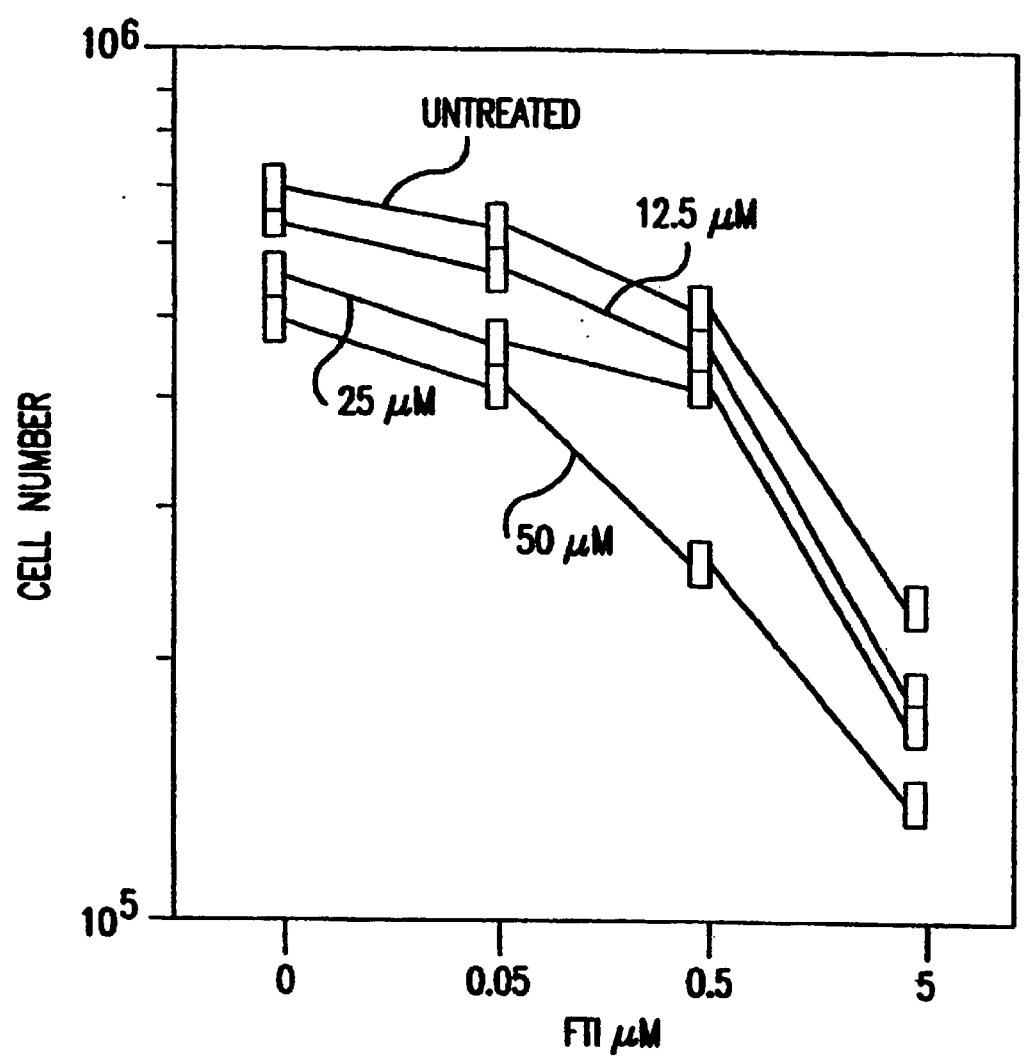
FIG. 30: Effect of a Farnesyl-protein Transferase Inhibitor in combination with estramustine on DU 145 Cells: Cell proliferation of DU 145 cells which were treated with various concentrations of estramustine for 4 hours. Cells were seeded 20,000/6 well cluster. After the treatment with estramustine, the cells were incubated for 7 days in the absence or presence of various concentrations of Compound A. See Protocol A in the "In vitro growth inhibition of human tumor cells assay."
Figure 31:
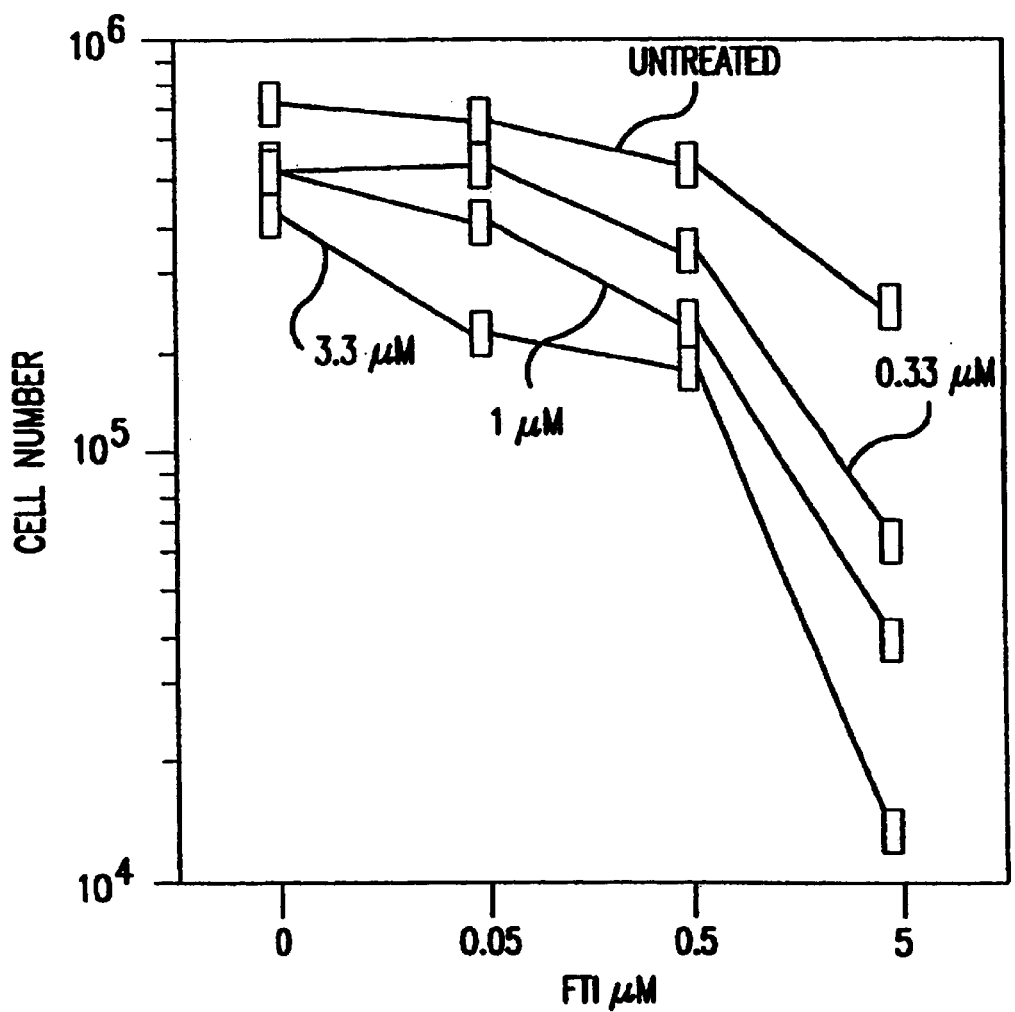
FIG. 31: Effect of a Farnesyl-protein Transferase Inhibitor in combination with cis-platinum on DU 145 Cells: Cell proliferation of DU 145 cells which were treated with various concentrations of cis-platinum for 4 hours. Cells were seeded 20,000/6 well cluster. After the treatment with cis-platinum, the cells were incubated for 7 days in the absence or presence of various concentrations of Compound A. See Protocol A in the "In vitro growth inhibition of human tumor cells assay."
Figure 32:
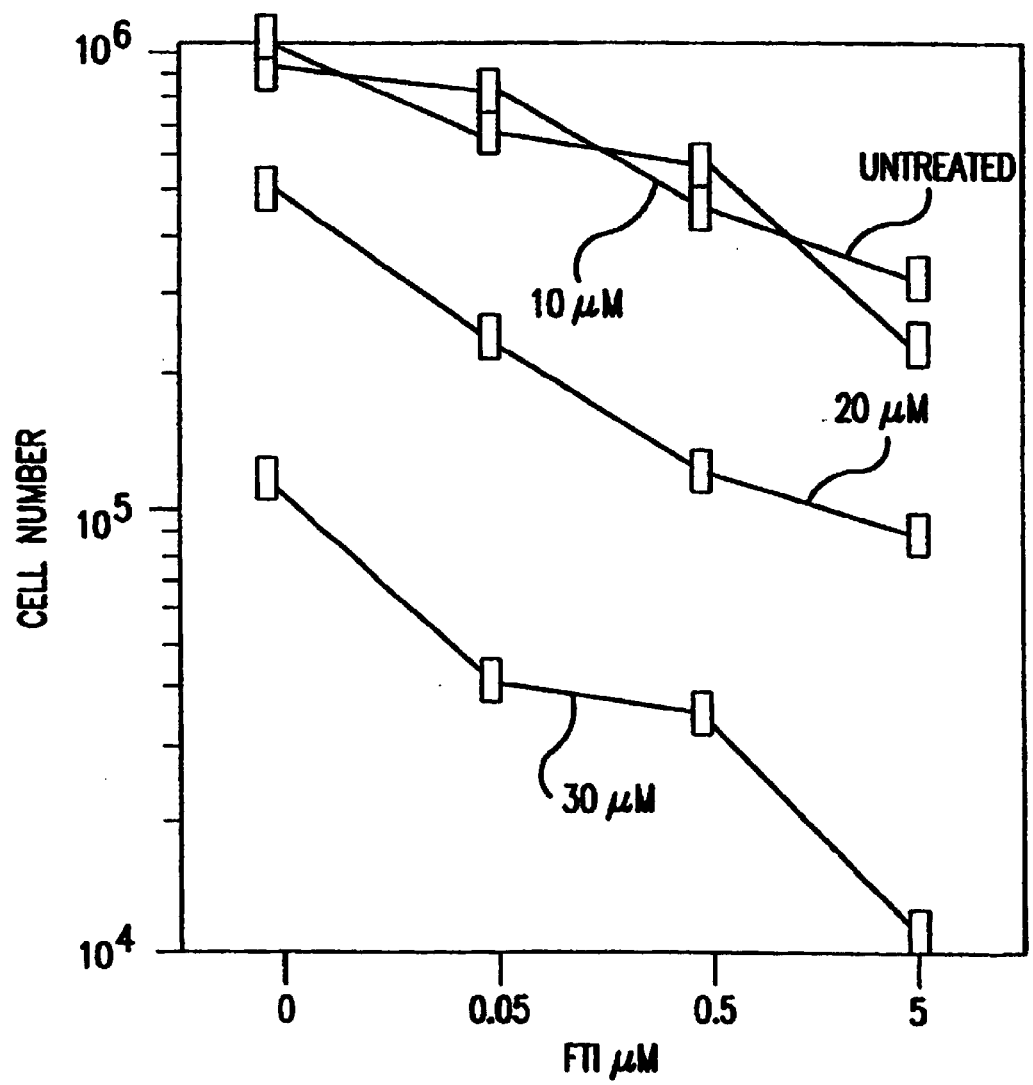
FIG. 32: Effect of a Farnesyl-protein Transferase Inhibitor in combination with bicalutamide on LNCaP Cells: Cell proliferation of LNCaP cells which were treated with various concentrations of bicalutamide for 4 hours. Cells were seeded 20,000/6 well cluster. After the treatment with bicalutamide, the cells were incubated for 7 days in the absence or presence of various concentrations of Compound A. See Protocol A in the "In vitro growth inhibition of human tumor cells assay."
Figure 33:
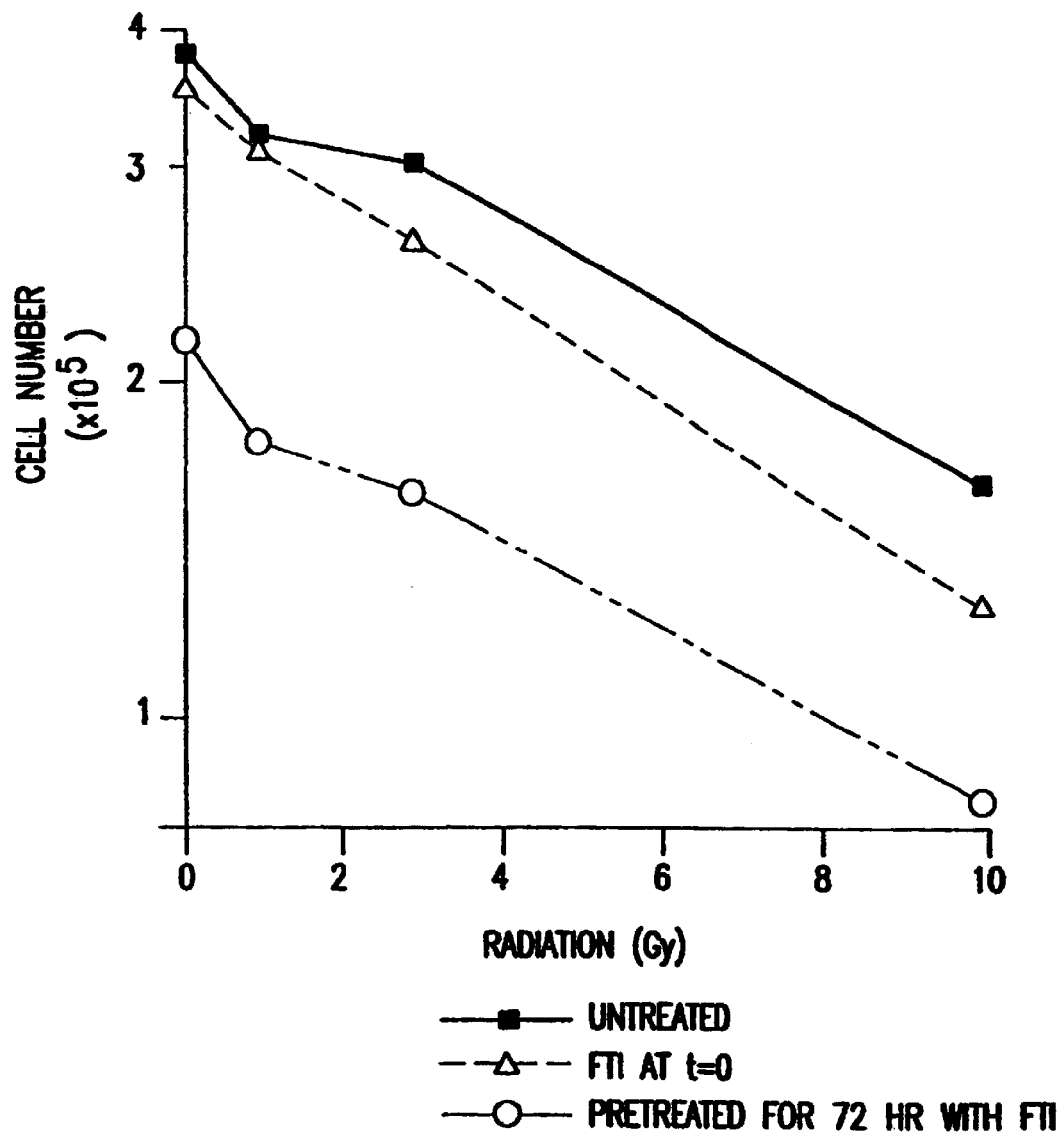
FIG. 33: Effect of a Farnesyl-protein Transferase Inhibitor in combination with γ-radiation on DU 145 Cells: Cell proliferation of DU 145 cells which were treated with various amounts of γ-radiation. Cells were seeded 20,000/6 well cluster. Cells were either pretreated with 20 mM Compound A, treated with 20 mM Compound A after irradiation or not treated with an FTI.

The present invention relates to a method of treating cancer which is comprised of admininstering to a mammalian patient in need of such treatment an effective amount of a combination of an antineoplastic agent and a prenyl-protein transferase inhibitor. The present method of treating cancer by simultaneously inhibiting protein prenylation and interfering with DNA replication and/or inducing apoptosis offers advantages over previously disclosed methods which utilize a prenyl-protein transferase inhibitor or an antineoplastic agent alone, in that the inhibitory activity and dosage of the instant combination of inhibitors of prenyl-protein transferase and anti-neoplastic agents can be individually varied depending on the nature of the cancer cells to be treated. Any compounds which act as an antineoplastic agent and any compounds which inhibit prenyl-protein transferase can be used in the instant method. Preferably the compounds utilized in the instant combination are an antineoplastic agent and a farnesyl-protein transferase inhibitor. When practicing the present method the antineoplastic agent and the inhibitor of prenyl-protein transferase may be administered either sequentially in any order or simultaneously.

It is anticipated that the therapeutic effect of the instant compositions may be achieved with smaller amounts of the antineoplastic agents and prenyl-protein transferase inhibitors than would be required if such antineoplastic agents and a prenyl-protein transferase inhibitors were administered alone, thereby avoiding any non-mechanism-based adverse toxicity effects which might result from administration of an amount of the single antineoplastic agent or prenyl-protein transferase inhibitor sufficient to achieve the same therapeutic effect. It is also anticipated that the instant compositions will achieve a synergistic therapeutic effect or will exhibit unexpected therapeutic advantage over the effect of any of the component compounds if administered alone.

As used herein the term an antineoplastic agent refers to compounds which either prevent cancer cells from multiplying by interfering with the cell's ability to replicate DNA or induce apoptosis in the cancerous cells.

The term prenyl-protein transferase inhibiting compound refers to compounds which antagonize, inhibit or counteract the expression of the gene coding a prenyl-protein transferase or the activity of the protein product thereof.

The term farnesyl protein transferase inhibiting compound likewise refers to compounds which antagonize, inhibit or counteract the expression of the gene coding farnesyl-protein transferase or the activity of the protein product thereof.

The term selective as used herein refers to the inhibitory activity of the particular compound against a prenyl-protein transferase activity or farnesyl-protein transferase activity. Preferably, for example, a selective inhibitor of farnesyl-protein transferase exhibits at least 20 times greater activity against farnesyl-protein transferase when comparing its activity against another receptor or enzymatic activity, respectively. More preferably the selectivity is at least 100 times or more.

The extent of selectivity of the two inhibitors that comprise the method of the instant invention may effect the advantages that the method of treatment claimed herein offers over previously disclosed methods of using a single antineoplastic agent or prenyl-protein transferase inhibitor for the treatment of cancer. In particular, use of two independent pharmaceutically active components that have complementary, essentially non-overlapping activities allows the person, utilizing the instant method of treatment to independently and accurately vary the inhibitory activity of the combination without having to synthesize a single drug having a particular pharmaceutical activity profile.

The term "synergistic" as used herein means that the effect achieved with the methods and compositions of this invention is greater than the sum of the effects that result from methods and compositions comprising the prenyl-protein transferase inhibitor and antineoplastic agent of this invention separately and in the amounts employed in the methods and compositions hereof. Such synergy between the two active ingredients enabling smaller doses to be given and preventing or delaying the build up of multi-drug resistance.

The preferred therapeutic effect provided by the instant composition is the treatment of cancer and specifically the inhibition of cancerous tumor growth and/or the regression of cancerous tumors. Cancers which are treatable in accordance with the invention described herein include cancers of the brain, breast, colon, genitourinary tract, lymphatic system, pancreas, rectum, stomach, larynx, liver, lung and prostate. More particularly, such cancers include histiocytic lymphoma, lung adenocarcinoma, pancreatic carcinoma, colo-rectal carcinoma, small cell lung cancers and neurological tumors.

The composition of this invention is also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the instant composition to a mammal in need of such treatment. For example, a component of NF-1 is a benign proliferative disorder.

The composition of the instant invention is also useful in the prevention of restenosis after percutaneous transluminal coronary angioplasty by inhibiting neointimal formation (C. Indolfi et al. Nature medicine, 1:541–545(1995).

The instant composition may also be useful in the treatment and prevention of polycystic kidney disease (D. L. Schaffner et al. American Journal of Pathology, 142:1051–1060 (1993) and B. Cowley, Jr. et al. FASEB Journal, 2:A3160 (1988)).

The pharmaceutical composition of this-invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic combination according to this invention, the selected combination or compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredients are combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The combinations of the instant invention may also be co-administered with other well known therapeutic agents that are selected for their particular usefulness against the condition that is being treated.

If formulated as a fixed dose, such combination products employ the combinations of this invention within the dosage range described below and the other pharmaceutically active agent(s) within its approved dosage range. Combinations of the instant invention may alternatively be used sequentially with known pharmaceutically acceptable agent(s) when a multiple combination formulation is inappropriate.

The instant invention encompasses a method of treatment wherein an antineoplastic agent and an inhibitor of prenyl-protein transferase are administered simultaneously or sequentially. Thus, while a pharmaceutical formulation comprising an antineoplastic agent and an inhibitor of prenyl-protein transferase may be advantageous for administering the combination for one particular treatment, sequential administration of the components of the combination may be advantageous in another treatment. It is also understood that the instant combination of antineoplastic agent and inhibitor of prenyl-protein transferase may be used in conjunction with other methods of treating cancer and/or tumors, including radiation therapy and surgery.

Radiation therapy, including x-rays or gamma rays which are delivered from either an externally applied beam or by implantation of tiny radioactive sources, may also be used in combination with an inhibitor of prenyl-protein transferase alone to treat cancer. The prenyl-protein transferase inhibitors may either be administered concurrently with the radiation therapy or may be administered prior to the application of the radiation.

In a particularly useful example of the method comprises of combining radiation therapy and administering an inhibitor of prenyl-protein transferase, a farnesyl-protein transferase inhibitor which is:

2(S)-[2(S)-[2(R)-Amino-3-mercapto]-propylamino-3(S)-methyl]-pentyloxy-3-phenylpropionyl-methionine sulfone isopropyl ester (Compound A);
is administered prior to the application of radiation therapy.

In another particularly useful example of the method comprises of combining radiation therapy and administering an inhibitor of prenyl-protein transferase, a farnesyl-protein transferase inhibitor which is:

1-(3-Chlorophenyl)-4-[1-(4-cyanobenzyl)-5-imidazolylmethyl]-2-piperazinone;
or a pharmaceutically acceptable salt thereof;
is administered prior to the application of radiation therapy.

In another particularly useful example of the method comprises of combining radiation therapy and administering an inhibitor of prenyl-protein transferase, a farnesyl-protein transferase inhibitor which is:

(R)-1-(3-Chlorophenyl)4-[1-(4-cyanobenzyl)-5-imidazolylmethyl]-5-[2-(ethanesulfonyl)methyl]-2-piperazinone;
or a pharmaceutically acceptable salt thereof;
is administered prior to the application of radiation therapy.

In another particularly useful example of the method comprises of combining radiation therapy and administering an inhibitor of prenyl-protein transferase, a farnesyl-protein transferase inhibitor which is:

4-[1-(5-Chloro-2-oxo-2H-[1,2']bipyridinyl-5'-ylmethyl)-1H-pyrrol-2-ylmethyl]-benzonitrile;
or a pharmaceutically acceptable salt thereof;
is -administered prior to the application of radiation therapy.

In another particularly useful example of the method comprises of combining radiation therapy and administering an inhibitor of prenyl-protein transferase, a farnesyl-protein transferase inhibitor which is:

1-[N-(1-(4-cyanobenzyl)-5-imidazolylmethyl)-N-(4-cyanobenzyl)amino]-4-(phenoxy)benzene;
or a pharmaceutically acceptable salt thereof;
is administered prior to the application of radiation therapy.

The present invention also encompasses a pharmaceutical composition useful in the treatment of cancer, comprising the administration of a therapeutically effective amount of the combinations of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's blood-stream by local bolus injection.

When a combination according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of an antineoplastic agent and a prenyl-protein transferase inhibitor are administered to a mammal undergoing treatment for cancer. Administration occurs in an amount of each type of inhibitor of between about 0.1 mg/kg of body weight to about 60 mg/kg of body weight per day, preferably of between 0.5 mg/kg of body weight to about 40 mg/kg of body weight per day. A particular therapeutic dosage that comprises the instant composition includes from about 0,01 mg to about 500mg of an antineoplastic agent and from about 0.01 mg to about 500mg of a prenyl-protein transferase inhibitor. Preferably, the dosage comprises from about 1 mg to about 100 mg of an antineoplastic agent and from about 1 mg to about 100 mg of a prenyl-protein transferase inhibitor.

Examples of an antineoplastic agent include, in general, microtubule-stabilising agents (such as paclitaxel (also known as Taxol®), docetaxel (also known as Taxotere®), epothilone A, epothilone B, desoxyepothilone A, desoxyepothilone B or their derivatives); microtubule-disruptor agents; alkylating agents, antimetabolites; a fusel poison; epidophyllotoxin; an antineoplastic enzyme; a topoisomerase inhibitor; procarbazine; mitoxantrone; platinum coordination complexes; biological response modifiers and growth inhibitors; hormonal/anti-hormonal therapeutic agents and haematopoietic growth factors.

Example classes of antineoplastic agents include, for example, the anthracycline family of drugs, the. vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, carminomycin, daunorubicin, aminopterin, methotrexate, methopterin, dichloromethotrexate, mitomycin C, porfiromycin,. 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, cisplatin, carboplatin, cyclophosphamide, bleomycin, tamoxifen, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

The preferred class of antineoplastic agents is the taxanes and the preferred antineoplastic agent is paclitaxel.

Examples of farnesyl-protein transferase inhibiting compounds include the following:

(a) a compound represented by formula (II-a) through (II-c):

(II-a)

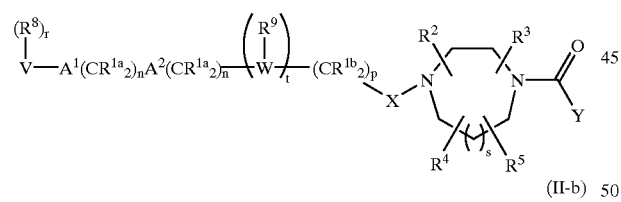

(II-b)

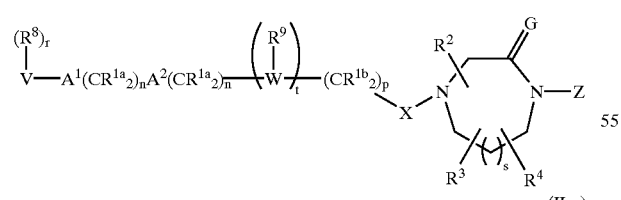

(II-c)

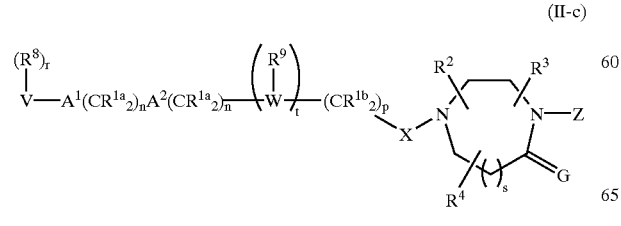

wherein with respect to formula (II-a):

(II-a)

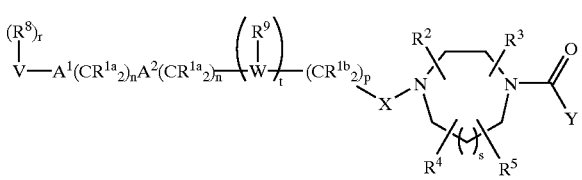

5 or a pharmaceutically acceptable salt thereof, $R^{1a}$ and $R^{1b}$ are independently selected from: p2 a) hydrogen,
b) aryl, heterocycle, $C_3$–$C_{10}$ cycloalkyl, $C_2$–C6 alkenyl, $C_2$–$C_6$ alkynyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—,
c) $C_1$–$C_6$ alkyl unsubstituted or substituted by aryl, heterocyclyl, $C_3$–$C_{10}$ cycloalkyl, $C_2$–$C_6$alkenyl, $C_2$–$C_6$ alkynyl, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)$—$NR^{10}$—;

$R^2$ and $R^3$ are independently selected from: H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle,

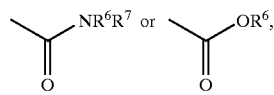

wherein the substituted group is substituted with one or more of:
1) aryl or heterocycle, unsubstituted or substituted with:
   a) $C_{1-4}$ alkyl,
   b) $(CH_2)_pOR^6$,
   c) $(CH_2)_pNR^6R^7$,
   d) halogen,
2) $C_{3-6}$ cycloalkyl,
3) $OR^6$,
4) $SR^6$, $S(O)R^6$, $SO_2R^6$,
5) —$NR^6R^7$, 6)
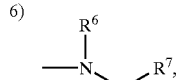

7)
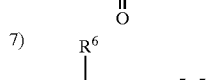

8)
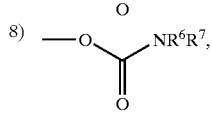

9) 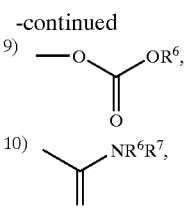

10) 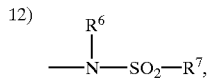

11) —SO$_2$—NR$^6$R$^7$,

12) 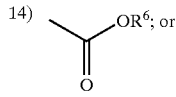

13) 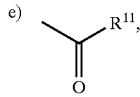

14)

$R^2$ and $R^3$ are attached to the same C atom and are combined to form —(CH$_2$)$_u$— wherein one of the carbon atoms is optionally replaced by a moiety selected from: O, S(O)$_m$, —NC(O)—, and —N(COR$^{10}$)—;

$R^4$ and $R^5$ are independently selected from H and CH$_3$; and any two of $R^2$, $R^3$, $R^4$ and $R^5$ are optionally attached to the same carbon atom;

$R^6$, $R^7$ and $R^{7a}$ are independently selected from: H; C$_{1-4}$ alkyl, C$_{3-6}$ cycloalkyl, heterocycle, aryl, aroyl, heteroaroyl, arylsulfonyl, heteroarylsulfonyl, unsubstituted or substituted with:
a) C$_{1-4}$ alkoxy,
b) aryl or heterocycle,
c) halogen,
d) HO, e)

f) —SO$_2$R$^{11}$, or
g) N(R$^{10}$)$_2$; or $R^6$ and $R^7$ may be joined in a ring;
$R^7$ and $R^{7a}$ may be joined in a ring;
$R^8$ is independently selected from:
a) hydrogen,
b) aryl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, CN, NO$_2$, R$^{10}$$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—, and
c) C$_1$–C$_6$ alkyl unsubstituted or substituted by aryl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NH—, CN, H$_2$N—C(NH)—, R$^{10}$C(O)—, R$^{10}$OC(O)—, N$_3$, —N(R$^{10}$)$_2$, or R$^{10}$OC(O)NH—;

$R^9$ is selected from:
a) hydrogen,
b) C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, CN, NO$_2$, (R$^{10}$)$_2$N—C—(NR$^{10}$)—, R$^{10}$C(O)—, R$^{10}$OC(O)—, N$_3$, —N(R$^{10}$)$_2$, or R$^{11}$OC(O)NR$^{10}$—, and
c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—;

$R^{10}$ is independently selected from hydrogen, C$_1$–C$_6$ alkyl, benzyl and aryl;

$R^{11}$ is independently selected from C$_1$–C$_6$ alkyl and aryl;

$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

V is selected from:
a) hydrogen,
b) heterocycle,
c) aryl,
d) C$_1$–C$_{20}$ alkyl wherein from 0 to 4 carbon atoms are replaced with a a heteroatom selected from O, S, and N, and
e) C$_2$–C$_{20}$ alkenyl, provided that V is not hydrogen if $A^1$ is S(O)$_m$ and V is not hydrogen if $A^1$ is a bond, n is 0 and $A^2$ is S(O)$_m$;

W is a heterocycle;

X is —CH$_2$—, —C(=O)—, or —S(=O)$_m$—;

Y is aryl, heterocycle, unsubstituted or substituted with one or more of:
1) C$_{1-4}$ alkyl, unsubstituted or substituted with:
   a) C$_{1-4}$ alkoxy,
   b) NR$^6$R$^7$,
   c) C$_{3-6}$ cycloalkyl,
   d) aryl or heterocycle,
   e) HO,
   f) —S(O)$_m$R$^6$, or
   g) —C(O)NR$^6$R$^7$,
2) aryl or heterocycle,
3) halogen,
4) OR$^6$,
5) NR$^6$R$^7$,
6) CN,
7) NO$_2$,
8) CF$_3$;
9) —S(O)$_m$R$^6$,
10) —C(O)NR$^6$R$^7$, or
11) C$_3$–C$_6$ cycloalkyl;

m is 0, 1 or 2;
n is 0, 1, 2, 3 or 4;
p is 0, 1, 2, 3 or 4;
r is 0 to 5, provided that r is 0 when V is hydrogen;
s is 0 or 1;
t is 0 or 1; and
u is 4 or 5;

with respect to formula (II-b):

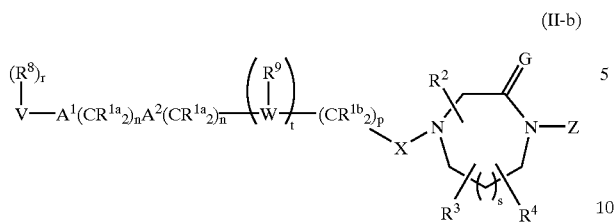

(II-b)

or a pharmaceutically acceptable salt thereof,
$R^{1a}$, $R^{1b}$, $R^{10}$, $R^{11}$, m, $R^2$, $R^3$, $R^6$, $R^7$, p, $R^{7a}$, u, $R^8$, $A^1$, $A^2$, V, W, X, n, p, r, s, t and u are as defined above with respect to formula (II-a);
$R^4$ is selected from H and $CH_3$;
and any two of $R^2$, $R^3$ and $R^4$ are optionally attached to the same carbon atom;
$R^9$ is selected from:
   a) hydrogen,
   b) alkenyl, alkynyl, perfluoroalkyl, F, Cl, Br, $R^{10}O$—, $R^{11}S(O)_m$—, $R^{10}C(O)NR^{10}$—, CN, $NO_2$, $(R^{10})_2N$—C—$(NR^{10})$—, $R^{10}C(O)$—, $R^{10}OC(O)$—, $N_3$, —$N(R^{10})_2$, or $R^{11}OC(O)NR^{10}$—, and
   c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;
G is $H_2$ or O;
Z is aryl, heteroaryl, arylmethyl, heteroarylmethyl, arylsulfonyl, heteroarylsulfonyl, unsubstituted or substituted with one or more of the following:
   1) $C_{1-4}$ alkyl, unsubstituted or substituted with:
      a) $C_{1-4}$ alkoxy,
      b) $NR^6R^7$,
      c) $C_{3-6}$ cycloalkyl,
      d) aryl or heterocycle,
      e) HO,
      f) —$S(O)_mR^6$, or
      g) —$C(O)NR^6R^7$,
   2) aryl or heterocycle,
   3) halogen,
   4) $OR^6$,
   5) $NR^6R^7$,
   6) CN,
   7) $NO_2$,
   8) $CF_3$;
   9) —$S(O)_mR^6$,
   10) —$C(O)NR^6R^7$, or
   11) $C_3$–$C_6$ cycloalkyl;
with respect to formula (II-c):

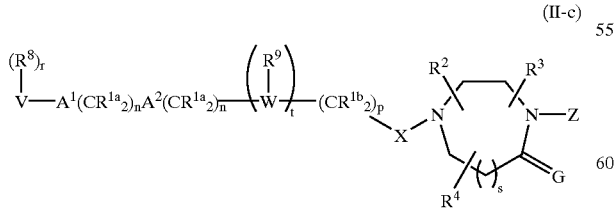

(II-c)

or a pharmaceutically acceptable salt thereof,
$R^{1a}$, $R^{1b}$, $R^{10}$, $R^{11}$, m, $R^2$, $R^3$, $R^6$, $R^7$, p, u, $R^{7a}$, $R^8$, $A^1$, $A^2$, V, W, X, n, r and t are as defined above with respect to formula (II-a);

$R^4$ is selected from H and $CH_3$;
and any two of $R^2$, $R^3$ and $R^4$ are optionally attached to the same carbon atom;
G is O;
Z is aryl, heteroaryl, arylmethyl, heteroarylmethyl, arylsulfonyl, heteroarylsulfonyl, unsubstituted or substituted with one or more of the following:
   1) $C_{1-4}$ alkyl, unsubstituted or substituted with:
      a) $C_{1-4}$ alkoxy,
      b) $NR^6R^7$,
      c) $C_{3-6}$ cycloalkyl,
      d) aryl or heterocycle,
      e) HO,
      f) —$S(O)_mR^6$, or
      g) —$C(O)NR^6R^7$,
   2) aryl or heterocycle,
   3) halogen,
   4) $OR^6$,
   5) $NR^6R^7$,
   6) CN,
   7) $NO_2$,
   8) $CF_3$;
   9) $S(O)_mR^6$,
   10) —$C(O)NR^6R^7$, or
   11) $C_3$–$C_6$ cycloalkyl;
and
s is 1;
(b) a compound represented by formula (II-d):

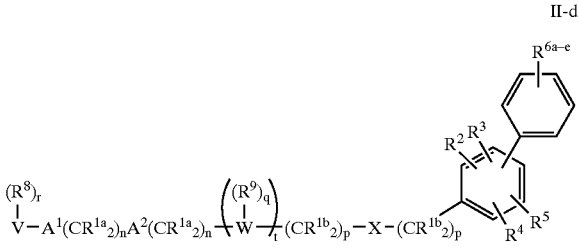

II-d wherein:
$R^{1a}$ and $R^{1b}$ are independently selected from:
   a) hydrogen,
   b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $R^{11}C(O)O$—, $(R^{10})_2NC(O)$—, $R^{10}_2N$—C$(NR^{10})$—, CN, $NO_2$, $R^{10}C(O)$—, $N_3$, —$N(R^{10})_2$, or $R^{11}OC(O)NR^{10}$—,
   c) unsubstituted or substituted $C_1$–$C_6$ alkyl wherein the substituent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}_2N$—C$(NR^{10})$—, CN, $R^{10}C(O)$—, $N_3$, —$N(R^{10})_2$, and $R^{11}OC(O)$—$NR^{10}$—;
$R^2$, $R^3$, $R^4$ and $R^5$ are independently selected from:
   a) hydrogen,
   b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{11}C(O)O$—, $R^{10}_2N$—C$(NR^{10})$—, CN, $NO_2$, $R^{10}C(O)$—, $N_3$, —$N(R^{10})_2$, or $R^{11}OC(O)NR^{10}$—,
   c) unsubstituted $C_1$–$C_6$ alkyl,
   d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{11}C(O)O$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$, $N_3$, —$N(R^{10})_2$, and $R^{11}OC(O)$—$NR^{10}$—;

any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—$CH_2$—, —$(CH_2)_4$— and —$(CH_2)_3$—; $R^7$ is selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
a) $C_{1-4}$ alkoxy,
b) aryl or heterocycle,
c) halogen,
d) HO, e) 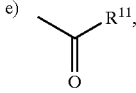

f) —$SO_2R^{11}$
g) $N(R^{10})_2$ or
h) $C_{1-4}$ perfluoroalkyl;

$R^8$ is independently selected from:
a) hydrogen,
b) aryl, substituted aryl, heterocycle, substituted heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—, and
c) $C_1$–$C_6$ alkyl unsubstituted or substituted by aryl, cyanophenyl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NH$—, $(R^{10})_2NC(O)$—, $R^{10}{}_2N$—$C(NR^{10})$—, CN, $R^{10}C(O)$—, $N_3$, —$N(R^{10})_2$, or $R^{10}OC(O)NH$—;

$R^9$ is independently selected from:
a) hydrogen,
b) $C_2$–$C_6$ alkenyl, $C_2$–$C_6$ alkynyl, $C_1$–$C_6$ perfluoroalkyl, F, Cl, Br, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—, and
c) $C_1$–$C_6$ alkyl unsubstituted or substituted by $C_1$–$C_6$ perfluoroalkyl, F, Cl, Br, $R^{10}O$—, $R^{11}S(O)_m$—, $R^{10}C$(O)$NR^{10}$—, $(R^{10})_2NC(O)$—, $R^{10}{}_2N$—$C(NR^{10})$—, CN, $R^{10}C(O)$—, $N_3$, —$N(R^{10})_2$, or $R^1$ $OC(O)NR^{10}$—;

$R^{10}$ is independently selected from hydrogen, $C_1$–$C_6$ alkyl, 2,2,2-trifluoroethyl, benzyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted hetaryl, $C_1$–$C_6$ perfluoroalkyl, 2-aminoethyl and 2,2,2-trifluoroethyl;

$A^1$ and $A^2$ are independently selected from: a bond, —CH=CH—, —C≡C—, —C(O)—, —C(O)$NR^{10}$—, —$NR^{10}C(O)$—, O, —$N(R^{10})$—, —$S(O)_2N(R^{10})$—, —$N(R^{10})S(O)_2$— or $S(O)_m$;

V is selected from:
a) hydrogen,
b) heterocycle,
c) aryl,
d) $C_2$–$C_{20}$ alkyl wherein from 0 to 4 carbon atoms are replaced with a a heteroatom selected from O, S, and N, and
e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

X is a bond, —CH=CH—, O, —C(=O)—, —C(O)$NR^7$—, —$NR^7C(O)$—, —C(O)O—, —OC(O)—, —C(O)$NR^7C(O)$—, —$NR^7$—, —$S(O)_2N(R^{10})$—, —$N(R^{10})S(O)_2$— or —S(=O)$_m$—;

m is 0, 1 or 2;
n is independently 0, 1, 2, 3 or 4;
p is independently 0, 1, 2, 3 or 4;
q is 0, 1, 2 or 3;
r is 0 to 5, provided that r is 0 when V is hydrogen; and
t is 0 or 1;

(c) a compound represented by formula (II-e):

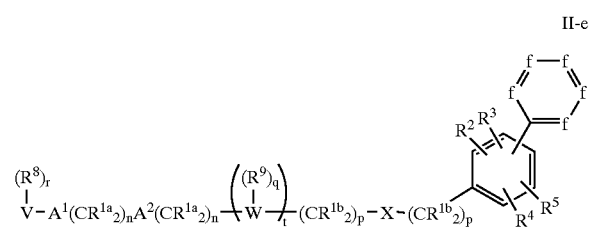

II-e wherein:
$R^{1a}$, $R^{1b}$, $R^2$, $R^3$, $R^4$, $R^5$, $R^7$, $R^8$, $R^9$, $R^{10}$, $R^{11}$, $A^1$, $A^2$, V, W, m, n, p, q, r and t are as previously defined with respect to formula (II-d);

from 1–3 of f(s) are independently N, and the remaining f's are independently $CR^6$; and each $R^6$ is independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{11}C(O)O$—, $R^{10}{}_2N$—$C(NR^{10})$—, CN, $NO_2$, $R^{10}C(O)$—, $N_3$, -$N(R^{10})_2$, or $R^{11}OC(O)NR^{10}$—, c) unsubstituted $C_1$–$C_6$ alkyl, d) substituted $C_1$—$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—; or any two of $R^6$ on adjacent carbon atoms are combined to form a diradical selected from —CH=CH—CH=CH—, —CH=CH—CH$_2$—, —(CH$_2$)$_4$— and —(CH$_2$)$_3$—;

(d) a compound represented by formula (II-f):

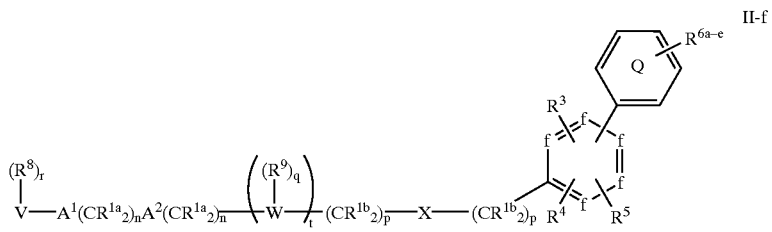
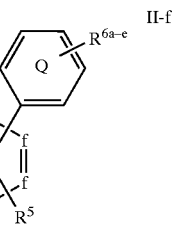

II-f wherein:

$R^3$, $R^4$, $R^5$, $R^{6a-e}$, $R^7$, $R^8$, $R^9$, $R^{10}$, $R^{11}$, $A^1$, $A^2$, V, W, m, n, p, q, r and t are as previously defined with respect to formula (II-d);

from 1–2 of f(s) are independently N, and the remaining f's are independently CH; and $R^1$ and $R^2$ are independently selected from:

a) hydrogen, b) aryl, heterocycle, $C_3$–$C_{10}$cycloalkyl, $C_2$–$C_6$ alkenyl, $C_2$–$C_6$ alkynyl, $R^{10}O$—, $R^{11}S(O)_m$—, $R^{10}C(O)NR^{10}$—, $R^{11}C(O)O$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—, c) unsubstituted or substituted $C_1$–$C_6$ alkyl wherein the substituent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—;

(f) a compound represented by formula (II-g):

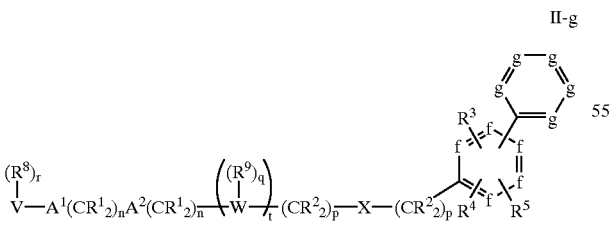

II-g wherein:

$R^3$, $R^4$, $R^5$, $R^7$, $R^8$, $R^9$, $R^{10}$, $R^{11}$, $A^1$, $A^2$, V, W, m, n, p, q, r and t are as previously defined with respect to formula (II-d);

from 1–2 of f(s) are independently N, and the remaining f's are independently CH;

from 1–3 of g(s) are independently N, and the remaining g's are independently $CR^6$;

$R^1$ and $R^2$ are independently selected from:

a) hydrogen, b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $R^{11}C(O)O$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—, c) unsubstituted or substituted $C_1$–$C_6$ alkyl wherein the substituent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—; and each $R^6$ is independently selected from:

a) hydrogen, b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{11}C(O)O$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—, c) unsubstituted $C_1$–$C_6$ alkyl, d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)$—$NR^{10}$—; or any two of $R^6$ on adjacent carbon atoms are combined to form a diradical selected from —CH=CH—CH=CH—, —CH=CH—CH$_2$—, —(CH$_2$)$_4$— and —(CH$_2$)$_3$—;

(g) a compound represented by formula (II-h):

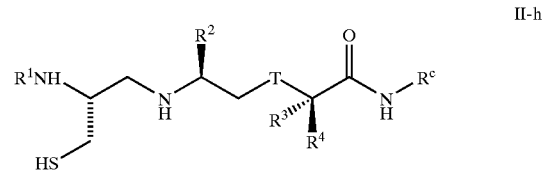

II-h wherein
R$^c$ is selected from:

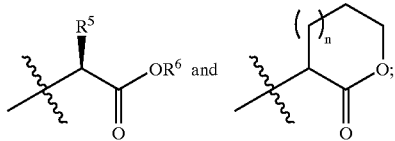

R$^1$ is hydrogen, an alkyl group, an aralkyl group, an acyl group, an aracyl group, an aroyl group, an alkylsulfonyl group, aralkylsulfonyl group or arylsulfonyl group, wherein alkyl and acyl groups comprise straight chain or branched chain hydrocarbons of 1 to 6 carbon atoms;
R$^2$ and R$^3$ are
the side chains of naturally occurring amino acids, including their oxidized forms which may be methionine sulfoxide or methionine sulfone, or in the alternative may be substituted or unsubstituted aliphatic, aromatic or heteroaromatic groups, such as allyl, cyclohexyl, phenyl, pyridyl, imidazolyl or saturated chains of 2 to 8 carbon atoms which may be branched or unbranched, wherein the aliphatic substitutents may be substituted with an aromatic. or heteroaromatic ring;
R$^4$ is hydrogen or an alkyl group, wherein the alkyl group comprises straight chain or branched chain hydrocarbons of 1 to 6 carbon atoms;
R$^5$ is selected from:
  a) a side chain of naturally occurring amino acids,
  b) an oxidized form of a side chain of naturally occurring amino acids selected from methionine sulfoxide and methionine sulfone,
  c) substituted or unsubstituted aliphatic, aromatic or heteroaromatic groups, such as allyl, cyclohexyl, phenyl, pyridyl, imidazolyl, or saturated chains of 2 to 8 carbon atoms which may be branched or unbranched, wherein the aliphatic substituent is optionally substituted with an aromatic or heteroaromatic ring, and
  d) —CH$_2$CH$_2$OH or —CH$_2$CH$_2$CH$_2$OH;
R$^6$ is a substituted or unsubstituted aliphatic, aromatic or heteroaromatic group such as saturated chains of 1 to 8 carbon atoms, which may be branched or unbranched, wherein the aliphatic substituent may be substituted with an aromatic or heteroaromatic ring;
T is O or S(O)$_m$;
m is 0, 1 or 2;
n is 0, 1 or 2;
(h) a compound represented by formula (II-i):

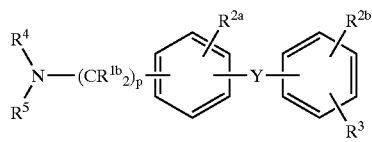

wherein:
R$^{1a}$ and R$^{1b}$ are independently selected from:
  a) hydrogen,
  b) unsubstituted or substituted aryl, unsubstituted or substituted heterocycle, unsubstituted or substituted C$_3$–C$_6$ cycloalkyl, C$_2$–C$_6$ alkenyl, C$_2$–C$_6$ alkynyl, R$^8$O—, R$^9$S(O)$_m$—, R$^8$C(O)NR$^8$—, CN, NO$_2$, (R$^8$)$_2$N—C(NR$^8$)—, R$^8$C(O)—, R$^8$OC(O)—, N$_3$, —N(R$^8$)$_2$, or R$^9$OC(O)NR$^8$—,
  c) C$_1$–C$_6$ alkyl unsubstituted or substituted by unsubstituted or substituted aryl, unsubstituted or substituted heterocyclic, unsubstituted or substituted C$_3$–C$_6$ cycloalkyl, C$_2$–C$_6$ alkenyl, C$_2$–C$_6$ alkynyl, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, or R$^9$OC(O)—NR$^8$—;
R$^{2a}$, R$^{2b}$ and R$^3$ are independently selected from:
  a) hydrogen,
  b) C$_1$–C$_6$ alkyl unsubstituted or substituted by C$_2$–C$_6$ alkenyl, R$^8$O—, R$^9$S(O)$_m$—, R$^8$C(O)NR$^8$—, CN, N$_3$, (R$^8$)$_2$N—C(NR$^8$), R$^8$C(O)—, R$^8$OC(O)—, —N(R$^8$)$_2$, or R$^9$OC(O)NR$^8$—,
  c) unsubstituted or substituted aryl, unsubstituted or substituted heterocycle, unsubstituted or substituted cycloalkyl, alkenyl, R$^8$O—, R$^9$S(O)$_m$—, R$^8$C(O)NR$^8$—, CN, NO$_2$, (R$^8$)$_2$N—C(NR$^8$)—, R$^8$C(O)—, R$^8$OC(O)—, N$_3$, —N(R$^8$)$_2$, halogen or R$^9$OC(O)NR$^8$—, and
  d) C$_1$–C$_6$ alkyl substituted with an unsubstituted or substituted group selected from aryl, heterocyclic and C$_3$–C$_{10}$ cycloalkyl;
R$^4$ and R$^5$ are independently selected from:
  a) hydrogen, and
  b)

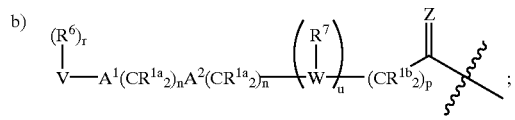

R$^6$ is independently selected from:
  a) hydrogen,
  b) unsubstituted or substituted aryl, unsubstituted or substituted heterocycle, unsubstituted or substituted C$_3$–C$_6$ cycloalkyl, C$_2$–C$_6$ alkenyl, C$_2$–C$_6$ alkynyl, C$_1$–C$_6$ perfluoroalkyl, F, Cl, Br, R$^8$O—, R$^9$S(O)$_m$—, R$^8$C(O)NR$^8$—, CN, NO$_2$, R$^8$$_2$N—C(NR$^8$)—, R$^8$C(O)—, R$^8$OC(O)—, N$_3$, —N(R$^8$)$_2$, or R$^9$OC(O)NR$^8$—, and
  c) C$_1$–C$_6$ alkyl unsubstituted or substituted by unsubstituted or substituted aryl, unsubstituted or substituted heterocycle, unsubstituted or substituted C$_3$–C$_6$ cycloalkyl, C$_2$–C$_6$ alkenyl, C$_2$–C$_6$ alkynyl, C$_1$–C$_6$ perfluoroalkyl, F, Cl, Br, R$^8$O—, R$^9$S(O)$_m$—, R$^8$C(O)NH—, CN, H$_2$N—C(NH)—, R$^8$C(O), R$^8$OC(O)—, N$_3$, —N(R$^8$)$_2$, or R$^8$OC(O)NH—;
R$^7$ is selected from:
  a) hydrogen,
  b) C$_2$–C$_6$ alkenyl, C$_2$–C$_6$ alkynyl, C$_1$–C$_6$ perfluoroalkyl, F, Cl, Br, R$^8$O—, R$^9$S(O)$_m$—, R$^8$C(O)NR$^8$—, CN, NO$_2$, (R$^8$)$_2$N—C—(NR$^8$)—, R$^8$C(O)—, R$^8$OC(O)—, N$_3$, —N(R$^8$)$_2$, or R$^9$OC(O)NR$^8$—, and
  c) C$_1$–C$_6$ alkyl unsubstituted or substituted by C$_1$–C$_6$ perfluoroalkyl, F, Cl, Br, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, or R$^9$OC(O)NR$^8$—;
R$^8$ is independently selected from hydrogen, C$_1$–C$_6$ alkyl, substituted or unsubstituted C$_1$–C$_6$ aralkyl and substituted or unsubstituted aryl;
R$^9$ is independently selected from C$_1$–C$_6$ alkyl and aryl;
R$^{10}$ is independently selected from hydrogen, C$_1$–C$_6$ alkyl, substituted or unsubstituted C$_1$–C$_6$ aralkyl and substituted or unsubstituted aryl;
A$^1$ and A$^2$ are independently selected from: a bond, —CH=CH—, —C≡C—, —C(O)—, —C(O)NR$^8$—, —NR⁸C(O)—, O, —N(R⁸)—, —S(O)₂N(R⁸)—, —N(R⁸)S(O)₂—, or S(O)$_m$;

V is selected from:
a) hydrogen,
b) heterocycle,
c) aryl,
d) C₁–C₂₀ alkyl wherein from 0 to 4 carbon atoms are replaced with a a heteroatom selected from O, S, and N, and
e) C₂–C₂₀ alkenyl, provided that V is not hydrogen if A¹ is S(O)$_m$ and V is not hydrogen if A¹ is a bond, n is 0 and A² is S(O)$_m$;

W is a heterocycle;

Y is selected from: a bond, —C(R¹⁰)═C(R¹⁰)—, —C≡C—, —C(O)—, —C(R¹⁰)₂—, —C(OR¹⁰)R¹⁰—, —CN(R¹⁰)₂R¹⁰—, —OC(R¹⁰)₂—, —NR¹⁰C(R¹⁰)₂—, —C(R¹⁰)₂O—, —C(R¹⁰)₂NR¹⁰—, —C(O)NR¹⁰—, —NR¹⁰C(O)—, O, —NC(O)R¹⁰—, —NC(O)OR¹⁰—, —S(O)₂N(R¹⁰)—, —N(R¹⁰)S(O)₂—, or S(O)$_m$;

Z is H₂ or O;

m is 0,1 or 2;

n is 0, 1, 2, 3 or 4;

p is 0, 1, 2, 3 or 4;

r is 0 to 5, provided that r is 0 when V is hydrogen; and u is 0 or 1;

(e) a compound represented by formula (II-m):

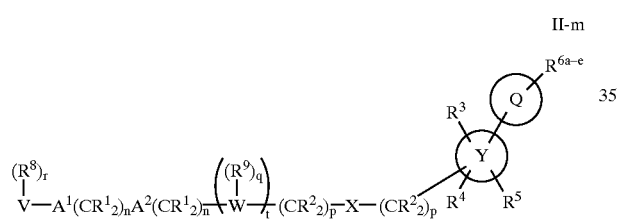

II-m wherein:

Q is a 4, 5, 6 or 7 membered heterocyclic ring which comprises a nitrogen atom through which Q is attached to Y and 0–2 additional heteroatoms selected from N, S and O, and which also comprises a carbonyl, thiocarbonyl, —C(═NR¹³)— or sulfonyl moiety adjacent to the nitrogen atom attached to Y;

Y is a 5, 6 or 7 membered carbocyclic ring wherein from 0 to 3 carbon atoms are replaced by a heteroatom selected from N, S and O, and wherein Y is attached to Q through a carbon atom;

R¹ and R² are independently selected from:
a) hydrogen,
b) aryl, heterocycle, C₃–C₁₀ cycloalkyl, C₂–C₆ alkenyl, C₂–C₆ alkynyl, R¹⁰O—, R¹¹S(O)$_m$—, R¹⁰C(O)NR¹⁰—, R¹¹C(O)O—, (R¹⁰)₂NC(O)—, R¹⁰₂N—C(NR¹⁰)—, CN, NO₂, R¹⁰C(O)—, N₃, —N(R¹⁰)₂, or R¹¹OC(O)NR¹⁰—,
c) unsubstituted or substituted C₁–C₆ alkyl wherein the substituent on the substituted C₁–C₆ alkyl is selected from unsubstituted or substituted aryl, heterocyclic, C₃–C₁₀ cycloalkyl, C₂–C₆ alkenyl, C₂–C₆ alkynyl, R¹⁰O—, R¹¹S(O)$_m$—, R¹⁰C(O)NR¹⁰—, (R¹⁰)₂NC(O)—, R¹⁰₂N—C(NR¹⁰)—, CN, R¹⁰C(O)—, N₃, —N(R¹⁰)₂, and R¹¹OC(O)—NR10—;

R³, R⁴ and R⁵ are independently selected from:
a) hydrogen,
b) unsubstituted or substituted aryl, unsubstituted or substituted heterocycle, C₃–C₁₀ cycloalkyl, C₂–C₆ alkenyl, C₂–C₆ alkynyl, halogen, C₁–C₆ perfluoroalkyl, R¹²O—, R¹¹S(O)$_m$—, R¹⁰C(O)NR10—, (R¹⁰)₂NC(O)—, R¹¹C(O)O—, R¹⁰₂N—C(NR¹⁰)—, CN, NO₂, R¹⁰C(O)—, N₃, —N(R¹⁰)₂, or R¹¹OC(O)NR¹⁰—,
c) unsubstituted C₁–C₆ alkyl,
d) substituted C₁–C₆ alkyl wherein the substituent on the substituted C₁–C₆ alkyl is selected from unsubstituted or substituted aryl, unsubstituted or substituted heterocyclic, C₃–C₁₀ cycloalkyl, C₂–C₆ alkenyl, C₂–C₆ alkynyl, R¹²O—, R¹¹(O)$_m$—, R¹⁰C(O)NR¹⁰—, (R¹⁰)₂NC(O)—, R¹⁰₂N—C(NR¹⁰)—, CN, R¹⁰C(O)—, N₃, —N(R¹⁰)₂, and R¹¹OC(O)—NR¹⁰—;

R⁶ᵃ, R⁶ᵇ, R⁶ᶜ, R⁶ᵈ and R⁶ᵉ are independently selected from:
a) hydrogen,
b) unsubstituted or substituted aryl, unsubstituted or substituted heterocycle, C₃–C₁₀ cycloalkyl, C₂–C₆ alkenyl, C₂–C₆ alkynyl, halogen, C₁–C₆ perfluoroalkyl, R¹²O—, R¹¹S(O)$_m$—, R¹⁰C(O)NR¹⁰—, (R¹⁰)₂NC(O)—, R¹¹S(O)₂NR¹⁰—, (R¹⁰)₂NS(O)₂—, R¹¹C(O)O—, R¹⁰₂N—C(NR¹⁰)—, CN, NO₂, R¹⁰C(O)—, N₃, —N(R¹⁰)₂, or R¹¹OC(O)NR¹⁰—,
c) unsubstituted C₁–C₆ alkyl,
d) substituted C₁–C₆ alkyl wherein the substituent on the substituted C₁–C₆ alkyl is selected from unsubstituted or substituted aryl, unsubstituted or substituted heterocyclic, C₃–C₁₀ cycloalkyl, C₂–C₆ alkenyl, C₂–C₆ alkynyl, R¹²O—, R¹¹S(O)$_m$—, R¹⁰C(O)NR¹⁰—, (R¹⁰)₂NC(O)—, R¹¹S(O)₂NR¹⁰—, (R¹⁰)₂NS(O)₂—, R¹⁰₂N—C(NR¹⁰)—, CN, R¹⁰C(O)—, N₃, —N(R¹⁰)₂, and R¹¹OC(O)—NR¹⁰—; or any two of R⁶ᵃ, R⁶ᵇ, R⁶ᶜ, R⁶ᵈ and R⁶ᵉ on adjacent carbon atoms are combined to form a diradical selected from —CH═CH—CH═CH—, —CH═CH—CH₂—, —(CH₂)₄— and —(CH₂)₃—;

R⁷ is selected from: H; C₁₋₄ alkyl, C₃₋₆ cycloalkyl, heterocycle, aryl, aroyl, heteroaroyl, arylsulfonyl, heteroarylsulfonyl, unsubstituted or substituted with:
a) C₁₋₄ alkoxy,
b) aryl or heterocycle, c) 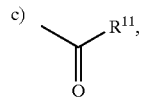

d) —SO₂R¹¹
e) N(R¹⁰)₂ or
f) C₁₋₄ perfluoroalkyl;

R⁸ is independently selected from:
a) hydrogen,
b) aryl, substituted aryl, heterocycle, substituted heterocycle, C₃–C₁₀ cycloalkyl, C₂–C₆ alkenyl, C₂–C₆ alkynyl, perfluoroalkyl, F, Cl, Br, R¹⁰O—, R¹¹S(O)$_m$—, R¹⁰C(O)NR¹⁰—, (R¹⁰)₂NC(O)—, R¹¹S(O)₂NR¹⁰—, (R¹⁰)₂NS(O)₂—, R¹⁰₂N—C(NR¹⁰)—, CN, NO₂, R¹⁰C(O)—, N₃, —N(R¹⁰)₂, or R¹¹OC(O)NR¹⁰—, and c) $C_1$–$C_6$ alkyl unsubstituted or substituted by aryl, cyanophenyl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{11}S(O)_2NR10$—, $(R^{10})_2NS(O)_2$—, $R^{10}_2N$—$C(NR^{10})$—, CN, $R^{10}C(O)$—, $N_3$, —$N(R^{10})_2$, or $R^{10}OC(O)NH$—;

$R^9$ is independently selected from:
a) hydrogen,
b) alkenyl, alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—, and
c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, or $R^{11}OC(O)NR^{10}$—;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteraryl, $C_1$–$C_6$ perfluoroalkyl, 2-aminoethyl and 2,2,2-trifluoroethyl;

$R^{13}$ is selected from hydrogen, $C_1$–$C_6$ alkyl, cyano, $C_1$–$C_6$ alkylsulfonyl and $C_1$–$C_6$ acyl;

$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

V is selected from:
a) hydrogen,
b) heterocycle,
c) aryl,
d) $C_1$–$C_{20}$ alkyl wherein from 0 to 4 carbon atoms are replaced with a heteroatom selected from O, S, and N, and
e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

X is a bond, —CH=CH—, O, —C(=O)—, —C(O)NR$^7$—, —NR$^7$C(O)—, —C(O)O—, —OC(O)—, —C(O)NR$^7$C(O)—, —NR7—, —S(O)$_2$N(R$^{10}$)—, —N(R$^{10}$)S(O)$_2$— or —S(=O)$_m$—;

m is 0, 1 or 2;
n is independently 0, 1, 2, 3 or 4;
p is independently 0, 1, 2, 3 or 4;
q is 0, 1, 2 or 3;
r is 0 to 5, provided that r is 0 when V is hydrogen; and
t is 0 or 1;

(f) a compound represented by formula (II-n):

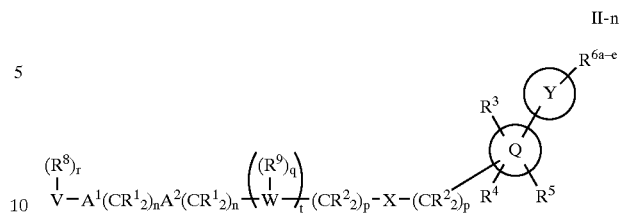

II-n wherein:

$R^1$, $R^2$, $R^3$, $R^4$, $R^5$, $R^{6a-e}$, $R^7$, $R^8$, $R^9$, $R^{10}$, $R^{11}$, $R^{12}$, $R^{13}$, $A^1$, $A^2$, V, W, m, n, p, q, r and t are as previously defined with respect to formula (II-m);

Q is a 4, 5, 6 or 7 membered heterocyclic ring which comprises a nitrogen atom through which Q is attached to Y and 0–2 additional heteroatoms selected from N, S and O, and which also comprises a carbonyl, thiocarbonyl, —C(=NR$^{13}$)— or sulfonyl moiety adjacent to the nitrogen atom attached to Y, provided that Q is not

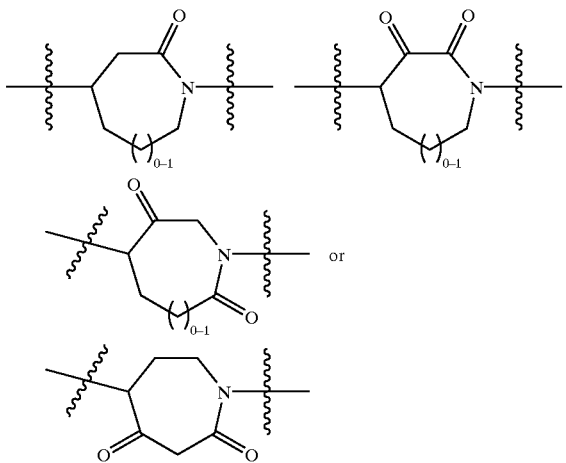

Y is a 5, 6 or 7 membered carbocyclic ring wherein from 0 to 3 carbon atoms are replaced by a heteroatom selected from N, S and O, and wherein Y is attached to Q through a carbon atom;

or a pharmaceutically acceptable salt or disulfide thereof.

Examples of compounds which selectively inhibit farnesyl protein transferase include the following:

2(S)-Butyl-1-(2,3-diaminoprop-1-yl)-1-(1-naphthoyl) piperazine;
1-(3-Amino-2-(2-naphthylmethylamino)prop-1-yl)-2(S)-butyl-4-(1-naphthoyl)piperazine;
2(S)-Butyl-1-{5-[1-(2-naphthylmethyl)]-4,5-dihydroimidazol}methyl4-(1-naphthoyl)piperazine;
1-[5-(1-Benzylimidazol)methyl)-2(S)-butyl4(1-naphthoyl) piperazine;
1-{5-[1-(4-nitrobenzyl)]imidazolylmethyl}-2(S)-butyl4-(1-naphthoyl)piperazine;
1-(3-Acetamidomethylthio-2(R)-aminoprop-1-yl)-2(S)-butyl-4-(1-naphthoyl)piperazine;
2(S)-Butyl- 1-[2-(1-imidazolyl)ethyl]sulfonyl-4-(1-naphthoyl)piperazine;

2(R)-Butyl-1-imidazolyl-4-methyl-4-( 1-naphthoyl)piperazine;
2(S)-Butyl-4-(1-naphthoyl)-1-(3-pyridylmethyl)piperazine;
1-2(S)-butyl-(2(R)-(4-nitrobenzyl)amino-3-hydroxypropyl)-4-(1-naphthoyl)piperazine;
1-(2(R)-Amino-3-hydroxyheptadecyl)-2(S)-butyl-4-(1-naphthoyl)-piperazine;
2(S)-Benzyl-1-imidazolyl-4-methyl-4-(1-naphthoyl)piperazine;
1-(2(R)-Amino-3-(3-benzylthio)propyl)-2(S)-butyl-4-(1-naphthoyl)piperazine;
1-(2(R)-Amino-3-[3-(4-nitrobenzylthio)propyl])-2(S)-butyl-4-(1-naphthoyl)piperazine;
2(S)-Butyl-1-[(4-imidazolyl)ethyl]-4-(1-naphthoyl)piperazine;
2(S)-Butyl-1-[(4-imidazolyl)methyl]-4-(1-naphthoyl)piperazine;
2(S)-Butyl-1-[(1-naphth-2-ylmethyl)-1H-imidazol-5-yl)acetyl]-4( 1-naphthoyl)piperazine;
2(S)-Butyl-1-[(1-naphth-2-ylmethyl)-1H-imidazol-5-yl)ethyl]-4-( 1-naphthoyl)piperazine;
1-(2(R)-Amino-3-hydroypropyl)-2(S)-butyl-4-(1-naphthoyl)piperazine;
1-(2(R)-Amino-4-hydroxybutyl)-2(S)-butyl-4(1-naphthoyl)piperazine;
1-(2-Amino-3-(2-benzyloxyphenyl)propyl)-2(S)-butyl-4-( 1-naphthoyl)piperazine;
1-(2-Amino-3-(2-hydroxyphenyl)propyl)-2(S)-butyl-4-(1-naphthoyl)piperazine;
1-[3-(4-imidazolyl)propyl]-2(S)-butyl-4-( 1-naphthoyl)-piperazine;
2(S)-n-Butyl-4-(2,3-dimethylphenyl)-1-(4-imidazolylmethyl) -piperazin-5-one;
2(S)-n-Butyl- 1-[1-(4-cyanobenzyl)imidazol-5-ylmethyl]-4-(2,3-dimethylphenyl)piperazin-5-one;
1-[1-(4Cyanobenzyl)imidazol-5-ylmethyl])(2,3-dimethylphenyl)-2(S)-(2-methoxyethyl)piperazin-5-one;
2(S)-n-Butyl-4-(1-naphthoyl)-1-[1-(1-naphthylmethyl)imidazol-5-ylmethyl]-piperazine;
2(S)-n-Butyl4-(1-naphthoyl)-1-[1-(2-naphthylmethyl)imidazol-5-ylmethyl]-piperazine;
2(S)-n-Butyl-1-[1-(4-cyanobenzyl)imidazol-5-ylmethyl]4-( 1-naphthoyl)piperazine;
2(S)-n-Butyl-1-[1-(4-methoxybenzyl)imidazol-5-ylmethyl]-4-(1-naphthoyl)piperazine;
2(S)-n-Butyl-1-[1-(3-methyl-2-butenyl)imidazol-5-ylmethyl]-4-(1-naphthoyl)piperazine;
2(S)-n-Butyl-1-[1-(4-fluorobenzyl)imidazol-5-ylmethyl]-4-( 1-naphthoyl)piperazine;
2(S)-n-Butyl-1-[1-(4-chlorobenzyl)imidazol-5-ylmethyl]-4-( 1-naphthoyl)piperazine;
1-[1-(4-Bromobenzyl)imidazol-5-ylmethyl]-2(S)-n-butyl-4-(1-naphthoyl)piperazine;
2(S)-n-Butyl-4-(1-naphthoyl)- 1-[1-(4-trifluoromethylbenzyl)imidazol -5-ylmethyl]-piperazine;
2(S)-n-Butyl-1-[1-(4-methylbenzyl)imidazol-5-ylmethyl]4-(1-naphthoyl)-piperazine;
2(S)-n-Butyl-1-[1-(3-methylbenzyl)imidazol-5-ylmethyl]-4-(1-naphthoyl)-piperazine;
1-[1-(4-Phenylbenzyl)imidazol-5-ylmethyl]-2(S)-n-butyl4-(1-naphthoyl)-piperazine;
2(S)-n-Butyl-4(1-naphthoyl)-1-[1-(2-phenylethyl)imidazol-5-ylmethyl]-piperazine;
2(S)-n-Butyl-4-(1-naphthoyl)-1-[1-(4-trifluoromethoxy)imidazol-5-ylmethyl]piperazine;
1-{[1(4cyanobenzyl)-1H-imidazol-5-yl]acetyl}-2(S)-n-butyl-4-(1-naphthoyl)piperazine;
(S)-1-(3-Chlorophenyl)-4-[1-(4-cyanobenzyl)-5-imidazolylmethyl]-5-[2-(methanesulfonyl)ethyl]-2-piperazinone;
(S)-1-(3-Chlorophenyl)-4-[1-(4-cyanobenzyl)-5-imidazolylmethyl]-5-[2-(ethanesulfonyl)ethyl]-2-piperazinone;
(R)-1-(3-Chlorophenyl)-4-[1-(4cyanobenzyl)-5-imidazolylmethyl]-5-[2-(ethanesulfonyl)methyl]-2-piperazinone;
(S)-1-(3-Chlorophenyl)-4-[1-(4-cyanobenzyl)-5-imidazolylmethyl]-5-[N-ethyl-2-acetamido]-2-piperazinone;
(±)-5-(2-Butynyl)-1-(3-chlorophenyl)-4-[1-(4-cyanobenzyl)-5-imidazolylmethyl]-2-piperazinone;
1-(3-Chlorophenyl)-4-[1-(4-cyanobenzyl)-5-imidazolylmethyl)-2-piperazinone;
5(S)-Butyl-4-[1-(4-cyanobenzyl-2-methyl)-5-imidazolylmethyl]-1-(2,3-dimethylphenyl)-piperazin-2-one;
4-[1-(2-(4-Cyanophenyl)-2-propyl)-5-imidazolylmethyl]-1-(3-chlorophenyl)-5(S)-(2-methylsulfonylethyl)piperazin-2-one;
5(S)-n-Butyl-4-[1-(4-cyanobenzyl)-5-imidazolylmethyl]-1-(2-methylphenyl)piperazin-2-one;
4-[1-(4-Cyanobenzyl)-5-imidazolylmethyl]-5(S)-(2-fluoroethyl)-1-(3-chlorophenyl)piperazin-2-one;
4-[3-(4-Cyanobenzyl)pyridin-4-yl]-1-(3-chlorophenyl)-5(S)-(2-methylsulfonylethyl)-piperazin-2-one;
4-[5-(4Cyanobenzyl)-1-imidazolylethyl]-1-(3-chlorophenyl)piperazin-2-one;
2(S)-[2(S)-[2(R)-Amino-3-mercapto]propylamino-3(S)-methyl]-pentyloxy-3-phenylpropionyl-homoserine lactone,
2(S)-[2(S)-[2(R)-Amino-3-mercapto]propylamino-3(S)-methyl]pentyloxy-3-phenylpropionyl-homoserine,
2(S)-[2(S)-[2(R)-Amino-3-mercapto]propylamino-3(S)-methyl]pentyloxy-2-methyl-3-phenylpropionyl-homoserine lactone,
2(S)-[2(S)-[2(R)-Amino-3-mercapto]propylamino-3(S-methyl]pentyloxy-2-methyl-3-phenylpropionyl-homoserine,
2(S)-[2(S)-[2(R)-Amino-3-mercapto]propylamino-3(S)-methyl]pentyloxy-4-pentenoyl-homoserine lactone,
2(S)-[2(S)-[2(R)-Amino-3-mercapto]propylamino-3 (S)-methyl]-pentyloxy-4-pentenoyl-homoserine,
2(S)-[2(S)-[2(R)-Amino-3-mercapto]propylamino-3(S)-methyl]pentyloxypentanoyl-homoserine lactone,
2(S)-[2(S)-[2(R)-Amino-3-mercapto]propylaniino-3 (S)-methyl]pentyloxypentanoyl-homoserine,
2(S)-[2(S)-[2(R)-Amino-3-mercapto]propylamino-3 (S)-methyl]5-pentyloxy-4-methylpentanoyl-homoserine lactone,
2(S)-[2(S)-[2(R)-Amino-3-mercapto]propylamino-3(S)-methyl]pentyloxy-4-methylpentanoyl-homoserine,
2(S)-[2(S)-[2(R)-Amino-3-mercapto]propylamino-3(S)-methyl]pentyloxy-3-methylbutanoyl-homoserine lactone,
2(S)-[2(S)-[2(R)-Amino-3-mercapto]propylamino-3(S)-methyl]pentyloxy-3-methylbutanoyl-homoserine,
2(S)-[2(S)-[2(R)-Amino-3-mercapto]propylamino-3(S)-methyl]pentyloxy-3-phenylbutanoyl-homoserine lactone,
2(S)-[2(S)-[2(R)-Amino-3-mercapto]propylamino-3(S)-methyl]-pentyloxy-3-phenylbutanoyl-homoserine,
2(S)-[2(S)-[2(R)-Amino-3-mercapto]propylamino3(S)-methyl]pentylthio-2-methyl-3-phenylpropionyl-homoserine lactone,
2(S)-[2(S)-[2(R)-Amino-3-mercapto]propylamino3(S)-methyl]pentylthio-2-methyl-3-phenylpropionyl-homoserine, 2(S)-[2(S)-[2(R)-Amino-3-mercapto]propylamino-3(S)-methyl]pentylsulfonyl-2-methyl-3-phenylpropionyl-homoserine lactone,
2(S)-[2(S)-[2(R)-Amino-3-mercapto]propylamino-3(S)-methyl]-pentylsulfonyl-2-methyl-3-phenylpropionyl-homoserine,
2(S)-[2(S)-[2(R)-Amino-3-mercapto]propylaniino-3(S)-methyl]-pentyloxy-3-phenylpropionyl-methionine methyl ester,
2(S-[2(S)-[2(R)-Amino-3-mercapto]propylamino-3(S)-methyl]pentyloxy-3-phenylpropionyl-methionine,
2(S)-[2(S)-[2(R)-Amino3-mercapto]propylamino-3(S)-methyl]pentyloxy-3-phenylpropionyl-methionine sulfone methyl ester (Compound 5),
2(S)-[2(S)-[2(R)-Amino-3-mercapto]propylamino3(S)-methyl]pentyloxy-3-phenylpropionyl-methionine sulfone (Compound 6),
2(S)-[2(S)-[2(R)-Amino-3-mercapto]propylamino-3(S)-methyl]-pentyloxy-3-phenylpropionyl-methionine sulfone isopropyl ester,
2-(S)-[2(S)-[2(R)-Amino-3-mercapto]propylamino-3(S)-methyl]-pentyloxy-3-naphth-2-yl-propionyt-methionine sulfone methyl ester,
2-(S)-[2(S)-[2(R)-Amino-3-mercapto]propylamino-3(S)-methyl]-pentyloxy-3-naphth-2-yl-propionyl-methionine sulfone,
2-(S)-[2(S)-[2(R)-Amino-3-mercapto]propylamino-3 (S)-methyl]pentyloxy-3-naphth-1-yl:propionyl-methionine sulfone methyl ester,
2-(S)-[2(S)-[2(R)-Amino-3-mercapto]propylamino-3(S)-methyl]pentyloxy-3-naphth-1-yl-propionyl-methionine sulfone,
2-(S)-[2(S)-[2(R-Amino-3-mercapto]propylamino-3 (S)-methyl]pentyloxy-3-methybutanoyl-methionine methyl ester.
2-(S)-[2(S)-[2(R)-Amino-3-mercapto]propylamino-3 (S)-methyl]pentyloxy-3-methybutanoyl-methionine,
Disulphide of 2(S)-[2(S)-[2(R)-Amino-3-mercapto]propylamino-3(S)methyl]pentyloxy-3-phenylpropionyl-homoserine lactone,
Disulphide of 2(S)-[2(S)-[2(R)-Amino-3-mercapto]propylamino-3(S)-methyl]pentyloxy-3-phenylpropionyl-homoserine,
Disulphide of 2(S)-[2(S)-[2(R)-Amino-3-mercapto]propylamino-3(S)methyl]pentyloxy-3-methylbutanoyl-methionine methyl ester
1-(4-Biphenylmethyl)-5-(4-cyanobenzyl)imidazole
1-(4-Cyanobenzyl)-5-(4'-phenylbenzamido)ethyl-imidazole
1-(2'-Trifluoromethyl-4-biphenylmethyl)-5-(4-cyanobenzyl)imidazole
1-(4-Biphenylethyl)-5-(4-cyanobenzyl)imidazole
1-(2'-Bromo-4-biphenylmethyl)-5-(4-cyanobenzyl) imidazole
1-(2'-Methyl-4-biphenylmethyl)-5-(4-cyanobenzyl) imidazole
1-(2'-Trifluoromethoxy-4-biphenyl methyl)-5-(4-cyanobenzyl) imidazole
1-(4-(3',5'-dichloro)-biphenylmethyl)-5-(4-cyanobenzyl) imidazole
-1-(2'-Methoxy-4-biphenylmethyl)-5-(4-cyanobenzyl) imidazole
1-(2'-Chloro-4-biphenylmethyl)-5-(4-cyanobenzyl) imidazole
1-(2-Chloro-4-biphenylmethyl)-5-(4-cyanobenzyl) imidazole
1-(3-Chloro-4-biphenylmethyl)-5-(4-cyanobenzyl) imidazole
1-(4-(3',5'-Bis-trifluoromethyl)-biphenylmethyl)-5-(4-cyanobenzyl) imidazole
1-(2'-Trifluoromethyl-4-biphenylmethyl) -5-(4-cyanobenzyl)-4-methylimidazole
1-(4-Biphenylmethyl)-5-(4-cyanophenyloxy)-imidazole
5-(4-Cyanophenyloxy)-1-(2'-methyl4-biphenylmethyl)-imidazole
5-(4-Biphenyloxy)-1-(4-cyanobenzyl)-imidazole
5-(2'-Methyl-4-biphenoxy)-1-(4-cyanobenzyl)-imidazole
5-(4-(3',5'-dichloro)biphenylmethyl)-1-(4-cyanobenzyl) imidazole
1-(4-biphenylmethyl)-5-(1-(R,S)-methoxy-1-(4-cyanophenyl)-methylimidazole
1-(4-Biphenylmethyl)-5-(1-(R,S)-hydroxy-1-(4-cyanophenyl)methylimidazole
1-(4-Biphenylmethyl)-5-(l-(R,S)-amino-1-(4cyanophenyl) methylimidazole
1-(4-biphenylmethyl)-5-(1-(R,S)-methoxy-1-(4-cyanophenyl)-methylimidazole
1-(4-Cyanobenzyl)-5-(1-hydroxy-1-(4-biphenyl)-methyl imidazole
1-(4Cyanobenzyl)-5-(1-oxo-1-(4-biphenyl)-methyl imidazole
1-(4-Cyanobenzyl)-5-(1-hydroxy-1-(3-fluoro-4-biphenyl)-methyl)-imidazole
1-(4-Cyanobenzyl)-5-(1-hydroxy-1-(3-biphenyl)methyl-imidazole
5-(2-[1,1'-Biphenyl]vinylene)-1-(4-cyanobenzyl)imidazole
1-[N-(1-(4-cyanobenzyl)-5-imidazolylmethyl)amino]-3-methoxy-4-phenylbenzene
1-(4-Biphenylmethyl)-5-(4-bromophenyloxy)-imidazole
1-(3'-Methyl-4-biphenylmethyl)-5-(4-cyanobenzyl) imidazole
1-(4'-Methylbiphenylmethyl)-5-(4-cyanobenzyl) imidazole
1-(3'-Trifluoromethyl-4-biphenylmethyl)-5-(4-cyanobenzyl) imidazole
1-(4'-Trifluoromethyl-4-biphenylmethyl)-5-(4-cyanobenzyl) imidazole
1-(3'-Chloro-4biphenylmethyl)-5-(4-cyanobenzyl) imidazole
1-(4'-Chloro-4-biphenylmethyl)-5-(4-cyanobenzyl) imidazole
1-(2'3'-Dichloro-4-biphenylmethyl)-5-(4-cyanobenzyl) imidazole
1-(2'4'-Dichloro-4-biphenylmethyl)-5-(4-cyanobenzyl) imidazole
1-(2'5'-Dichloro-4-biphenylmethyl)-5-(4-cyanobenzyl) imidazole
1-(3'-Trifluoromethoxy-4-biphenylmethyl)-5-(4-cyanobenzyl) imidazole
1-(2'-Fluoro-4biphenylmethyl)-5-(4-cyanobenzyl) imidazole
1-(4-(2'-Trifluoromethylphenyl)-2-Chlorophenylmethyl)-5-(4-cyanobenzyl) imidazole
1-{1-(4-(2'-trifluoromethylphenyl)phenyl)ethyl}-5-(4-cyanobenzyl) imidazole
1-(2'-Trifluoromethyl-4-biphenylpropyl)-5-(4-cyanobenzyl) imidazole
1-(2'-N-t-Butoxycarbonylamino-4-biphenylmethyl)-5-(4-cyanobenzyl) imidazole
1-(2'-Aminomethyl4-biphenylmethyl)-5-(4-cyanobenzyl) imidazole
1-(2'-Acetylaminomethyl-4-biphenylmethyl)-5-(4-cyanobenzyl) imidazole
1-(2'-Methylsulfonylaminomethyl-4-biphenylmethyl)-5-(4-cyanobenzyl) imidazole
1-(2'-Ethylaminomethyl-4-biphenylmethyl)-5-(4cyanobenzyl) imidazole 1-(2'-Phenylaminomethyl4-biphenylmethyl)-5-(4-cyanobenzyl) imidazole
1-(2'-Glycinylaminomethyl-4-biphenylmethyl)-5-(4-cyanobenzyl) imidazole
1-(2'-Methyl-4-biphenylmethyl)-2-chloro-5-(4-cyanobenzyl) imidazole
1-(2'-Methyl-4-biphenylmethyl)-4-chloro-5-(4-cyanobenzyl) imidazole
1-(3'-Chloro-2-methyl4-biphenylmethyl)-4-(4-cyanobenzyl)imidazole
1-(3'-Chloro-2-methyl-4-biphenylmethyl)-5-(4-cyanobenzyl)imidazole
1-(3'-Trifluoromethyl-2-methyl-4-biphenylmethyl)-4-(4-cyanobenzyl) imidazole
1-(3'-Trifluoromethyl-2-methyl-4-biphenylmethyl)-5-(4-cyanobenzyl)imidazole
1-(3'-Methoxy-2-methyl-4-biphenylmethyl)-5-(4-cyanobenzyl)imidazole
1-(2'-Chloro-4'-fluoro-4-biphenylmethyl)-5-(4-cyanobenzyl)imidazole
1-(2'-Ethyl-4-biphenylmethyl)-5-(4-cyanobenzyl)imidazole
1-(2'-(2-Propyl)4-biphenylmethyl)-5-(4-cyanobenzyl) imidazole
1-(2'-(2-Methyl-2-propyl)-4-biphenylmethyl)-5-(4-cyanobenzyl)imidazole
1-(2'-Ethyl-4-biphenylmethyl)-5-(4-(1H-tetrazol-5-yl))benzyl)imidazole
1-[1-(4-Cyanobenzyl)imidazol-5-ylmethoxy]-4-(2'-methylphenyl)-2-(3-N-phthalimido-1-propyl)benzene
1-(3',5'-Ditrifluoromethyl-2-methyl-4-biphenylmethyl)-5-(4-cyanobenzyl)imidazole
1-(3',5'-Chloro-2-methyl-4-biphenylmethyl)-5-(4-cyanobenzyl)imidazole
1-(3',5'-Dimethyl-2-methyl-4-biphenylmethyl)-5-(4-cyanobenzyl)imidazole
1-(3-(N-Boc-aminomethyl)-4-biphenylmethyl)-5-(4-cyanobenzyl)-imidazole
1-(3-Aminomethyl-4-biphenylmethyl)-5-(4-cyanobenzyl) imidazole
1-(4-Cyanobenzyl)-2-methyl-5-(2'-methylbiphenyl-4-yloxy)imidazole
5-(4-Cyanobenzyl)-1-(3-cyano-2'-trifluoromethylbiphenyl-4-ylmethyl)-imidazole
2-Amino-5-(biphenyl-4-ylmethyl)-1-(4-cyanobenzyl) imidazole
2-Amino- 1-(biphenyl-4-ylmethyl)-5-(4-cyanobenzyl) imidazole
1-(3-Butylbiphenyl-4-ylmethyl)-5-(4-cyanobenzyl)-imidazole
1-(3-Propylbiphenyl-4-ylmethyl)-5-(4-cyanobenzyl)-imidazole
1-(4-Biphenylmethyl)-4-(4-cyanobenzyl-2-methylimidazole
1-(4Cyanobenzyl)-5-[(3-fluoro-4-biphenyl)methyl]imidazole
1-(4Cyanobenzyl)-5-[1-(4-biphenyl)-1-hydroxy]ethyl-2-methylimidazole
1-(4-Cyanobenzyl)-5-(4-biphenylmethyl)-2-methylimidazole
1-(4Cyanobenzyl)-5-[1-(4-biphenyl)]ethyl-2-methyl imidazole
1-(4-Cyanobenzyl-5-[1-(4-biphenyl)]vinylidene-2-methylimidazole and
1-(4-Cyanobenzyl)-5-[2-(4-biphenyl)]vinylene-2-methylimidazole
1-(4-[Pyrid-2-yl]phenylmethyl)-5-(4-cyanobenzyl) imidazole
1-(4-[3-Methylpyrazin-2-yl]phenylmethyl)-5-(4-cyanobenzyl)imidazole
1-(4-(Pyrimidinyl-5-yl)phenylmethyl)-5-(4-cyanobenzyl) imidazole
1-(2-Phenylpyrid-5-ylmethyl)-5-(4-cyanobenzyl)imidazole
1-(2-Phenyl-N-Oxopyrid-5-ylmethyl)-5-(4-cyanobenzyl) imidazole
1-(3-Phenylpyrid-6-ylmethyl)-5-(4-cyanobenzyl)imidazole
1-(3-Phenyl-N-Oxopyrid-6-ylmethyl)-5-(4-cyanobenzyl) imidazole
1-(2-(3-Trifluoromethoxyphenyl)-pyrid-5-ylmethyl)-5-(4-cyanobenzyl)imidazole
1-(2-(2-Trifluoromethylphenyl)-pyrid-5-ylmethyl)-5-(4-cyanobenzyl)imidazole
1-(3-Phenyl-2-Chloropyrid-6-ylmethyl)-5-(4-cyanobenzyl) imidazole
1-(3-Phenyl-4chloropyrid-6-ylmethyl)-5-(4-cyanobenzyl) imidazole.
1-(2-Amino-3-phenylpyrid-6-ylmethyl)-5-(4-cyanobenzyl) imidazole
1-(2-[Pyrid-2-yl]pyrid-5-ylmethyl)-5-(4-cyanobenzyl) imidazole
N-{1-(4-Cyanobenzyl)-1H-imidazol-5-yl)methyl}-5-(pyrid-2-yl)-2-amino-pyrimidine
N,N-bis(4-Imidazolemethyl)amino-3-[(3-carboxyphenyl)oxy]benzene
N,N-bis(4Imidazolemethyl)amino4-[(3-carboxyphenyl)oxy]benzene
N,N-bis(4-Imidazolemethyl)amino-3-[(3-carbomethoxyphenyl)-oxy]benzene
N,N-bis(4-Imidazolemethyl)amino4[(3-carbomethoxyphenyl)-oxy]benzene
N-(4-Imidazolemethyl)-N-(4-nitrobenzyl)aminomethyl-3-[(3-carboxyphenyl)oxy]benzene
N-(4-Imidazolemethyl)-N-(4-nitrobenzyl)aminomethyl-3-[(3-carbomethoxyphenyl)oxy]benzene
N-(4-Imidazolemethyl)-N-(4-nitrobenzyl)amino-3-(phenoxy)benzene
N-(4-Imidazolemethyl)-N-(4-nitrobenzyl)amino-4-(phenoxy)benzene
N-(4-Imidazolemethyl)-N-(4-nitrobenzyl)amino-4-(phenylthio)benzene
N-Butyl-N-[1-(4cyanobenzyl)-5-imidazolemethyl]amino4-(phenoxy)benzene
N-[1-(4-Cyanobenzyl)-5-imidazolemethyl] amino4-(phenoxy)benzene
N-(4-Imidazolemethyl)amino-3-[(3-carboxyphenyl)oxy]benzene
1-[N-(1-(4-cyanobenzyl)-5-imidazolylmethyl)-N-(4-cyanobenzyl)amino]-4-(phenoxy)benzene
(±)4-[(4-imidazolylmethyl)amino]pentyl-1-(phenoxy)benzene
1-[(N-(1-(4-cyanobenzyl)-5-imidazolylmethyl)-N-(n-butyl) amino)methyl]4-(phenoxy)benzene
4-[N-(1-(4-cyanobenzyl)-S-imidazolylmethyl)-N-(n-butyl) amino]-1-(phenylthio)benzene
(±)-4-[N-(1-(4-cyanobenzyl)-4-imidazolylmethyl)-N-(n-butyl) amino]1-(phenylsulfinyl)benzene
3-[N-(4-imidazolylmethyl)-N-(n-butyl)amino]-N-(phenyl) benzenesulfonamide and
1-[N-(1-(4-cyanobenzyl)-5-imidazolylmethyl)amino]-3-methoxy-4-phenylbenzene
4-[3-[4-(-2-Oxo-2-H-pyridin-1-yl)benzyl]-3-H-imidazol4-ylmethyl]benzonitrile
4-[3-[4-Methyl-2-oxo-2-H-pyridin- 1-yl)benzyl]-3-H-imidazol-4-ylmethyl]benzonitrile
4-[3-[4-(-2-Oxo-piperidin-1-yl)benzyl]-3-H-imidazol-4-ylmethyl]benzonitrile 4-{3-[3-Methyl-4-(2-oxopiperidin-1-yl)-benzyl]-3-H-imidizol-4-ylmethyl}-benzonitrile
(4-{3-[4-(2-Oxo-pyrrolidin-1-yl)-benzyl]-3H-imidizol-4-ylmethyl}-benzonitrile
4-{3-[4-(3-Methyl-2-oxo-2-H-pyrazin-1-yl)-benzyl-3-H-imidizol-4-ylmethyl}-benzonitrile
4-{3-[2-Methoxy4-(2-oxo-2-H-pyridin-1-yl)-benzyl]-3-H-imidizol4-ylmethyl}-benzonitrile
4-{1-[4(5-Chloro-2-oxo-2H-pyridin-1-yl)-benzyl]-1H-pyrrol-2-ylmethyl}-benzonitrile
4-[1-(2-Oxo-2H-[1,2']bipyridinyl-5'-ylmethyl)-1H-pyrrol-2-ylmethyl]-benzonitrile
4-[1-(5-Chloro-2-oxo-2H-[1,2']bipyridinyl-5'-ylmethyl)-1H-pyrrol-2-ylmethyl]-benzonitrile
4-[3-(2-Oxo- 1-phenyl-1,2-dihydropyridin-4-ylmethyl)-3H-imidazol-4-ylmethyl]benzonitrile
4-{3-[1-(3-Chloro-phenyl)-2-oxo-1,2-dihydropyridin-4-ylmethyl]-3H-imidazol-4-ylmethyl}benzonitrile or a pharmaceutically acceptable salt, disulfide or optical isomer thereof.

Specific examples of a farnesyl-protein transferase inhibitor is

2(S)-[2(S)[2(R)-Amino-3-mercapto]-propylamino-3(S)-methyl]-pentyloxy-3-phenylpropionyl-methionine sulfone isopropyl ester (Compound A)

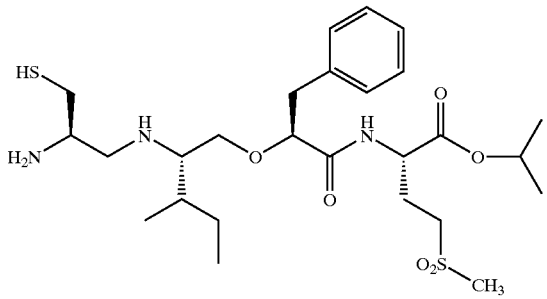

1-(3-Chlorophenyl)-4-[1-(4-cyanobenzyl)-5-imidazolylmethyl]-2-piperazinone;
(R)-1-(3-Chlorophenyl)-4-[1-(4-cyanobenzyl)-5-imidazolylmethyl]-5-[2-(ethanesulfonyl)methyl]-2-piperazinone;
4-[1-(5-Chloro-2-oxo-2H- [1,2']bipyridinyl-5'-ylmethyl)-1H-pyrrol-2-ylmethyl]-benzonitrile and
1-[N-(1-(4-cyanobenzyl)-5-imidazolylmethyl)-N-(4-cyanobenzyl)amino]4-(phenoxy)benzene;
or a pharmaceutically acceptable salt, disulfide or optical isomer thereof.

A particularly useful example of the instant method comprises administering an effective amount of a combination of paclitaxel and a farnesyl-protein transferase inhibitor which is:

2(S)-[2(S)-[2(R)-Amino-3-mercapto]-propylamino-3(S)-methyl]-pentyloxy-3-phenylpropionyl-methionine sulfone isopropyl ester (Compound A).

Another particularly useful example of the instant method comprises administering an effective amount of a combination of vinblastine and a farnesyl-protein transferase inhibitor which is:

2(S)-[2(S)-[2(R)-Amino-3-mercapto)-propylamino-3(S)-methyl]-pentyloxy-3-phenylpropionyl-methionine sulfone isopropyl ester (Compound A).

Another particularly useful example of the instant method comprises administering an effective amount of a combination of 5-fluorouracil and a farnesyl-protein transferase inhibitor which is:

2(S)-[2(S)-[2(R)-Amino-3-mercapto]-propylamino-3(S)-methyl]-pentyloxy-3-phenylpropionyl-methionine sulfone isopropyl ester (Compound A).

Another particularly useful example of the instant method comprises administering an effective amount of a combination of colchicine and a farnesyl-protein transferase inhibitor which is:

2(S)-[2(S)-[2(R)-Amino-3-mercapto]-propylamino-3(S)-methyl]-pentyloxy-3-phenylpropionyl-methionine sulfone isopropyl ester (Compound A).

Another particularly useful example of the instant method comprises administering an effective amount of a combination of estramustine and a farnesyl-protein transferase inhibitor which is:

2(S)-[2(S)-[2(R)-Amino-3-mercapto]-propylamino-3(S)-methyl]-pentyloxy-3-phenylpropionyl-methionine sulfone isopropyl ester (Compound A).

Another particularly useful example of the instant method comprises administering an effective amount of a combination of etoposide and a farnesyl-protein transferase inhibitor which is:

2(S)-[2(S)-[2(R)-Amino-3-mercapto]-propylamino-3(S)-methyl]-pentyloxy-3-phenylpropionyl-methionine sulfone isopropyl ester (Compound A).

Another particularly useful example of the instant method comprises administering an effective amount of a combination of doxorubicin and a farnesyl-protein transferase inhibitor which is:

2(S)-[2(S)-[2(R)-Amino-3-mercapto]-propylamino-3(S)-methyl]-pentyloxy-3-phenylpropionyl-methionine sulfone isopropyl ester (Compound A).

Another particularly useful example of the instant method comprises administering an effective amount of a combination of cis-platinum and a farnesyl-protein transferase inhibitor which is:

2(S)-[2(S)-[2(R)-Amino-3-mercapto]-propylamino-3(S)-methyl]-pentyloxy-3-phenylpropionyl-methionine sulfone isopropyl ester (Compound A).

Another particularly useful example of the instant method comprises administering an effective amount of a combination of bicalutamide and a farnesyl-protein transferase inhibitor which is:

2(S)-[2(S)-[2(R)-Amino-3-mercapto]-propylamino-3(S)-methyl]-pentyloxy-3-phenylpropionyl-methionine sulfone isopropyl ester (Compound A).

Another particularly useful example of the instant method comprises administering an effective amount of a combination of epothilone A and a farnesyl-protein transferase inhibitor which is:

2(S)-[2(S)-[2(R)-Amino-3-mercapto]-propylamino-3(S)-methyl]-pentyloxy-3-phenylpropionyl-methionine sulfone isopropyl ester (Compound A).

Another particularly useful example of the instant method comprises administering an effective amount of a combination of epothilone B and a farnesyl-protein transferase inhibitor which is:

2(S)-[2(S)-[2(R)-Amino-3-mercapto]-propylamino-3(S)-methyl]-pentyloxy-3-phenylpropionyl-methionine sulfone isopropyl ester (Compound A).

Another particularly useful example of the instant method comprises administering an effective amount of a combination of desoxyepothilone A and a farnesyl-protein transferase inhibitor which is:

2(S)-[2(S)-[2(R)-Amino-3-mercapto]-propylamino-3(S)-methyl]-pentyloxy-3-phenylpropionyl-methionine sulfone isopropyl ester (Compound A).

Another particularly useful example of the instant method comprises administering an effective amount of a combination of desoxyepothilone B and a farnesyl-protein transferase inhibitor which is:

2(S)-[2(S)-[2(R)-Amino-3-mercapto]-propylamino-3(S)-methyl]-pentyloxy-3-phenylpropionyl-methionine sulfone isopropyl ester (Compound A).

A particularly useful example of the instant method comprises administering an effective amount of a combination of paclitaxel and a farnesyl-protein transferase inhibitor which is:

1-(3-Chlorophenyl)-4-[1-(4-cyanobenzyl)-5-imidazolylmethyl]-2-piperazinone;
or a pharmaceutically acceptable salt thereof.

Another particularly useful example of the instant method comprises administering an effective amount of a combination of vinblastine and a farnesyl-protein transferase inhibitor which is:

1-(3-Chlorophenyl)4-[1-(4-cyanobenzyl)-5-imidazolylmethyl]-2-piperazinone;
or a pharmaceutically acceptable salt thereof.

Another particularly useful example of the instant method comprises administering an effective amount of a combination of 5-fluorouracil and a farnesyl-protein transferase inhibitor which is:

1-(3-Chlorophenyl)-4-[ 1-(4-cyanobenzyl)-5-imidazolylmethyl]-2-piperazinone;
or a pharmaceutically acceptable salt thereof.

Another particularly useful example of the instant method comprises administering an effective amount of a combination of colchicine and a farnesyl-protein transferase inhibitor which is:

1-(3-Chlorophenyl)-4-[1-(4-cyanobenzyl)-5-imidazolylmethyl]-2-piperazinone;
or a pharmaceutically acceptable salt thereof.

Another particularly useful example of the instant method comprises administering an effective amount of a combination of estramustine and a farnesyl-protein transferase inhibitor which is:

1-(3-Chlorophenyl)-4-[1-(4-cyanobenzyl)-5-imidazolylmethyl]-2-piperazinone;
or a pharmaceutically acceptable salt thereof.

Another particularly useful example of the instant method comprises administering an effective amount of a combination of etoposide and a farnesyl-protein transferase inhibitor which is:

1-(3-Chlorophenyl)-4-[1-(4-cyanobenzyl)-5-imidazolylmethyl]-2-piperazinone;
or a pharmaceutically acceptable salt thereof.

Another particularly useful example of the instant method comprises administering an effective amount of a combination of doxorubicin and a farnesyl-protein transferase inhibitor which is:

1-(3-Chlorophenyl)-4-[1-(4-cyanobenzyl)-5-imidazolylmethyl]-2-piperazinone;
or a pharmaceutically acceptable salt thereof.

Another particularly useful example of the instant method comprises administering an effective amount of a combination of cis-platinum and a farnesyl-protein transferase inhibitor which is:

1-(3-Chlorophenyl)-4-[1-(4-cyanobenzyl)-5-imidazolylmethyl]-2-piperazinone;
or a pharmaceutically acceptable salt thereof.

Another particularly useful example of the instant method comprises administering an effective amount of a combination of bicalutamide and a farnesyl-protein transferase inhibitor which is:

1-(3-Chlorophenyl)-4-[1-(4-cyanobenzyl)-5-imidazolylmethyl]-2-piperazinone;
or a pharmaceutically acceptable salt thereof.

Another particularly useful example of the instant method comprises administering an effective amount of a combination of epothilone A and a farnesyl-protein transferase inhibitor which is:

1-(3-Chlorophenyl)-4-[1-(4-cyanobenzyl)-5-imidazolylmethyl]-2-piperazinone;
or a pharmaceutically acceptable salt thereof.

Another particularly useful example of the instant method comprises administering an effective amount of a combination of epothilone B and a farnesyl-protein transferase inhibitor which is:

1-(3-Chlorophenyl)-4-[1-(4-cyanobenzyl)-5-imidazolylmethyl]-2-piperazinone;
or a pharmaceutically acceptable salt thereof.

Another particularly useful example of the instant method comprises administering an effective amount of a combination of desoxyepothilone A and a farnesyl-protein transferase inhibitor which is:

1-(3-Chlorophenyl)4-[1-(4-cyanobenzyl)-5-imidazolylmethyl]-2-piperazinone;
or a pharmaceutically acceptable salt thereof.

Another particularly useful example of the instant method comprises administering an effective amount of a combination of desoxyepothilone B and a farnesyl-protein transferase inhibitor which is:

1-(3-Chlorophenyl)-4-[1-(4-cyanobenzyl)-5-imidazolylmethyl]-2-piperazinone;
or a pharmaceutically acceptable salt thereof.

A particularly useful example of the instant method comprises administering an effective amount of a combination of paclitaxel and a farnesyl-protein transferase inhibitor which is:

(R)-1-(3-Chlorophenyl)-4-[1-(4-cyanobenzyl)-5-imidazolylmethyl]-5-[2-(ethanesulfonyl)methyl]-2-piperazinone;
or a pharmaceutically acceptable salt thereof.

Another particularly useful example of the instant method comprises administering an effective amount of a combination of vinblastine and a farnesyl-protein transferase inhibitor which is:

(R)-1-(3-Chlorophenyl)-4-[1-(4-cyanobenzyl)-5-imidazolylmethyl]-5-[2-(ethanesulfonyl)methyl]-2-piperazinone;
or a pharmaceutically acceptable salt thereof.

Another particularly useful example of the instant method comprises administering an effective amount of a combination of 5-fluorouracil and a farnesyl-protein transferase inhibitor which is:

(R)-1-(3-Chlorophenyl)-4-[1-(4-cyanobenzyl)-5-imidazolylmethyl]-5-[2-(ethanesulfonyl)methyl]-2-piperazinone;
or a pharmaceutically acceptable salt thereof.

Another particularly useful example of the instant method comprises administering an effective amount of a combination of colchicine and a farnesyl-protein transferase inhibitor which is:

(R)-1-(3-Chlorophenyl)-4-[1-(4-cyanobenzyl)-5-imidazolylmethyl]-5-[2-(ethanesulfonyl)methyl]-2-piperazinone;
or a pharmaceutically acceptable salt thereof.

Another particularly useful example of the instant method comprises administering an effective amount of a combination of estramustine and a farnesyl-protein transferase inhibitor which is:

(R)-1-(3-Chlorophenyl)A-[1-(4-cyanobenzyl)-5-imidazolylmethyl]-5-[2-(ethanesulfonyl)methyl]-2-piperazinone;
or a pharmaceutically acceptable salt thereof.

Another particularly useful example of the instant method comprises administering an effective amount of a combination of etoposide and a farnesyl-protein transferase inhibitor which is:

(R)-1-(3-Chlorophenyl)-4-[1-(4-cyanobenzyl)-5-imidazolylmethyl]-5-[2-(ethanesulfonyl)methyl]-2-piperazinone;
or a pharmaceutically acceptable salt thereof.

Another particularly useful example of the instant method comprises administering an effective amount of a combination of doxorubicin and a farnesyl-protein transferase inhibitor which is:

(R)-1-(3-Chlorophenyl)-4-[1-(4-cyanobenzyl)-5-imidazolylmethyl]-5-[2-(ethanesulfonyl)methyl]-2-piperazinone;
or a pharmaceutically acceptable salt thereof.

Another particularly useful example of the instant method comprises administering an effective amount of a combination of cis-platinum and a farnesyl-protein transferase inhibitor which is:

(R)-1-(3-Chlorophenyl)4-[1-(4-cyanobenzyl)-5-imidazolylmethyl]-5-[2-(ethanesulfonyl)methyl]-2-piperazinone;
or a pharmaceutically acceptable salt thereof.

Another particularly useful example of the instant method comprises administering an effective amount of a combination of bicalutamide and a farnesyl-protein transferase inhibitor which is:

(R)-1-1-(3-Chlorophenyl)-4-[1-(4-cyanobenzyl)-5-imidazolylmethyl]-5-[2-(ethanesulfonyl)methyl]-2-piperazinone;
or a pharmaceutically acceptable salt thereof.

Another particularly useful example of the instant method comprises administering an effective amount of a combination of epothilone A and a farnesyl-protein transferase inhibitor which is:

(R)-1-(3-Chlorophenyl)-4-[1-(4-cyanobenzyl)-5-imidazolylmethyl]-5-[2-(ethanesulfonyl)methyl]-2-piperazinone;
or a pharmaceutically acceptable salt thereof.

Another particularly useful example of the instant method comprises administering an effective amount of a combination of epothilone B and a farnesyl-protein transferase inhibitor which is:

(R)-1-(3-Chlorophenyl)-4-[1-(4-cyanobenzyl)-5-imidazolylmethyl]-5-[2-(ethanesulfonyl)methyl]-2-piperazinone;
or a pharmaceutically acceptable salt thereof.

Another particularly useful example of the instant method comprises administering an effective amount of a combination of desoxyepothilone A and a farnesyl-protein transferase inhibitor which is:

(R)-1-(3-Chlorophenyl)4-[1-(4-cyanobenzyl)-5-imidazolylmethyl]-5-[2-(ethanesulfonyl)methyl]-2-piperazinone;
or a pharmaceutically acceptable salt thereof.

Another particularly useful example of the instant method comprises administering an effective amount of a combination of desoxyepothilone B and a farnesyl-protein transferase inhibitor which is:

(R)-1-(3-Chlorophenyl)-4-[1-(4-cyanobenzyl)-5-imidazolylmethyl]-5-[2-(ethanesulfonyl)methyl]-2-piperazinone;
or a pharmaceutically acceptable salt thereof.

Another particularly useful example of the instant method comprises administering an effective amount of a combination of paclitaxel and a farnesyl-protein transferase inhibitor which is:

4-[1-(5-Chloro-2-oxo-2H-[1,2']bipyridinyl-5'-ylmethyl)-1H-pyrrol-2-ylmethyl]-benzonitrile;
or a pharmaceutically acceptable salt thereof.

Another particularly useful example of the instant method comprises administering an effective amount of a combination of vinblastine and a farnesyl-protein transferase inhibitor which is:

4-[1-(5-Chloro-2-oxo-2H-[1,2']bipyridinyl-5'-ylmethyl)-1H-pyrrol-2-ylmethyl]-benzonitrile;
or a pharmaceutically acceptable salt thereof.

Another particularly useful example of the instant method comprises administering an effective amount of a combination of 5-fluorouracil and a farnesyl-protein transferase inhibitor which is:

4-[1-(5-Chloro-2-oxo-2H-[1,2']bipyridinyl-5'-ylmethyl)-1H-pyrrol-2-ylmethyl]-benzonitrile;
or a pharmaceutically acceptable salt thereof.

Another particularly useful example of the instant method comprises administering an effective amount of a combination of colchicine and a farnesyl-protein transferase inhibitor which is:

4-[1-(5-Chloro-2-oxo-2H-[1,2']bipyridinyl-5'-ylmethyl)-1H-pyrrol-2-ylmethyl]-benzonitrile;
or a pharmaceutically acceptable salt thereof.

Another particularly useful example of the instant method comprises administering an effective amount of a combination of estramustine and a farnesyl-protein transferase inhibitor which is:

4-[1-(5-Chloro-2-oxo-2H-[1,2']bipyridinyl-5'-ylmethyl)-1H-pyrrol-2-ylmethyl]-benzonitrile;
or a pharmaceutically acceptable salt thereof.

Another particularly useful example of the instant method comprises administering an effective amount of a combination of etoposide and a farnesyl-protein transferase inhibitor which is:

4-[1-(5-Chloro-2-oxo-2H-[1,2']bipyridinyl-5'-ylmethyl)-1H-pyrrol-2-ylmethyl]-benzonitrile;
or a pharmaceutically acceptable salt thereof.

Another particularly useful example of the instant method comprises administering an effective amount of a combination of doxorubicin and a farnesyl-protein transferase inhibitor which is:

4-[1-(5-Chloro-2-oxo-2H-[1,2']bipyridinyl-5'-ylmethyl)-1H-pyrrol-2-ylmethyl]-benzonitrile;
or a pharmaceutically acceptable salt thereof.

Another particularly useful example of the instant method comprises administering an effective amount of a combination of cis-platinum and a farnesyl-protein transferase inhibitor which is:

4-[1-(5-Chloro-2-oxo-2H-[1,2']bipyridinyl-5'-ylmethyl)-1H-pyrrol-2-ylmethyl]-benzonitrile;
or a pharmaceutically acceptable salt thereof.

Another particularly useful example of the instant method comprises administering an effective amount of a combination of bicalutamide and a farnesyl-protein transferase inhibitor which is:

4-[11-(5-Chloro-2-oxo-2H-[1,2']bipyridinyl-5'-ylmethyl)-1H-pyrrol-2-ylmethyl]-benzonitrile;
or a pharmaceutically acceptable salt thereof.

Another particularly useful example of the instant method comprises administering an effective amount of a combination of epothilone A and a farnesyl-protein transferase inhibitor which is:

4-[1-(5-Chloro-2-oxo-2H-[1,2']bipyridinyl-5'-ylmethyl)-1H-pyrrol-2-ylmethyl]-benzonitrile;
or a pharmaceutically acceptable salt thereof.

Another particularly useful example of the instant method comprises administering an effective amount of a combination of epothilone B and a farnesyl-protein transferase inhibitor which is:

4-[1-(5-Chloro-2-oxo-2H-[1,2']bipyridinyl-5'-ylmethyl)-1H-pyrrol-2-ylmethyl]-benzonitrile;
or a pharmaceutically acceptable salt thereof.

Another particularly useful example of the instant method comprises administering an effective amount of a combination of desoxyepothilone A and a farnesyl-protein transferase inhibitor which is:

4-[1-(5-Chloro-2-oxo-2H-[1,2']bipyridinyl-5'-ylmethyl)-1H-pyrrol-2-ylmethyl]-benzonitrile;
or a pharmaceutically acceptable salt thereof.

Another particularly useful example of the instant method comprises administering an effective amount of a combination of desoxyepothilone B and a farnesyl-protein transferase inhibitor which is:

4-[1-(5-Chloro-2-oxo-2H-[1,2']bipyridinyl-5'-ylmethyl)-1H-pyrrol-2-ylmethyl]-benzonitrile;
or a pharmaceutically acceptable salt thereof.

Another particularly useful example of the instant method comprises administering an effective amount of a combination of paclitaxel and a farnesyl-protein transferase inhibitor which is:

1-[N-(1-(4-cyanobenzyl)-5-imidazolylmethyl)-N-(4-cyanobenzyl)amino]4-(phenoxy)benzene;
or a pharmaceutically acceptable salt thereof.

Another particularly useful example of the instant method comprises administering an effective amount of a combination of vinblastine and a farnesyl-protein transferase inhibitor which is:

1-[N-(1-(4-cyanobenzyl)-5-imidazolylmethyl)-N-(4-cyanobenzyl)amino]-4-(phenoxy)benzene;
or a pharmaceutically acceptable salt thereof.

Another particularly useful example of the instant method comprises administering an effective amount of a combination of 5-fluorouracil and a farnesyl-protein transferase inhibitor which is:

1-[N-(1-(4-cyanobenzyl)-5-imidazolylmethyl)-N-(4-cyanobenzyl)amino]-4-(phenoxy)benzene;
or a pharmaceutically acceptable salt thereof.

Another particularly useful example, of the instant method comprises administering an effective amount of a combination of colchicine and a farnesyl-protein transferase inhibitor which is:

1-[N-(1-(4-cyanobenzyl)-5-imidazolylmethyl)-N-(4-cyanobenzyl)amino]-4-(phenoxy)benzene;
or a pharmaceutically acceptable salt thereof.

Another particularly useful example of the instant method comprises administering an effective amount of a combination of estramustine and a farnesyl-protein transferase inhibitor which is:

1-[N-(1-(4-cyanobenzyl)-5-imidazolylmethyl)-N-(4-cyanobenzyl)amino]-4-(phenoxy)benzene;
or a pharmaceutically acceptable salt thereof.

Another particularly useful example of the instant method -comprises administering an effective amount of a combination of etoposide and a farnesyl-protein transferase inhibitor which is:

1-[N-(1-(4-cyanobenzyl)-5-imidazolylmethyl)-N-(4-cyanobenzyl)amino]4-(phenoxy)benzene;
or a pharmaceutically acceptable salt thereof.

Another particularly useful example of the instant method comprises administering an effective amount of a combination of doxorubicin and a farnesyl-protein transferase inhibitor which is:

1-[N-(1-(4-cyanobenzyl)-5-imidazolylmethyl)-N-(4-cyanobenzyl)amino]4(phenoxy)benzene;
or a pharmaceutically acceptable salt thereof.

Another particularly useful example of the instant method comprises administering an effective amount of a combination of cis-platinum and a farnesyl-protein transferase inhibitor which is:

1-[N-(1-(4-cyanobenzyl)-5-imidazolylmethyl)-N-(4-cyanobenzyl)amino]A(phenoxy)benzene;
or a pharmaceutically acceptable salt thereof.

Another particularly useful example of the instant method comprises administering an effective amount of a combination of bicalutamide and a farnesyl-protein transferase inhibitor which is:

1-[N-(1-(4-cyanobenzyl)-5-imidazolylmethyl)-N-(4-cyanobenzyl)amino]4(phenoxy)benzene;
or a pharmaceutically acceptable salt thereof.

Another particularly useful example of the instant method comprises administering an effective amount of a combination of epothilone A and a farnesyl-protein transferase inhibitor which is:

1[N-(1-(4-cyanobenzyl)-5-imidazolylmethyl)-N-(4-cyanobenzyl)amino]-4-(phenoxy)benzene;
or a pharmaceutically acceptable salt thereof.

Another particularly useful example of the instant method comprises administering an effective amount of a combination of epothilone B and a farnesyl-protein transferase inhibitor which is:

1-[N-(1-(4-cyanobenzyl)-5-imidazolylmethyl)-N-(4-cyanobenzyl)amino]4-(phenoxy)benzene;
or a pharmaceutically acceptable salt thereof.

Another particularly useful example of the instant method comprises administering an effective amount of a combination of desoxyepothilone A and a farnesyl-protein transferase inhibitor which is:

1-[N-(1-(4cyanobenzyl)-5-imidazolylmethyl)-N-(4-cyanobenzyl)amino]4-(phenoxy)benzene;
or a pharmaceutically acceptable salt thereof.

Another particularly useful example of the instant method comprises administering an effective amount of a combination of desoxyepothilone B and a farnesyl-protein-transferase-inhibitor which is:

1-[N-(1-(4-cyanobenzyl)-5-imidazolylmethyl)-N-(4-cyanobenzyl)amino]-4-(phenoxy)benzene;
or a pharmaceutically acceptable salt thereof.

Compounds which are described as inhibitors of farnesyl-protein transferase and may therefore useful in the present invention, and methods of synthesis thereof, can be found in the following patents, pending applications and publications, which are herein incorporated by reference:

WO 95/32987 published on 7 Dec. 1995;
U.S. Pat. No. 5,420,245;
U.S. Pat. No. 5,523,430;
U.S. Pat. No. 5,532,359;
U.S. Pat. No. 5,510,510;
U.S. Pat. No. 5,589,485;
U.S. Pat. No. 5,602,098;
European Pat. Publ. 0 618 221;
European Pat. Publ. 0 675 112;
European Pat. Publ. 0 604 181;
European Pat. Publ. 0 696 593;
WO 94/19357;
WO 95/08542;
WO 95/11917;
WO 95/12612;
WO 95/12572;
WO 95/10514 and U.S. Pat. No. 5,661,152;
WO 95/10515;
WO 95/10516;
WO 95/24612;
WO 95/34535;
WO 95/25086;
WO 96/05529;
WO 96/06138;
WO 96106193;

WO 96/16443;
WO 96/21701;
WO 96/21456;
WO 96/22278;
WO 96/24611;
WO 96/24612;
WO 96/05168;
WO 96/05169;
WO 96/00736 and U.S. Pat. No. 5,571,792 granted on Nov. 5, 1996;
WO 96/17861;
WO 96/33159;
WO 96/34850;
WO 96/34851;
WO 96/30017;
WO 96/30018;
WO 96/30362;
WO 96/30363;
WO 96/31111;
WO 96/31477;
WO 96/31478;
WO 96/31501;
WO 97/00252;
WO 97/03047;
WO 97/03050;
WO 97/04785;
WO 97102920;
WO 97/17070;
WO 97/23478;
WO 97/26246;
WO 97/30053;
WO 97/44350;
WO 98/02436; and
U.S. Pat. No. 5,532,359 granted on Jul. 2, 1996.

Compounds which are inhibitors of farnesyl-protein transferase and are therefore useful in the present invention, and methods of synthesis thereof, can be found in the following patents, pending applications and publications, which are herein incorporated by reference:

U.S. Pat. No. 5,238,922 granted on Aug. 24, 1993;
U.S. Pat. No. 5,340,828 granted on Aug. 23, 1994;
U.S. Pat. No. 5,480,893 granted on Jan. 2, 1996;
U.S. Pat. No. 5,352,705 granted on Oct. 4, 1994;
U.S. Pat. No. 5,504,115 granted on Apr. 2, 1996;
U.S. Pat. No. 5,536,750 granted on Jul. 16, 1996;
U.S. Pat. No. 5,504,212 granted on Apr. 2, 1996;
U.S. Pat. No. 5,439,918 granted on Aug. 8, 1995;
U.S. Pat. No. 5,686,472 granted on Nov. 11, 1997;
U.S. Pat. No. 5,736,539 granted on Apr. 4, 1998;
U.S. Pat. No. 5,576,293 granted on Nov. 19, 1996;
U.S. Pat. No. 5,468,733 granted on Nov. 21, 1995;
WO 96/06609 (Mar. 3, 1996) and U.S. Ser. No. 08/298,478 filed on Aug. 24, 1994;
U.S. Pat. No. 5,585,359 granted on Dec. 17, 1996
U.S. Pat. No. 5,523,456 granted on Jun. 4, 1996;
U.S. Pat. No. 5,661,161 granted on Aug. 26, 1997;
U.S. Pat. No. 5,571,835 granted on Nov. 5, 1996;
U.S. Pat. No. 5,491,164 granted on February 13, 1996;
U.S. Pat. No. 5,652,257 granted on Jul. 29, 1997;
U.S. Pat. No. 5,631,280 granted on May 20, 1997;
U.S. Pat. No. 5,578,629 granted on Nov. 26, 1996;
U.S. Pat. No. 5,627,202 granted on May 6, 1997;
WO 96130343 (Oct. 3, 1996); U.S. Ser. No. 08/412,829 filed on Mar. 29, 1995; and U.S. Ser. No. 08/470,690 filed on Jun. 6, 1995; and U.S. Ser. No. 08/600,728 filed on February 28, 1996;
U.S. Pat. No. 5,624,936 granted on Apr. 29, 1997;
U.S. Pat. No. 5,534,537 granted on Jul. 9, 1996;
U.S. Pat. No. 5,710,171 granted on Apr. 29, 1997;
WO 96139137 (Dec. 12, 1996); U.S. Ser. No. 08/468,160 filed on Jun. 6, 1995; U.S. Ser. No. 08/652,055 filed on May 23, 1996; U.S. Ser. No. 08/960,248 filed Oct. 29, 1997;
U.S. Pat. No. 5,703,241 granted on Dec. 30, 1997;
WO 97/18813; U.S. Ser. No. 08/749,254 filed on Nov. 15, 1996;
WO 97/27854 (Aug. 7, 1997); U.S. Ser. No. 60/010,799 filed on Jan. 30, 1996; U.S. Ser. No. 08/786,520 filed on Jan. 21, 1997; U.S. Ser. No. 09/015,823 filed on Jan. 29, 1998;
WO 97/27752 (Aug. 7, 1997); U.S. Ser. No. 60/010,860 filed on Jan. 30, 1996; U.S. Ser. No. 08/84,556 filed on Jan. 21, 1997; U.S. Ser. No. 09/030,223 filed on Feb. 25, 1998;
WO 97/27853 (Aug. 7, 1997); U.S. Ser. No. 60/011,081 filed on Jan. 30, 1996; U.S. Ser. No. 08/786,519 filed on Jan. 21, 1997; U.S. Ser. No. 09/445,054;
WO 97/27852 (Aug. 7, 1997); U.S. Ser. No. 60/010,798 filed on Jan. 30, 1996; U.S. Ser. No. 08/786,516 filed on Jan. 21, 1997;
WO 97/36888 (Oct. 9, 1997); U.S. Ser. No. 60/014,587 filed on Apr. 3, 1996; U.S. Ser. No. 08/823,919 filed on Mar. 25, 1997;
WO 97/36889 (Oct. 9, 1997); U.S. Ser. No. 60/014,589 filed on Apr. 3, 1996; U.S. Ser. No. 08/823,923 filed on Mar. 25, 1997;
WO 97/36876 (Oct. 9, 1997); U.S. Ser. No. 60/014,592 filed on Apr. 3, 1996; U.S. Ser. No. 08/834,671 filed on Apr. 1, 1997;
WO 97/36593 (Oct. 9, 1997); U.S. Ser. No. 60/014,593 filed on Apr. 3, 1996; U.S. Ser. No. 08/827,485, filed on Mar. 27, 1997;
WO 97/36879 (Oct. 9, 1997); U.S. Ser. No. 60/014,594 filed on Apr. 3, 1996; U.S. Ser. No. 08/823,920 filed on Mar. 25, 1997;
WO 97/36583 (Oct. 9, 1997); U.S. Ser. No. 60/014,668 filed on Apr. 3, 1996; U.S. Ser. No. 08/824,588 filed on Mar. 26, 1997;
WO 97/36592 (Oct. 9, 1997); U.S. Ser. No. 60/014,775 filed on Apr. 3, 1996; U.S. Ser. No. 08/826,292 filed on Mar. 27, 1997;
WO 97/36584 (Oct. 9, 1997); U.S. Ser. No. 60/014,776 filed on Apr. 3, 1996; U.S. Ser. No. 08/824,427 filed on Mar. 26, 1997; U.S. Ser. No. 60/014,777 filed on Apr. 3, 1996; U.S. Ser. No. 08/826,317 filed on Mar. 27, 1997;
WO 97/38665 (Oct. 23, 1997); U.S. Ser. No. 60/014,791 filed on Apr. 3, 1996; U.S. Ser. No. 08/831,308 filed on Apr. 1, 1997;
WO 97/36591 (Oct. 9, 1997); U.S. Ser. No. 60/014,792 filed on Apr. 3, 1996; U.S. Ser. No. 08/827,482, filed on Mar. 27, 1997;
WO 97/36605 (Oct. 9, 1997); U.S. Ser. No. 60/014,793 filed on Apr. 3, 1996; U.S. Ser. No. 08/823,934 filed on Mar. 25, 1997;
WO 97/37877 (Oct. 9, 1997); U.S. Ser. No. 60/014,794 filed on Apr. 3, 1996; U.S. Ser. No. 08/834,675 filed on Apr. 1, 1997;
WO 97/37900 (Oct. 9, 1997); U.S. Ser. No. 60/014,798 filed on Apr. 3, 1996; U.S. Ser. No. 08/823,929 filed on Mar. 25, 1997;
WO 97/36891 (Oct. 9, 1997); U.S. Ser. No. 60/014,774 filed on Apr. 3, 1996; U.S. Ser. No. 08/826,291 filed on Mar. 27, 1997;
WO 97/36886 (Oct. 9, 1997); U.S. Ser. No. 60/022,332 filed on Jul. 24, 1996; U.S. Ser. No. 08/823,919, filed on Mar. 27, 1997;

WO 97/36881 (Oct. 9, 1997); U.S. Ser. No. 60/022,340 filed on Jul. 24, 1996; U.S. Ser. No. 08/827,486, filed on Mar. 27, 1997;

WO 97/36585 (Oct. 9, 1997); U.S. Ser. No. 60/022,341 filed on Jul. 24, 1996; U.S. Ser. No. 08/826,251 filed on Mar. 27, 1997;

WO 97/36898 (Oct. 9, 1997); U.S. Ser. No. 60/022,342 filed on Jul. 24, 1996; U.S. Ser. No. 08/825,293 filed on Mar. 27, 1997;

WO 97/36897 (Oct. 9, 1997); U.S. Ser. No. 60/022,558 filed on Jul. 24, 1996; U.S. Ser. No. 08/827,476, filed on Mar. 27, 1997;

WO 97136874 (Oct. 9, 1997);

WO 97/36585 (Oct. 9, 1997); U.S. Ser. No. 60/022,586 filed on Jul. 24, 1996; U.S. Ser. No. 08/827,484, filed on Mar. 27, 1997;

WO 97136890 (Oct. 9, 1997); U.S. Ser. No. 60/022,587 filed on Jul. 24, 1996; U.S. Ser. No. 08/831,105 filed on Apr. 1, 1997;

WO 97/36901 (Oct. 9, 1997); U.S. Ser. No. 60/022,647 filed on Jul. 24, 1996; U.S. Ser. No. 08/827,483, filed on Mar. 27, 1997;

U.S. Ser. No. 60/032,126 filed on Dec. 5, 1996; U.S. Ser. No. 08/985,732, filed on Dec. 4, 1997;

U.S. Ser. No. 60/032,428 filed on Dec. 5, 1996; U.S. Ser. No. 08/985,124, filed on Dec. 4, 1997;

U.S. Ser. No. 60/032,578 filed on Dec. 5, 1996; U.S. Ser. No. 08/985,337, filed on Dec. 4, 1997;

U.S. Ser. No. 60/032,579 filed on Dec. 5, 1996; U.S. Ser. No. 08/985,320, filed on Dec. 5, 1997;

U.S. Ser. No. 60/033,990, filed on Dec. 30, 1996; U.S. Ser. No. 08/995,744, filed on Dec. 22, 1997; and U.S. Ser. No. 60/033,991, filed on Dec. 30, 1996; U.S. Ser. No. 08/985,124, filed on Dec. 5, 1997.

All patents, publications and pending patent applications identified are hereby incorporated by reference.

With respect to the compounds of formulas II-a through II-n the following definitions apply:

The term "alkyl" refers to a monovalent alkane (hydrocarbon) derived radical containing from 1 to 15 carbon atoms unless otherwise defined. It may be straight, branched or cyclic. Preferred straight or branched alkyl groups include methyl, ethyl, propyl, isopropyl, butyl and t-butyl. Preferred cycloalkyl groups include cyclopentyl and cyclohexyl.

When substituted alkyl is present, this refers to a straight, branched or cyclic alkyl group as defined above, substituted with 1–3 groups as defined with respect to each variable.

Heteroalkyl refers to an alkyl group having from 2–15 carbon atoms, and interrupted by from 1–4 heteroatoms selected from O, S and N.

The term "alkenyl" refers to a hydrocarbon radical straight, branched or cyclic containing from 2 to 15 carbon atoms and at least one carbon to carbon double bond. Preferably one carbon to carbon double bond is present, and up to four non-aromatic (non-resonating) carbon-carbon double bonds may be present Examples of alkenyl groups include vinyl, allyl, iso-propenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like. Preferred alkenyl groups include ethenyl, propenyl, butenyl and cyclohexenyl. As described above with respect to alkyl, the straight, -branched or cyclic portion of the alkenyl group may contain double bonds and may be substituted when a substituted alkenyl group is provided.

The term "alkynyl" refers to a hydrocarbon radical straight, branched or cyclic, containing from 2 to 15 carbon atoms and at least one carbon to carbon triple bond. Up to three carbon-carbon triple bonds may be present. Preferred alkynyl groups include ethynyl, propynyl and butynyl. As described above with respect to alkyl, the straight, branched or cyclic portion of the alkynyl group may contain triple bonds and may be substituted when a substituted alkynyl group is provided.

Aryl refers to aromatic rings e.g., phenyl, substituted phenyl and like groups as well as rings which are fused, e.g., naphthyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted as defined below. Preferred substituted aryls include phenyl and naphthyl substituted with one or two groups. With regard to the farnesyl transferase inhibitors, "aryl" is intended to include any stable monocyclic, bicyclic or tricyclic carbon ring(s) of up to 7 members in each ring, wherein at least one ring is aromatic. Examples of aryl groups include phenyl, naphthyl, anthracenyl, biphenyl, tetrahydronaphthyl, indanyl, phenanthrenyl and the like.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms. The heteroaryl group is optionally substituted with up to three groups.

Heteroaryl thus includes aromatic and partially aromatic groups which contain one or more heteroatoms. Examples of this type are thiophene, purine, imidazopyridine, pyridine, oxazole, thiazole, oxazine, pyrazole, tetrazole, imidazole, pyridine, pyrimidine, pyrazine and triazine. Examples of partially aromatic groups are tetrahydro-imidazo[4,5-c]pyridine, phthalidyl and saccharinyl, as defined below.

With regard to the farnesyl transferase inhibitors, the term heterocycle or heterocyclic, as used herein, represents a stable 5- to 7-membered monocyclic or stable 8- to 11-membered bicyclic or stable 11–15 membered tricyclic heterocycle ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, pyridonyl, pyrazinyl, pyrazolidinyl, pyrazolyl, pyrimidinyl, pyrrolidinyl, pyrrolyl, quinazolinyl, quinolinyl, quinolinyl N-oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, thienofuryl, thienothienyl, and thienyl. Preferably, heterocycle is selected from imidazolyl, 2-oxopyrrolidinyl, piperidyl, pyridyl and pyrrolidinyl.

With regard to the farnesyl transferase inhibitors, the terms "substituted aryl", "substituted heterocycle" and "substituted cycloalkyl" are intended to include the cyclic group which is substituted with 1 or 2 substitutents selected from the group which includes but is not limited to F, Cl, Br, $CF_3$, $NH_2$, $N(C_1-C_6$ alkyl$)_2$, $NO_2$, CN, $(C_1-C_6$ alkyl$)O$—, —OH, $(C_1-C_6$ alkyl$)S(O)_m$—, $(C_1-C_6$ alkyl$)C(O)NH$—, $H_2N$—C(NH)—, $(C_1-C_6$ alkyl$)C(O)$—, $(C_1-C_6$ alkyl$)OC(O)$—, $N_3$, $(C_1-C_6$ alkyl$)OC(O)NH$— and $C_1-C_{20}$ alkyl.

In the present method, amino acids which are disclosed are identified both by conventional 3 letter and single letter abbreviations as indicated below:

| Alanine | Ala | A |
|---|---|---|
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The compounds used in the present method may have asymmetric centers and occur as racemates, racemic mixtures, and as individual diastereomers, with all possible isomers, including optical isomers, being included in the present invention. Unless otherwise specified, named amino acids are understood to have the natural "L" stereoconfiguration.

With respect to the farnesyl-protein transferase inhibitors of the formulas II-d and II-f, the substituent illustrated by the structure

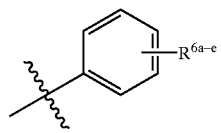

is a simplified representation of a phenyl ring having five (5) substituents (hydrogens and/or non-hydrogens) and may also be represented by the structure:

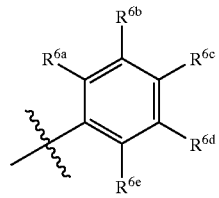

With respect to the farnesyl-protein transferase inhibitors of the formulas II-d and II-f, the moiety described as

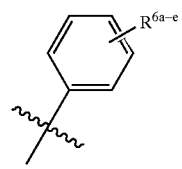

where any two of $R^{6a}$, $R^{6b}$, $R^{6c}$, $R^{6d}$ and $R^{6e}$ on adjacent carbon atoms are combined to form a diradical selected from —CH=CH—CH=CH, —CH=CH—CH—, —$(CH_2)_4$— and —$(CH_2)_4$—includes the following structures:

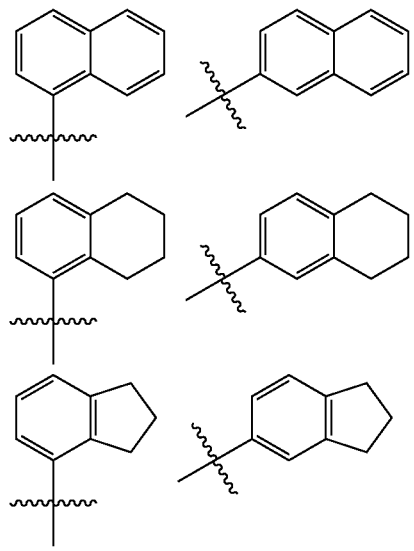

It is understood that such fused ring moieties may be further substituted by the remaining $R^{6a}$, $R^{6b}$, $R^{6c}$, $R^{6d}$ and/or $R^{6e}$ as defined hereinabove.

With respect to the farnesyl-protein transferase inhibitors of the formulas II-e and II-g, the moieties designated by the following structures:

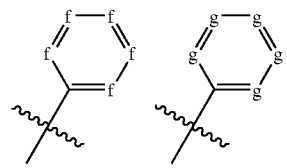

represent an aromatic 6-membered heterocyclic ring and includes the following ring systems:

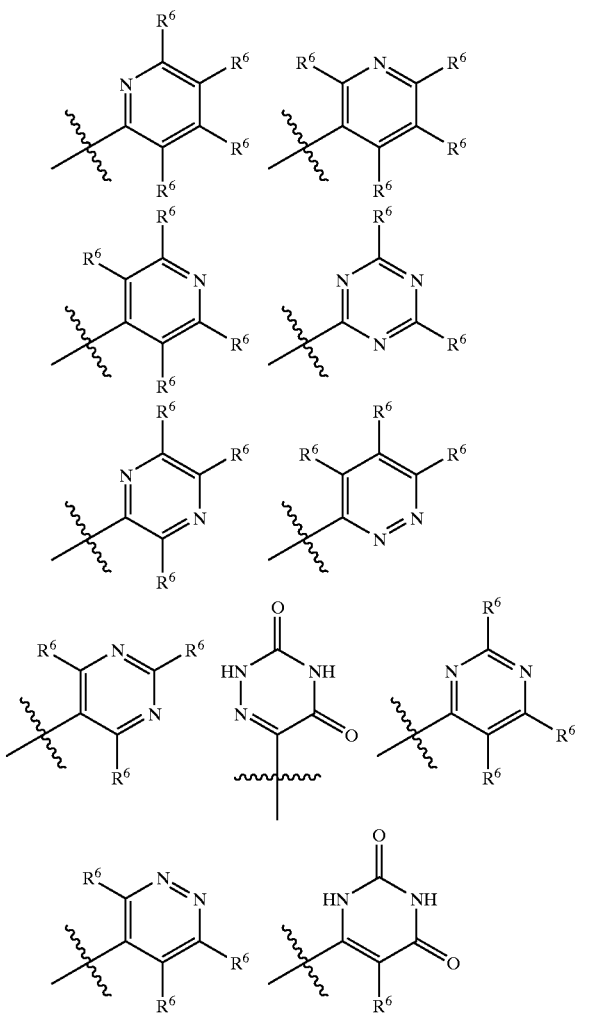

wherein $R^6$ is as defined hereinabove.

With respect to the farnesyl-protein transferase inhibitors of the formulas II-e and II-g, the moieties designated by the following structures:

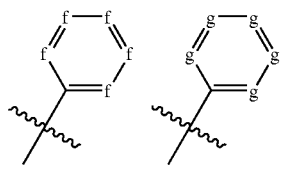

where any two of $R^6$ on adjacent carbon atoms are combined to form a diradical selected from —CH═CH—CH═CH—, —CH═CH—CH—, —(CH$_2$)$_4$— and —(CH$_2$)$_4$—include, but are not limited to the following structures:

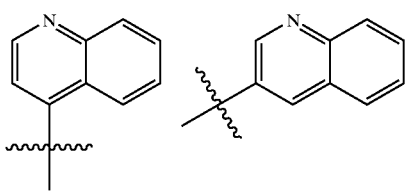

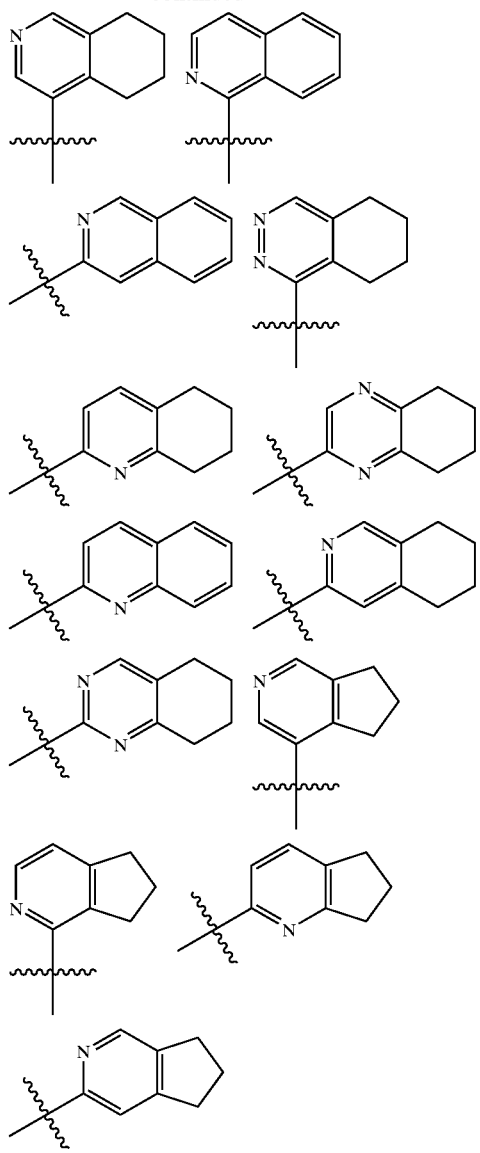

It is understood that such fused ring moieties may be further substituted by the remaining $R^6$s as defined hereinabove.

With respect to the farnesyl-protein transferase inhibitors of the formulas II-f and II-g, the moiety designated by the following structure:

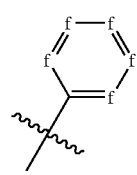

represents an aromatic 6-membered heterocyclic ring and includes the following ring systems:

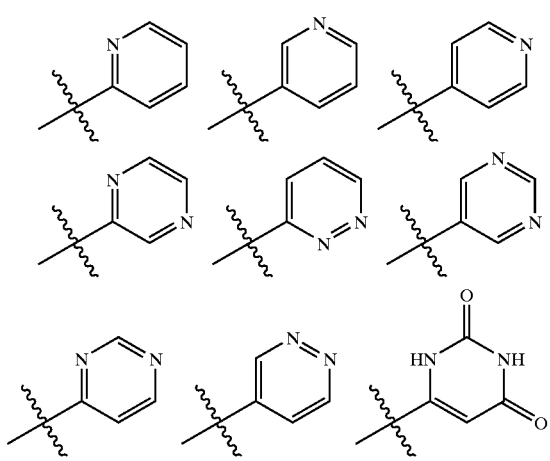

wherein it is understood that one of the ring carbon atoms is substituted with

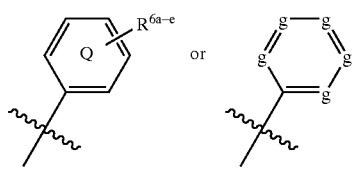

respectively.

With respect to the farnesyl-protein transferase inhibitors of the formula II-m, the substituent illustrated by the structure:

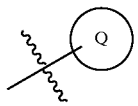

represents a 4, 5, 6 or 7 membered heterocyclic ring which comprises a nitrogen atom through which Q is attached to Y and 0–2 additional heteroatoms selected from N, S and O, and which also comprises a carbonyl, thiocarbonyl, —C(=NR$^{13}$)— or sulfonyl moiety adjacent to the nitrogen atom attached to Y and includes the following ring systems:

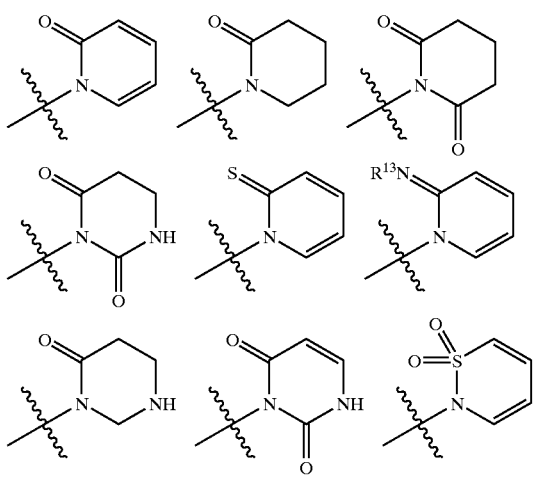

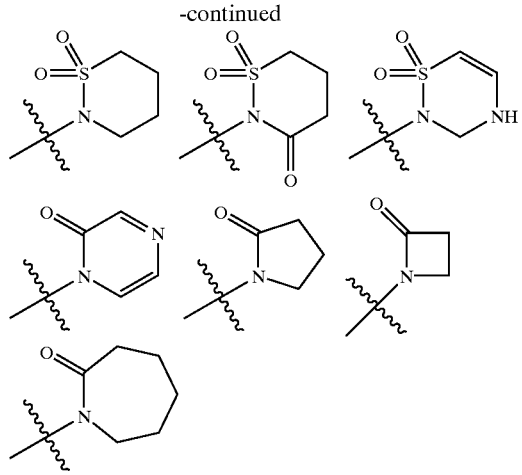

It is understood that such rings may be substituted by R$^{6a}$, R$^{6b}$, R$^{6c}$, R$^{6d}$ and/or R$^{6e}$ as defined hereinabove.

With respect to the farnesyl-protein transferase inhibitors of the formula II-m, the moiety described as where any two of R$^{6a}$, R$^{6b}$, R$^{6c}$, R$^{6d}$ and R$^{6e}$ on adjacent carbon atoms are combined to form a diradical selected from —CH=CH—CH=CH, —CH=CH—CH—, —(CH$_2$)4— and —(CH2)4- includes, but is not limited to, the following structures:

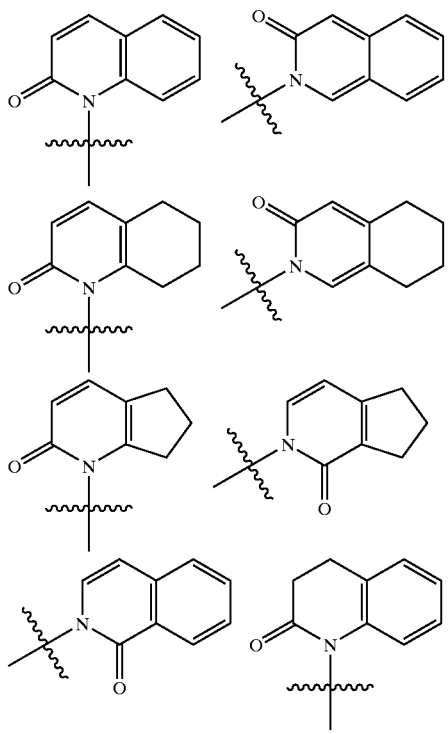

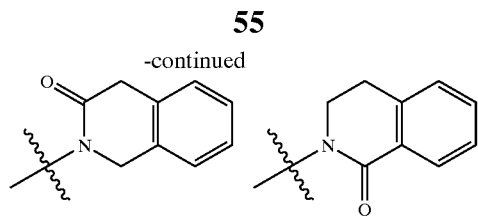

It is understood that such fused ring moieties may be further substituted by the remaining $R^{6a}$, $R^{6b}$, $R^{6c}$, $R^{6d}$ and/or $R^{6e}$ as defined hereinabove.

With respect to the farnesyl-protein transferase inhibitors of the formula II-m, the substituent illustrated by the structure:

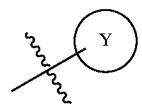

represents a 5, 6 or 7 membered carbocyclic ring wherein from 0 to 3 carbon atoms are replaced by a heteroatom selected from N, S and O, and wherein Y is attached to Q through a carbon atom and includes the following ring systems:

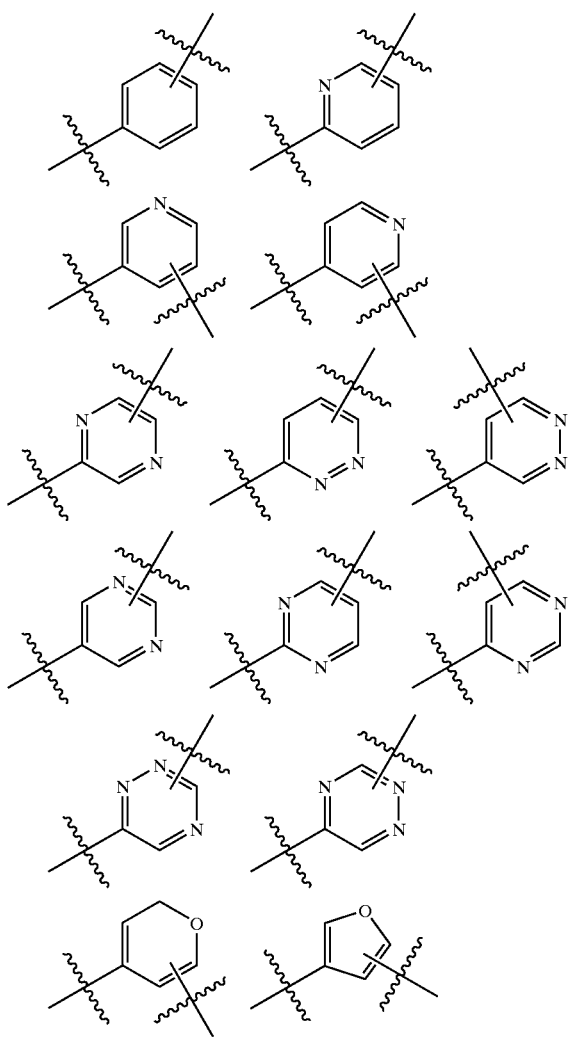

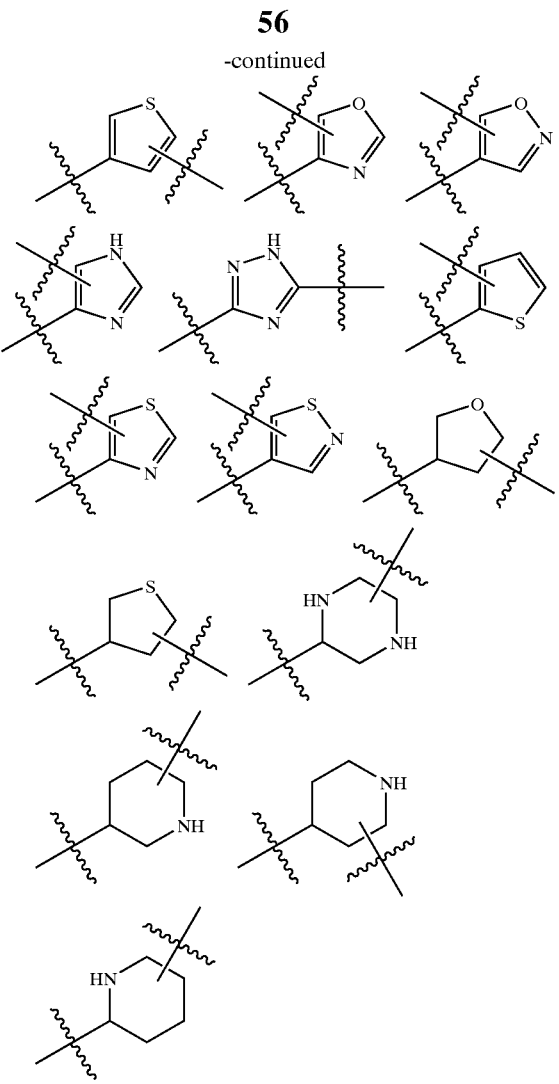

With respect to the farnesyl-protein transferase inhibitors of the formula II-n, the substituent illustrated by the structure:

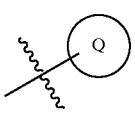

represents a 4, 5, 6 or 7 membered heterocyclic ring which comprises a nitrogen atom through which Q is attached to Y and 0–2 additional heteroatoms selected from N, S and O, and which also comprises a carbonyl, thiocarbonyl, —C(=NR$^{13}$)— or sulfonyl moiety adjacent to the nitrogen atom attached to Y and includes the following ring systems:

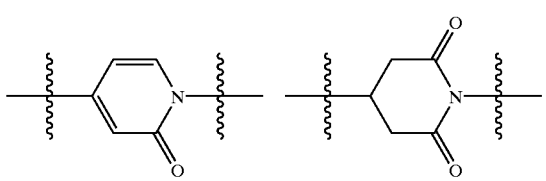

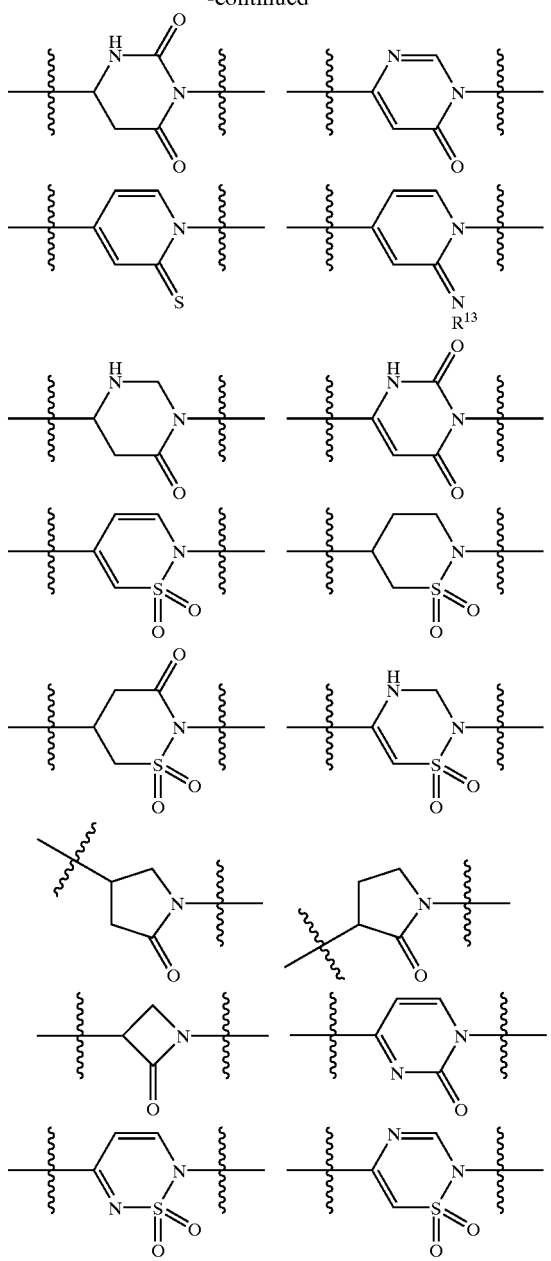

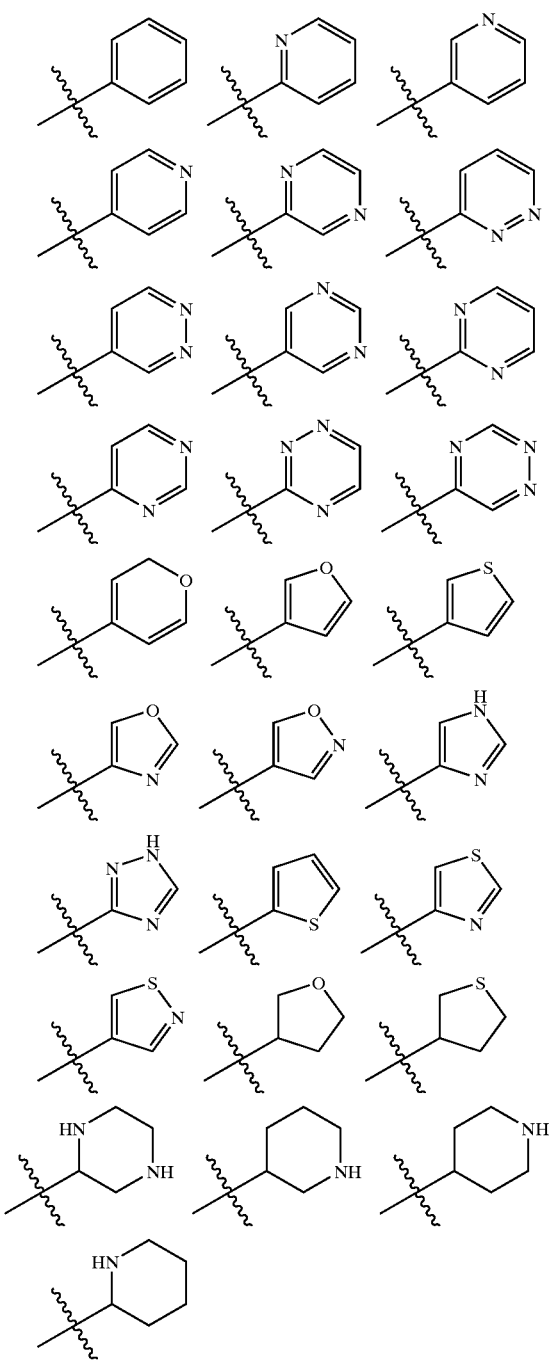

With respect to the farnesyl-protein transferase inhibitors of the formula II-n, the substituent illustrated by the structure:

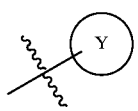

represents a 5-, 6- or 7-membered carbocyclic ring wherein from 0 to 3 carbon atoms are replaced by a heteroatom selected from N, S and O, and wherein Y is attached to Q through a carbon atom and includes the following ring systems:

With respect to the farnesyl-protein transferase inhibitors of the formula II-n, the moiety described as

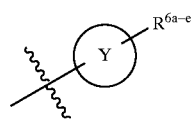

where any two of $R^{6a}$, $R^{6b}$, $R^{6c}$, $R^{6b}$ and $R^{6e}$ on adjacent carbon atoms are combined to form a diradical selected from —CH=CH—CH=CH, —CH=CH—CH—, —(CH$_2$)$_4$— and —(CH$_2$)$_4$—includes, but is not limited to, the following structures:

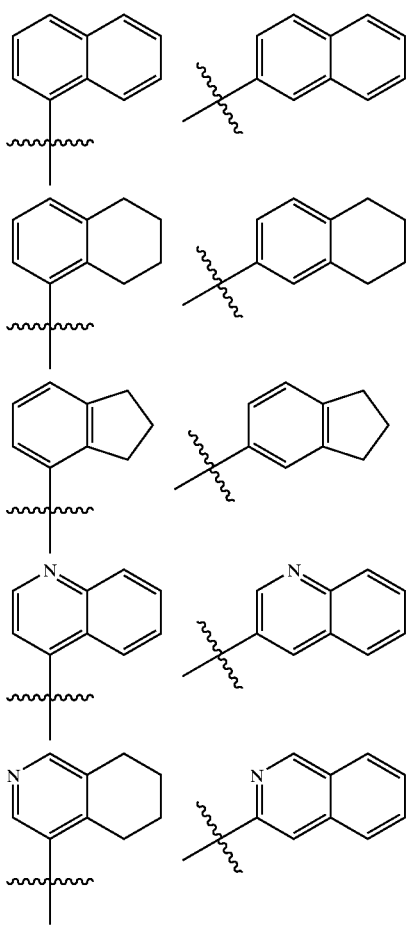

It is understood that such fused ring moieties may be further substituted by the remaining $R^{6a}$, $R^{6b}$, $R^{6c}$, $R^{6d}$ and/or $R^{6e}$ as defied hereinabove.

When $R^2$ and $R^3$ are combined to form —$(CH_2)_u$—, cyclic moieties are formed. Examples of such cyclic moieties include, but are not limited to:

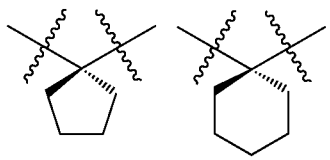

In addition, such cyclic moieties may optionally include a heteroatom(s). Examples of such heteroatom-containing cyclic moieties include, but are not limited to:

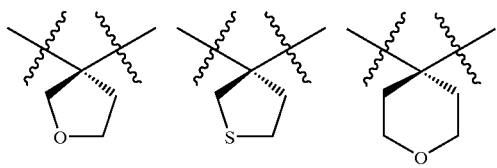

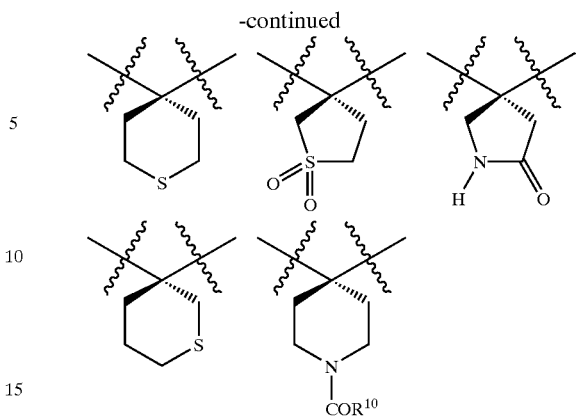

When $R^6$ and $R^7$, $R^7$ and $R^{7a}$, or are combined to form —$(CH_2)_u$—, cyclic moieties are formed. Examples of such cyclic moieties include, but are not limited to:

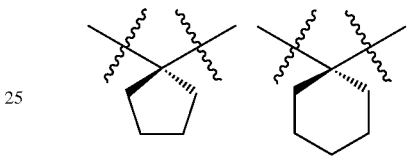

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenyl-acetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^{10}$, Z, n, etc.) at a particular location in a molecule be independent of its definitions elsewhere in that molecule. Thus, —$N(R^{10})2$ represents —NHH, —$NHCH_3$, —$NHC_2H_5$, etc. It is understood that substituents and substitution patterns on the compounds of the instant invention can be selected by one of ordinary skill in the art to provide compounds that are chemically stable and that can be readily synthesized by techniques known in the art as well as those methods set forth below.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The compounds of formula (II-h) can be synthesized from their constituent amino acids by conventional peptide synthesis techniques, and the additional methods described below. Standard methods of peptide synthesis are disclosed, for example, in the following works: Schroeder et al., "*The Peptides*", Vol. I, Academic Press 1965, or Bodanszky et al., "*Peptide Synthesis*", Interscience Publishers, 1966, or McOmie (ed.) "*Protective Groups in Organic Chemistry*", Plenum Press, 1973, or Barany et al., "The Peptides: Analysis, Synthesis, Biology" 2, Chapter 1, Academic Press, 1980, or Stewart et al., "Solid Phase Peptide Synthesis", Second Edition, Pierce Chemical Company, 1984. Also useful in exemplifying syntheses of specific unnatural amino acid residues are European Pat. Appl. No. 0 350 163 A2 (particularly page 51–52) and J. E. Baldwin et al. Tetrahedron, 50:5049–5066 (1994). With regards to the synthesis of instant compounds containing a (β-acetylamino)alanine residue at the C-terminus, use of the commercially available $N_\alpha$-Z-L-2,3-diaminopropionic acid (Fluka) as a starting material is preferred.

Abbreviations used in the description of the chemistry and in the Examples that follow are:

| | |
|---|---|
| $Ac_2O$ | Acetic anhydride; |
| Boc | t-Butoxycarbonyl; |
| DBU | 1,8-diazabicyclo[5.4.0]undec-7-ene; |
| DMAP | 4-Dimethylaminopyridine; |
| DME | 1,2-Dimethoxyethane; |
| DMF | Dimethylformamide; |
| EDC | 1-(3-dimethylaminopropyl)-3-ethyl-carbodiimide-hydrochloride; |
| HOBT | 1-Hydroxybenzotriazole hydrate; |
| $Et_3N$ | Triethylamine; |
| EtOAc | Ethyl acetate; |
| FAB | Fast atom bombardment; |
| HOOBT | 3-Hydroxy-1,2,2-benzotriazin-4(3H)-one; |
| HPLC | High-performance liquid chromatography; |
| MCPBA | m-Chloroperoxybenzoic acid; |
| MsCl | Methanesulfonyl chloride; |
| NaHMDS | Sodium bis(trimethylsilyl)amide; |
| Py | Pyridine; |
| TFA | Trifluoroacetic acid; |
| THF | Tetrahydrofuran. |

The compounds are useful in various pharmaceutically acceptable salt forms. The term "pharmaceutically acceptable salt" refers to those salt forms which would be apparent to the pharmaceutical chemist i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients in combination with pharmaceutically acceptable carriers.

Pharmaceutically acceptable salts include conventional non-toxic salts or quarternary ammonium salts formed, e.g., from non-toxic inorganic or organic acids. Non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, sulfanilic, 2-acetoxybenzoic, fumaric, toluenesulfonic, methanesulfonic, ethane disulfonic, oxalic, isethionic, trifluoroacetic and the like.

The pharmaceutically acceptable salts of the present invention can be synthesized by conventional chemical methods. Generally, the salts are prepared by reacting the free base or acid with stoichiometric amounts or with an excess of the desired salt-forming inorganic or organic acid or base, in a suitable solvent or solvent combination.

The farnesyl transferase inhibitors of formula (II-a) through (II-c) can be synthesized in accordance with Schemes 1–22, in addition to other standard manipulations such as ester hydrolysis, cleavage of protecting groups, etc., as may be known in the literature or exemplified in the experimental procedures. Substituents R, $R^a$ and $R^b$, as shown in the Schemes, represent the substituents $R^2$, $R^3$, $R^4$, and $R^5$; however their point of attachment to the ring is illustrative only and is not meant to be limiting.

These reactions may be employed in a linear sequence to provide the compounds of the invention or they may be used to synthesize fragments which are subsequently joined by the alkylation reactions described in the Schemes.

Synopsis of Schemes 1–22:

The requisite intermediates are in some cases commercially available, or can be prepared according to literature procedures, for the most part. In Scheme 1, for example, the synthesis of 2-alkyl substituted piperazines is outlined, and is essentially that described by J. S. Kiely and S. R. Priebe in Organic Preparations and Proceedings Int., 1990, 22, 761–768. Boc-protected amino acids I, available commercially or by procedures known to those skilled in the art, can be coupled to N-benzyl amino acid esters using a variety of dehydrating agents such as DCC (dicyclohexycarbodiimide) or EDC.HCl (1-ethyl-3-(3-dimethylaminopropyl) carbodiimide hydrochloride) in a solvent such as methylene chloride, chloroform, dichloroethane, or in dimethylformamide. The product II is then deprotected with acid, for example hydrogen chloride in chloroform or ethyl acetate, or trifluoroacetic acid in methylene chloride, and cyclized under weakly basic conditions to give the diketopiperazine III. Reduction of III with lithium aluminum hydride in refluxing ether gives the piperazine IV, which is protected as the Boc derivative V. The N-benzyl group can be cleaved under standard conditions of hydrogenation, e.g., 10% palladium on carbon at 60 psi hydrogen on a Parr apparatus for 24–48 h. The product VI can be treated with an acid chloride, or a carboxylic acid under standard dehydrating conditions to furnish the carboxamides VII; a final acid deprotection as previously described gives the intermediate VIII (Scheme 2). The intermediate VIII can be reductively alkylated with a variety of aldehydes, such as IX. The aldehydes can be prepared by standard procedures, such as that described by O. P. Goel, U. Krolls, M. Stier and S. Kesten in Organic Syntheses, 1988, 67, 69–75, from the appropriate amino acid (Scheme 3). The reductive alkylation can be accomplished at pH 5–7 with a variety of reducing agents, such as sodium triacetoxyborohydride or sodium cyanoborohydride in a solvent such as dichloroethane, methanol or dimethylformamide. The product X can be deprotected to give the final compounds XI with trifluoroacetic acid in methylene chloride. The final product XI is isolated in the salt form, for example, as a trifluoroacetate, hydrochloride or acetate salt, among others. The product diamine XI can further be selectively protected to obtain XII, which can subsequently be reductively alkylated with a second aldehyde to obtain XIII. Removal of the protecting group, and conversion to cyclized products such as the dihydroimidazole XV can be accomplished by literature procedures.

Alternatively, the protected piperazine intermediate VII can be reductively alkylated with other aldehydes such as 1-trityl-4-imidazolyl-carboxaldehyde or 1-trityl-4-imidazolylacetaldehyde, to give products such as XVI (Scheme 4). The trityl protecting group can be removed from XVI to give XVII, or alternatively, XVI can first be treated with an alkyl halide then subsequently deprotected to give the alkylated imidazole XVIII. Alternatively, the intermediate VIII can be acylated or sulfonylated by standard techniques. The imidazole acetic acid XIX can be converted to the acetate XXI by standard procedures, and XXI can be first reacted with an alkyl halide, then treated with refluxing methanol to provide the regiospecifically alkylated imidazole acetic acid ester XXII. Hydrolysis and reaction with piperazine VIII in the presence of condensing reagents such as 1-(3-dimethylaminopropyl)-3-ethylcarbodiimide (EDC) leads to acylated products such as XXIV.

If the piperazine VIII is reductively alkylated with an aldehyde which also has a protected hydroxyl group, such as XXV in Scheme 6, the protecting groups can be subsequently removed to unmask the hydroxyl group (Schemes 6, 7). The alcohol can be oxidized under standard conditions to e.g. an aldehyde, which can then be reacted with a variety of organometallic reagents such as Grignard reagents, to obtain secondary alcohols such as XXIX. In addition, the fully deprotected amino alcohol XXX can be reductively alkylated (under conditions described previously) with a variety of aldehydes to obtain secondary amines, such as XXXI (Scheme 7), or tertiary amines.

The Boc protected amino alcohol XXVII can also be utilized to synthesize 2-aziridinylmethylpiperazines such as XXXII (Scheme 8). Treating XXVII with 1,1'-sulfonyldiimidazole and sodium hydride in a solvent such as dimethylformamide led to the formation of aziridine XXXII. The aziridine reacted in the presence of a nucleophile, such as a thiol, in the presence of base to yield the ring-opened product XXXIII.

In addition, the piperazine VIII can be reacted with aldehydes derived from amino acids such as O-alkylated tyrosines, according to standard procedures, to obtain compounds such as XXXIX. When R' is an aryl group, XXXIX can first be hydrogenated to unmask the phenol, and the amine group deprotected with acid to produce XL. Alternatively, the amine protecting group in XXXIX can be removed, and O-alkylated phenolic amines such as XLI produced.

Depending on the identity of the amino acid I, various side chains can be incorporated into the piperazine. For example when I is the Boc-protected β-benzyl ester of aspartic acid, the intermediate diketopiperazine XLII where n=1 and R=benzyl is obtained, as shown in Scheme 10. Subsequent lithium aluminum hydride reduction reduces the ester to the alcohol XLIII, which can then be reacted with a variety of alkylating agents such as an alkyl iodide, under basic conditions, for example, sodium hydride in dimethylformamide or tetrahydrofuran. The resulting ether XLIV can then be carried on to final products as described in Schemes 3–9.

N-Aryl piperazines can be prepared as described in Scheme 11. An aryl amine XLV is reacted with bis-chloroethyl amine hydrochloride (XLVI) in refluxing n-butanol to furnish compounds XLVII. The resulting piperazines XLVII can then be carried on to final products as described in Schemes 3–9.

Piperazin-5-ones can be prepared as shown in Scheme 12. Reductive amination of Boc-protected amino aldehydes XLIX (prepared from I as described previously) gives rise to compound L. This is then reacted with bromoacetyl bromide under Schotten-Baumann conditions; ring closure is effected with a base such as sodium hydride in a polar aprotic solvent such as dimethylformamide to give LI. The carbamate protecting group is removed under acidic conditions such as trifluoroacetic acid in methylene chloride, or hydrogen chloride gas in methanol or ethyl acetate, and the resulting piperazine can then be carried on to final products as described in Schemes 3–9.

The isomeric piperazin-3-ones can be prepared as described in Scheme 13. The imine formed from arylcarboxamides LII and 2-aminoglycinal diethyl acetal (LIII) can be reduced under a variety of conditions, including sodium triacetoxyborohydride in dichloroethane, to give the amine LIV. Amino acids I can be coupled to amines LIV under standard conditions, and the resulting amide LV when treated with aqueous acid in tetrahydrofuran can cyclize to the unsaturated LVI. Catalytic hydrogenation under standard conditions gives the requisite intermediate LVII, which is elaborated to final products as described in Schemes 3–9.

Access to alternatively substituted piperazines is described in Scheme 14. Following deprotection with trifluoroacetic acid, the N-benzyl piperazine V can be acylated with an aryl carboxylic acid. The resulting N-benzyl aryl carboxamide LIX can be hydrogenated in the presence of a catalyst to give the piperazine carboxamide LX which can then be carried on to final products as described in Schemes 3–9.

Reaction Scheme 15 provides an illustrative example the synthesis of compounds of the instant invention wherein the substituents $R^2$ and $R^3$ are combined to form —$(CH_2)_a$—. For example, 1-aminocyclohexane-1-carboxylic acid LXI can be converted to the spiropiperazine LXVI essentially according to the procedures outlined in Schemes 1 and 2. The piperazine intermediate LXIX can be deprotected as before, and carried on to final products as described in Schemes 3–9. It is understood that reagents utilized to provide the substituent Y which is 2-(naphthyl) and the imidazolylalkyl substituent may be readily replaced by other reagents well known in the art and readily available to provide other N-substituents on the piperazine.

The aldehyde XLIX from Scheme 12 can also be reductively alkylated with an aniline as shown in Scheme 16. The product LXXI can be converted to a piperazinone by acylation with chloroacetyl chloride to give LXXII, followed by base-induced cyclization to LXXIII. Deprotection, followed by reductive alkylation with a protected-imidazole carboxaldehyde leads to LXXV, which can be alkylation with an arylmethylhalide to give the imidazolium salt LXXVI. Final removal of protecting groups by either solvolysis with a lower alkyl alcohol, such as methanol, or treatment with triethylsilane in methylene chloride in the presence of trifluoroacetic acid gives the final product LXXVII.

Scheme 17 illustrates the use of an optionally substituted homoserine lactone LXXIX to prepare a Boc-protected piperazinone LXXXII. Intermediate LXXXII may be deprotected and reductively alkylated or acylated as illustrated in the previous Schemes. Alternatively, the hydroxyl moiety of intermediate LXXXII may be mesylated and displaced by a suitable nucleophile, such as the sodium salt of ethane thiol, to provide an intermediate LXXXIII. Intermediate LXXXII may also be oxidized to provide the carboxylic acid on intermediate LXXXIV, which can be utilized form an ester or amide moiety.

Amino acids of the general formula LXXXVI which have a sidechain not found in natural amino acids may be prepared by the reactions illustrated in Scheme 18 starting with the readily prepared imine LXXXV.

Schemes 19–22 illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.

SCHEME 1
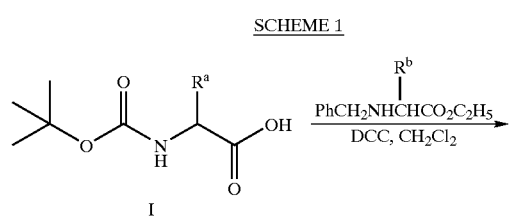
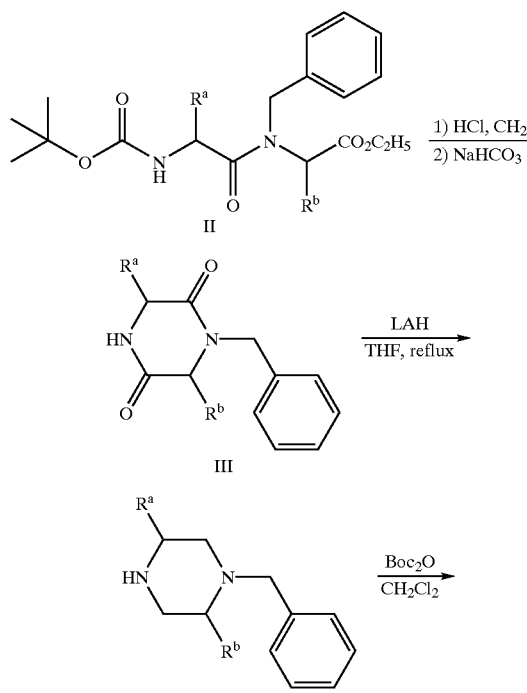
SCHEME 2
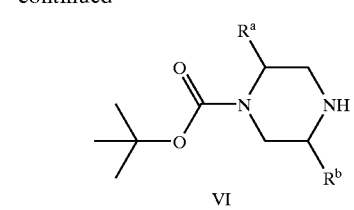
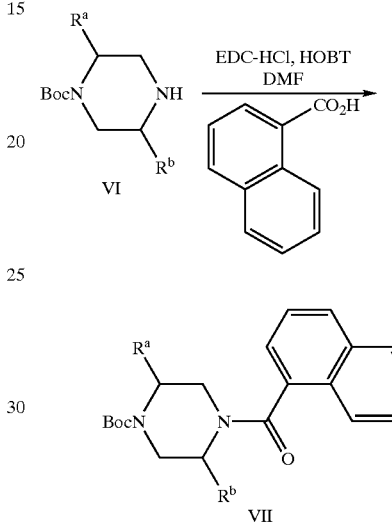
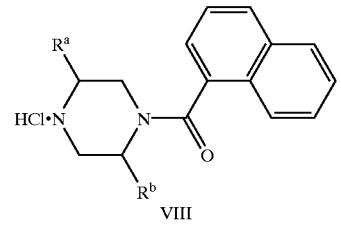
SCHEME 3
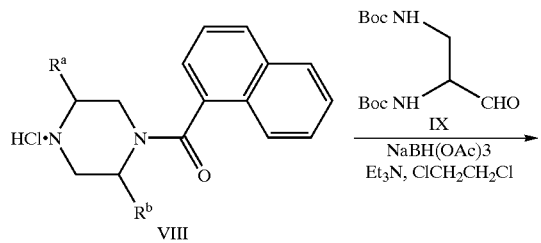

-continued
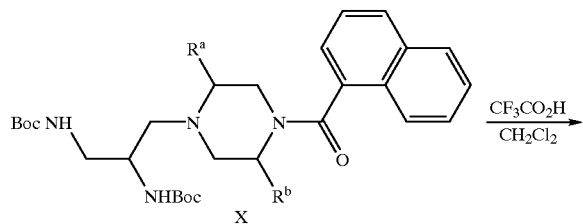
X
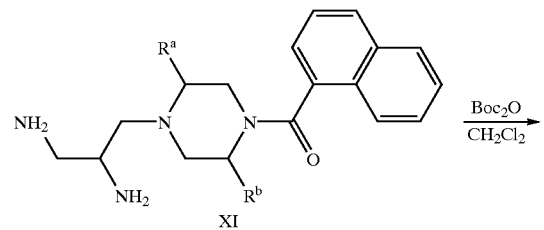
XI
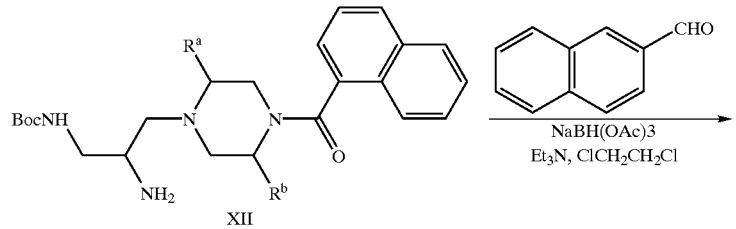
XII
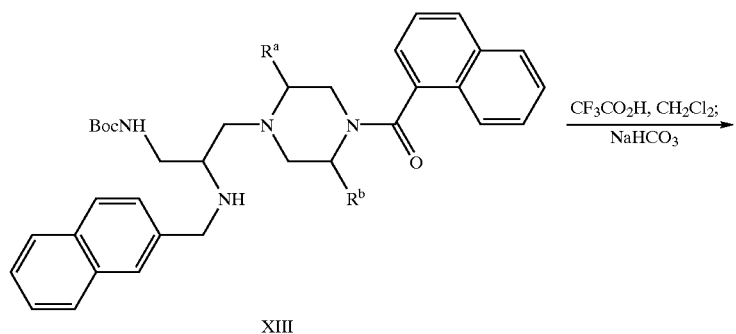
XIII
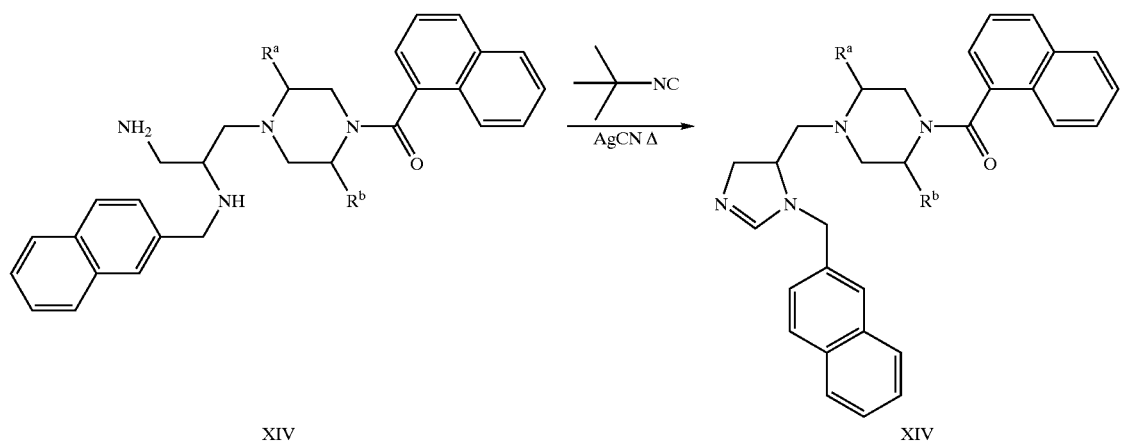
XIV                                   XIV

SCHEME 4

SCHEME 5

SCHEME 6

-continued
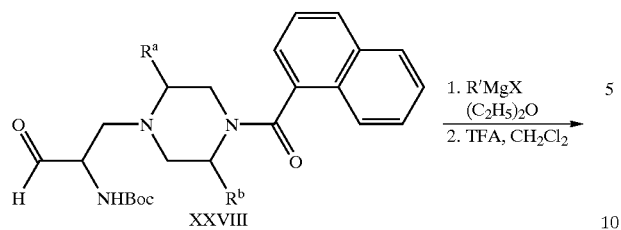
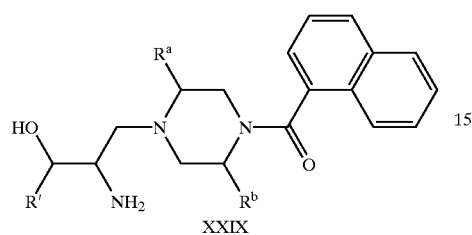
SCHEME 7
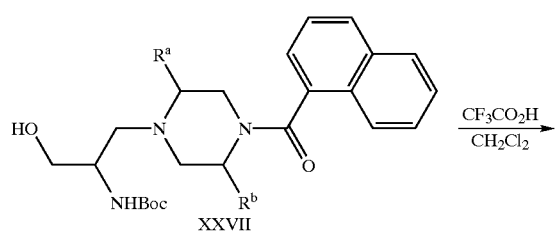
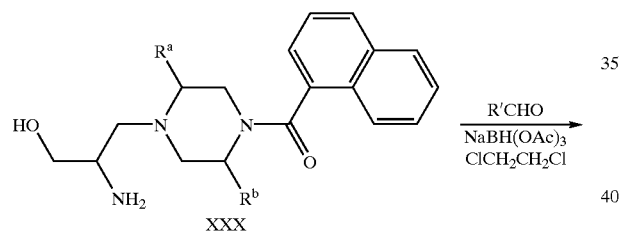
-continued
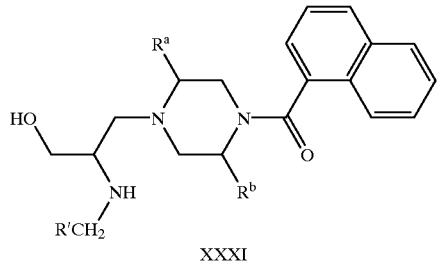
SCHEME 8
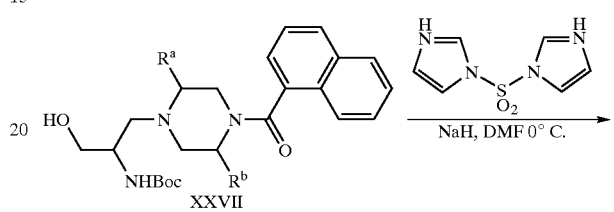
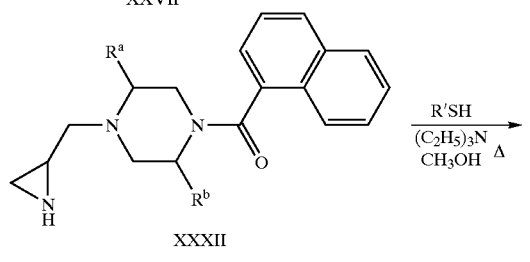
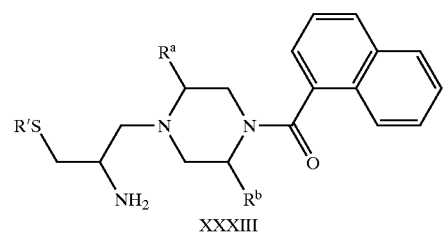
SCHEME 9
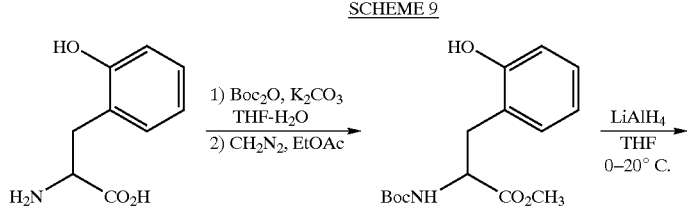
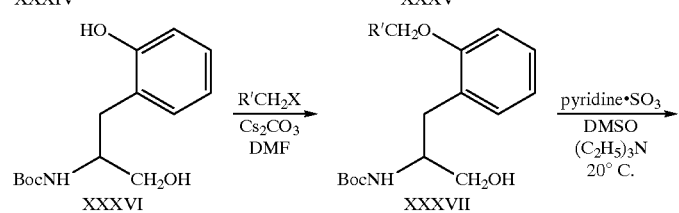

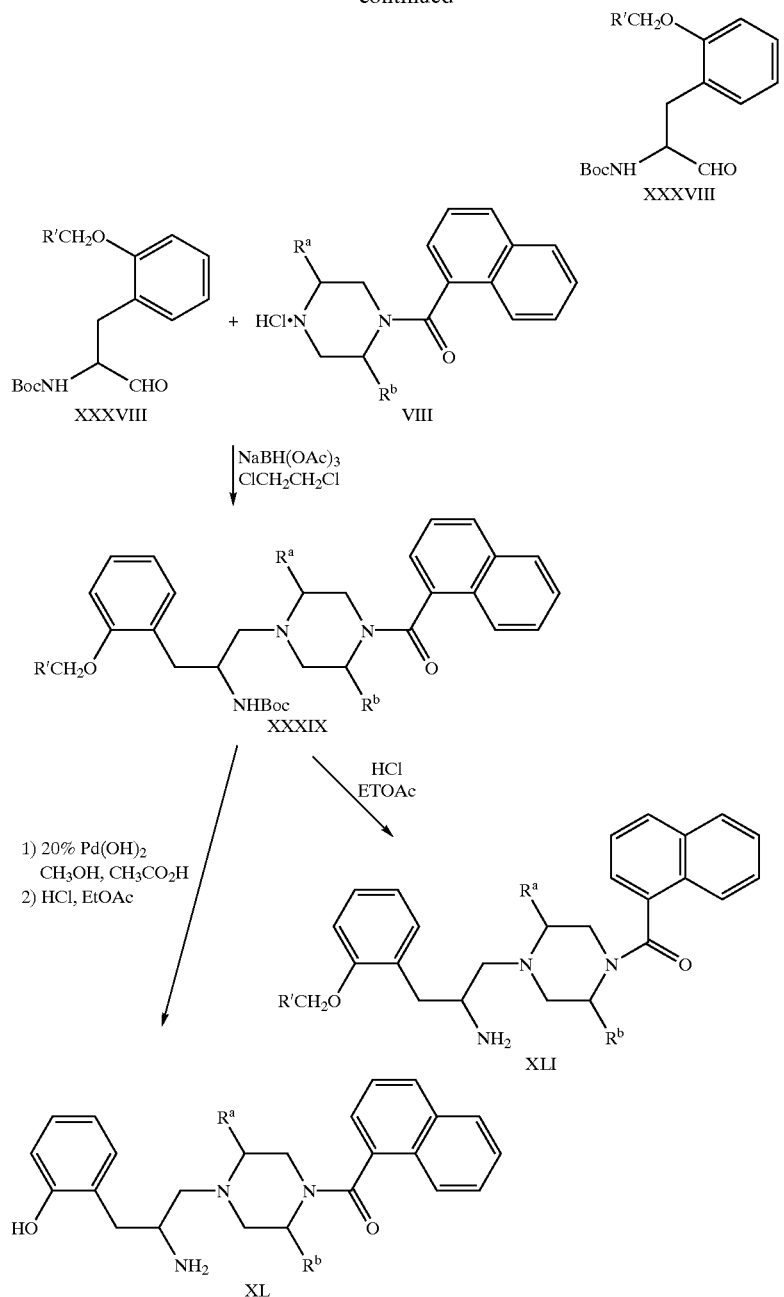
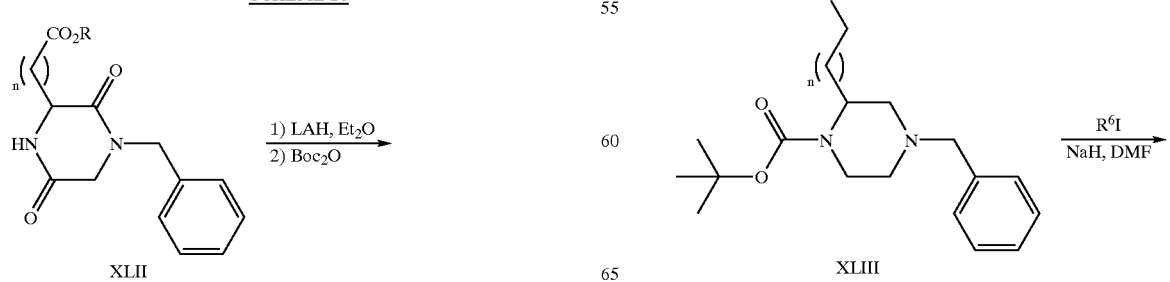
SCHEME 10

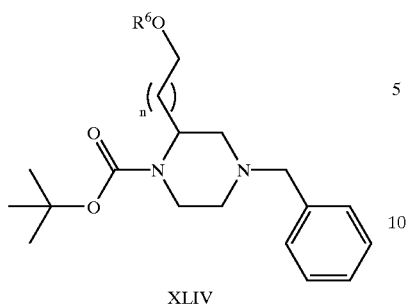
XLIV
SCHEME 11
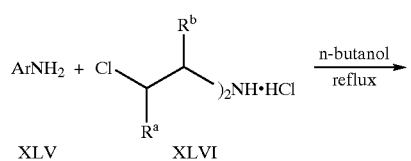
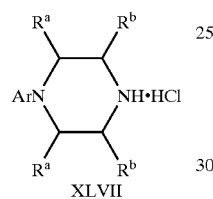
XLVII
SCHEME 12
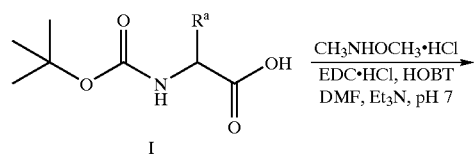
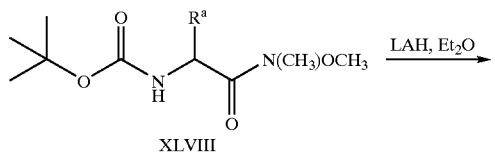
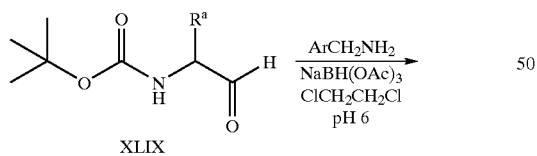
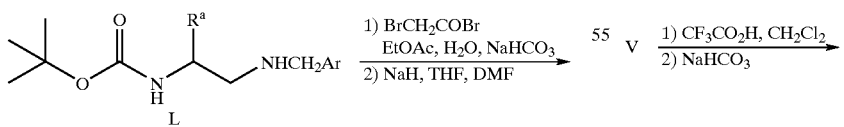
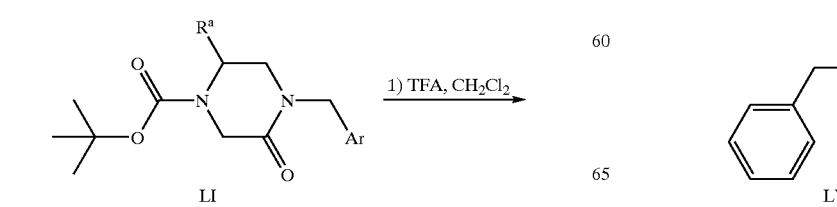
LI
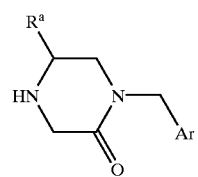
SCHEME 13
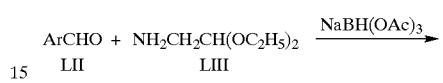
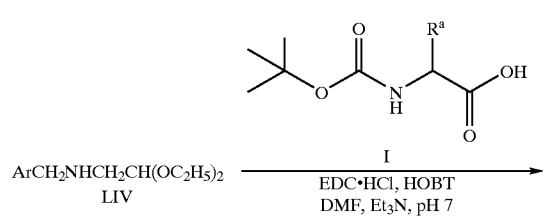
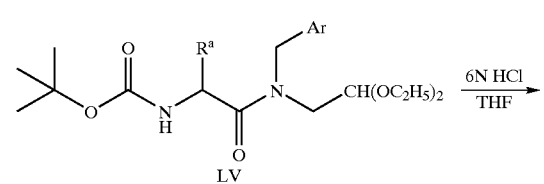
LV
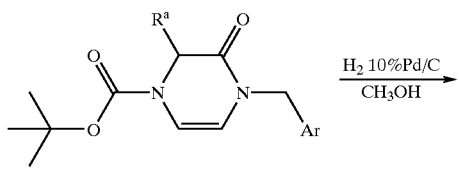
LVI
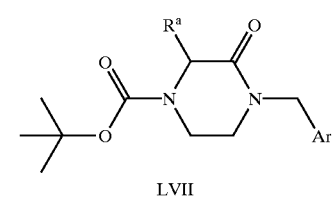
LVII
SCHEME 14
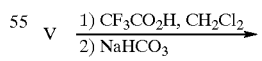
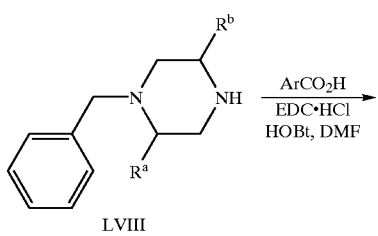
LVIII

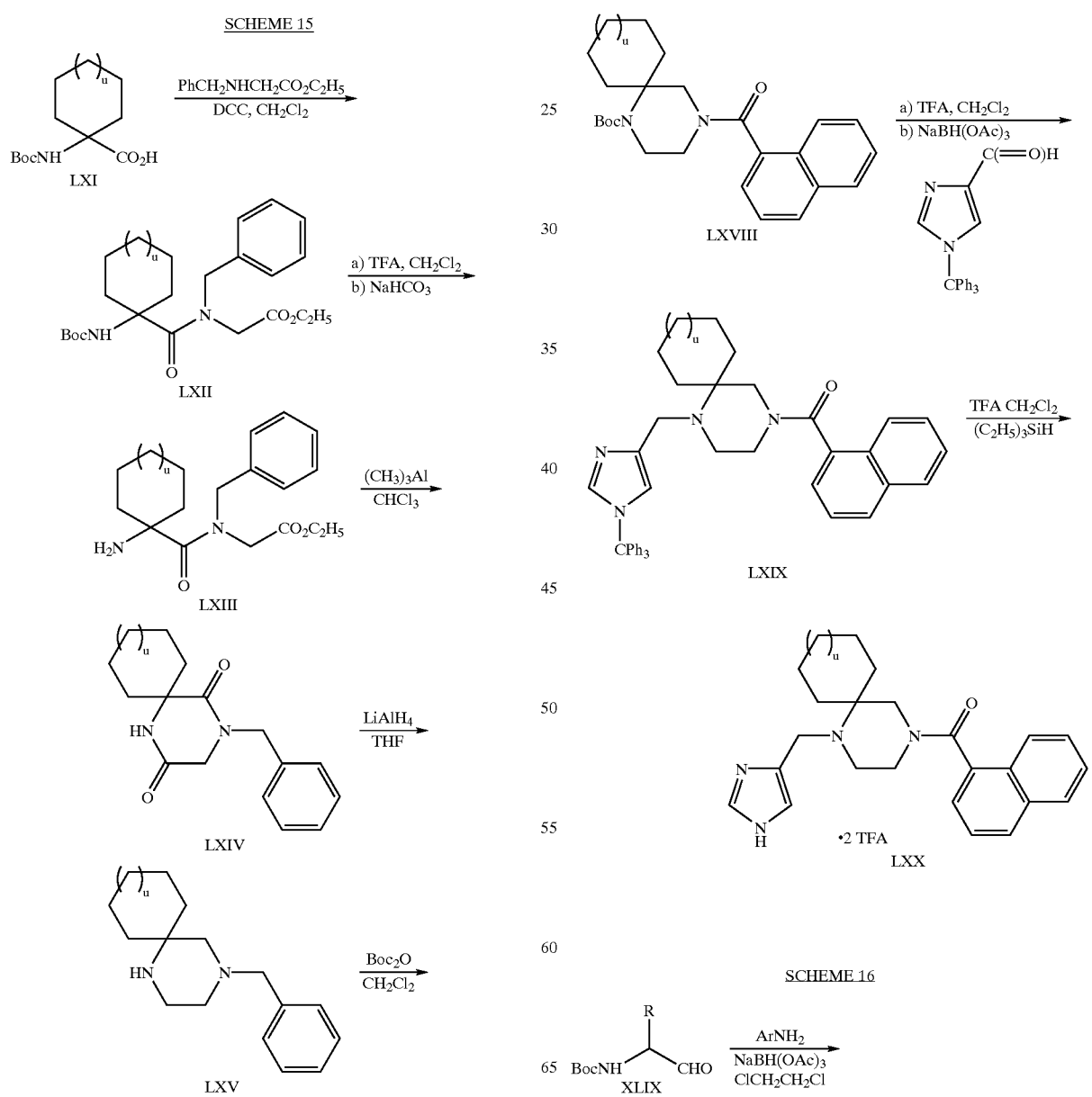

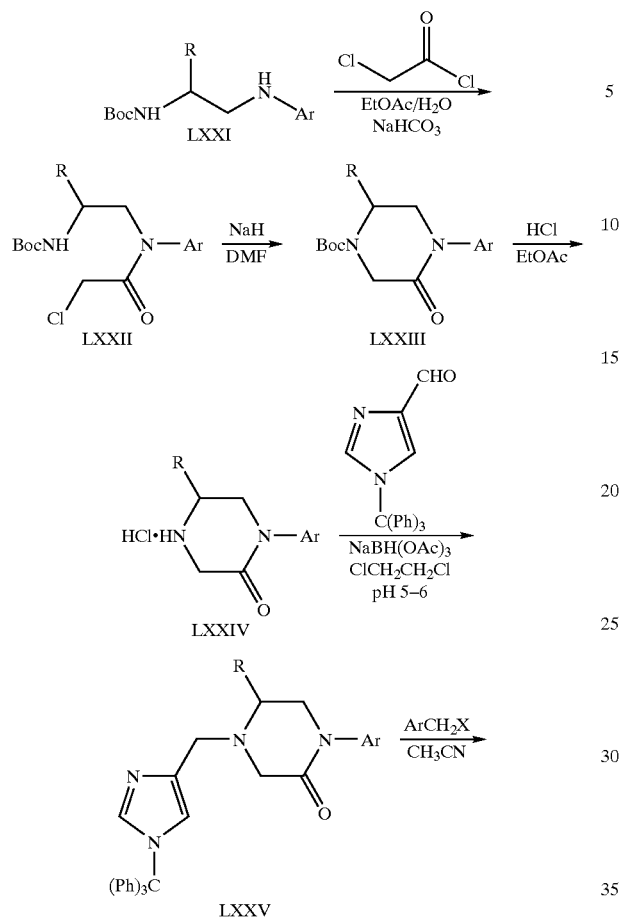
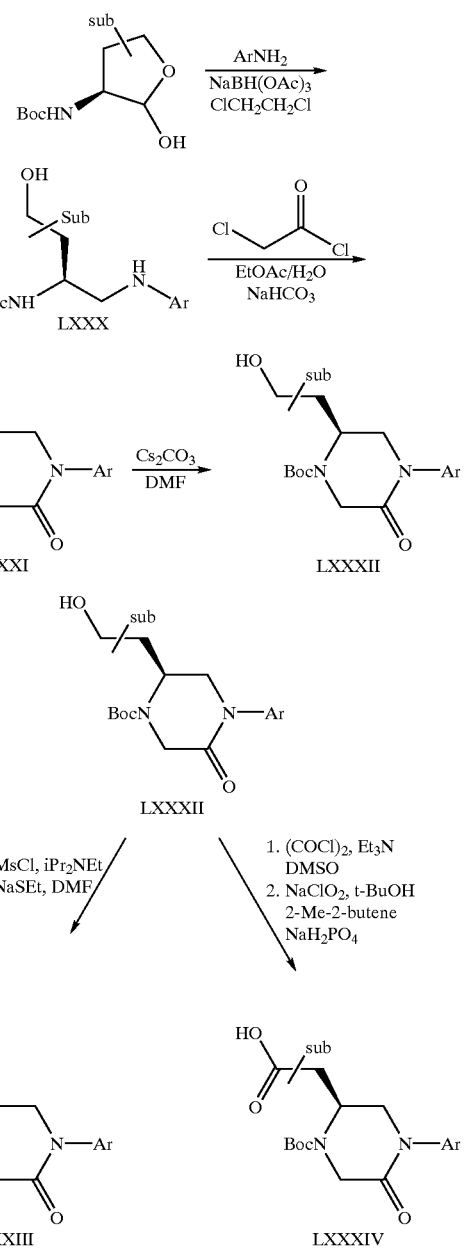
SCHEME 17
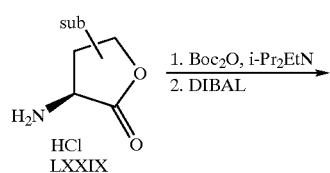
SCHEME 18
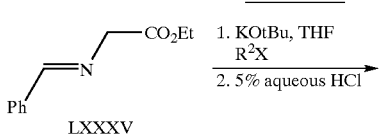
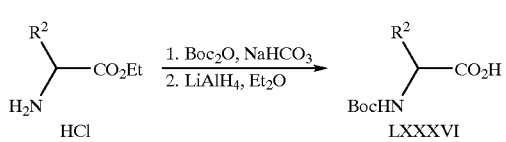

REACTION SCHEME 19
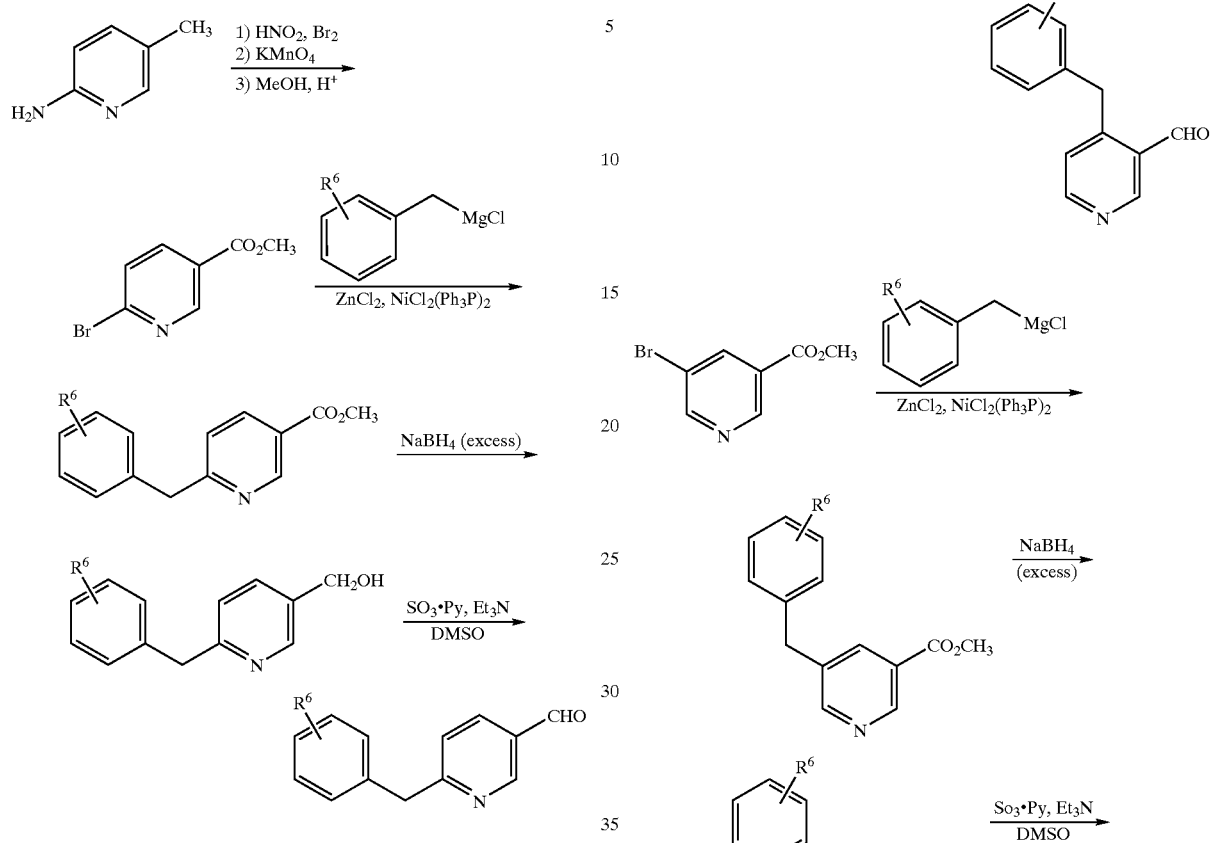
REACTION SCHEME 20
REACTION SCHEME 21
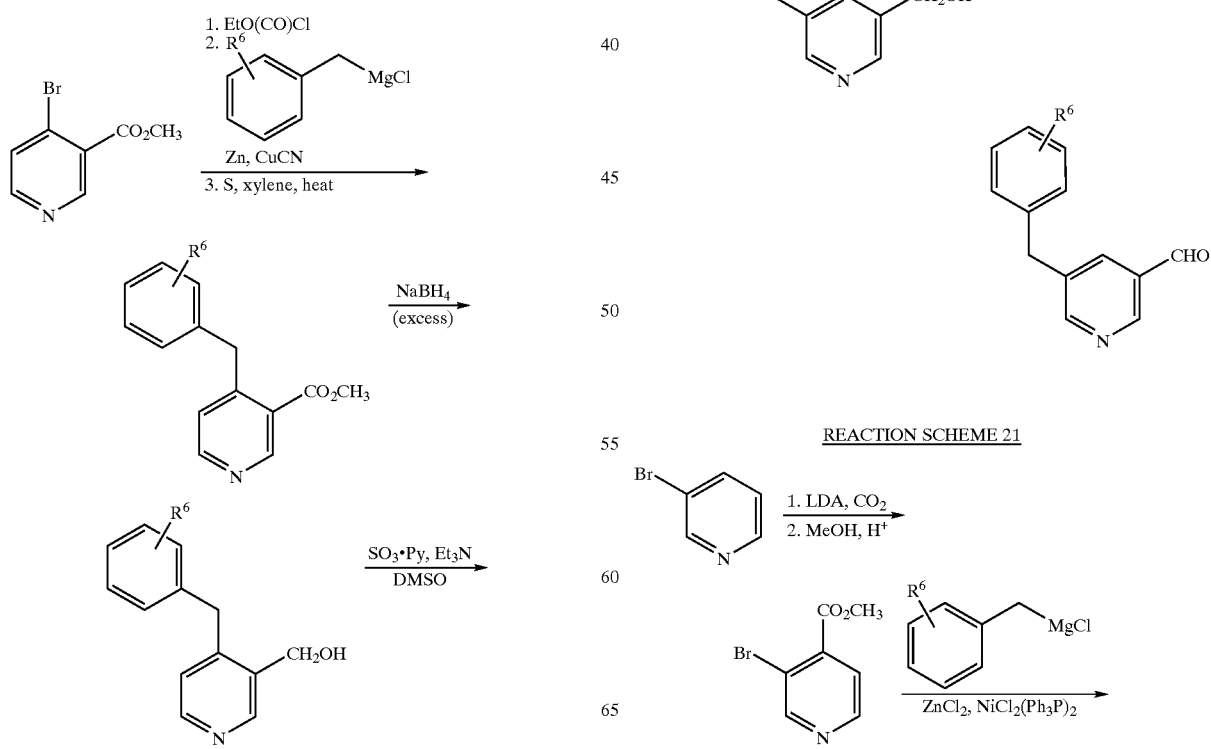

-continued

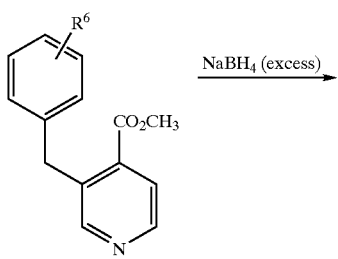

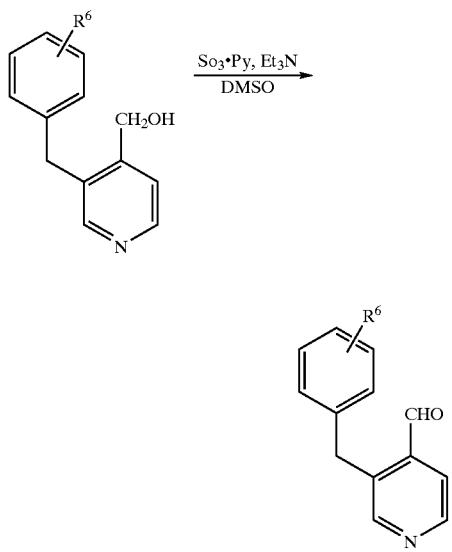

REACTION SCHEME 22

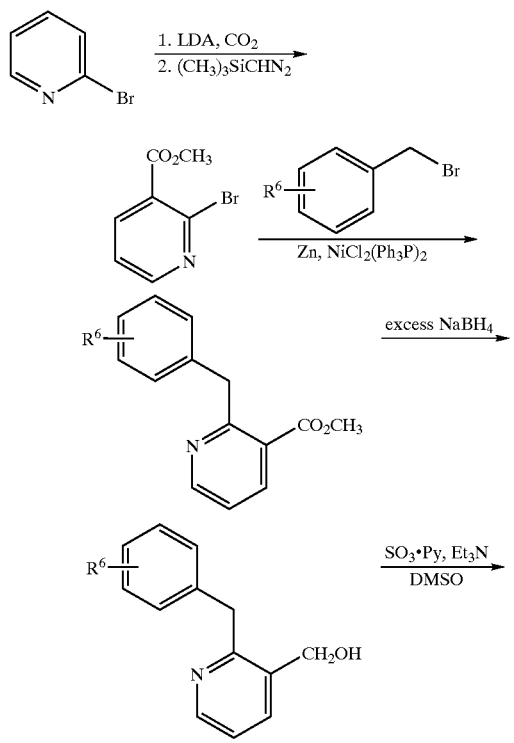

-continued

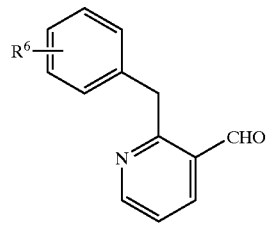

The farnesyl transferase inhibitors of formula (II-d) can be synthesized in accordance with Schemes 23–36, in addition to other standard manipulations such as ester hydrolysis, cleavage of protecting groups, etc., as may be known in the literature or exemplified in the experimental procedures. Substituents $R^2$, $R^6$ and $R^8$, as shown in the Schemes, represent the substituents $R^2$, $R^3$, $R^4$, $R^5$, $R^{6a}$, $R^{6b}$, $R^{6c}$, $R^{6d}$ and $R^8$; although only one such $R^2$, $R^6$ or $R^8$ is present in the intermediates and products of the schemes, it is understood that the reactions shown are also applicable when such aryl or heteroaryl moieties contain multiple substituents. The compounds referred to in the Synopsis of Schemes 23–36 by Roman numerals are numbered starting sequentially with I and ending with XXV.

These reactions may be employed in a linear sequence to provide the compounds of the invention or they may be used to synthesize fragments which are subsequently joined by the alkylation reactions described in the Schemes. Aryl-aryl coupling is generally described in "Comprehensive Organic Functional Group Transformations," Katritsky et al. eds., pp 472–473, Pergamon Press (1995).

Synopsis of Schemes 23–36:

The requisite intermediates are in some cases commercially available, or can be prepared according to literature procedures, for the most part. Schemes 23–35 illustrate synthesis of the compounds of the formula II-d which incorporate a preferred benzylimidazolyl sidechain. In Scheme 23, for example, a biaryl intermediate that is not commercially available may be synthesized by methods known in the art. Thus, a suitably substituted phenyl boronic acid I may be reacted under Suzuki coupling conditions (*Pure Appl. Chem.*, 63:419 (1991)) with a suitably substituted halogenated benzoic acid, such as 4-bromobenzoic acid, to provide the biaryl carboxylic acid II. The acid may be reduced and the triflate of the intermediate alcohol III may be formed in situ and coupled to a suitably substituted benzylimidazolyl IV to provide, after deprotection, the instant compound V.

Schemes 24–27 illustrate other methods of synthesizing the key alcohol intermediates, which can then be processed as described in Scheme 23. Thus, Scheme 24 illustrates the analogous series of biaryl alcohol forming reactions starting with the halogenated biarylaldehyde.

Scheme 25 illustrates the reaction wherein the "terminal" phenyl moiety is employed in the Suzuki coupling as the halogenated reactant. Such a coupling reaction is also compatible when one of the reactants incorporates a suitably protected hydroxyl functionality as illustrated in Scheme 26.

Negishi chemistry (*Org. Synth.*, 66:67 (1988)) may also be employed to form the biaryl component of the instant compounds, as shown in Scheme 27. Thus, a suitably substituted zinc bromide adduct may be coupled to a suitably substituted aryl halide in the presence of nickel (II) to provide the biaryl VII. The aryl halide and the zinc bromide adduct may be selected based on the availability of the starting reagents.

Scheme 28 illustrates the preparation of a suitably substituted biphenylmethyl bromide which could also be utilized in the reaction with the protected imidazole as described in Scheme 1.

As illustrated in Scheme 29, the sequence of coupling reactions may be modified such that the biphenyl bond is formed last. Thus, a suitably substituted imidazole may first be alkylated with a suitably substituted benzyl halide to provide intermediate VIII. Intermediate VIII can then undergo Suzuki type coupling to a suitably substituted phenyl boronic acid.

Scheme 30 illustrates synthesis of an instant compound wherein a non-hydrogen $R^{9b}$ is incorporated in the instant compound. Thus, a readily available 4-substituted imidazole IX may be selectively iodinated to provide the 5-iodoimidazole X. That imidazole may then be protected and coupled to a suitably substituted benzyl moiety to provide intermediate XI. Intermediate XI can then undergo the alkylation reactions that were described hereinabove.

Scheme 31 illustrates synthesis of instant compounds that incorporate a preferred imidazolyl moiety connected to the biaryl via an alkyl amino, sulfonamide or amide linker. Thus, the 4-aminoalkylimidazole XII, wherein the primary amine is protected as the phthalimide, is selectively alkylated- then deprotected to provide the amine XIII. The amine XIII may then react under conditions well known in the art with various activated biaryl moieties to provide the instant compounds shown.

Compounds of the instant invention wherein the $A^1(CR^{1a}{}_2)_nA^2(CR^{1a}{}_2)_n$ linker is oxygen may be synthesized by methods known in the art, for example as shown in Scheme 32. The suitably substituted phenol XIV may be reacted with methyl N-(cyano)methanimidate to provide the 4-phenoxyimidazole XV. After selective protection of one of the imidazolyl nitrogens, the intermediate XVI can undergo alkylation reactions as described for the benzylimidazoles hereinabove.

Scheme 33 illustrates an analogous series of reactions wherein the $(CR^{1b}{}_2)_pX(CR^{1b}2)_p$ linker of the instant compounds is oxygen. Thus, a suitably substituted haloaryl alcohol, such as, is reacted with methyl N-(cyano) methanimidate to provide intermediate XVI. Intermediate XVI is then protected and, if desired to form a compound of a preferred embodiment, alkylated with a suitably protected benzyl. The intermediate XVII can then be coupled to a second aryl moiety by Suzuki chemistry to provide the instant compound.

Compounds of the instant invention wherein the $A^1(CR^{1a}{}_2)_nA^2(CR^{1a}{}_2)_n$ linker is a substituted methylene may be synthesized by the methods shown in Scheme 34. Thus, the N-protected imidazolyl iodide XVIII is reacted, under Grignard conditions with a suitably protected benzaldehyde to provide the alcohol XIX. Acylation, followed by the alkylation procedure illustrated in the Schemes above (in particular, Scheme 23) provides the instant compound XX. If other $R^1$ substituents are desired, the acetyl moiety can be manipulated as illustrated in the Scheme.

Grignard chemistry may also be employed to form a substituted alkyl linker between the biaryl and the preferred W (imidazolyl) as shown in Scheme 35. Similar substituent manipulation as shown in Scheme 34 may be performed on the fully functionalized compound which incorporates an $R^{1b}$ hydroxyl moiety.

Scheme 36 illustrates reactions wherein the moiety

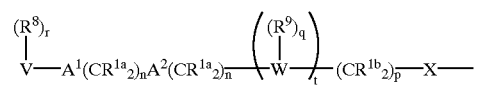

incorporated in the compounds of the instant invention is represented by other than a substituted imidazole-containing group.

Thus, the intermediates whose synthesis are illustrated in Schemes hereinabove and other biheteroaryl intermediates obtained commercially or readily synthesized, can be coupled with a variety of aldehydes. The aldehydes can be prepared by standard procedures, such as that described by O. P. Goel, U. Krolls, M. Stier and S. Kesten in *Organic Syntheses*, 1988, 67, 69–75, from the appropriate amino acid (Scheme 14). Grignard chemistry may be utilized, as shown in Scheme 36, to incorporate the biaryl moiety. Thus, a suitably substituted biaryl Grignard reagent is reacted with an aldehyde to provide the C-alkylated instant compound XXI. Compound XXI can be deoxygenated by methods known in the art, such as a catalytic hydrogention, then deprotected with trifluoroacetic acid in methylene chloride to give the final compound XXII. The final product XXII may be isolated in the salt form, for example, as a trifluoroacetate, hydrochloride or acetate salt, among others. The product diamine XXII can further be selectively protected to obtain XXIII, which can subsequently be reductively alkylated with a second aldehyde to obtain XXIV. Removal of the protecting group, and conversion to cyclized products such as the dihydroimidazole XXV can be accomplished by literature procedures.

Incorporation of other moieties via the appropriate aldehyde starting material may be performed as illustrated in Scheme 36 and the intermediates manipulated as illustrated above in Schemes 4–9.

SCHEME 23

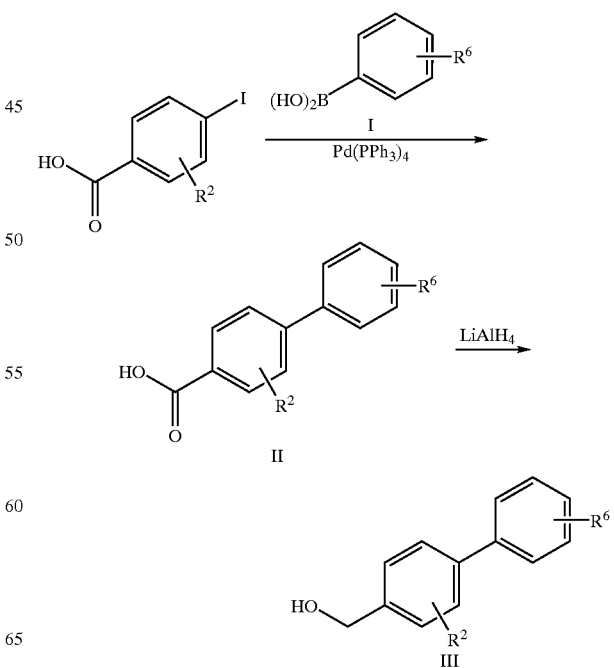

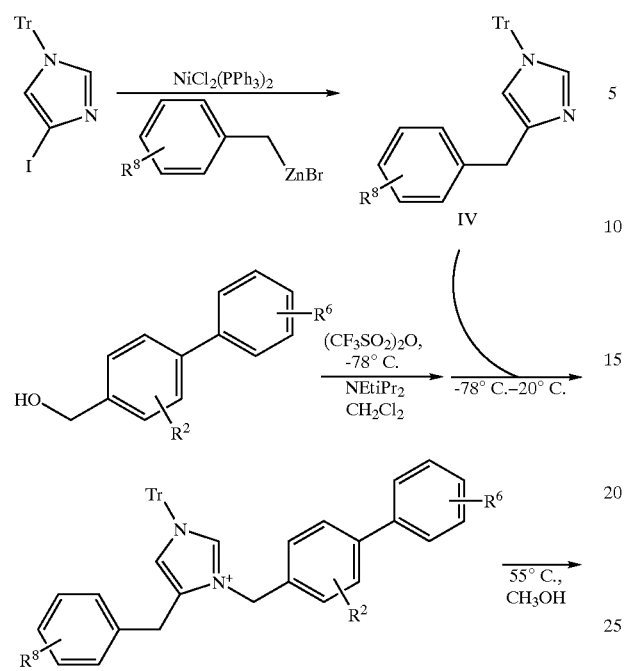
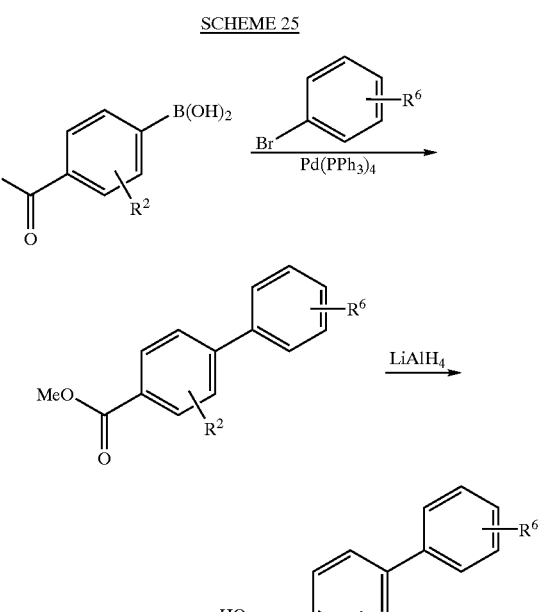
SCHEME 25
SCHEME 24
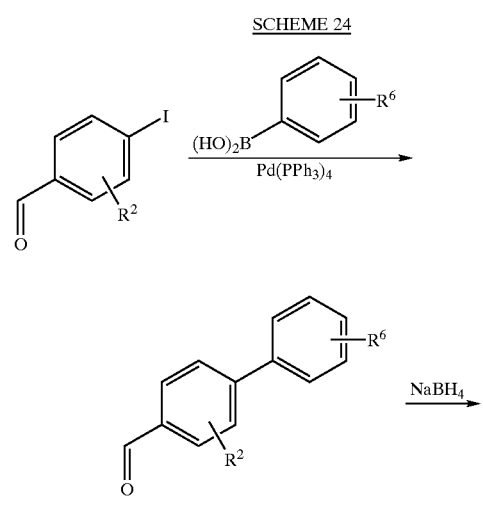
SCHEME 26
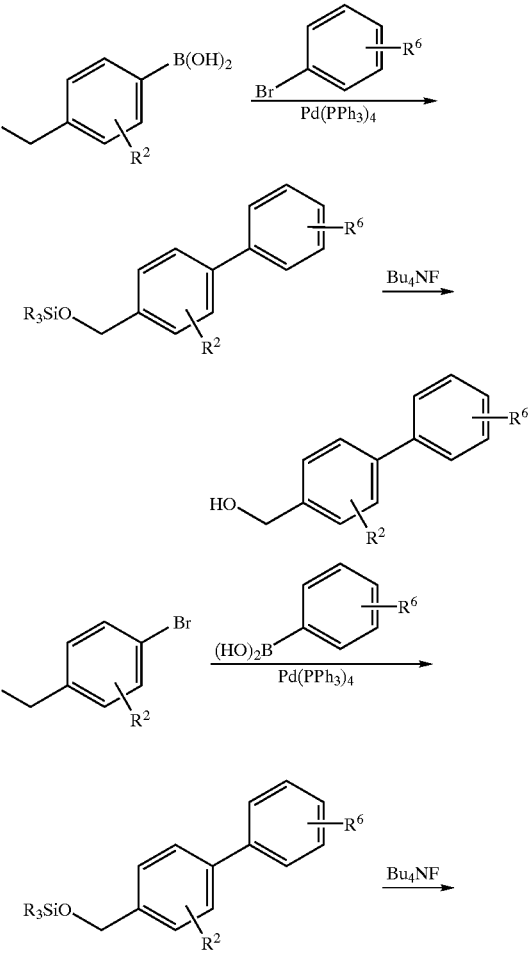

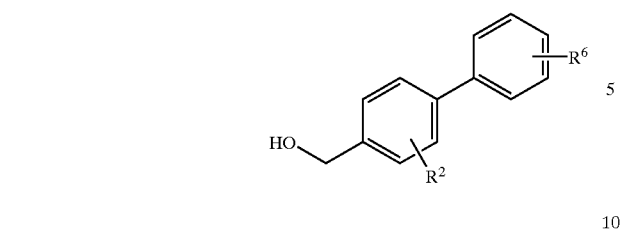
SCHEME 27
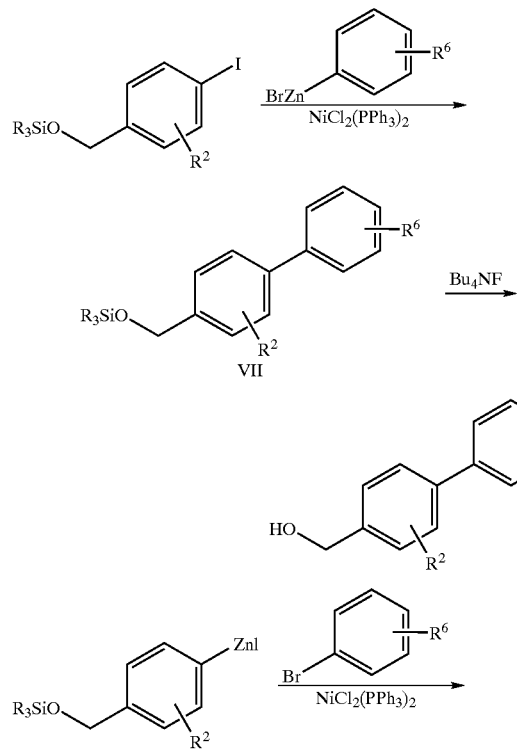
SCHEME 28
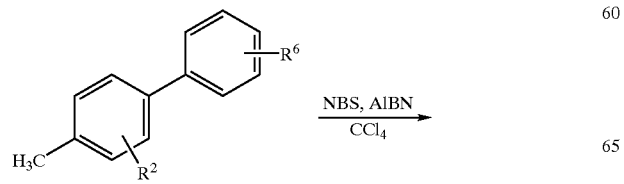
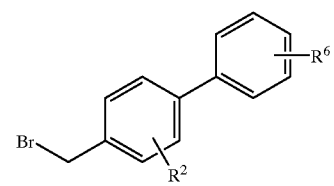
SCHEME 29
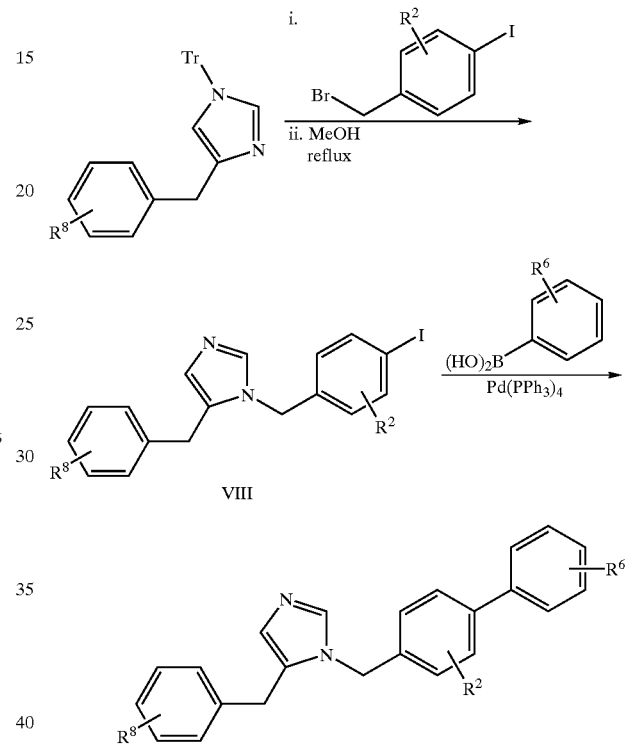
SCHEME 30
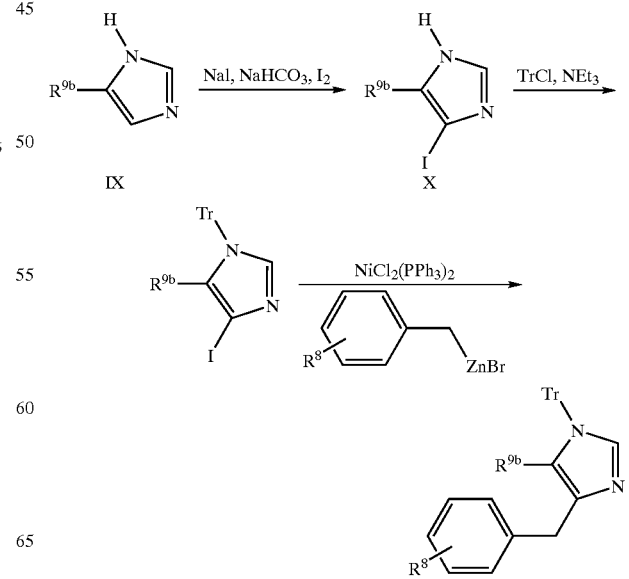

91
-continued
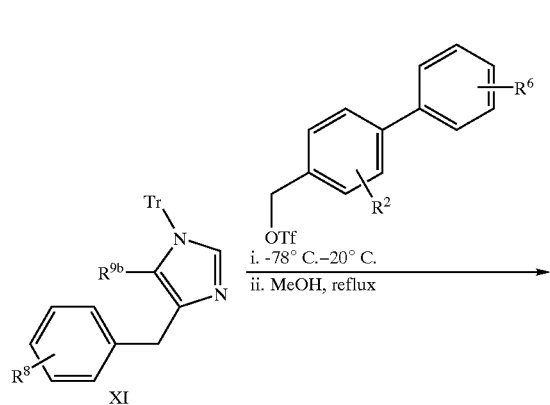
XI
SCHEME 31
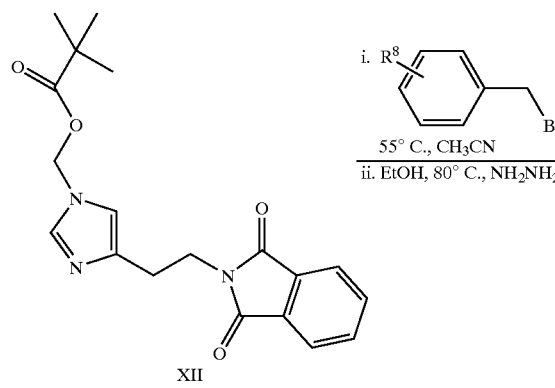
XII
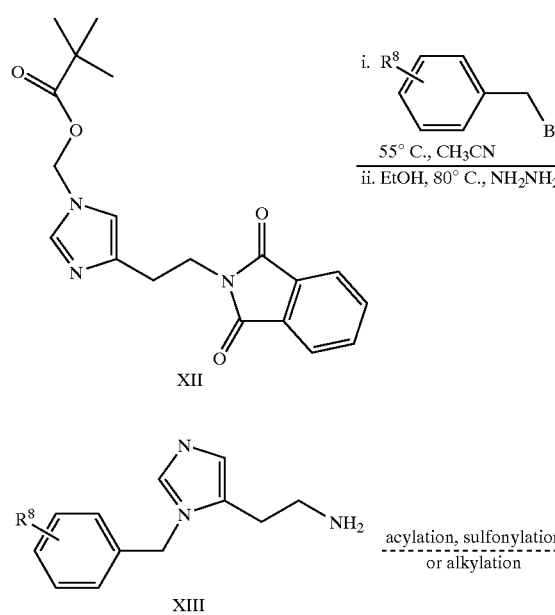
XIII
92
-continued
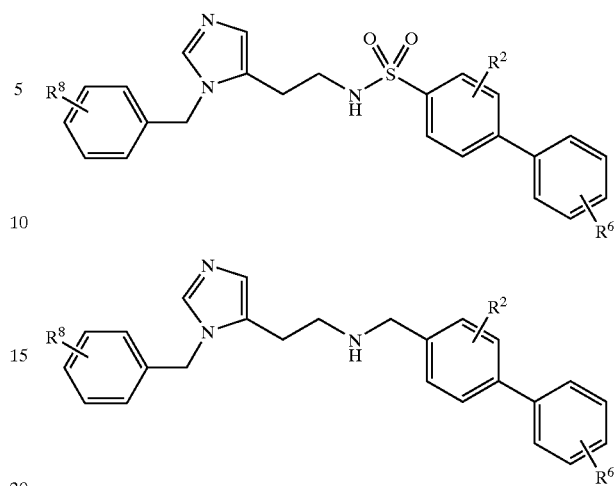
SCHEME 32
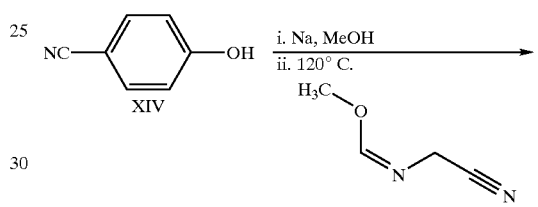
XIV
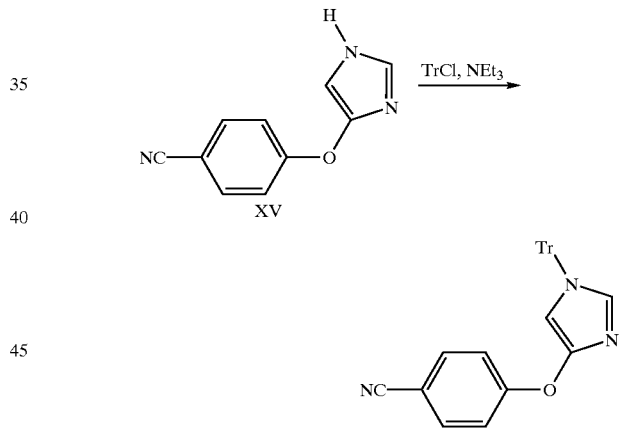
XV
XVI
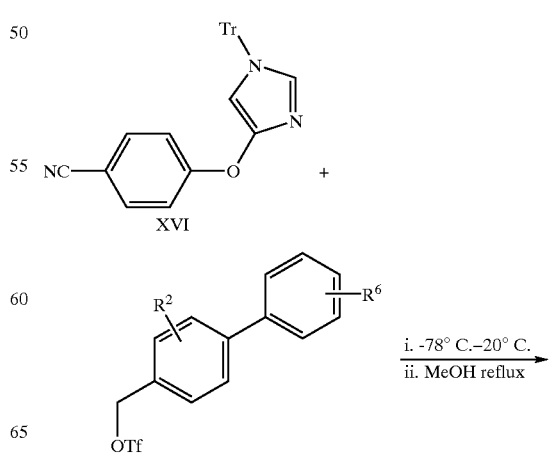
XVI
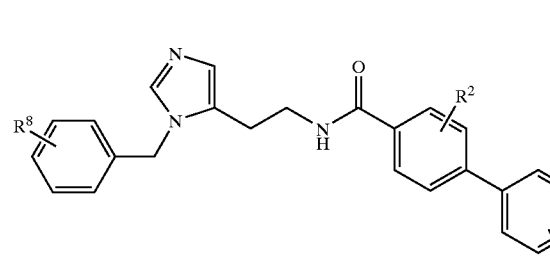

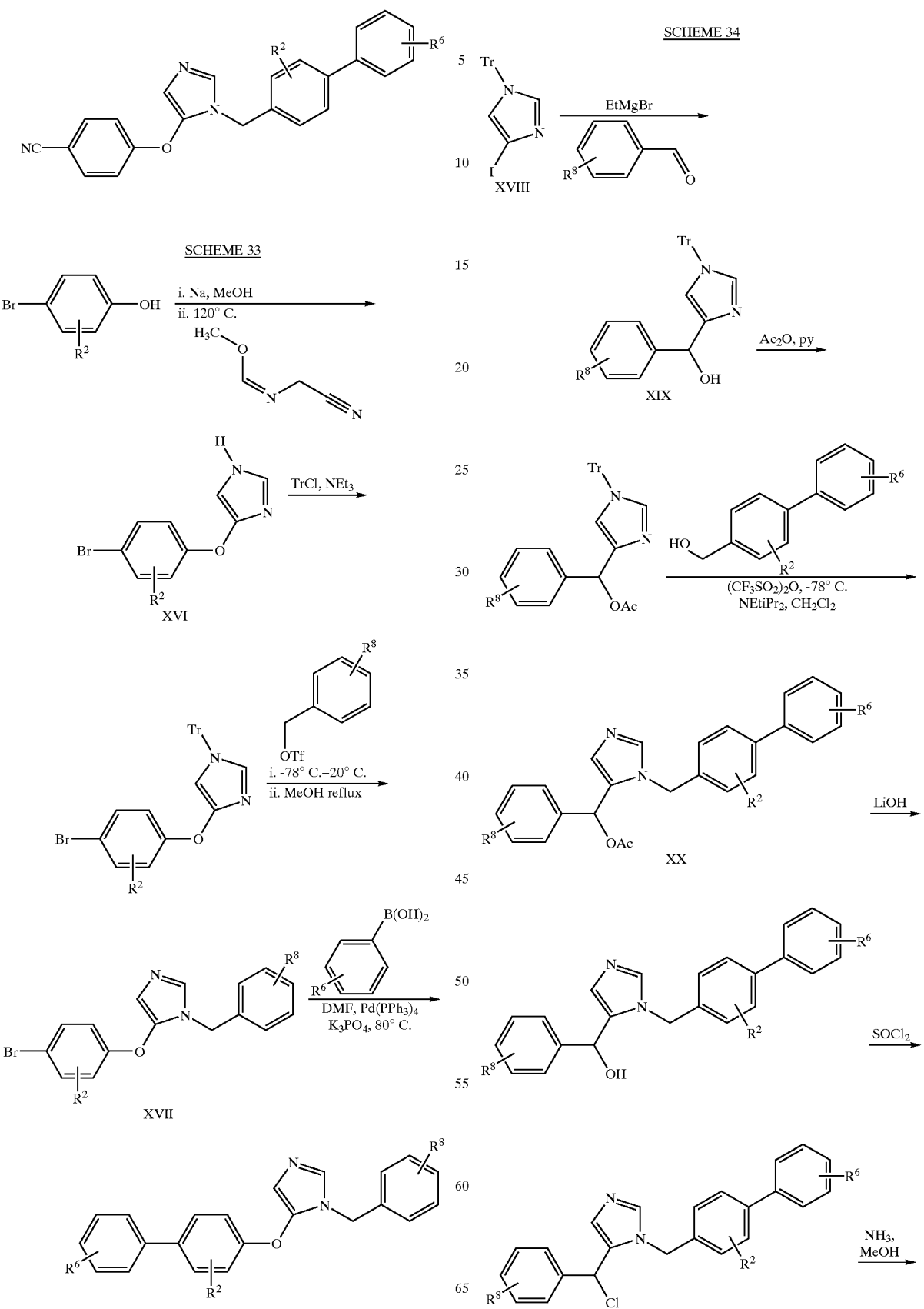

SCHEME 35

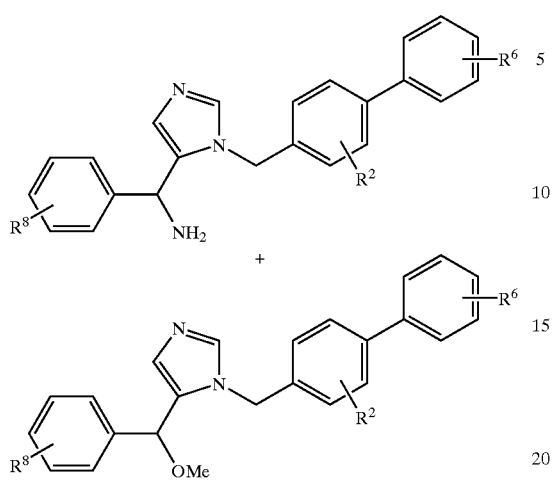

SCHEME 36

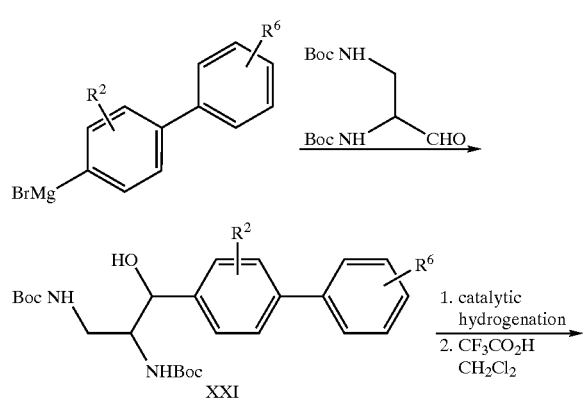

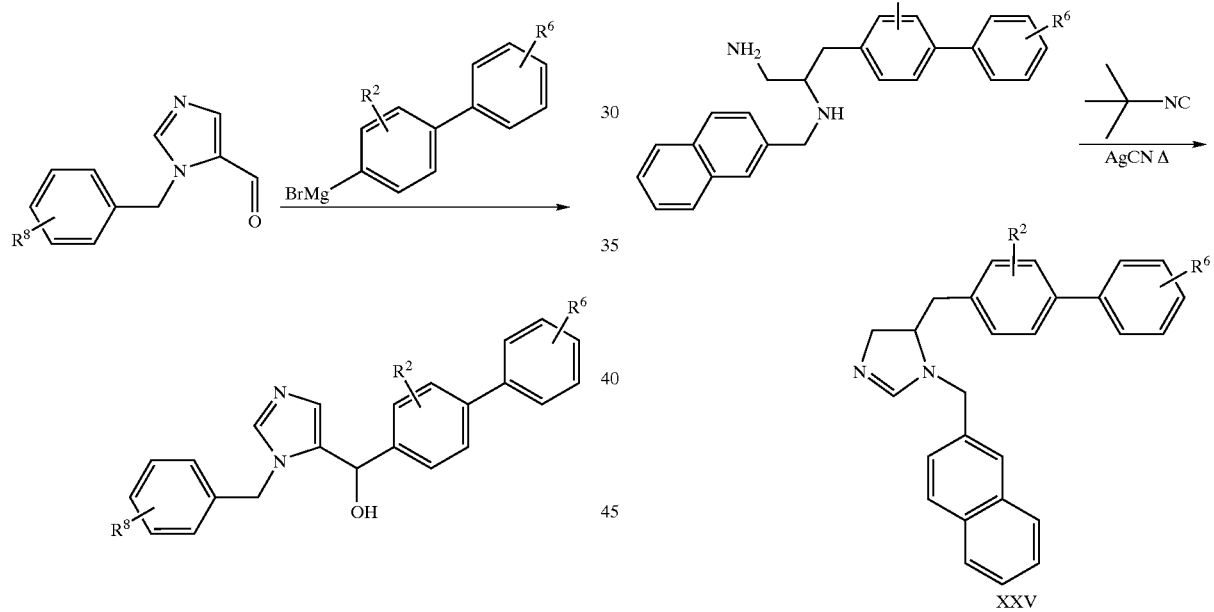

The farnesyl transferase inhibitors of formula (II-e) can be synthesized in accordance with Schemes 37–52, in addition to other standard manipulations such as ester hydrolysis, cleavage of protecting groups, etc., as may be known in the literature or exemplified in the experimental procedures. Substituents $R^2$, $R^6$ and $R^8$, as shown in the Schemes, represent the substituents $R^2$, $R^3$, $R^4$, $R^5$, $R^6$ and $R^8$; although only one such $R^2$, $R^6$ or $R^8$ is present in the intermediates and products of the schemes, it is understood that the reactions shown are also applicable when such aryl or heteroaryl moieties contain multiple substituents. The compounds referred to in the Synopsis of Schemes 37–52 by Roman numerals are numbered starting sequentially with I and ending with XXV.

These reactions may be employed in a linear sequence to provide the compounds of the invention or they may be used to synthesize fragments which are subsequently joined by the alkylation reactions described in the Schemes. Other reactions useful in the preparation of heteroaryl moieties are described in "Comprehensive Organic Chemistry, Volume 4: Heterocyclic Compounds" ed. P. G. Sammes, Oxford (1979) and references therein. Aryl-aryl coupling is generally described in "Comprehensive Organic Functional Group Transformations," Katritsky et al. eds., pp 472–473, Pergamon Press (1995).

Synopsis of Schemes 37–52:

The requisite intermediates are in some cases commercially available, or can be prepared according to literature procedures, for the most part. Schemes 37–51 illustrate synthesis of the instant arylheteroaryl compound which incorporate a preferred benzylimidazolyl side-chain. Thus, in Scheme 37, for example, a arylheteroaryl intermediate that is not commercially available may be synthesized by methods known in the art. Thus, a suitably substituted pyridyl boronic acid I may be reacted under Suzuki coupling conditions (*Pure Appl. Chem.*, 63:419 (1991)) with a suitably substituted halogenated benzoic acid, such as 4-bromobenzoic acid, to provide the arylheteroaryl carboxylic acid II. The acid may be reduced and the triflate of the intermediate alcohol III may be formed in situ and coupled to a suitably substituted benzylimidazolyl IV to provide, after deprotection, the instant compound V.

Schemes 38–41 illustrate other methods of synthesizing the key alcohol intermediates, which can then be processed as described in Scheme 1. Thus, Scheme 38 illustrates the analogous series of arylheteroaryl alcohol forming reactions starting with the halogenated arylaldehyde.

Scheme 39 illustrates the reaction wherein the "terminal" heteroaryl moiety is employed in the Suzuki coupling as the halogenated reactant. Such a coupling reaction is also compatible when one of the reactants incorporates a suitably protected hydroxyl functionality as illustrated in Scheme 40.

Negishi chemistry (*Org. Synth.*, 66:67 (1988)) may also be employed to form the arylheteroaryl component of the instant compounds, as shown in Scheme 41. Thus, a suitably substituted zinc bromide adduct may be coupled to a suitably substituted aryl halide in the presence of nickel (II) to provide the arylheteroaryl VII. The heteroaryl halide and the zinc bromide adduct may be selected based on the availability of the starting reagents.

Scheme 42 illustrates the preparation of the suitably substituted arylheteroaryl methanol. from the pyridyltoluene.

Scheme 43 illustrates the preparation of the suitably substituted pyrazinylaryl methanol starting with alanine.

As illustrated in Scheme 44, the sequence of coupling reactions may be modified such that the arylheteroaryl bond is formed last. Thus, a suitably substituted imidazole may first be alkylated with a suitably substituted benzyl halide to provide intermediate VII. Intermediate VIII can then undergo Suzuki type coupling to a suitably substituted heteroaryl boronic acid.

Scheme 45 illustrates synthesis of an instant compound wherein a non-hydrogen $R^{9b}$ is incorporated in the instant compound. Thus, a readily available 4substituted imidazole IX may be selectively iodinated to provide the 5-iodoimidazole X. That imidazole may then be protected and coupled to a suitably substituted benzyl moiety to provide intermediate XI. Intermediate XI can then undergo the alkylation reactions that were described hereinabove.

Scheme 46 illustrates synthesis of instant compounds that incorporate a preferred imidazolyl moiety connected to the arylheteroaryl via an alkyl amino, sulfonamide or amide linker. Thus, the 4-aminoalkylimidazole XII, wherein the primary amine is protected as the phthalimide, is selectively alkylated then deprotected to provide the amine XIII. The amine XIII may then react under conditions well known in the art with various activated arylheteroaryl moieties to provide the instant compounds shown.

Compounds of the instant invention wherein the $A^1(CR^{1a}{}_2)_n A^2(CR^{1a}{}_2)_n$ linker is oxygen may be synthesized by methods known in the art, for example as shown in Scheme 47. The suitably substituted phenol XIV may be reacted with methyl N-(cyano)methanimidate to provide the 4-phenoxyimidazole XV. After selective protection of one of the imidazolyl nitrogens, the intermediate XVI can undergo alkylation reactions as described for the phenylmethylimidazoles hereinabove.

Scheme 48 illustrates an analogous series of reactions wherein the $(CR^{1b}{}_2)_p X(CR^{1b}{}_2)_p$ linker of the instant compounds is oxygen. Thus, a suitably substituted haloaryl alcohol, such as 4-bromophenol, is reacted with methyl N-(cyano)methanimidate to provide intermediate XVI. Intermediate XVI is then protected and, if desired to form a compound of a preferred embodiment, alkylated with a suitably protected benzyl. The intermediate XVII can then be coupled to a heteroaryl moiety by Suzuki chemistry to provide the instant compound.

Compounds of the instant invention wherein the $A^1(CR^{1a}{}_2)_n A^2(CR^{1a}{}_2)_n$ linker is a substituted methylene may be synthesized by the methods shown in Scheme 49. Thus, the N-protected imidazolyl iodide XVIII is reacted, under Grignard conditions with a suitably protected benzaldehyde to provide the alcohol XIX. Acylation, followed by the alkylation procedure illustrated in the Schemes above (in particular, Scheme 37) provides the instant compound XX. If other $R^1$ substituent s are desired, the acetyl moiety can be manipulated as illustrated in the Scheme.

Addition of various nucleophiles to an imidazolyl aldehyde may also be employed to form a substituted alkyl linker between the arylheteroaryl and the preferred W (imidazolyl) as shown in Scheme 50. Thus a halogenated arylheteroaryl, such as 4-(3-pyridyl)bromobenzene, may undergo metal halogen exchange followed by reaction with a suitably substituted imidazolyl aldehyde and acteylation to form the alcohol. Then, similar substituent manipulation as shown in Scheme 49 may be performed on a fully functionalized compound which incorporates an $R^2$ hydroxyl moiety.

Scheme 51 illustrates the synthesis of a suitably substituted pyrimidinebromobenzene, which may be employed in the reaction illustrated in Scheme 49. This reaction and other reactions useful in the preparation of heteroaryl moieties are described in "Comprehensive Organic Chemistry, Volume 4: Heterocyclic Compounds" ed. P. G. Sammes, Oxford (1979).

Schemes 52 illustrates reactions wherein the moiety

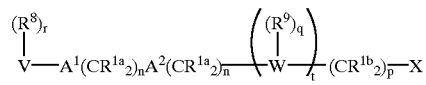

incorporated in the compounds of the instant invention is represented by other than a substituted imidazole-containing group.

Thus, the intermediates whose synthesis are illustrated in Schemes hereinabove and other arylheteroaryl intermediates obtained commercially or readily synthesized, can be coupled with a variety of aldehydes. The aldehydes can be prepared by standard procedures, such as that described by O. P. Goel, U. Krolls, M. Stier and S. Kesten in *Organic Syntheses*, 1988, 67, 69–75, from the appropriate amino acid. Metalation chemistry may be utilized, as shown in Scheme 52, to incorporate the arylheteroaryl moiety. Thus, a suitably substituted arylheteroaryl lithium reagent, prepared in situ, is reacted with an aldehyde to provide the C-alkylated instant compound XXI. Compound XXI can be deoxygenated by methods known in the art, such as a catalytic hydrogention, then deprotected with trifluoroacetic acid in methylene chloride to give the final compound XXII. The final product XXII may be isolated in the salt form, for example, as a trifluoroacetate, hydrochloride or acetate salt, among others. The product diamine XXII can further be selectively protected to obtain XXIII, which can subsequently be reductively alkylated with a second aldehyde to obtain XXIV. Removal of the protecting group, and conversion to cyclized products such as the dihydroimidazole XXV can be accomplished by literature procedures.

Incorporation of other moieties via the appropriate aldehyde starting material may be performed as illustrated in Scheme 52 and the intermediates manipulated as illustrated above in Schemes 4–9.

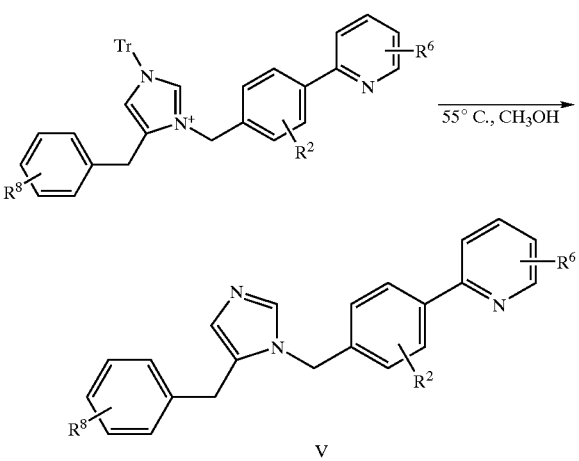

SCHEME 37

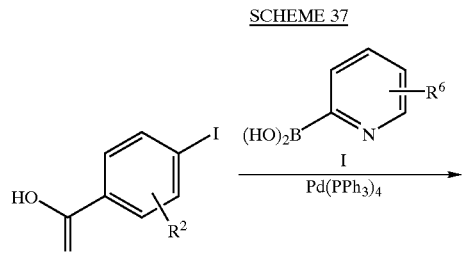

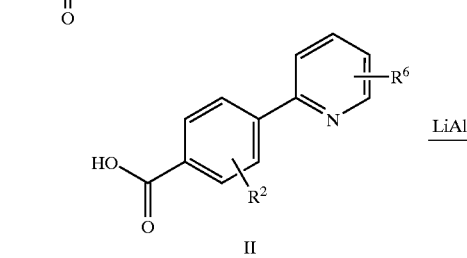

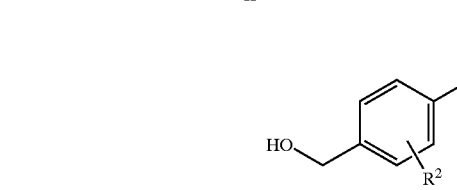

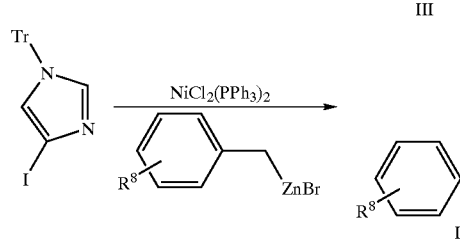

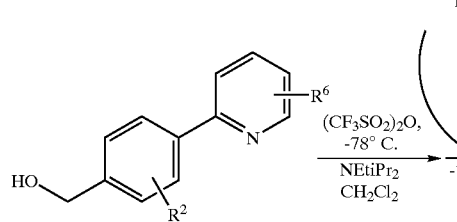

SCHEME 38

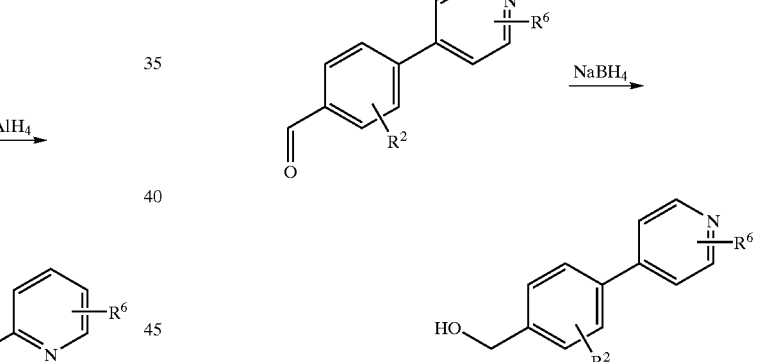

SCHEME 39

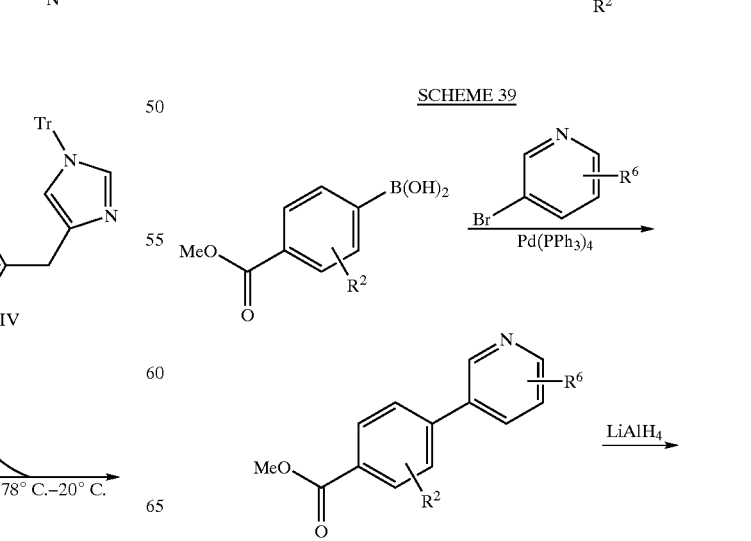

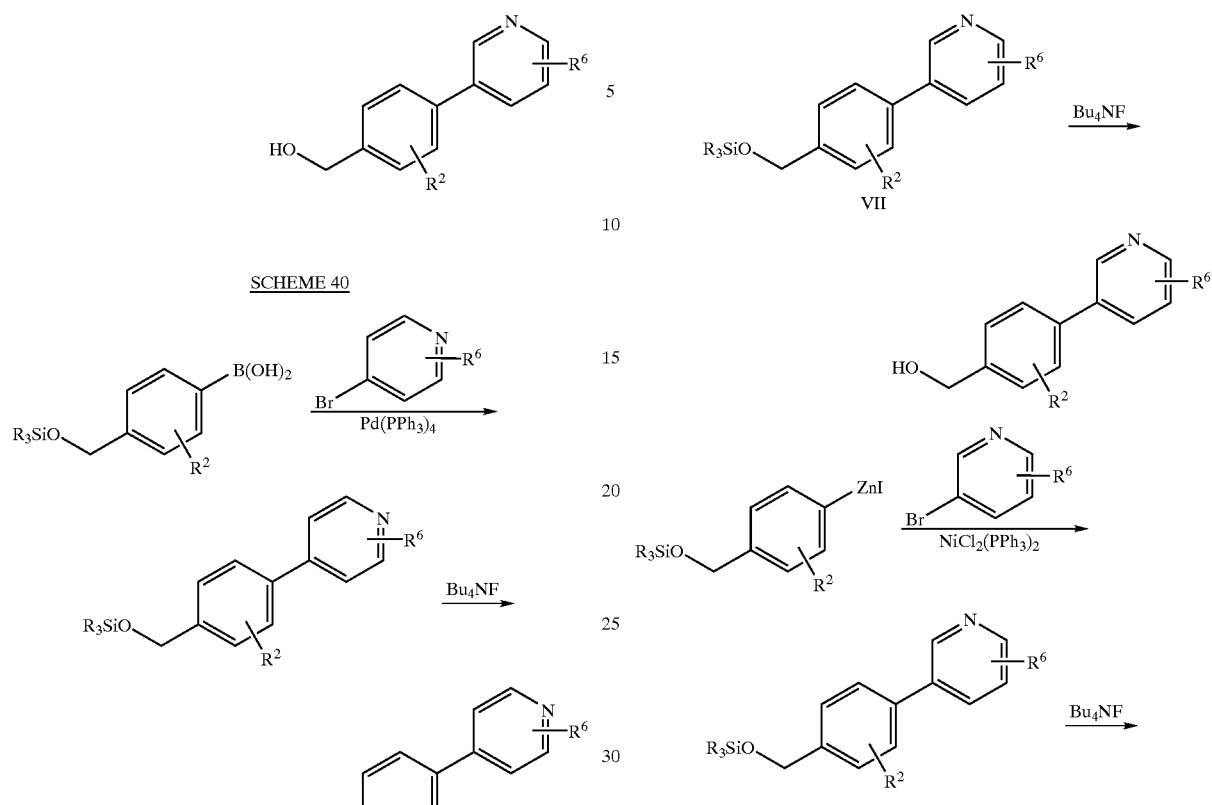
SCHEME 40
SCHEME 41
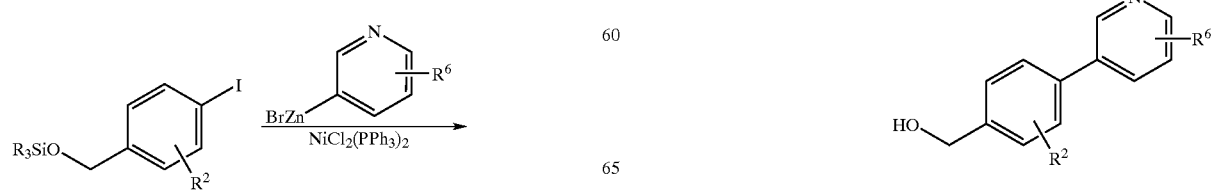
SCHEME 42
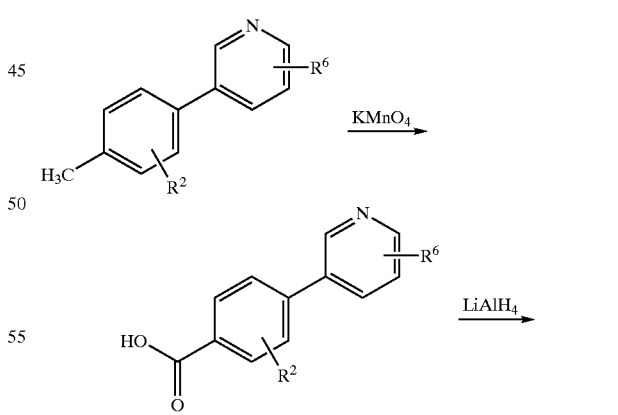

SCHEME 43
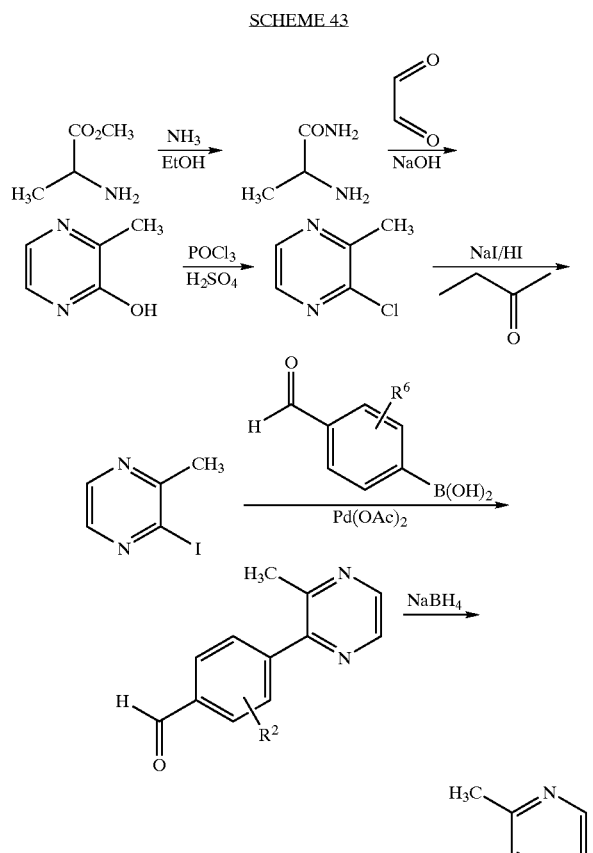
SCHEME 44
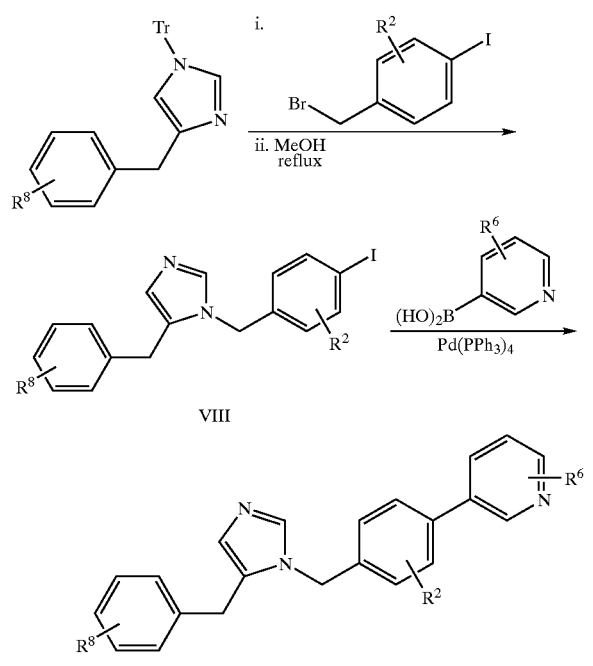
SCHEME 45
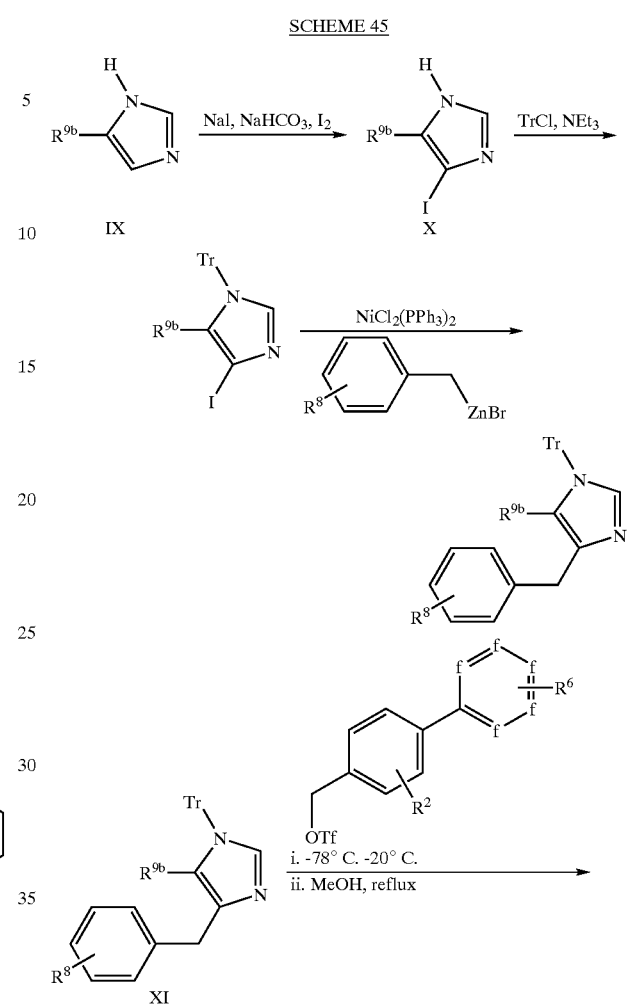
SCHEME 46
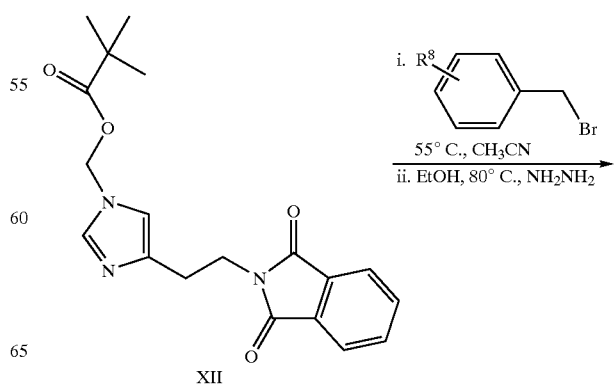

105
-continued
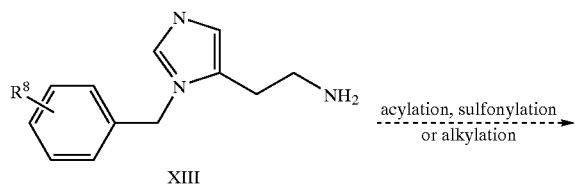
XIII
acylation, sulfonylation or alkylation
----→
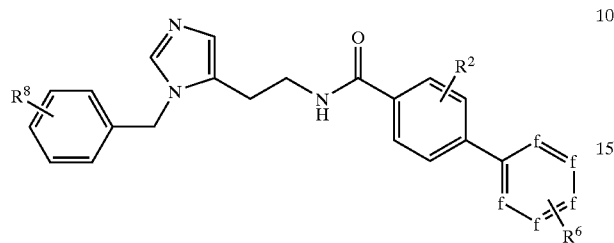
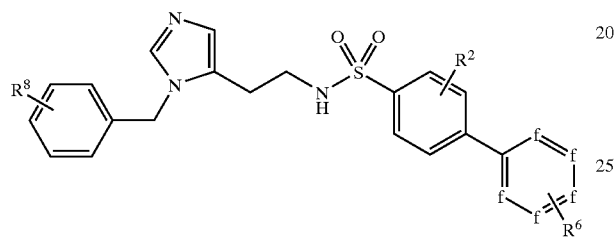
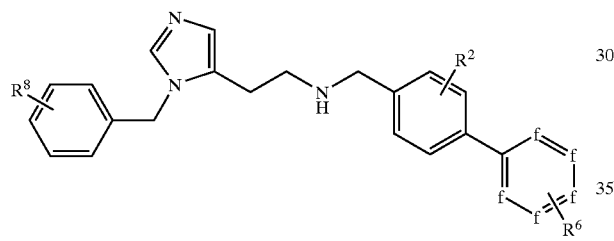
SCHEME 47
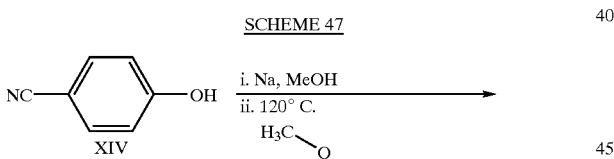
XIV
i. Na, MeOH
ii. 120° C.
----→
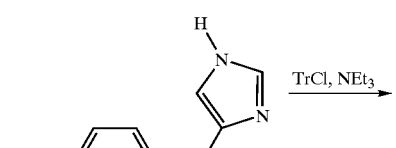
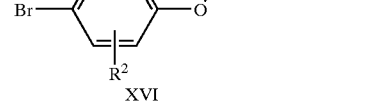
XV
TrCl, NEt₃
----→
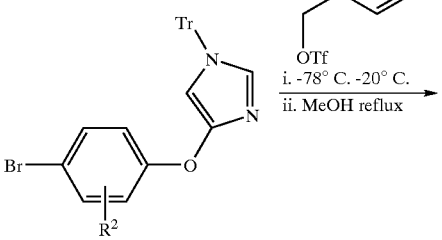
XVI
106
-continued
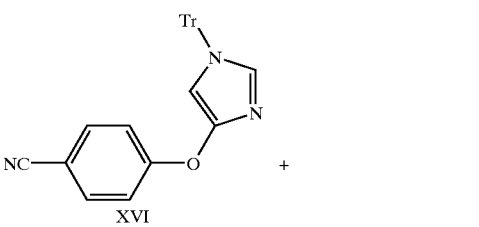
XVI
+
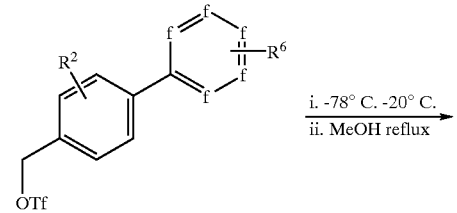
i. -78° C. -20° C.
ii. MeOH reflux
----→
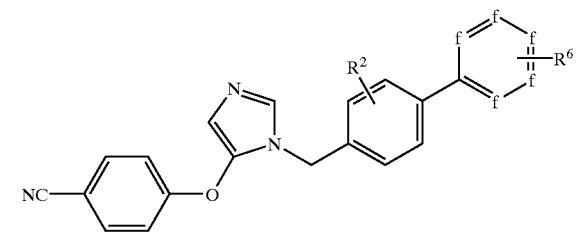
SCHEME 48
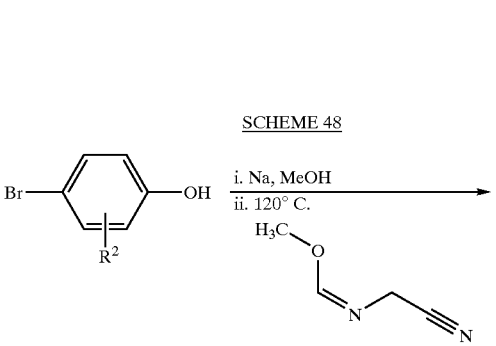
i. Na, MeOH
ii. 120° C.
----→
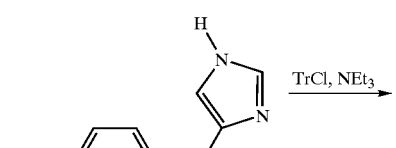
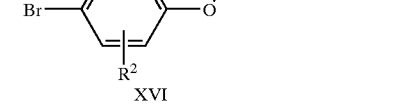
XVI
TrCl, NEt₃
----→
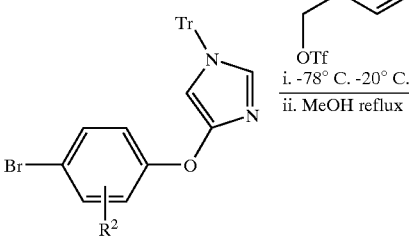
OTf
i. -78° C. -20° C.
ii. MeOH reflux
----→

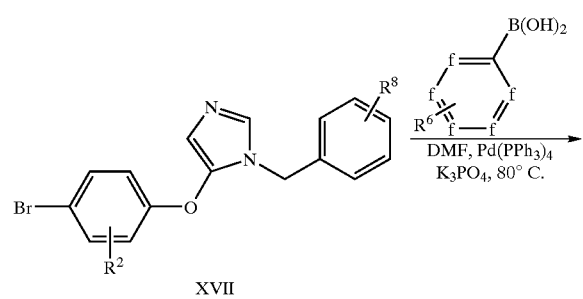
XVII
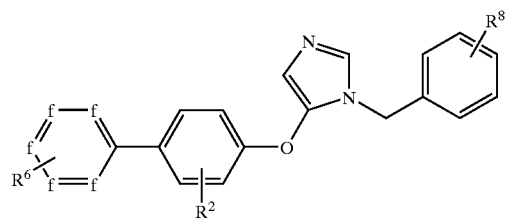
SCHEME 49
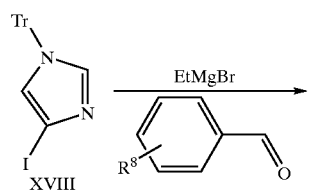
XVIII
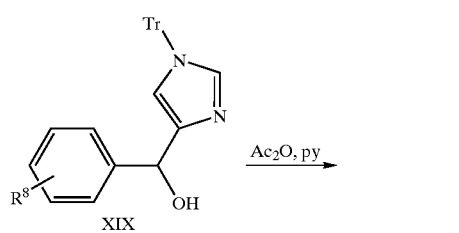
XIX
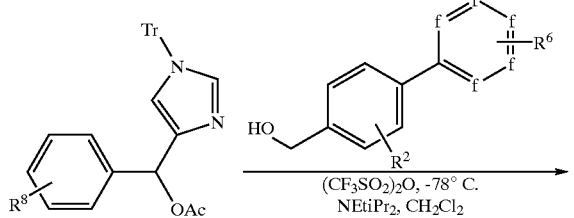
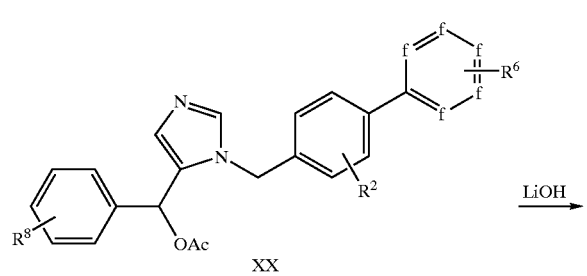
XX
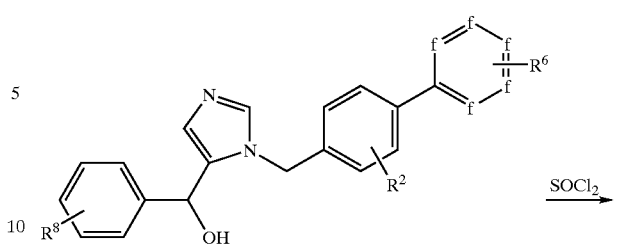
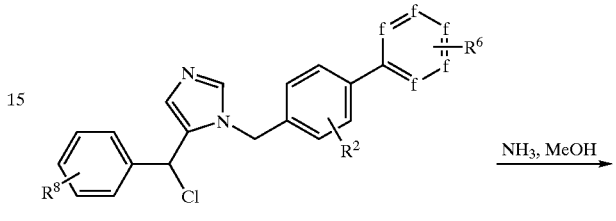
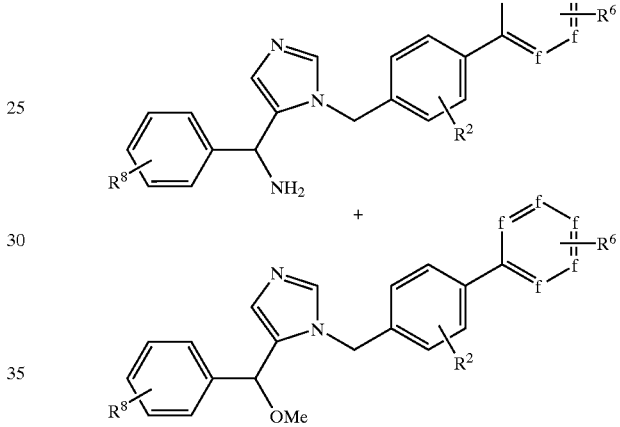
SCHEME 50
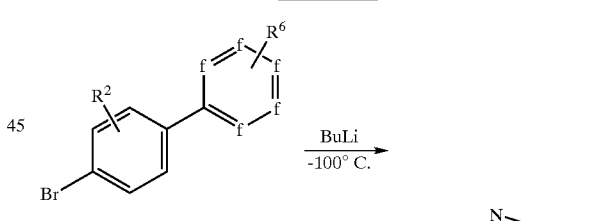
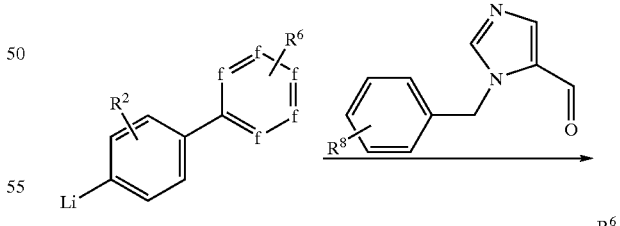
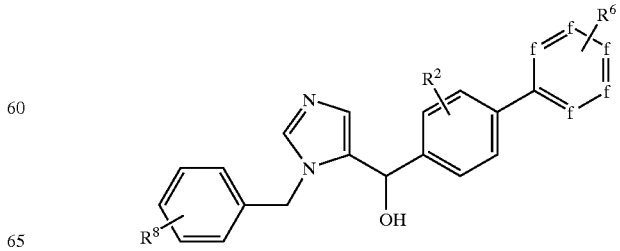

SCHEME 51

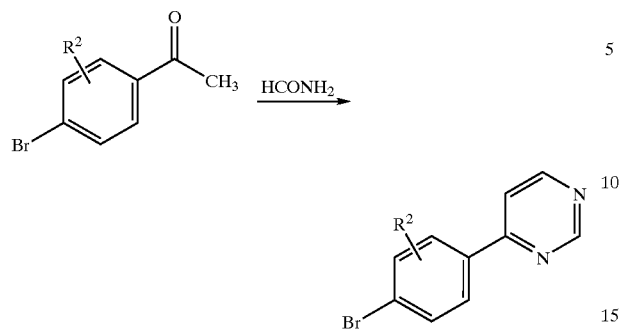

SCHEME 52

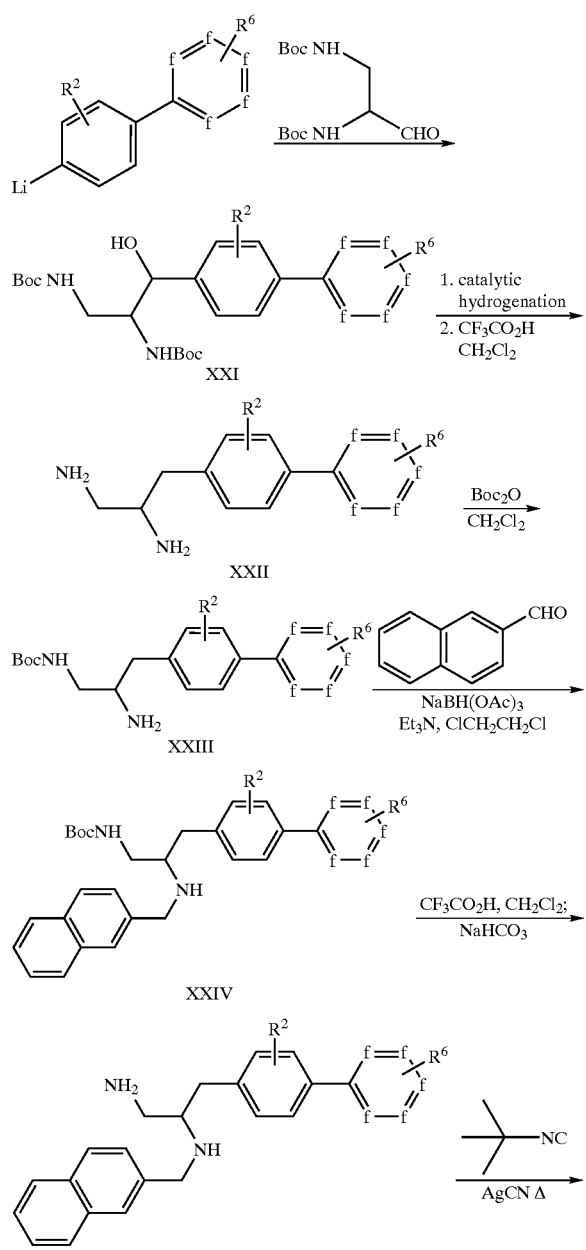

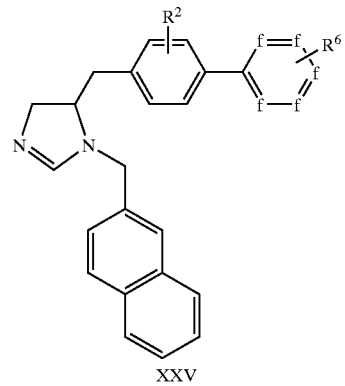

XXV

The farnesyl transferase inhibitors of formula (II-f) can be synthesized in accordance with Schemes 53–66, in addition to other standard manipulations such as ester hydrolysis, cleavage of protecting groups, etc., as may be known in the literature or exemplified in the experimental procedures. Substituents $R^3$, $R^6$ and $R^8$, as shown in the Schemes, represent the substituents $R^3$, $R^4$, $R^5$, $R^{6a}$, $R^{6b}$, $R^{6c}$, $R^{6d}$, $R^{6e}$ and $R^8$; although only one such $R^3$, $R^6$ or $R^8$ is present in the intermediates and products of the schemes, it is understood that the reactions shown are also applicable when such aryl or heteroaryl moieties contain multiple substituents. The compounds referred to in the Synopsis of Schemes 53–66 by Roman numerals are numbered starting sequentially with I and ending with XXX.

These reactions may be employed in a linear sequence to provide the compounds of the invention or they may be used to synthesize fragments which are subsequently joined by the alkylation reactions described in the Schemes. The reactions described in the Schemes are illustrative only and are not meant to be limiting. Other reactions useful in the preparation of heteroaryl moieties are described in "Comprehensive Organic Chemistry, Volume 4: Heterocyclic Compounds" ed. P. G. Sammes, Oxford (1979) and references therein. Aryl-aryl coupling is generally described in "Comprehensive Organic Functional Group Transformations," Katritsky et al. eds., pp 472–473, Pergamon Press (1995).

Synopsis of Schemes 53–66:

The requisite intermediates are in some cases commercially available, or can be prepared according to literature procedures, for the most part. Schemes 53–64 illustrate synthesis of the instant arylheteroaryl compound which incorporate a preferred benzylimidazolyl sidechain. Thus, in Scheme 53, for example, a arylheteroaryl intermediate that is not commercially available may be synthesized by methods known in the art. Thus, a suitably substituted phenyl boronic acid I may be reacted under Suzuki coupling conditions (Pure Appl. Chem., 63:419 (1991)) with a suitably substituted halogenated nicotinic acid, such as 4-bromonicotinic acid, to provide the arylheteroaryl carboxylic acid II. The acid may be reduced and the triflate of the intermediate alcohol III may be formed in situ and coupled to a suitably substituted benzylimidazolyl IV to provide, after deprotection, the instant compound V.

Schemes 54–55 illustrate other methods of synthesizing the key alcohol intermediates, which can then be processed as described in Scheme 53. Thus, Scheme 54 illustrates the analogous series of arylheteroaryl alcohol forming reactions starting with the methyl nicotinate boronic acid and the "terminal" phenyl moiety employed in the Suzuki coupling as the halogenated reactant. Such a coupling reaction is also compatible when one of the reactants incorporates a suitably protected hydroxyl functionality as illustrated in Scheme 55.

Negishi chemistry (*Org. Synth.*, 66:67 (1988)) may also be employed to form the arylheteroaryl component of the instant compounds, as shown in Scheme 56. Thus, a suitably substituted zinc bromide adduct may be coupled to a suitably substituted heteroaryl halide in the presence of nickel (II) to provide the arylheteroaryl VII. The heteroaryl halide and the zinc bromide adduct may be selected based on the availability of the starting reagents.

Scheme 57 illustrates the preparation of a suitably substituted 3-hydroxymethyl-5-phenyl pyridine which could also be utilized in the reaction with the protected imidazole as described in Scheme 53. An Alternative preparation of a suitably substituted 5-hydroxymethyl-2-phenyl pyridine is also illustrated.

As illustrated in Scheme 58, the sequence of coupling reactions may be modified such that the aryl-heteroaryl bond is formed last. Thus, a suitably substituted imidazole may first be alkylated with a suitably substituted benzyl halide to provide intermediate VIII. Intermediate VIII can then undergo Suzuki type coupling to a suitably substituted phenyl boronic acid.

Scheme 59 illustrates synthesis of an instant compound wherein a non-hydrogen $R^{9b}$ is incorporated in the instant compound. Thus, a readily available 4-substituted imidazole IX may be selectively iodinated to provide the 5-iodoimidazole X. That imidazole may then be protected and coupled to a suitably substituted benzyl moiety to provide intermediate XI. Intermediate XI can then undergo the alkylation reactions that were described hereinabove.

Scheme 60 illustrates synthesis of instant compounds that incorporate a preferred imidazolyl moiety connected to the biaryl via an alkyl amino, sulfonamide or amide linker. Thus, the 4-aminoalkyl-imidazole XII, wherein the primary amine is protected as the phthalimide, is selectively alkylated then deprotected to provide the amine XIII. The amine XIII may then react under conditions well known in the art with various activated arylheteroaryl moieties to provide the instant compounds shown.

Compounds of the instant invention wherein the $A^1(CR^1_2)_nA^2(CR^1_2)_n$ linker is oxygen may be synthesized by methods known in the art, for example as shown in Scheme 61. The suitably substituted phenol XIV may be reacted with methyl N-(cyano)methanimidate to provide the 4-phenoxyimidazole XV, After selective protection of one of the imidazolyl nitrogens, the intermediate XVI can undergo alkylation reactions as described for the benzylimidazoles hereinabove.

Scheme 62 illustrates an analogous series of reactions wherein the $(CR^2_2)_pX(CR^2_2)_p$ linker of the instant compounds is oxygen. Thus, a suitably substituted halopyridinol, such as 3-chloro-2-pyridinol, is reacted with methyl N-(cyano)methanimidate to provide intermediate XVI. Intermediate XVI is then protected and, if desired to form a compound of a preferred embodiment, alkylated with a suitably protected benzyl. The intermediate XVII can then be coupled to a aryl moiety by Suzuki chemistry to provide the instant compound.

Compounds of the instant invention wherein the $A^1(CR^1_2)_nA^2(CR^1_2)_n$ linker is a substituted methylene may be synthesized by the methods shown in Scheme 63. Thus, the N-protected imidazolyl iodide XVIII is reacted, under Grignard conditions with a suitably protected benzaldehyde to provide the alcohol XIX. Acylation, followed by the alkylation procedure illustrated in the Schemes above (in particular, Scheme 53) provides the instant compound XX. If other $R^1$ substituents are desired, the acetyl moiety can be manipulated as illustrated in the Scheme.

Addition of various nucleophiles to an imidazolyl aldehyde may also be employed to form a substituted alkyl linker between the biheteroaryl and the preferred W (imidazolyl) as shown in Scheme 64. Thus a sutiably substituted phenyl lithium can be reacted with pyridine to form the 2-substituted N-lithio-1,2-dihydropyridine XXa. Intermediate XXa can then react with a aldehyde to provide a suitably substituted instant compound. Similar substituent manipulation as shown in Scheme 63 may be performed on the fully functionalized compound which incorporates an $R^2$ hydroxyl moiety.

Scheme 65 illustrate reactions wherein the moiety

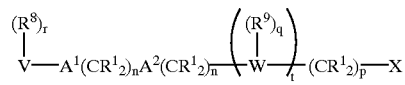

incorporated in the compounds of the instant invention is represented by other than a substituted imidazole-containing group.

Thus, the intermediates whose synthesis are illustrated in Schemes hereinabove and other arylheteroaryl intermediates obtained commercially or readily synthesized, can be coupled with a variety of aldehydes. The aldehydes can be prepared by standard procedures, such as that described by O. P. Goel, U. Krolls, M. Stier and S. Kesten in *Organic Syntheses*, 1988, 67, 69–75, from the appropriate amino acid. Lithioheteroaryl chemistry may be utilized, as shown in Scheme 65, to incorporate the arylheteroaryl moiety. Thus, a suitably substituted arylheteroaryl N-lithio reagent is reacted with an aldehyde to provide the C-alkylated instant compound XXI. Compound XXI can be deoxygenated by methods known in the art, such as a catalytic hydrogention, then deprotected with trifluoroacetic acid in methylene chloride to give the final compound XXII. The final product XXII may be isolated in the salt form, for example, as a trifluoroacetate, hydrochloride or acetate salt, among others. The product diamine XXII can further be selectively protected to obtain XXIII, which can subsequently be reductively alkylated with a second aldehyde to obtain XXIV. Removal of the protecting group, and conversion to cyclized products such as the dihydroimidazole XXV can be accomplished by literature procedures.

If the arylheteroaryl subunit reagent is reacted with an aldehyde which also has a protected hydroxyl group, such as XXVI in Scheme 66, the protecting groups can be subsequently removed to unmask the hydroxyl group. The alcohol can be oxidized under standard conditions to e.g. an aldehyde, which can then be reacted with a variety of organometallic reagents such as alkyl lithium reagents, to obtain secondary alcohols such as XXX.

Incorporation of other moieties via the appropriate aldehyde starting material may be performed as illustrated in Scheme 65–66 and the intermediates manipulated as illustrated above in Schemes 4–9.

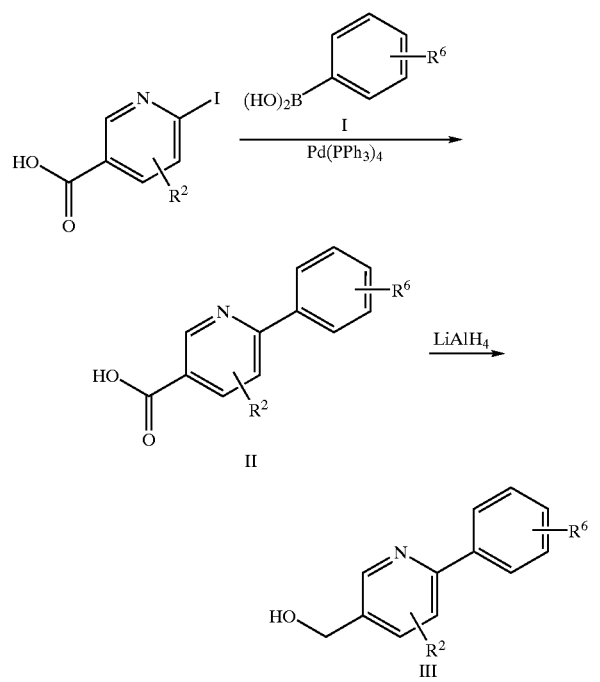
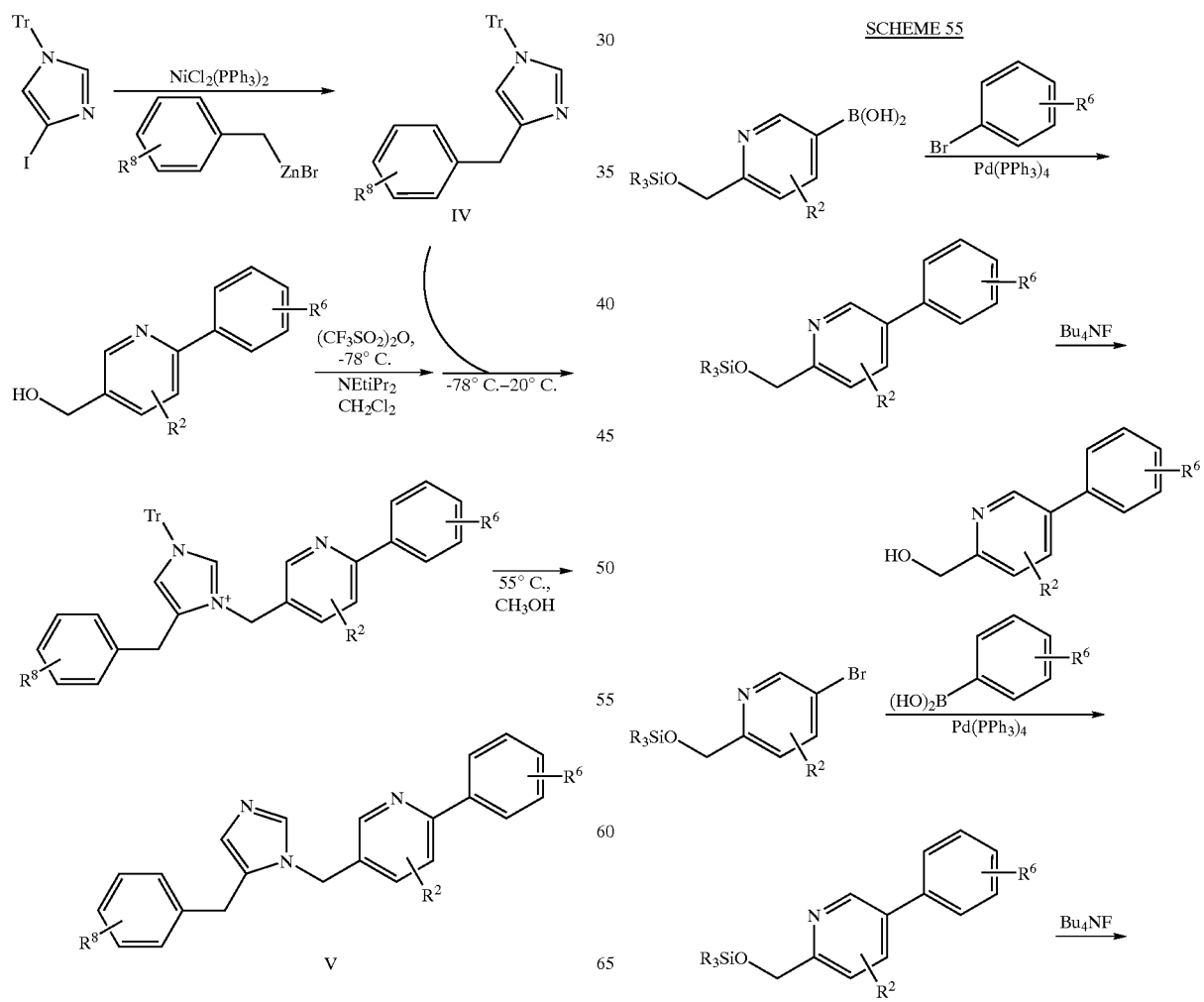
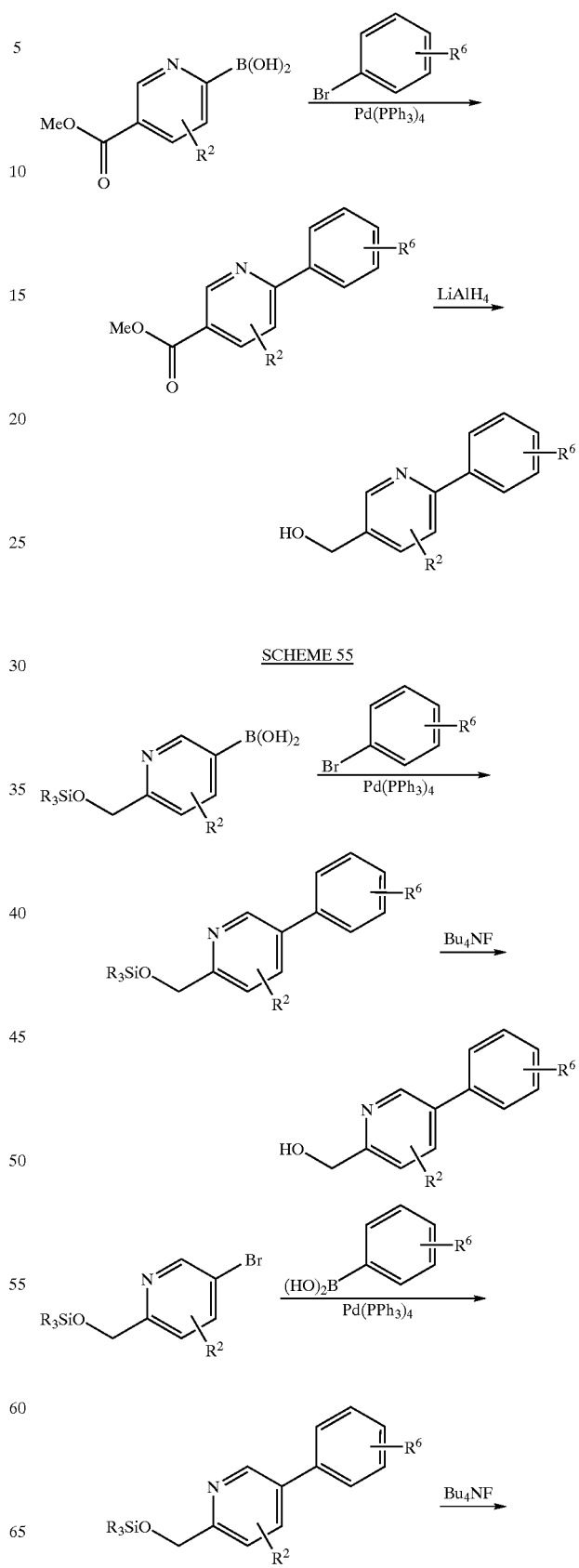

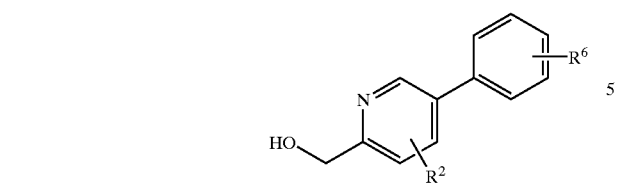
SCHEME 56
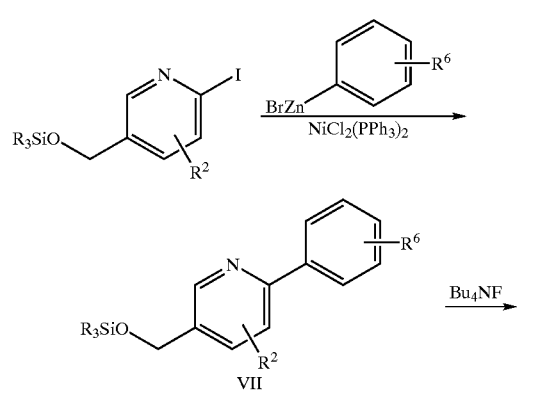
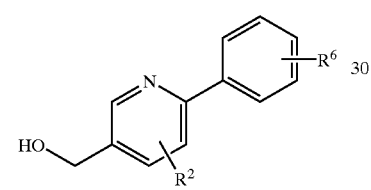
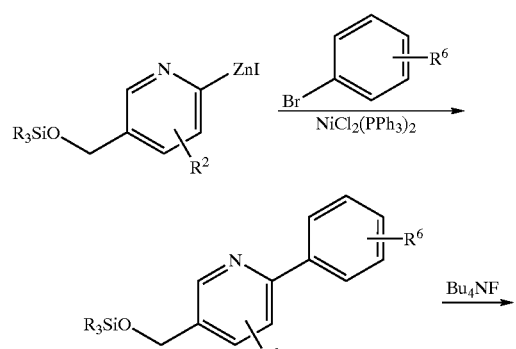
SCHEME 57
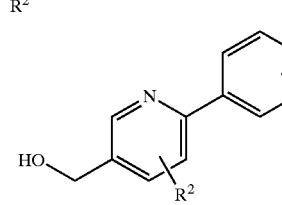
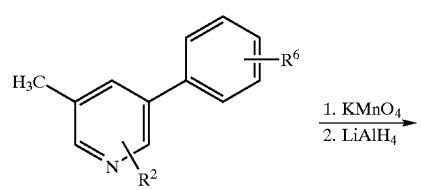
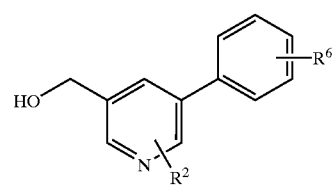
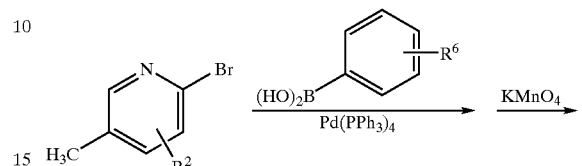
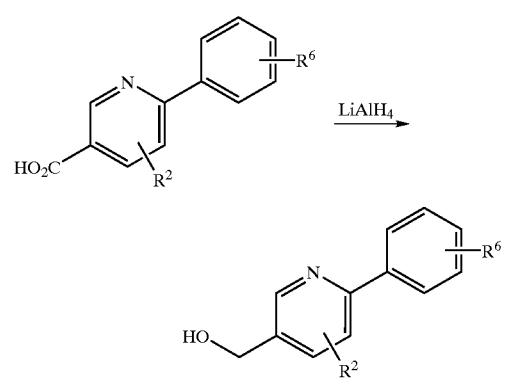
SCHEME 58
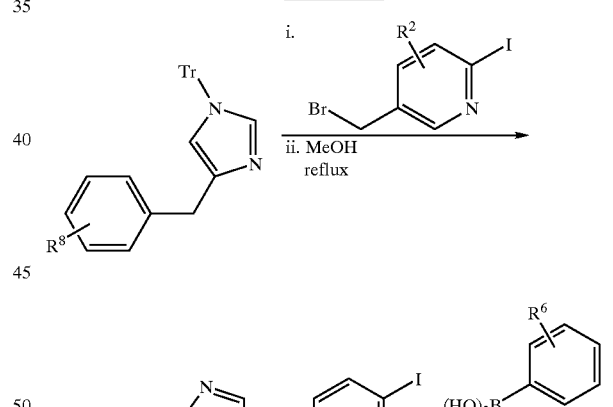
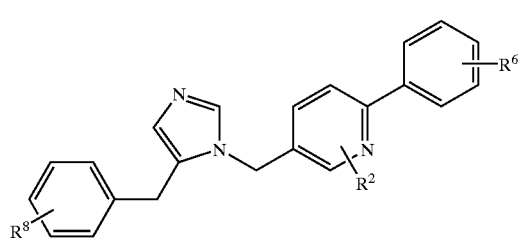

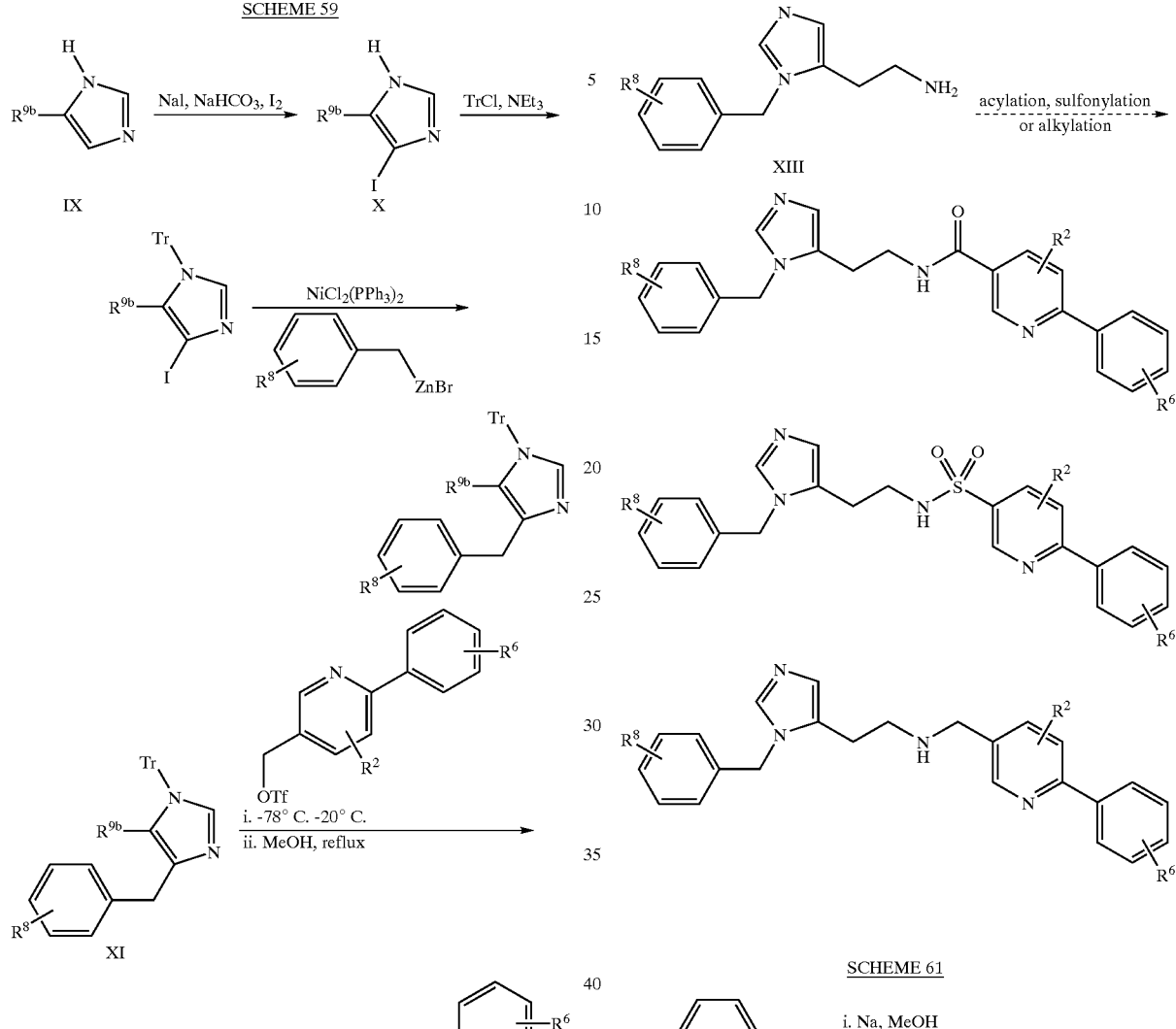
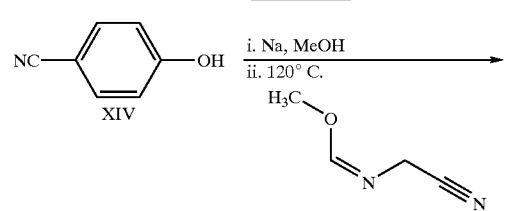
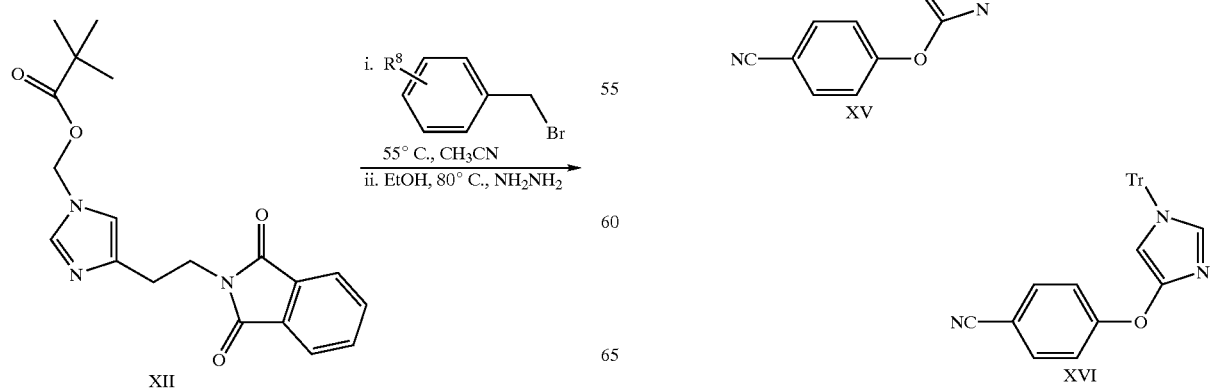

119
-continued
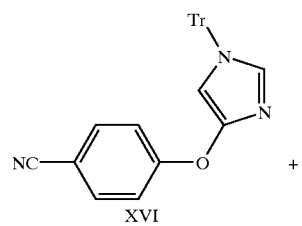
+
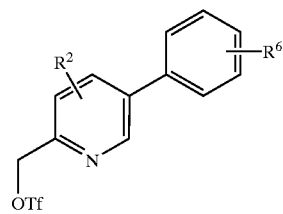
i. −78° C. −20° C.
ii. MeOH reflux
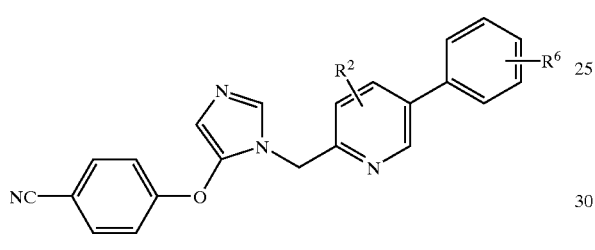
SCHEME 62
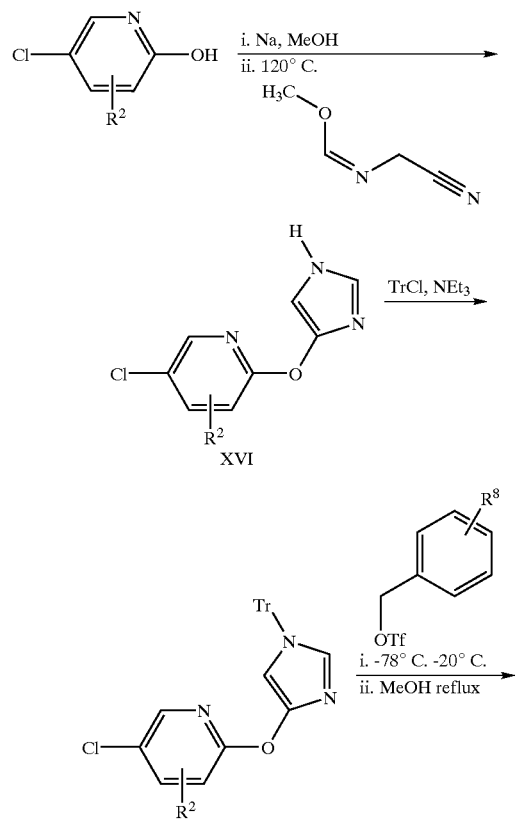
120
-continued
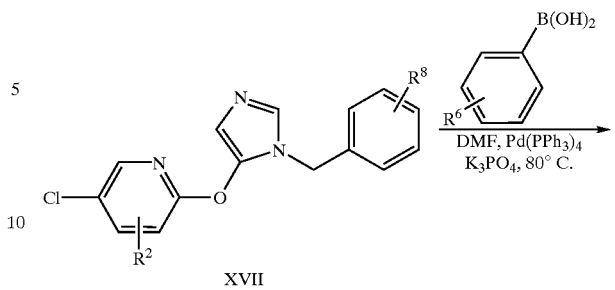
DMF, Pd(PPh₃)₄
K₃PO₄, 80° C.
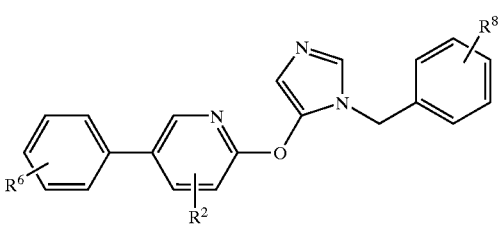
SCHEME 63
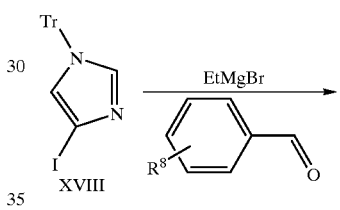
EtMgBr
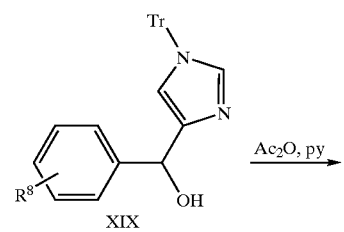
Ac₂O, py
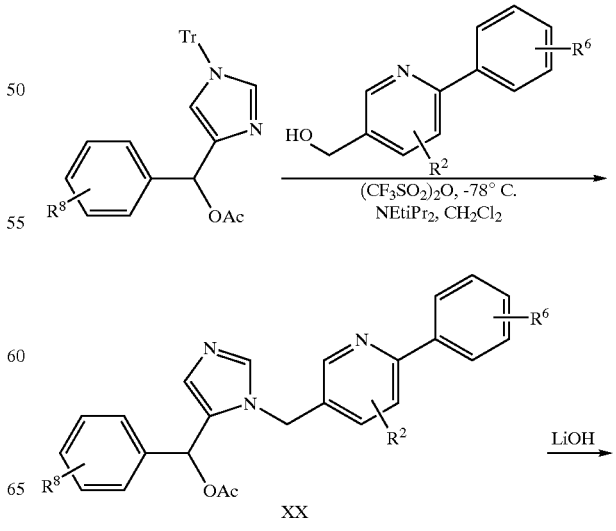
LiOH

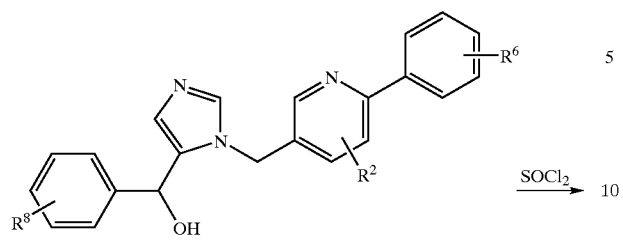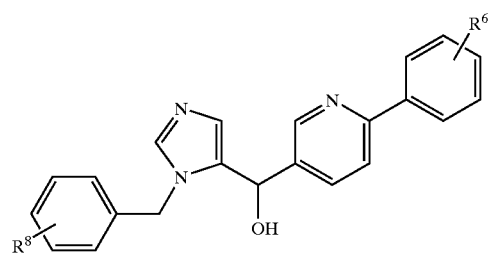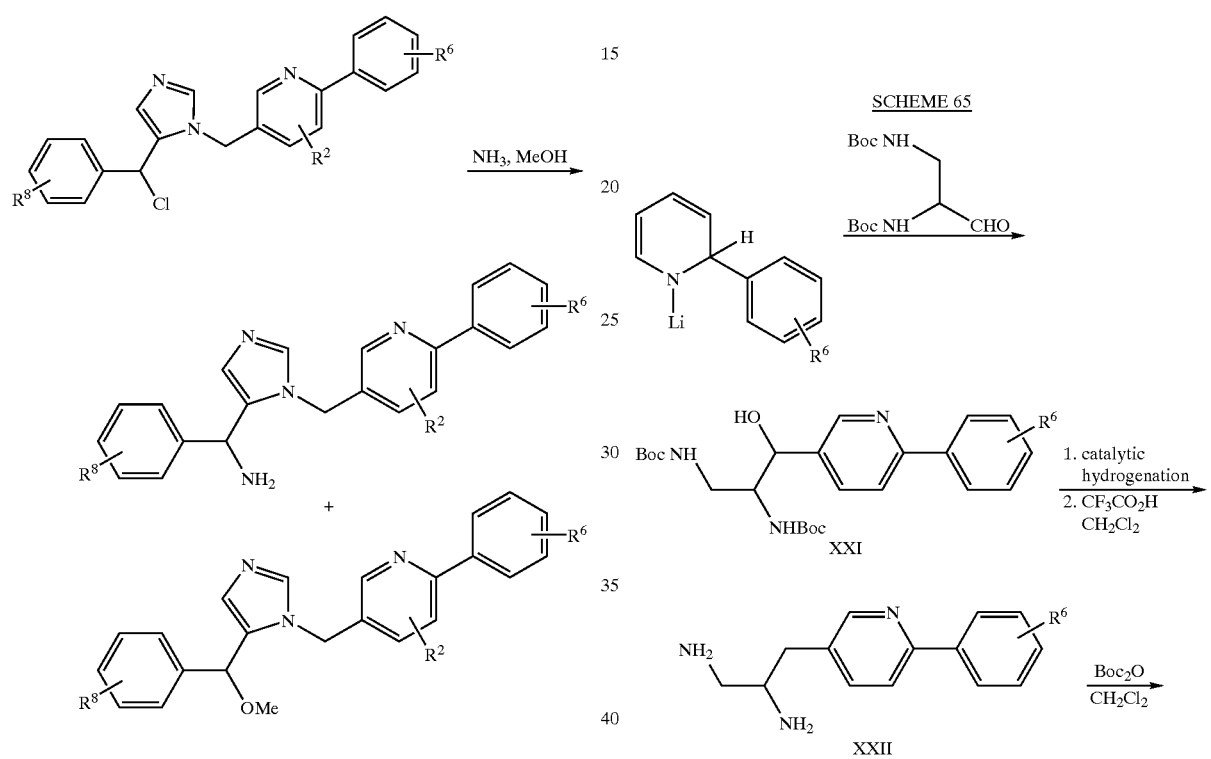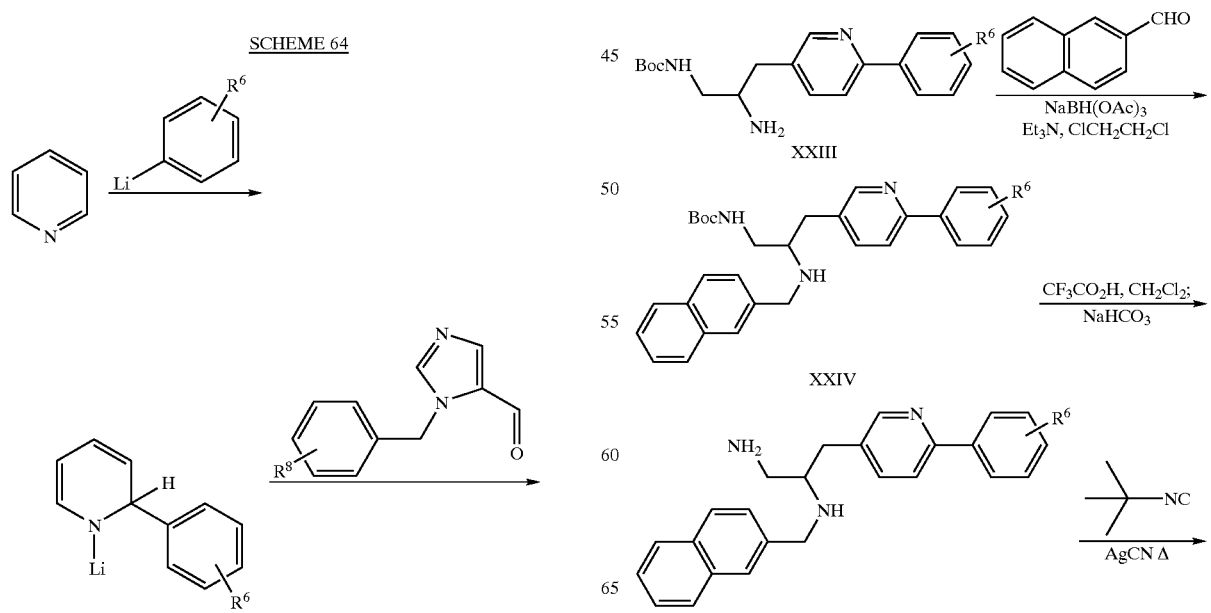

123

-continued

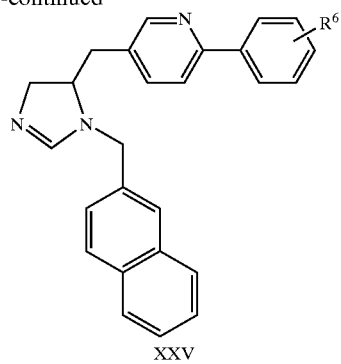

XXV

SCHEME 66

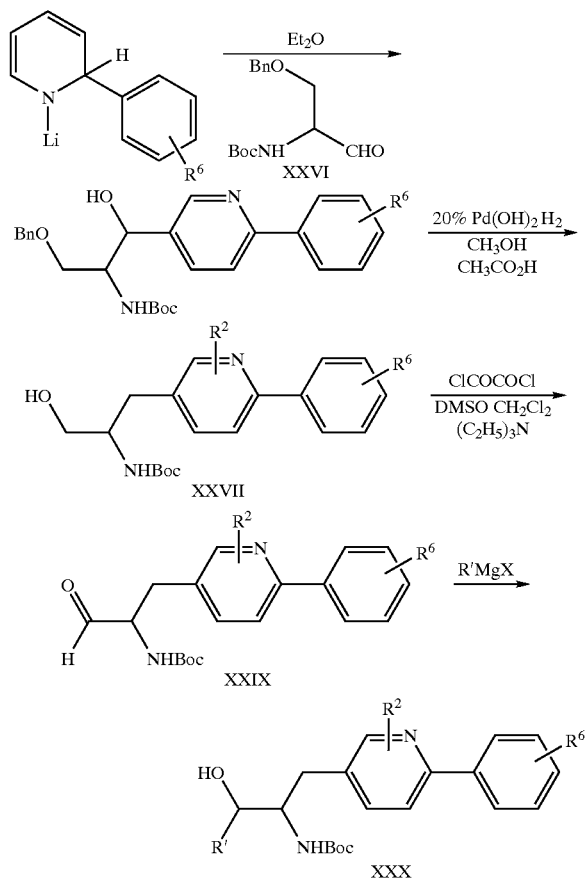

The farnesyl transferase inhibitors of formula (II-g) can be synthesized in accordance with Schemes 67–78, in addition to other standard manipulations such as ester hydrolysis, cleavage of protecting groups, etc., as may be known in the literature or exemplified in the experimental procedures. Substituents $R^3$, $R^6$ and $R^8$, as shown in the Schemes, represent the substituents $R^3$, $R^4$, $R^5$, $R^6$ and $R^8$; although only one such $R^3$, $R^6$ or $R^8$ is present in the intermediates and products of the schemes, it is understood that the reactions shown are also applicable when such aryl or heteroaryl moieties contain multiple substituents. The compounds referred to in the Synopsis of Schemes 67–78 by Roman numerals are numbered starting sequentially with I and ending with XX.

124

These reactions may be employed in a linear sequence to provide the compounds of the invention or they may be used to synthesize fragments which are subsequently joined by the alkylation reactions described in the Schemes. The reactions described in the Schemes are illustrative only and are not meant to be limiting. Other reactions useful in the preparation of heteroaryl moieties are described in "Comprehensive Organic Chemistry, Volume 4: Heterocyclic Compounds" ed. P. G. Sammes, Oxford (1979) and references therein. Aryl-aryl coupling is generally described in "Comprehensive Organic Functional Group Transformations," Katritsky et al. eds., pp 472473, Pergamon Press (1995).

Synopsis of Schemes 67–78:

The requisite intermediates are in some cases commercially available, or can be prepared according to literature procedures, for the most part. Schemes 67–78 illustrate synthesis of the instant biheteroaryl compound which incorporate a preferred benzylimidazolyl sidechain. Thus, in Scheme 67, for example, a biheteroaryl intermediate that is not commercially available may be synthesized by methods known in the art. Thus, a suitably substituted pyridyl boronic acid I may be reacted under Suzuki coupling conditions (Pure Appl. Chem., 63:419 (1991)) with a suitably substituted halogenated nicotinic acid, such as 4-bromonicotinic acid, to provide the biheteroaryl carboxylic acid II. The acid may be reduced and the triflate of the intermediate alcohol III may be formed in situ and coupled to a suitably substituted benzylimidazolyl IV to provide, after deprotection, the instant compound V.

Schemes 68–71 illustrate other methods of synthesizing the key alcohol intermediates, which can then be processed as described in Scheme 67. Thus, Scheme 68 illustrates the analogous series of biheteroaryl alcohol forming reactions starting with the methyl nicotinate boronic acid and the "terminal" heteroaryl moiety employed in the Suzuki coupling as the halogenated reactant. Such a coupling reaction is also compatible when one of the reactants incorporates a suitably protected hydroxyl functionality as illustrated in Scheme 69.

Negishi chemistry (Org. Synth., 66:67 (1988)) may also be employed to form the biheteroaryl component of the instant compounds, as shown in Scheme 70. Thus, a suitably substituted zinc bromide -adduct may be coupled to a suitably substituted heteroaryl halide in the presence of nickel (II) to provide the biheteroaryl VII. The heteroaryl halide and the zinc bromide adduct may be selected based on the availability of the starting reagents.

Scheme 71 illustrates the preparation of the pyridylmethanol intermediate starting with the 3-methyl pyridine.

As illustrated in Scheme 72, the sequence of coupling reactions may be modified such that the heteroaryl-heteroaryl bond is formed last. Thus, a suitably substituted imidazole may first be alkylated with a suitably substituted benzyl halide to provide intermediate VIII. Intermediate VIII can then undergo Suzuki type coupling to a suitably substituted pyridyl boronic acid.

Scheme 73 illustrates synthesis of an instant compound wherein a non-hydrogen $R^{9b}$ is incorporated in the instant compound. Thus, a readily available 4substituted imidazole IX may be selectively iodinated to provide the 5-iodoimidazole X. That imidazole may then be protected and coupled to a suitably substituted benzyl moiety to provide intermediate XI. Intermediate XI can then undergo the alkylation reactions that were described hereinabove.

Scheme 74 illustrates synthesis of instant compounds that incorporate a preferred imidazolyl moiety connected to the biaryl via an alkyl amino, sulfonamide or amide linker. Thus, the 4-aminoalkylimidazole XII, wherein the primary amine is protected as the phthalimide, is selectively alkylated then deprotected to provide the amine XIII. The amine XIII may then react under conditions well known in the art with various activated biheteroaryl moieties to provide the instant compounds shown.

Compounds of the instant invention wherein the $A^1(CR^1{}_2)_nA^2(CR^1{}_2)_n$ linker is oxygen may be synthesized by methods known in the art, for example as shown in Scheme 75. The suitably substituted phenol XIV may be reacted with methyl N-(cyano)methanimidate to provide the 4-phenoxyimidazole XV. After selective protection of one of the imidazolyl nitrogens, the intermediate XVI can undergo alkylation reactions as described for the benzylimidazoles hereinabove.

Scheme 76 illustrates an analogous series of reactions wherein the $(CR^2{}_2)_pX(CR^2{}_2)_p$ linker of the instant compounds is oxygen. Thus, a suitably substituted halopyridinol, such as 3-chloro-2-pyridinol, is reacted with methyl N-(cyano)methanimidate to provide intermediate XVI. Intermediate XVI is then protected and, if desired to form a compound of a preferred embodiment, alkylated with a suitably protected benzyl. The intermediate XVII can then be coupled to a heteroaryl moiety by Suzuki chemistry to provide the instant compound.

Compounds of the instant invention wherein the $A^1(CR^1{}_2)_nA^2(CR^1{}_2)_n$ linker is a substituted methylene may be synthesized by the methods shown in Scheme 77. Thus, the N-protected imidazolyl iodide XVIII is reacted, under Grignard conditions with a suitably protected benzaldehyde to provide the alcohol XIX. Acylation, followed by the alkylation procedure illustrated in the Schemes above (in particular, Scheme 67) provides the instant compound XX. If other $R^1$ substituents are desired, the acetyl moiety can be manipulated as illustrated in the Scheme.

Scheme 78 illustrates the use of halogenated 2-amino-pyrimidine in the preparation of compounds of the instant invention.

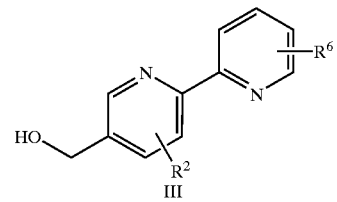

III

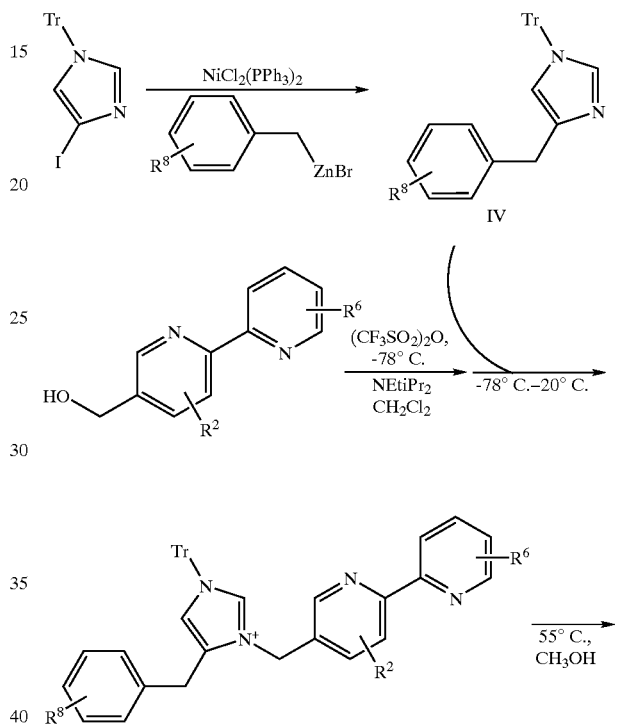

V

SCHEME 67

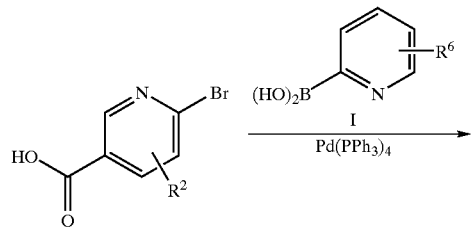

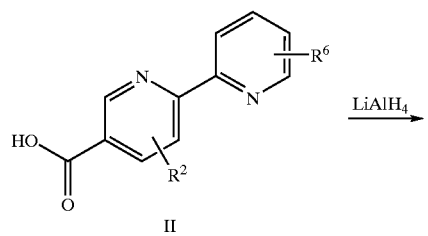

II

SCHEME 68

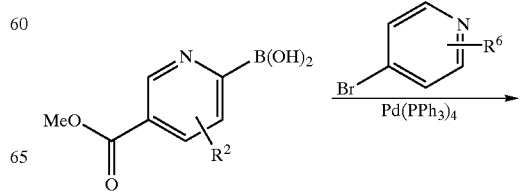

127
-continued
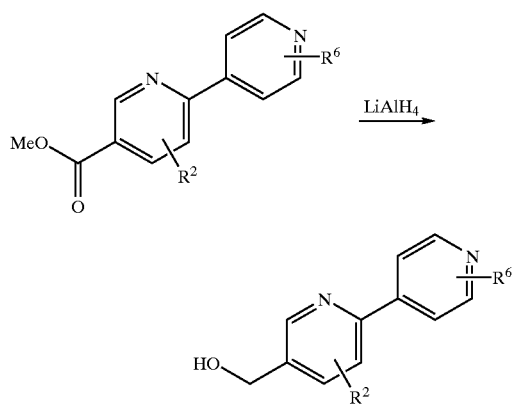
SCHEME 69
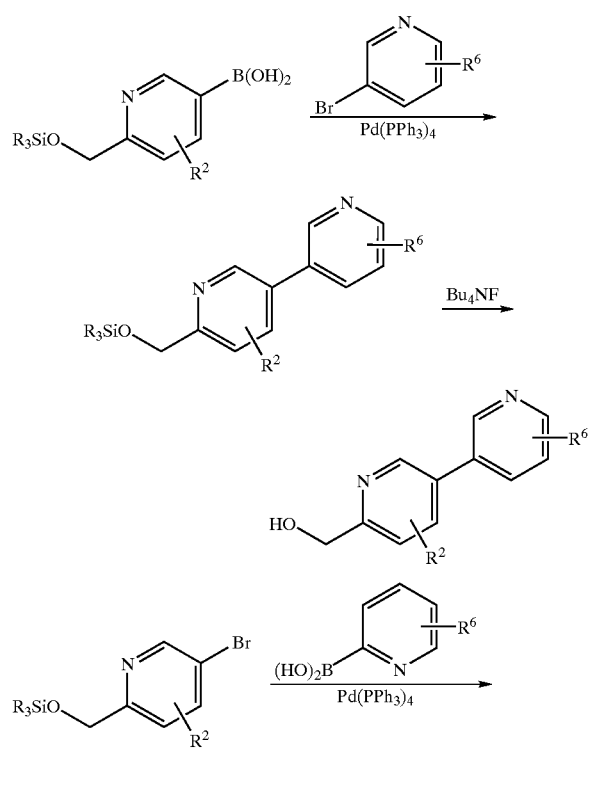
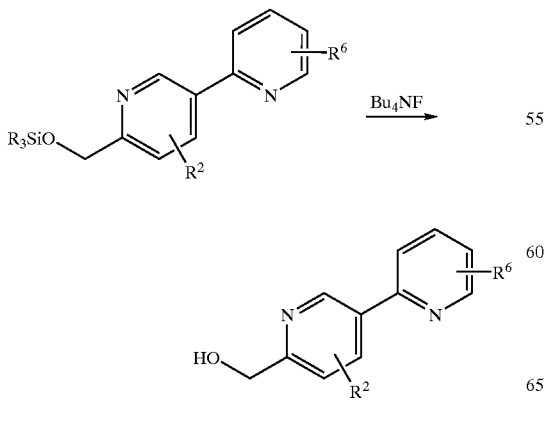
128
SCHEME 70
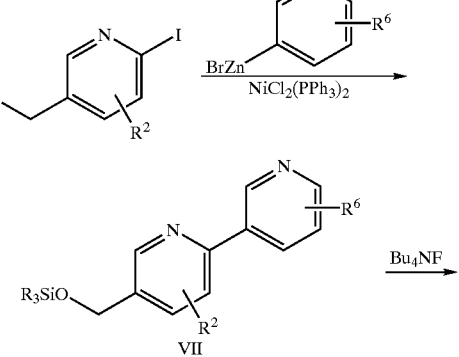
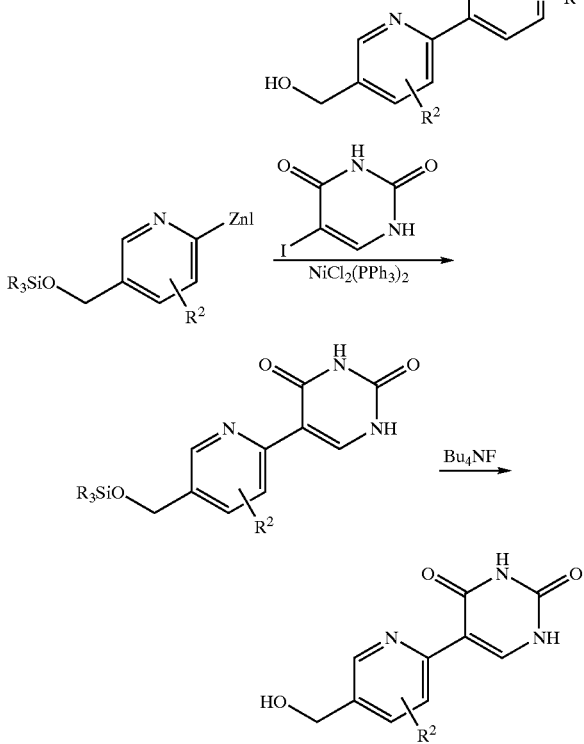
SCHEME 71
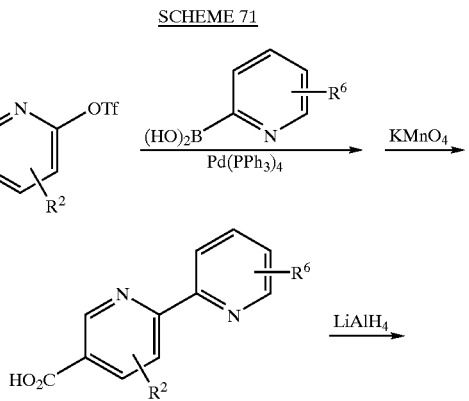

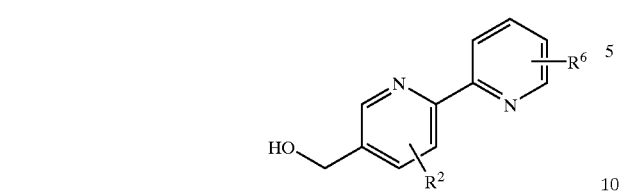
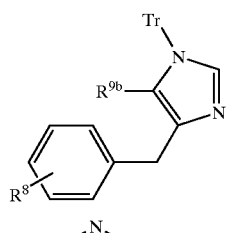
SCHEME 72
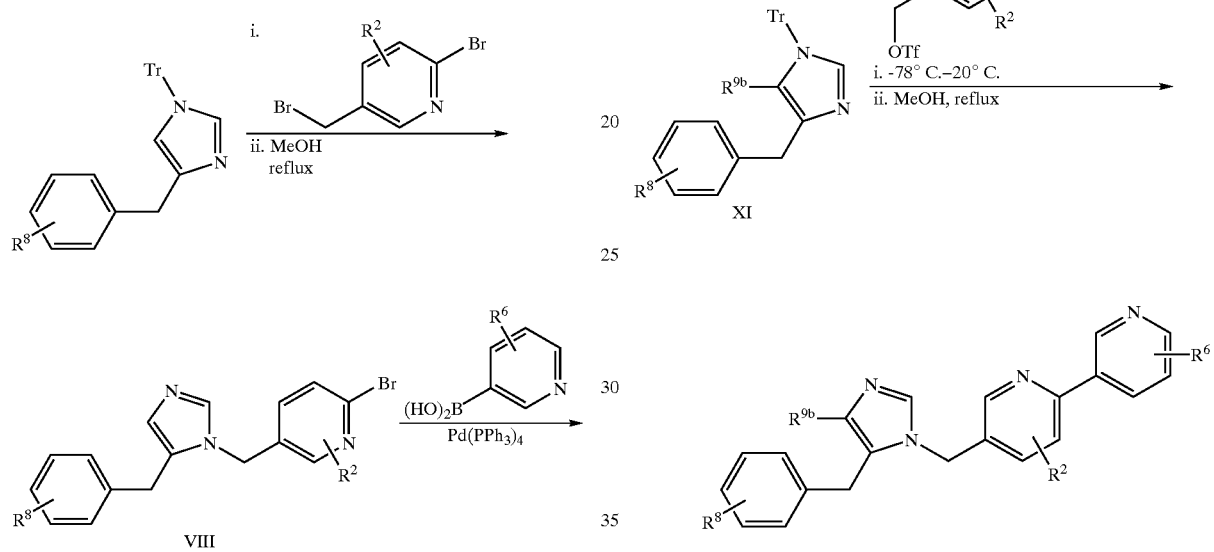
SCHEME 73
SCHEME 74
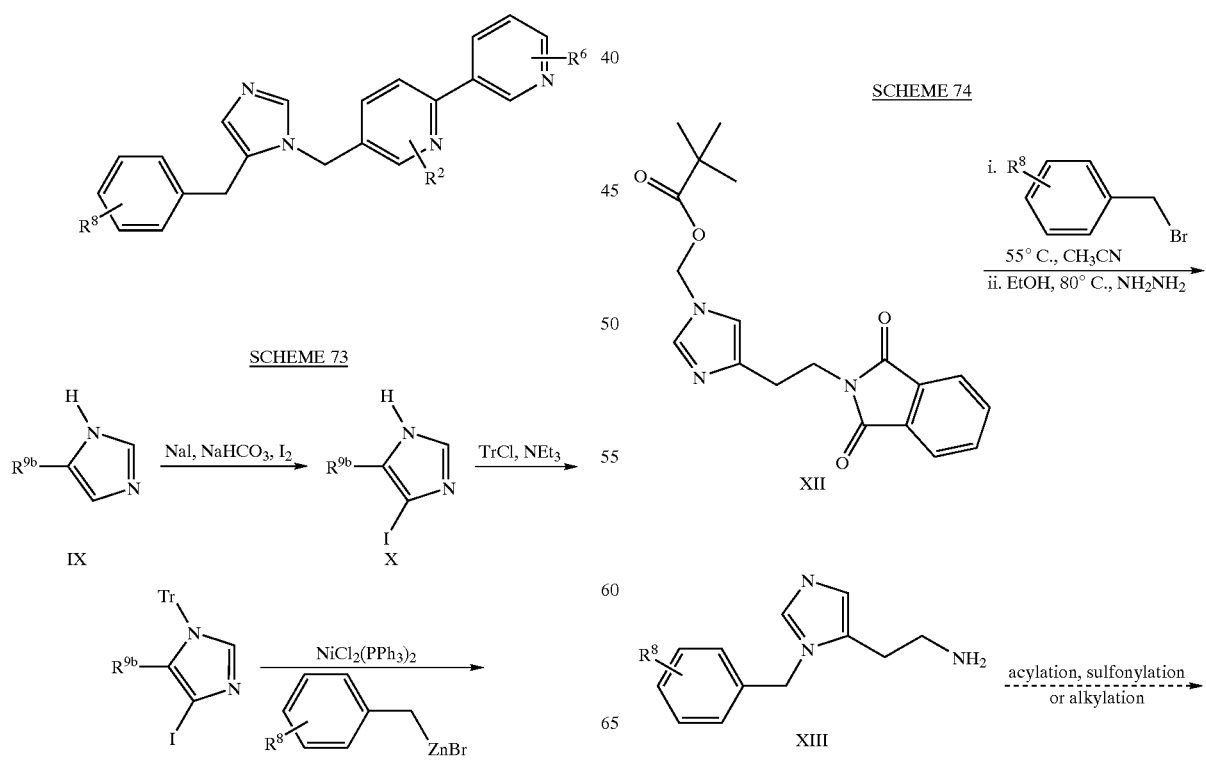

131
-continued
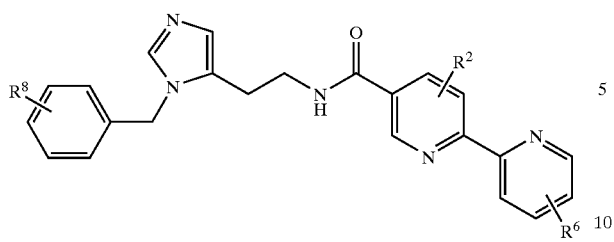
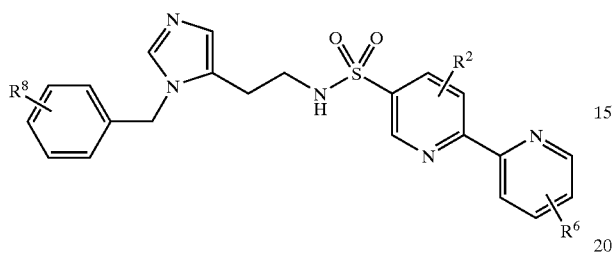
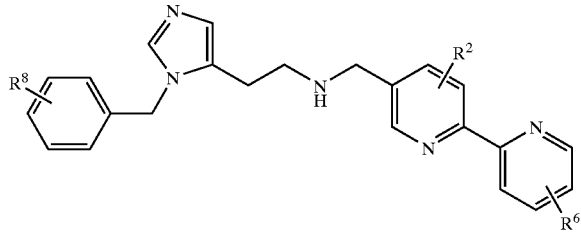
SCHEME 75
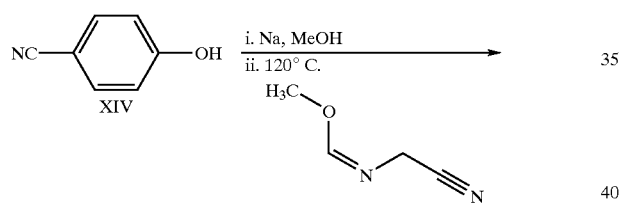
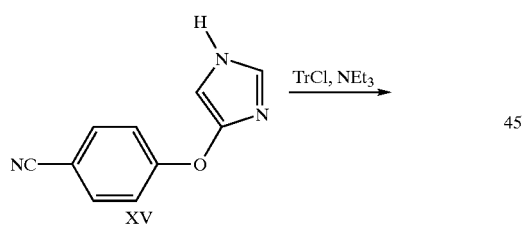
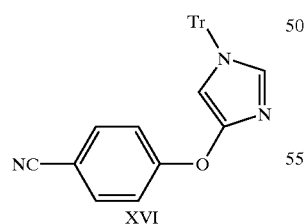
132
-continued
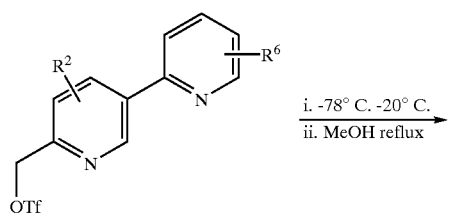
i. -78° C. -20° C.
ii. MeOH reflux
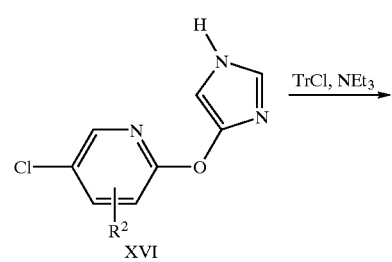
SCHEME 76
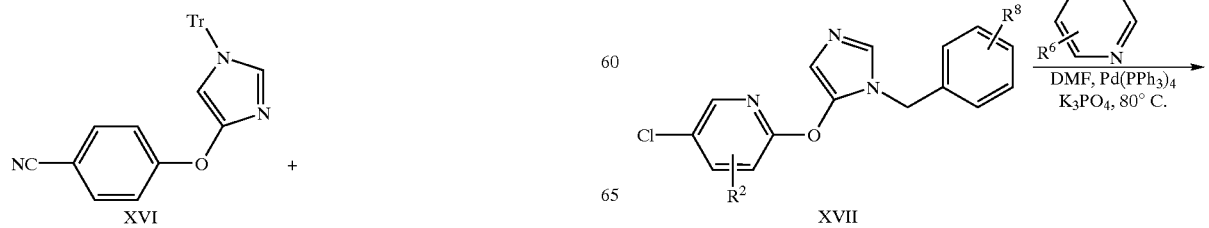

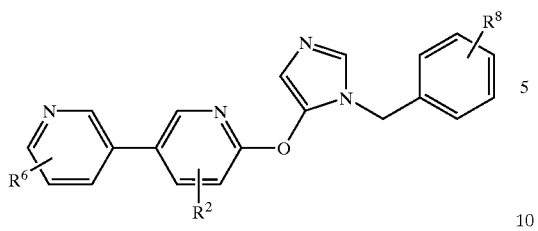

SCHEME 77

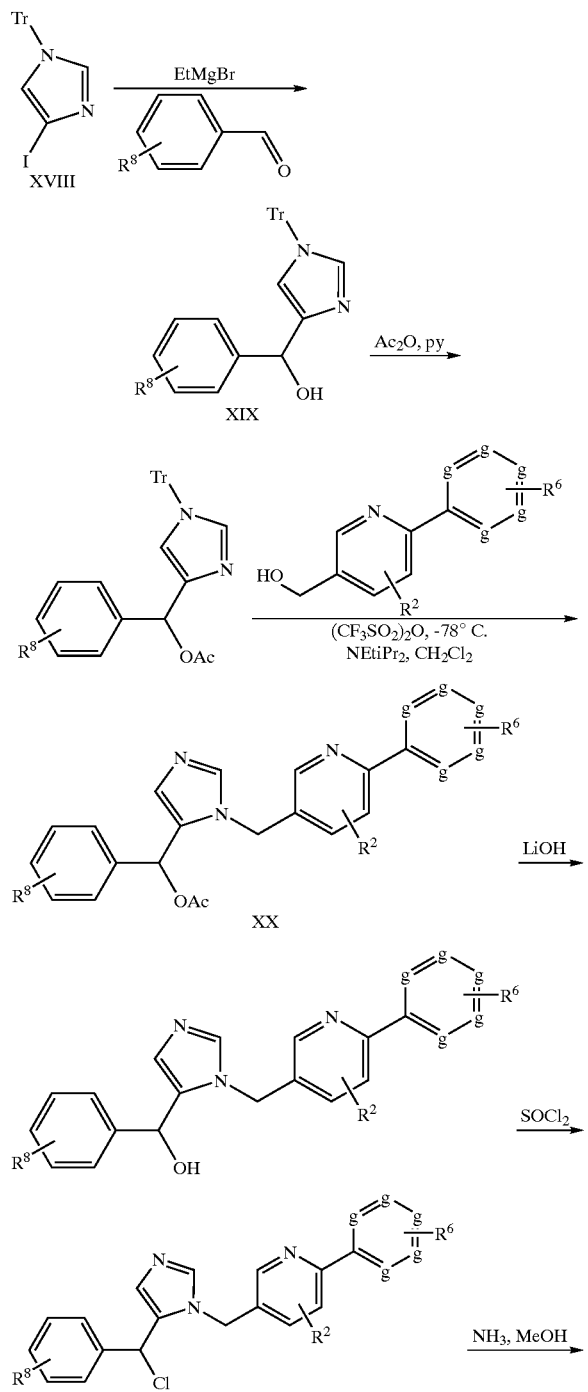

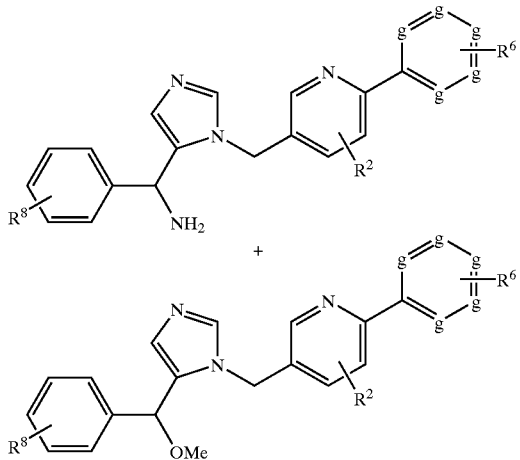

SCHEME 78

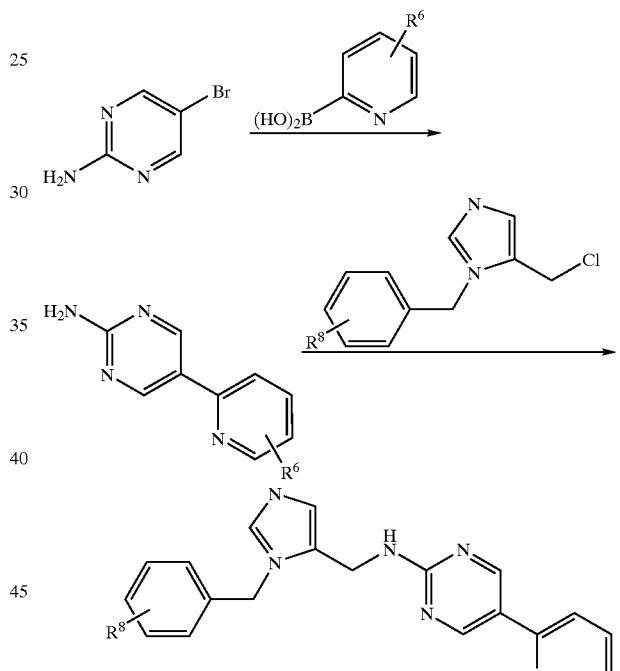

The farnesyl transferase inhibitors of formula (II-j) can be synthesized in accordance with Schemes 79–88, in addition to other standard manipulations such as ester hydrolysis, cleavage of protecting groups, etc., as may be known in the literature or exemplified in the experimental procedures. Substituents $R^3$, $R^6$ and $R^8$, as shown in the Schemes, represent the substituents $R^3$, $R^4$, $R^5$, $R^{6a}$, $R^{6b}$, $R^{6c}$, $R^{6d}$, $R^{6e}$ and $R^8$; although only one such $R^3$, $R^6$ or $R^8$ is present in the intermediates and products of the schemes, it is understood that the reactions shown are also applicable when such aryl or heterocyclic moieties contain multiple substituents.

These reactions may be employed in a linear sequence to provide the compounds of the invention or they may be used to synthesize fragments which are subsequently joined by the alkylation reactions described in the Schemes. The reactions described in the Schemes are illustrative only and are not meant to be limiting. Other reactions useful in the preparation of heteroaryl moieties are described in "Comprehensive Organic Chemistry, Volume 4: Heterocyclic Compounds" ed. P. G. Sammes, Oxford (1979) and references therein.

Synopsis of Schemes 79–88:

The requisite intermediates are in some cases commercially available, or can be prepared according to literature procedures. Schemes 79–88 illustrate synthesis of the instant bicyclic compounds which incorporate a preferred benzylimidazolyl side chain. Thus, in Scheme 79, for example, a bicyclic intermediate that is not commercially available may be synthesized by methods known in the art. Thus, a suitably substituted pyridinone I may be reacted under coupling conditions with a suitably substituted iodobenzyl alcohol to provide the intermediate alcohol 2. The intermediate alcohol 2 may converted to the corresponding bromide 3. The bromide 3 may be coupled to a suitably substituted benzylimidazolyl 4 to provide, after deprotection, the instant compound 5.

Schemes 80–82 illustrate methods of synthesizing related or analogous key alcohol intermediates, which can then be processed as described in Scheme 79. Thus, Scheme 80 illustrates pyridinonylpyridyl alcohol forming reactions starting with the suitably substituted iodonicotinate 6.

Scheme 81 illustrates preparation of the intermediate alcohol 9 wherein the terminal lactam ring is saturated. Acylation of a suitably substituted 4-aminobenzyl alcohol 7 with a suitably substituted brominated acyl chloride provides the bisacylated intermediate 8. Closure of the lactam ring followed by saponifiaction of the remaining acyl group provides the intermediate alcohol. Preparation of the homologous saturated lactam 10 is illustrated in Scheme 82.

Scheme 83 illustrates the synthesis of the alcohol intermediate 13 which incorporates a terminal pyrazinone moiety. Thus, the amide of a suitably substituted amino acid 11 is formed and reacted with glyoxal to form the pyrazine 12, which then undergoes the Ullmann coupling to form intermediate 13.

Scheme 84 illustrates synthesis of an instant compound wherein a non-hydrogen $R^{9b}$ is incorporated in the instant compound. Thus, a readily available 4-substituted imidazole 14 may be selectively iodinated to provide the 5-iodoimidazole 15. That imidazole may then be protected and coupled to a suitably substituted benzyl moiety to provide intermediate 16. Intermediate 16 can then undergo the alkylation reactions that were described hereinabove.

Scheme 85 illustrates synthesis of instant compounds that incorporate a preferred imidazolyl moiety connected to the bicyclic moiety via an alkyl amino, sulfonamide or amide linker. Thus, the 4-aminoalkylimidazole 17, wherein the primary amine is protected as the phthalimide, is selectively alkylated then deprotected to provide the amine 18. The amine 18 may then react under conditions well known in the art with various activated bicyclic moieties to provide the instant compounds shown.

Compounds of the instant invention wherein the $A^1(CR^1{}_2)_nA^2(CR^1{}_2)_n$ linker is oxygen may be synthesized by methods known in the art, for example as shown in Scheme 86. The suitably substituted phenol 19 may be reacted with methyl N-(cyano)methanimidate to provide the 4phenoxyimidazole 20. After selective protection of one of the imidazolyl nitrogens, the intermediate 21 can undergo alkylation reactions as described for the benzylimidazoles hereinabove.

Compounds of the instant invention wherein the $A^1(CR^1{}_2)_nA^2(CR^1{}_2)_n$ linker is a substituted methylene may be synthesized by the methods shown in Scheme 87. Thus, the N-protected imidazolyl iodide 22 is reacted, under Grignard conditions with a suitably protected benzaldehyde to provide the alcohol 23. Acylation, followed by the alkylation procedure illustrated in the Schemes above (in particular, Scheme 79) provides the instant compound 24. If other $R^1$ substituents are desired, the acetyl moiety can be manipulated as illustrated in the Scheme.

Scheme 88 illustrates incorporation of an acetyl moiety as the $(CR^2{}_2)_pX(CR^2{}_2)_p$ linker of the instant compounds. Thus the readily available methylphenone 25 undergoes the Ullmann reaction and the acetyl is brominated to provide intermediate 26. Reaction with the imidazolyl reagent 4 provides, after deprotection, the instant compound 27.

SCHEME 79

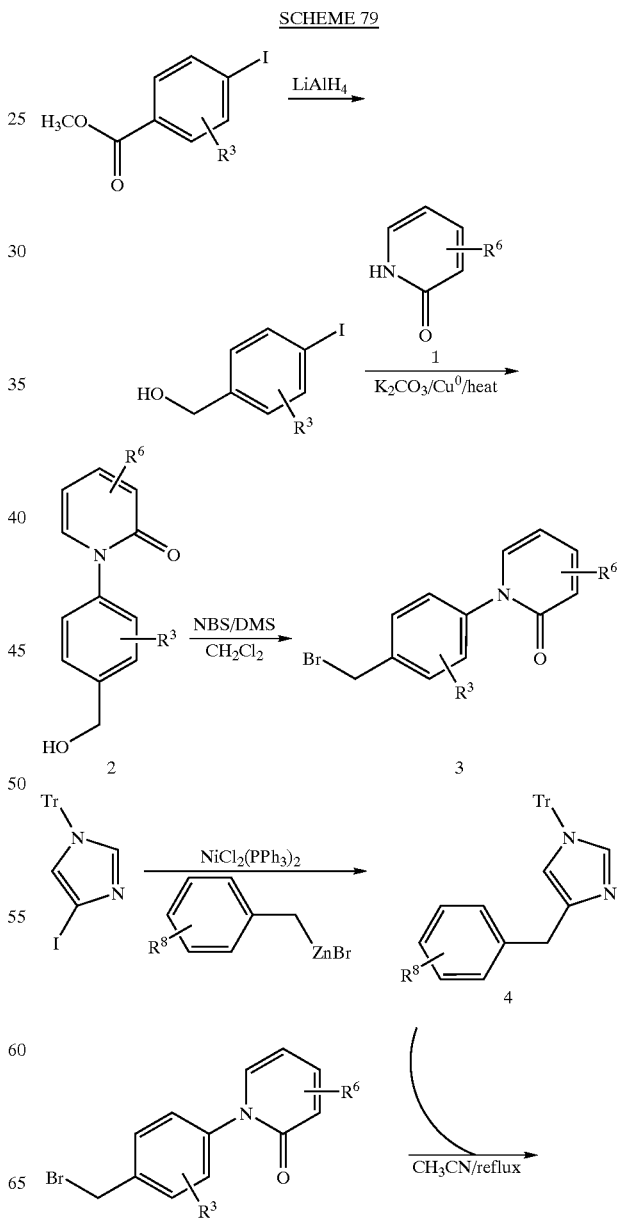

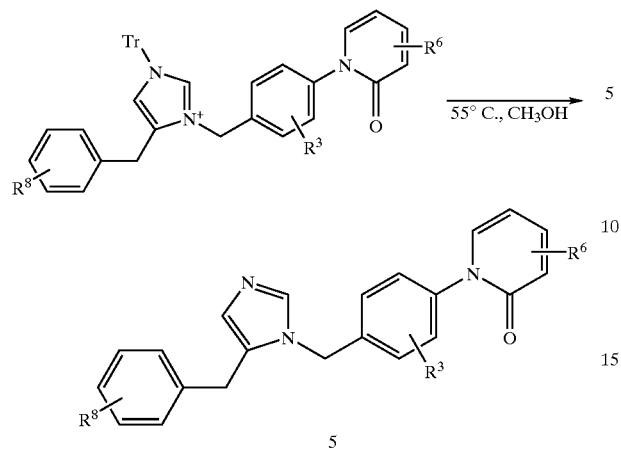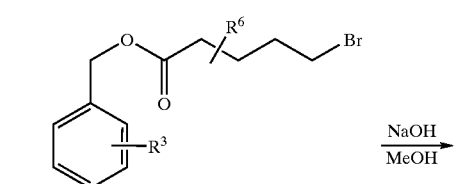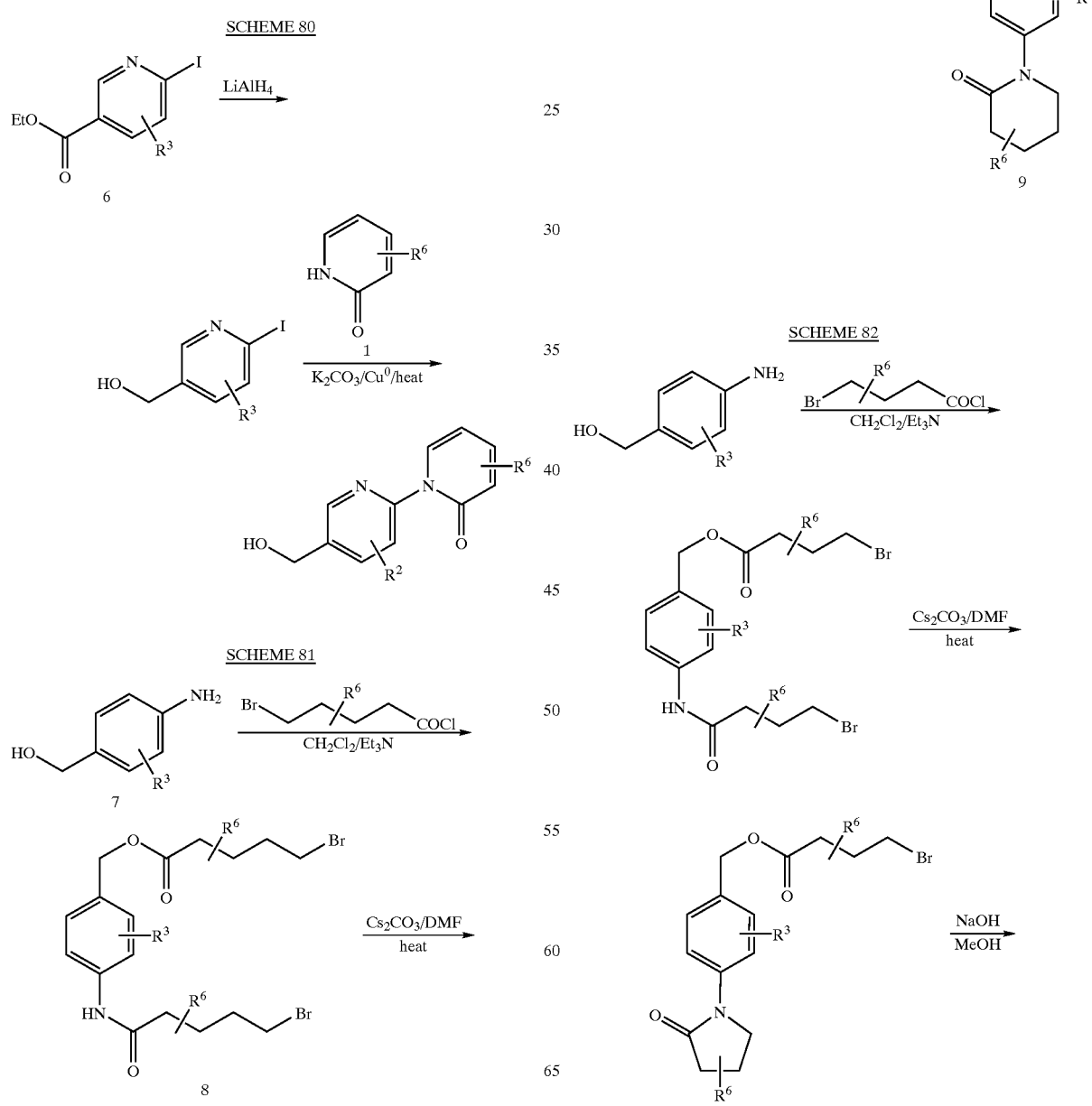

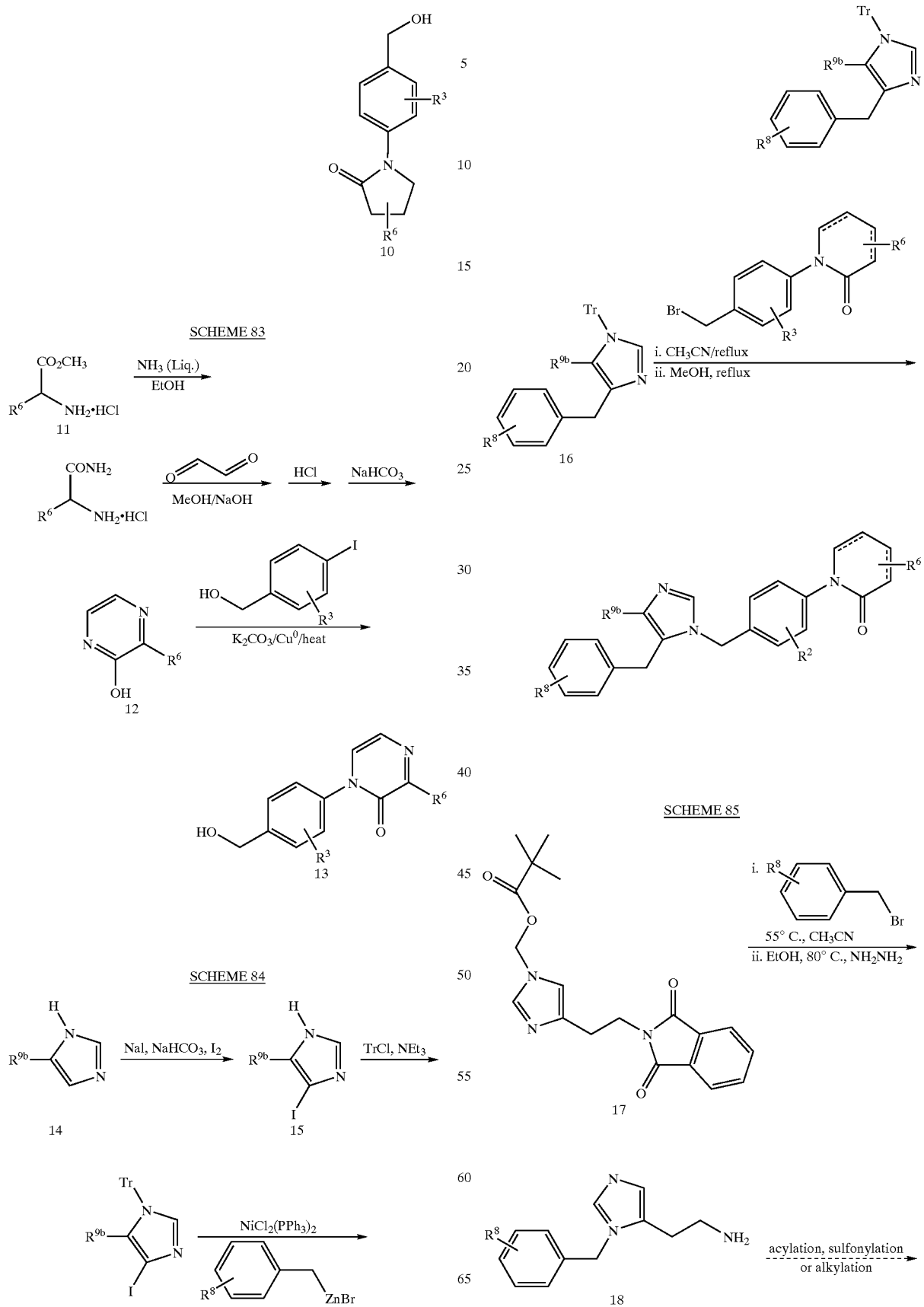

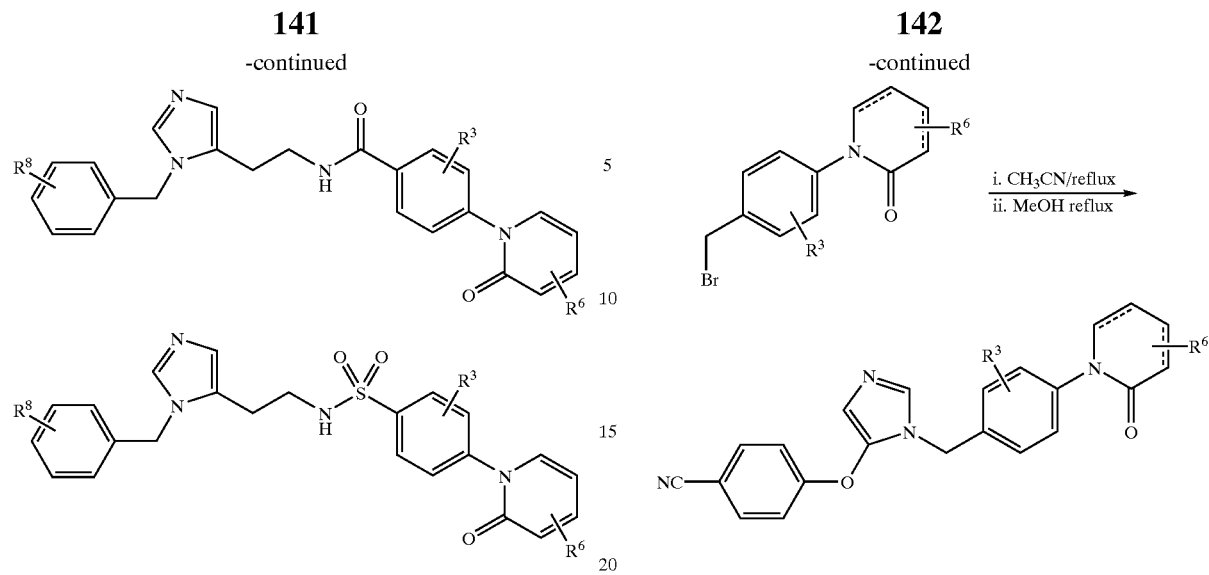
SCHEME 86
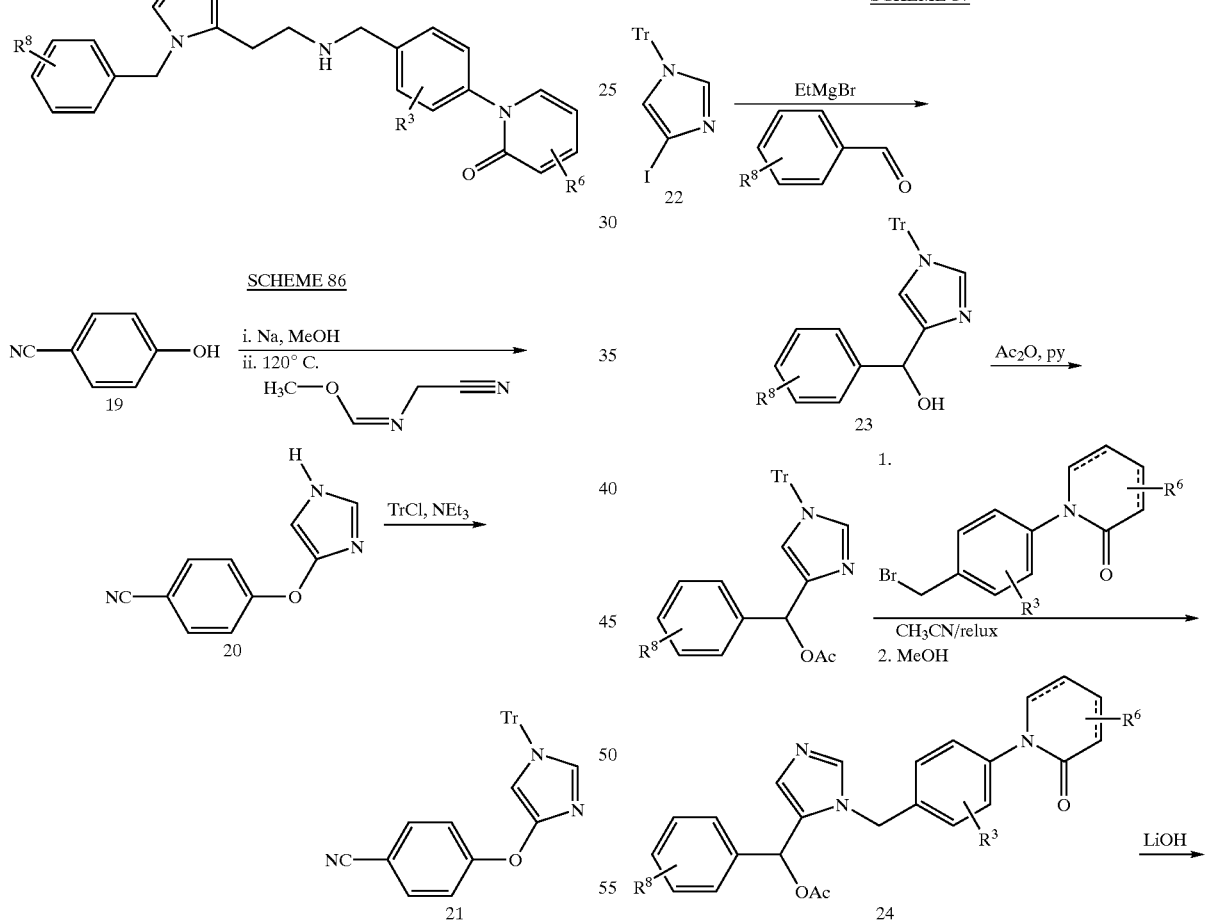
SCHEME 87
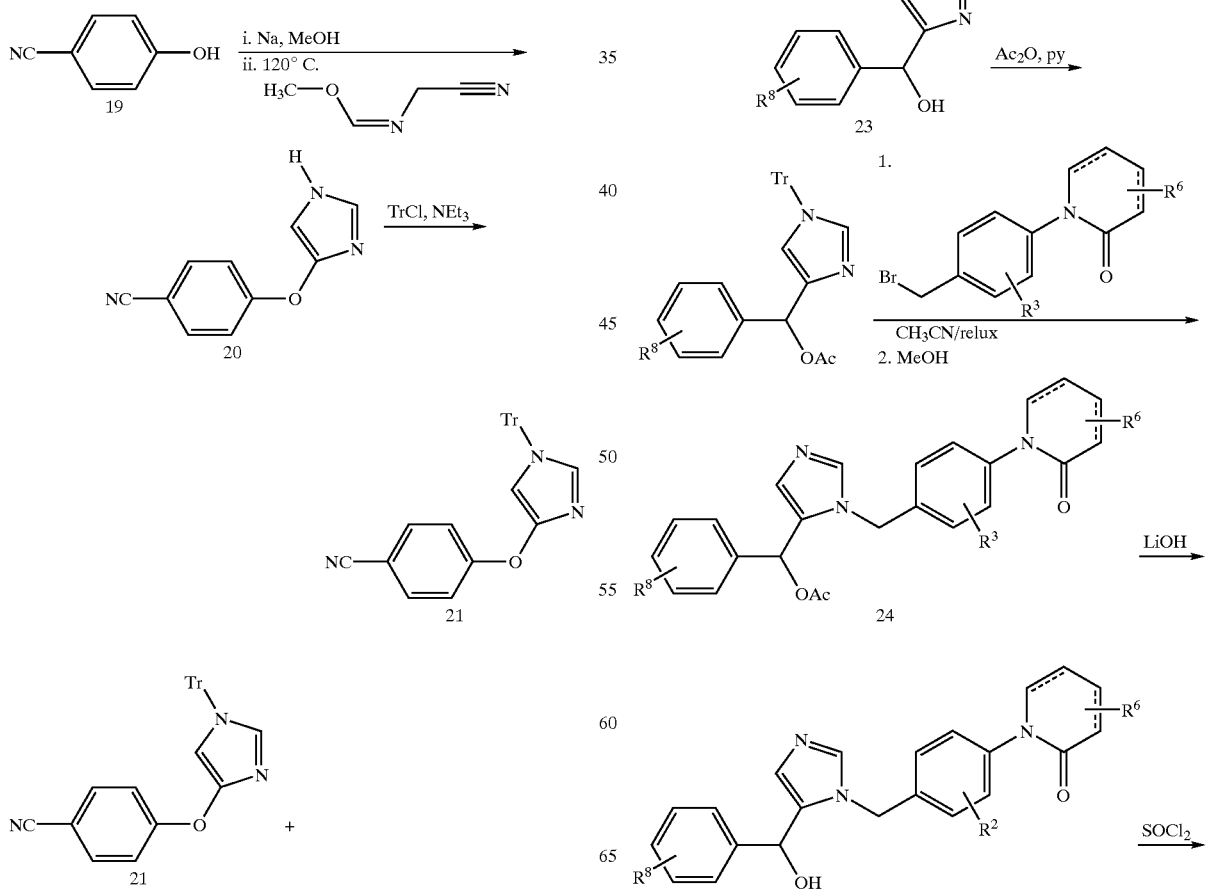

-continued

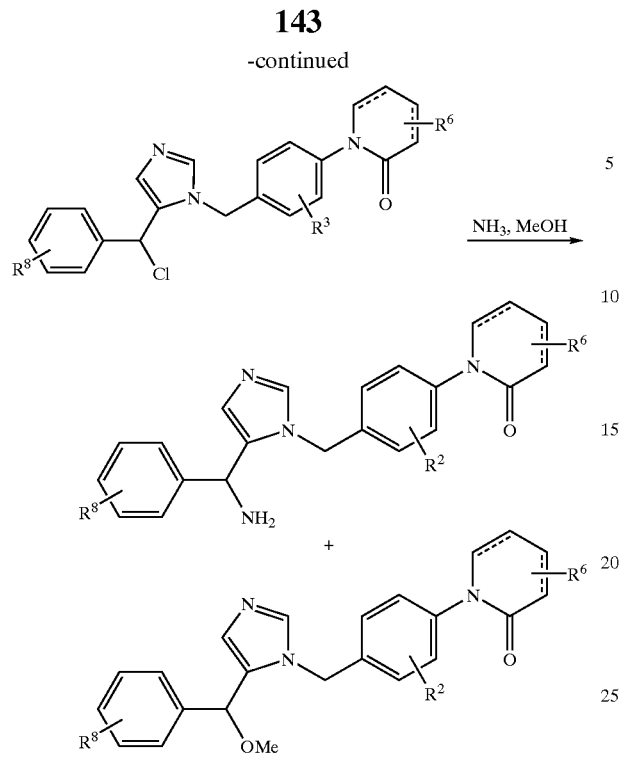

SCHEME 88

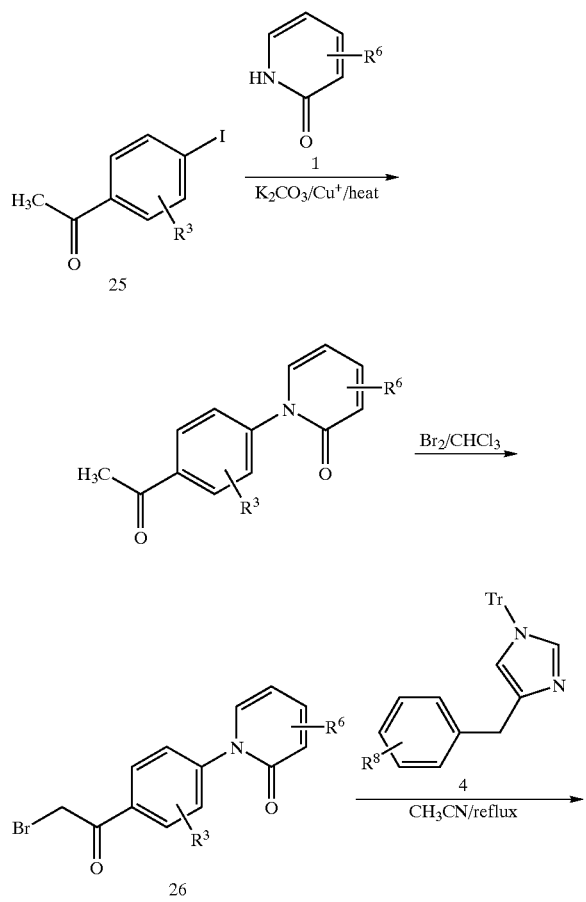

-continued

The farnesyl transferase inhibitors of formula (II-k) can be synthesized in accordance with Schemes 89–97, in addition to other standard manipulations such as ester hydrolysis, cleavage of protecting groups, etc., as may be known in the literature or exemplified in the experimental procedures. Substituents $R^3$, $R^6$ and $R^8$, as shown in the Schemes, represent the substituents $R^3$, $R^4$, $R^5$, $R^{6a}$, $R^{6b}$, $R^{6c}$, $R^{6d}$, $R^{6e}$ and $R^8$; although only one such $R^3$, $R^6$ or $R^8$ is present in the intermediates and products of the schemes, it is understood that the reactions shown are also applicable when such aryl or heterocyclic moieties contain multiple substituents.

These reactions may be employed in a linear sequence to provide the compounds of the invention or they may be used to synthesize fragments which are subsequently joined by the alkylation reactions described in the Schemes. The reactions described in the Schemes are illustrative only and are not meant to be limiting. Other reactions useful in the preparation of heteroaryl moieties are described in "Comprehensive Organic Chemistry, Volume 4: Heterocyclic Compounds" ed. P. G. Sammes, Oxford (1979) and references therein.

Synopsis of Schemes 89–97:

The requisite intermediates are in some cases commercially available, or can be prepared according to literature procedures. Schemes 89–96 illustrate synthesis of the instant bicyclic compounds which incorporate a preferred benzylimidazolyl side-chain. Thus, in Scheme 89, for example, a bicyclic intermediate that is not commercially available may be synthesized by methods known in the art. Thus, a suitably substituted pyridinonyl alcohol 29 may be synthesized starting from the corresponding isonicotinate 28 according to procedures described by Boekelhiede and Lehn (*J. Org. Chem.*, 26:428–430 (1961)). The alcohol is then protected and reacted under Ullmann coupling conditions with a suitably substituted phenyl iodide, to provide the intermediate bicyclic alcohol 30. The intermediate alcohol 30 may converted to the corresponding bromide 31. The bromide 31 may be coupled to a suitably substituted benzylimidazolyl 32 to provide, after deprotection, the instant compound 33.

Schemes 90–92 illustrate methods of synthesizing related or alcohol intermediates, which can then be processed as described in Scheme 89. Thus, Scheme 90 illustrates preparation of a pyridyl-pyridinonyl alcohol and thienylpyridinonyl alcohol starting with the suitably substituted halogenated heterocycles.

Scheme 91 illustrates preparation of the intermediate bromide 36 wherein the preferred pyridinone is replced by a saturated lactam. Acylation of a suitably substituted aniline 34 with a suitably substituted brominated acyl chloride provides the acylated intermediate 35. Closure of the lactam ring provides the intermediate alcohol, which is converted to the bromide as described above.

Scheme 92 illustrates synthesis of an instant compound wherein a non-hydrogen $R^{9b}$ is incorporated in the instant compound. Thus, a readily available 4-substituted imidazole 37 may be selectively iodinated to provide the 5-iodoimidazole 38. That imidazole 38 may then be protected and coupled to a suitably substituted benzyl moiety to provide intermediate 39. Intermediate 39 can then undergo the alkylation reactions that were described hereinabove.

Scheme 93 illustrates synthesis of instant compounds that incorporate a preferred imidazolyl moiety connected to the biaryl via an alkyl amino, sulfonamide or amide linker. Thus, the 4-aminoalkylimidazole 40, wherein the primary amine is protected as the phthalimide, is selectively alkylated then deprotected to provide the amine 41. The amine 41 may then react under conditions well known in the art with various activated arylheteroaryl moieties to provide the instant compounds shown.

Compounds of the instant invention wherein the $A^1(CR^1{}_2)_nA^2(CR^1{}_2)_n$ linker is oxygen may be synthesized by methods known in the art, for example as shown in Scheme 94. The suitably substituted phenol 42 may be reacted with methyl N-(cyano)methanimidate to provide the 4-phenoxyimidazole 43. After selective protection of one of the imidazolyl nitrogens, the intermediate 44 can undergo alkylation reactions as described for the benzylimidazoles hereinabove.

Compounds of the instant invention wherein the $A^1(CR^1{}_2)_nA^2(CR^1{}_2)_n$ linker is a substituted methylene may be synthesized by the methods shown in Scheme 95. Thus, the N-protected imidazolyl iodide 45 is reacted, under Grignard conditions with a suitably protected benzaldehyde to provide the alcohol 46. Acylation, followed by the alkylation procedure illustrated in the Schemes above (in particular, Scheme 89) provides the instant compound 47. If other RI substituents are desired, the acetyl moiety can be manipulated as illustrated in the Scheme.

Scheme 96 illustrates incorporation of an acetyl moiety as the $(CR^2{}_2)_pX(CR^2{}_2)_p$ linker of the instant compounds.

Thus, the suitably substituted acetyl pyridine 48 is converted to the corresponding pyridinone and undergoes the Ullmann reaction with a suitably substituted phenyl iodide. The acetyl is then brominated to provide intermediate 49. Reaction with the imidazolyl reagent 32 provides, after deprotection, the instant compound 50.

Scheme 97 illustrate reactions wherein the moiety

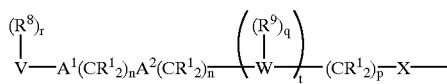

incorporated in the compounds of the instant invention is represented by other than a substituted imidazole-containing group.

Thus, the intermediates whose synthesis are illustrated in the Schemes, and other pyridinonecarbocyclic and pyridinoneheterocyclic intermediates obtained commercially or readily synthesized, can be coupled with a variety of aldehydes. The aldehydes can be prepared by standard procedures, such as that described by O. P. Goel, U. Krolls, M. Stier and S. Kesten in *Organic Syntheses,* 1988, 67, 69–75, from the appropriate amino acid. Knochel chemistry may be utilized, as shown in Scheme 97, to incorporate the arylpyridinone moiety. Thus, a suitably substituted 4-(bromo)-pyridine is converted to the corresponding pyridinone 51 as described above and the pyridinone is coupled to a suitably substituted phenyl iodide as previously described above. The resulting bromide 52 is treated with zinc(O) and the resulting zinc bromide reagent 53 is reacted with an aldehyde to provide the C-alkylated instant compound 54. Compound 54 can be deoxygenated by methods known in the art, such as a catalytic hydrogention, then deprotected with trifluoroacetic acid in methylene chloride to give the final compound 55. The compound 55 may be isolated in the salt form, for example, as a trifluoroacetate, hydrochloride or acetate salt, among others. The product diamine 55 can further be selectively protected to obtain 56, which can subsequently be reductively alkylated with a second aldehyde to obtain compound 57. Removal of the protecting group, and conversion to cyclized products such as the dihydroimidazole 58 can be accomplished by literature procedures.

SCHEME 89

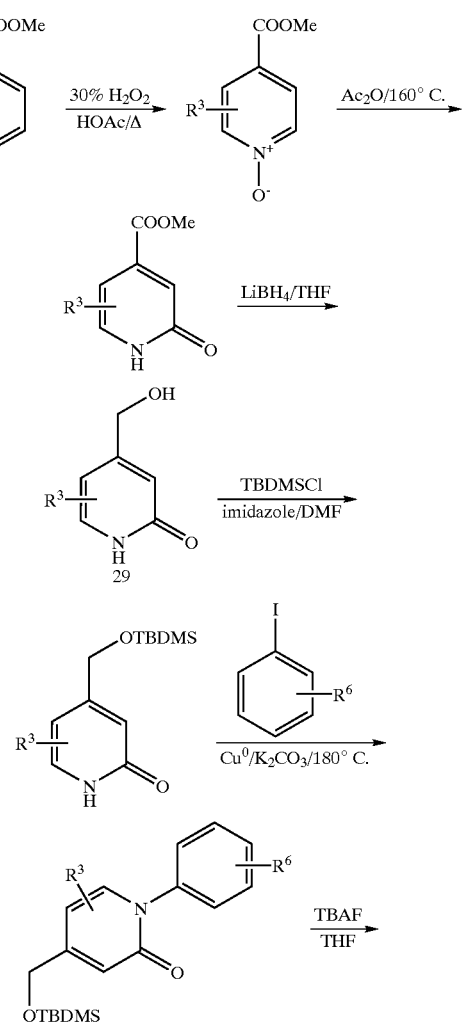

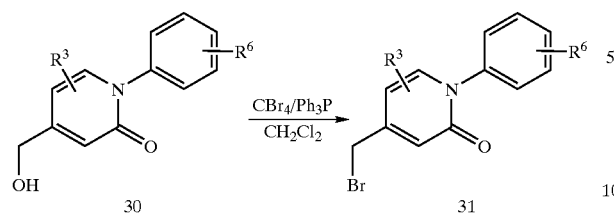
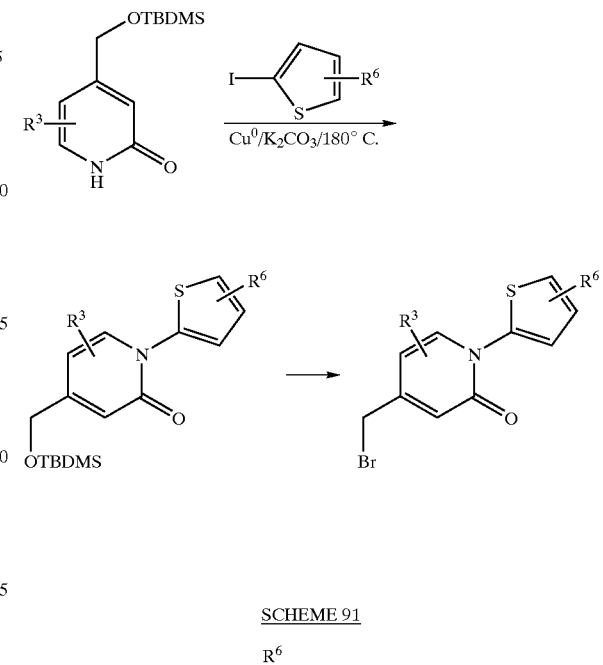
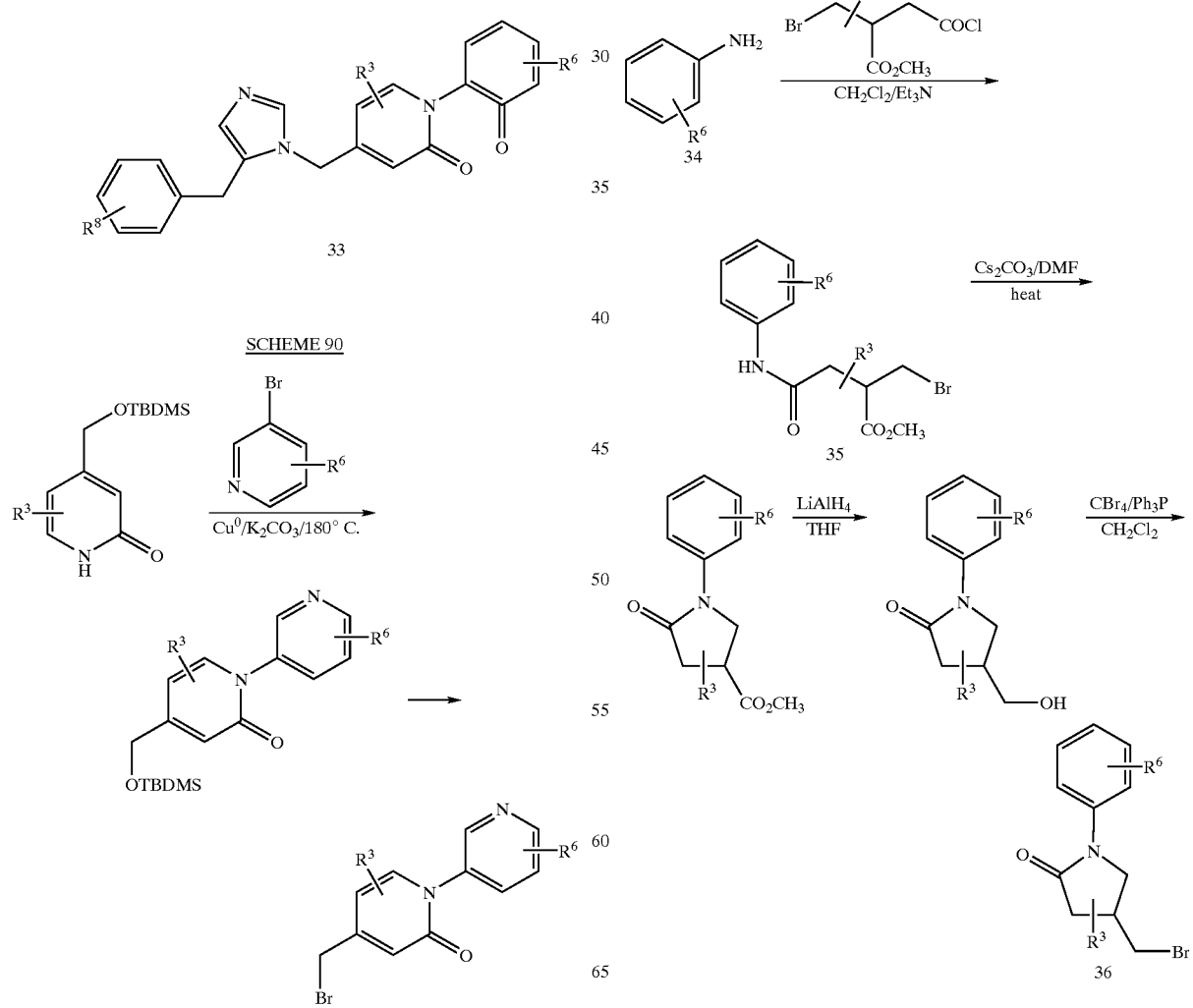

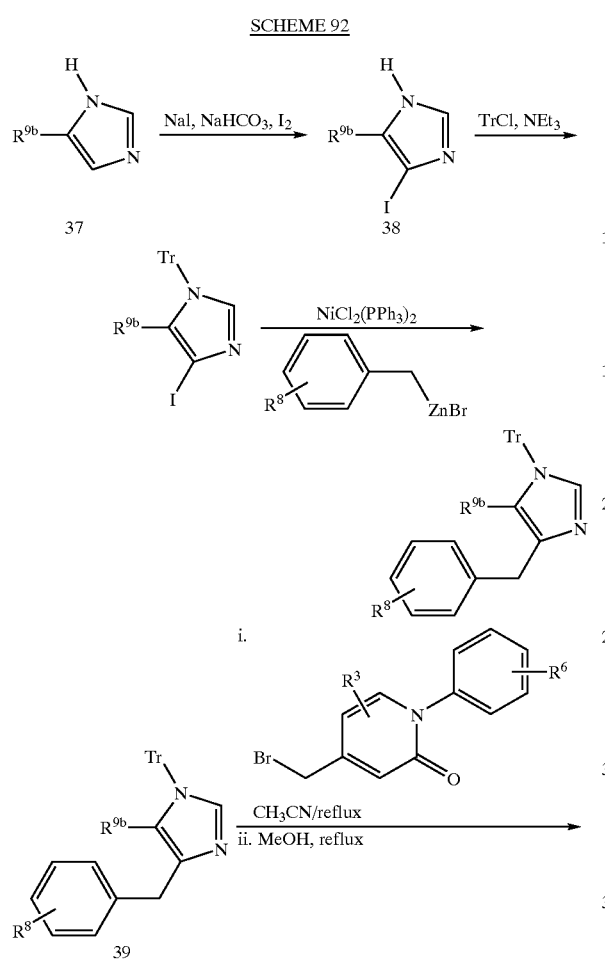
SCHEME 92
SCHEME 93
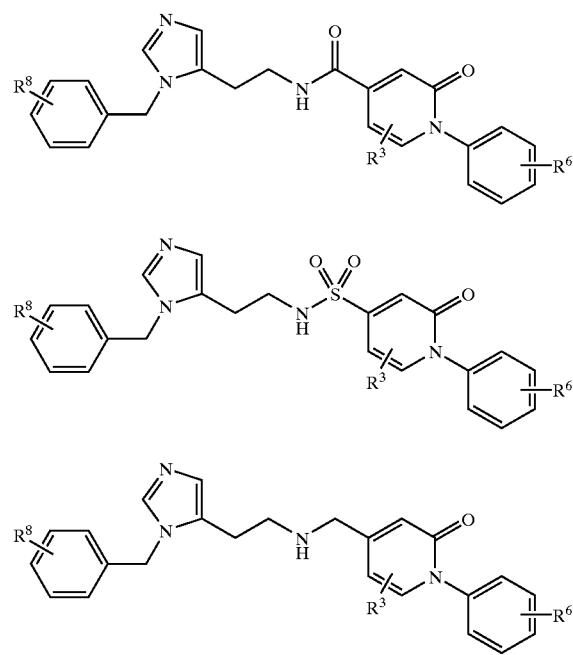
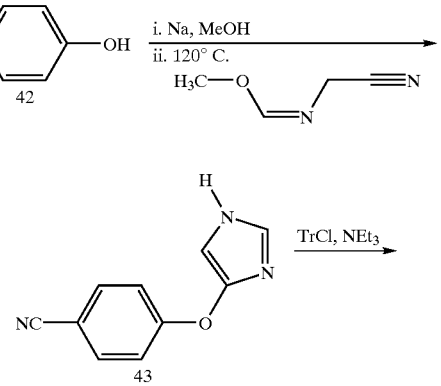
SCHEME 94
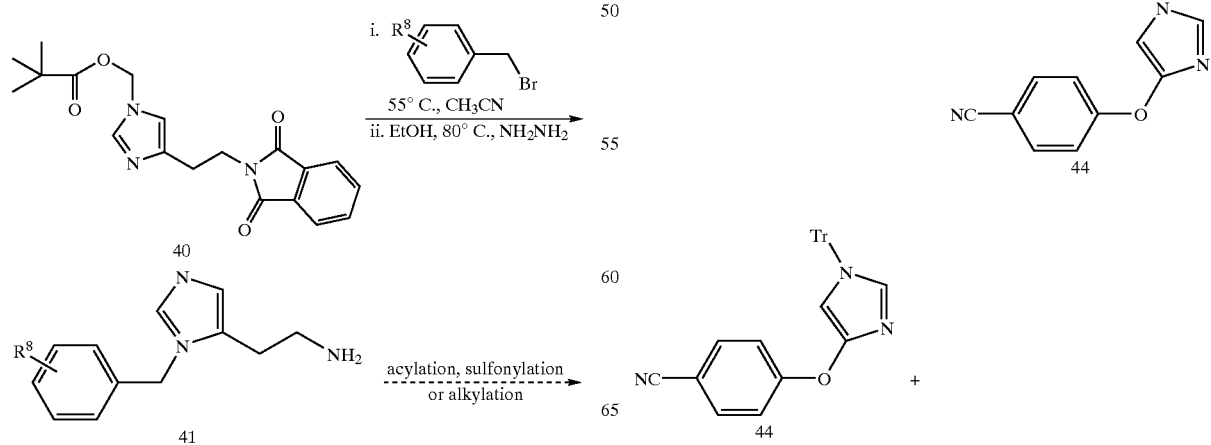

151
-continued
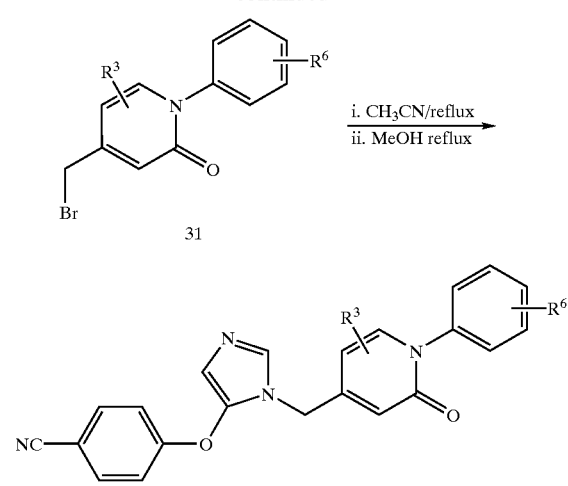
SCHEME 95
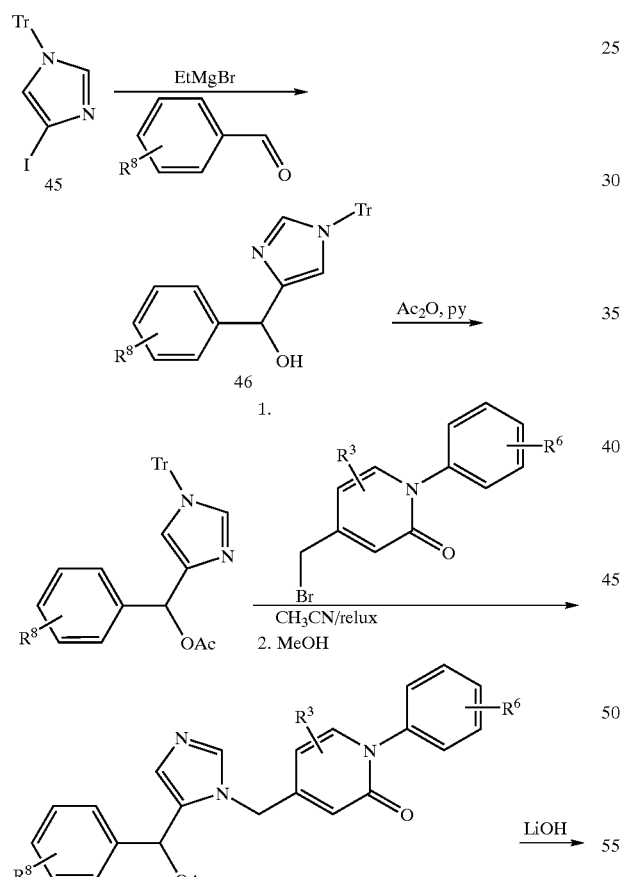
152
-continued
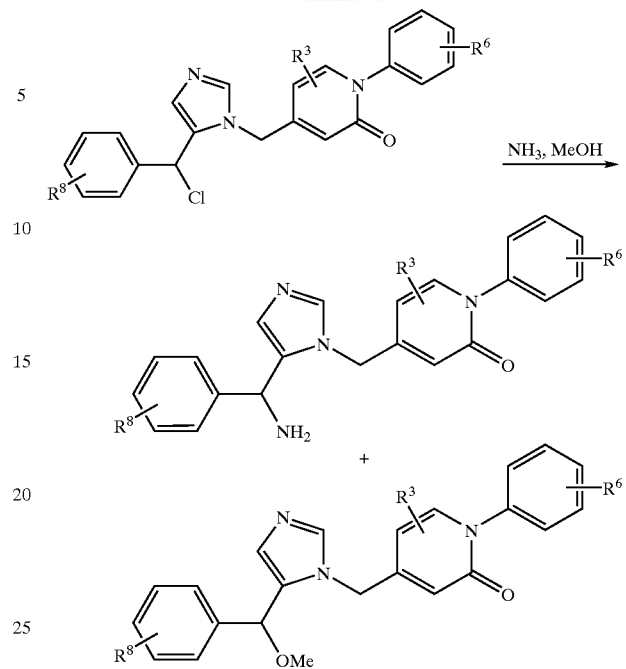
SCHEME 96
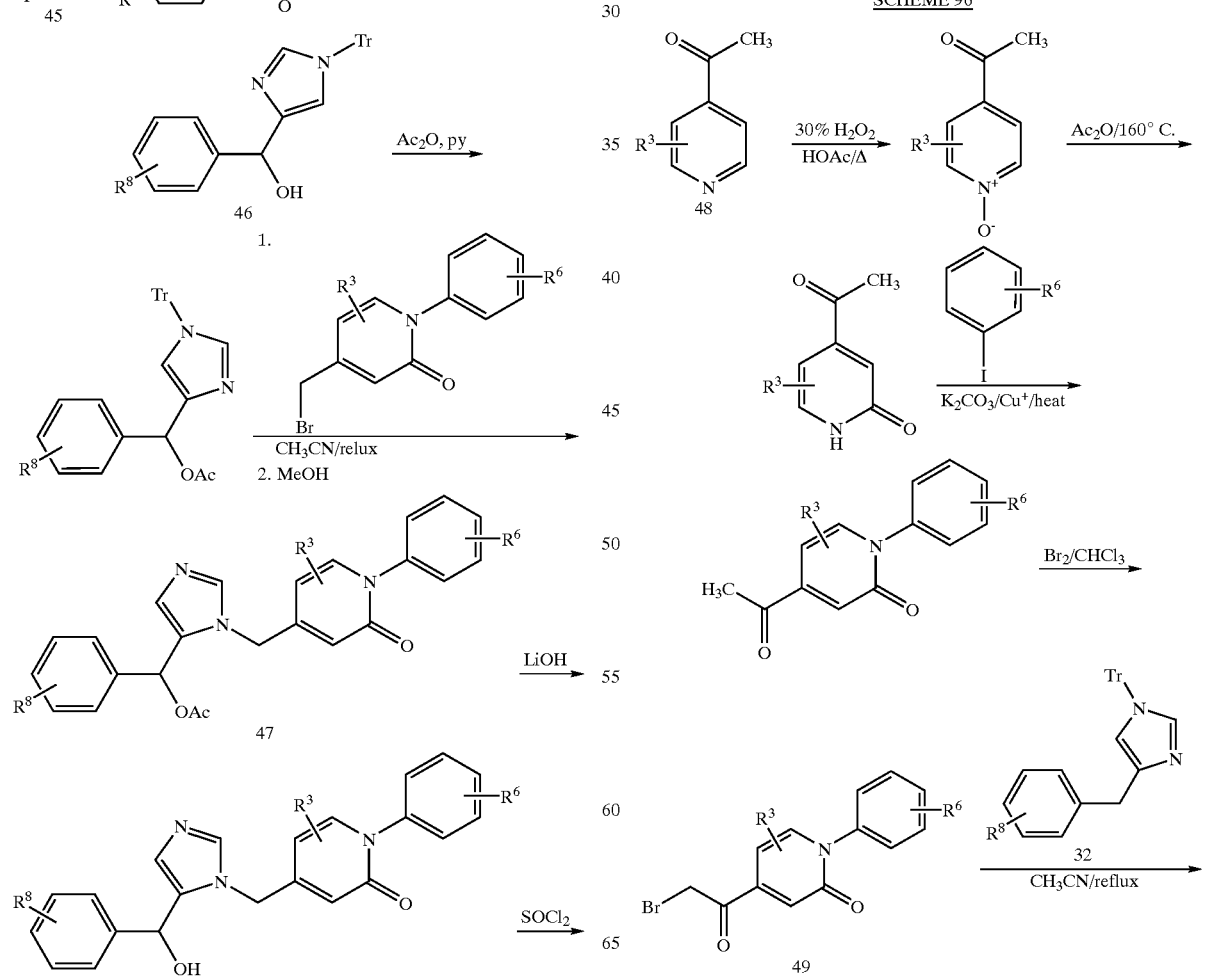

-continued

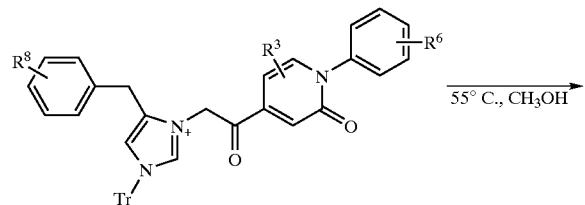

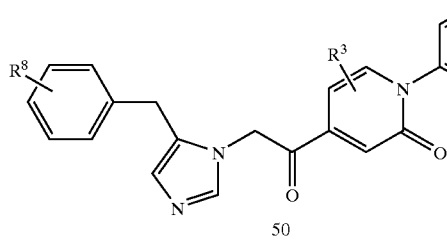

SCHEME 97

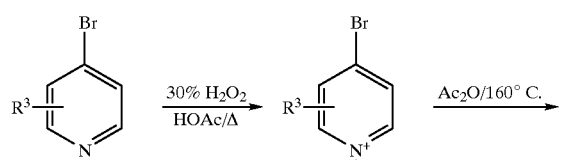

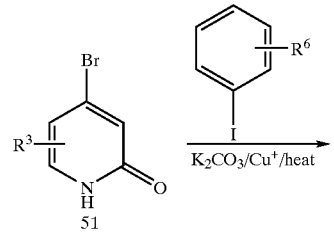

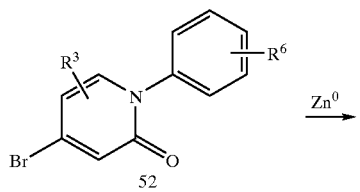

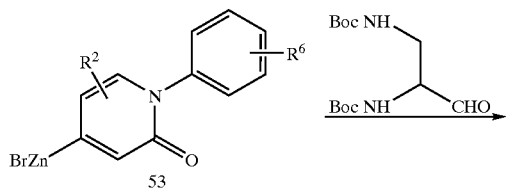

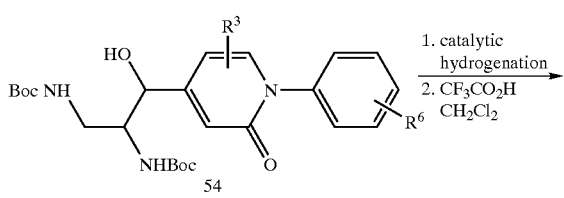

-continued

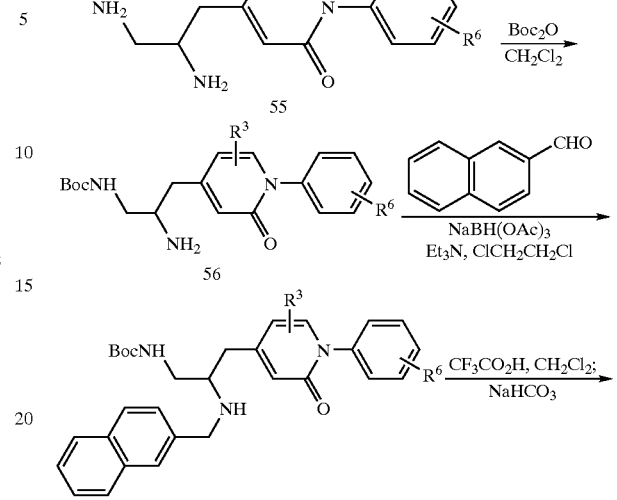

The farnesyl transferase inhibitors of formula (II-i) can be synthesized in accordance with Reaction Schemes, in addition to other *standard manipulations such as ester hydrolysis, cleavage of protecting groups, etc., as may be known in the literature or exemplified in the experimental procedures. Some key reactions utilized to form the amino-diphenyl moiety of the instant compounds are shown.

These reactions may be employed in a linear sequence to provide the compounds of the invention or they may be used to synthesize fragments which are subsequently joined by the alkylation reactions described in the Reaction Schemes.

Reaction Schemes A–P describe the preparation of appropriately substituted aniline intermediates that may be further functionalized by the methods described in Reaction Schemes Q–Y to provide the compounds of the instant invention.

Reaction Schemes A–D illustrate use of Ullman reactions to provide diphenyl ethers, amines and sulfides from readily available fully substituted phenols/thiophenols/anilines and aryl halides. In such syntheses, the desired amine moiety is typically masked as a nitro group which is subsequently reduced by techniques well known in the art. An alternative synthesis of the diphenyl ethers which employs para-nitro fluorobenzene is shown in Reaction Scheme E.

Reaction Scheme F illustrates standard acid-amine coupling to provide the fully substituted N-phenylbenzamides. Reaction Scheme G illustrates formation of the aminomethyl spacer via a reductive amination of a suitably substituted benzaldehyde.

Reaction Scheme H illustrates coupling of suitably substituted anilines with readily available phenylsulfonyl chlorides. Access to aminobenzophenones is illustrated in Reaction Scheme I, which also illustrates the reduction of the carbonyl to provide the unsubstituted methyl spacer. An alternative method of forming the benzophenone intermediates is illustrated in Reaction Scheme J. Also shown in Reaction Scheme J is reductive amination of the resulting carbonyl to provide the amine substituted methyl spacer. Another method of forming the benzophenone intermediates, illustrated in Reaction Scheme K, is a Stille reaction with an aryl stannane.

Reaction Schemes L and M illustrate palladium mediated formation of olefin and acetylene spacer units. Reaction Scheme N illustrates formation of an appropriately substituted benzyl ether. Reaction Scheme P illustrates the use of the Claisen rearrangement to provide methyl spacers having substituents such as a vinyl group which can be further functionalized.

REACTION SCHEME A

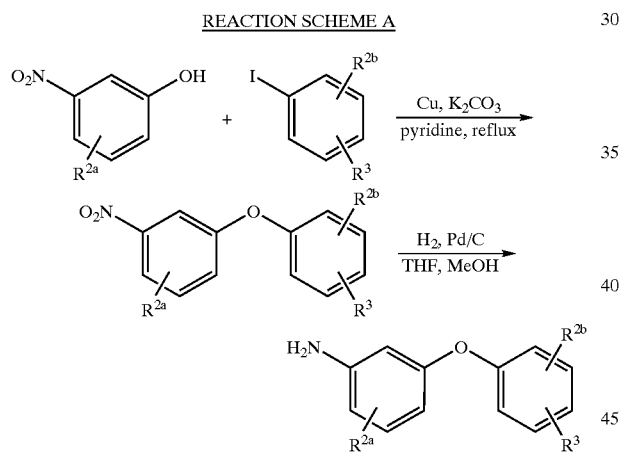

REACTION SCHEME B

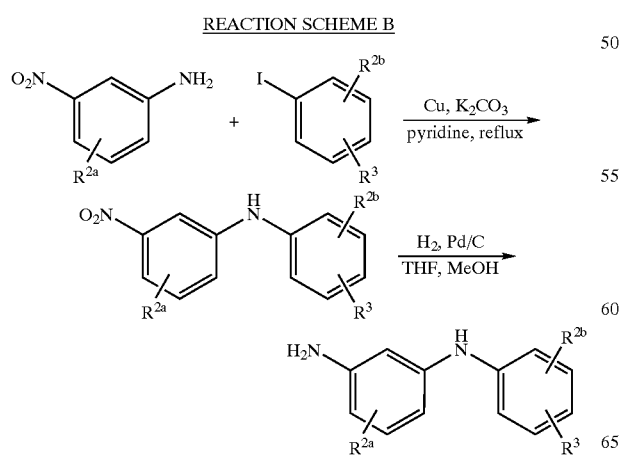

REACTION SCHEME C

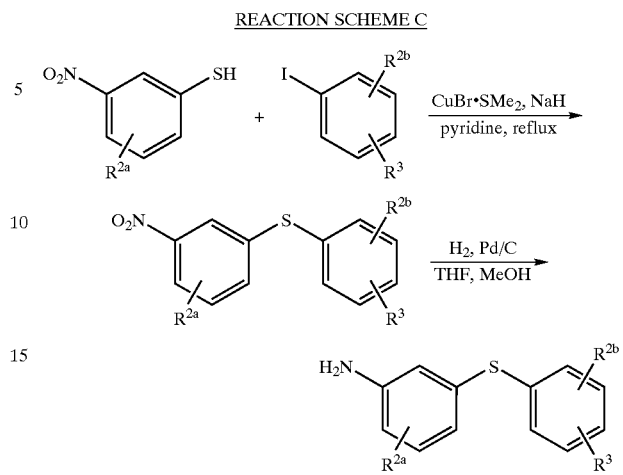

REACTION SCHEME D

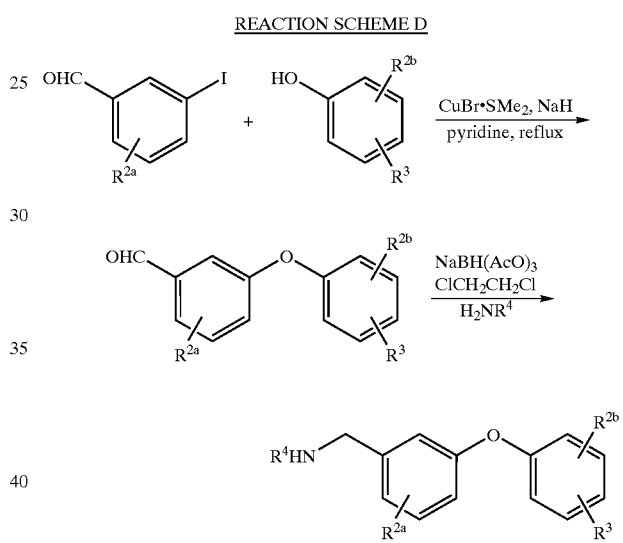

REACTION SCHEME E

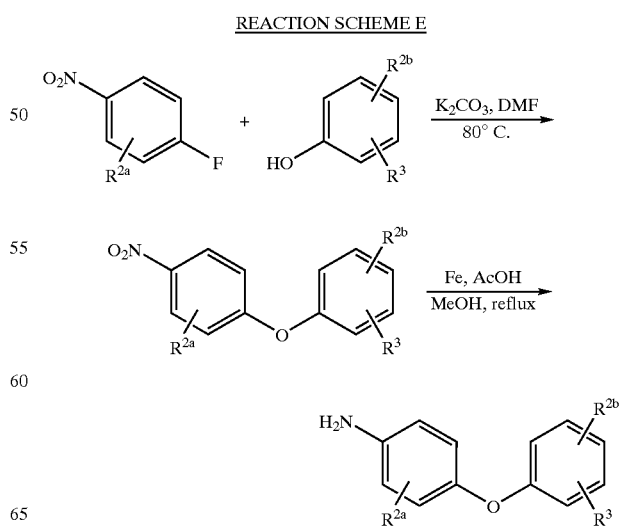

REACTION SCHEME F
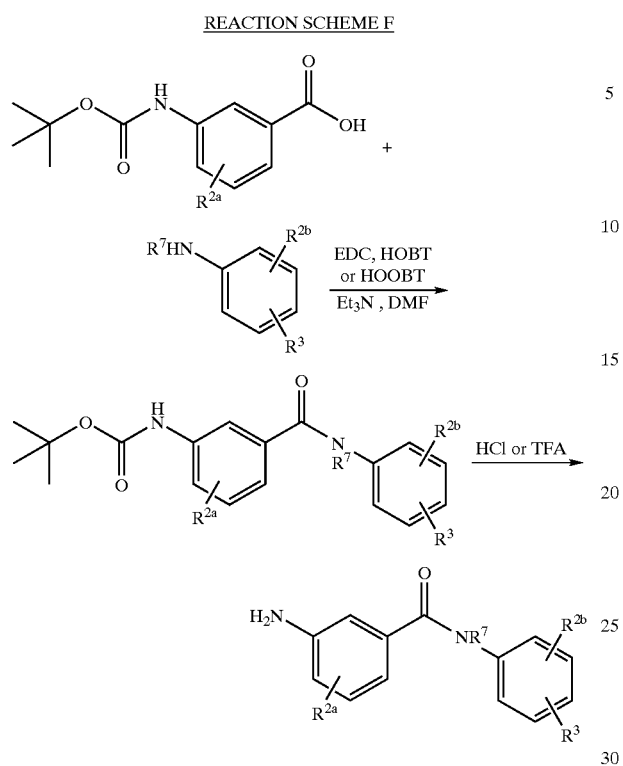
REACTION SCHEME G
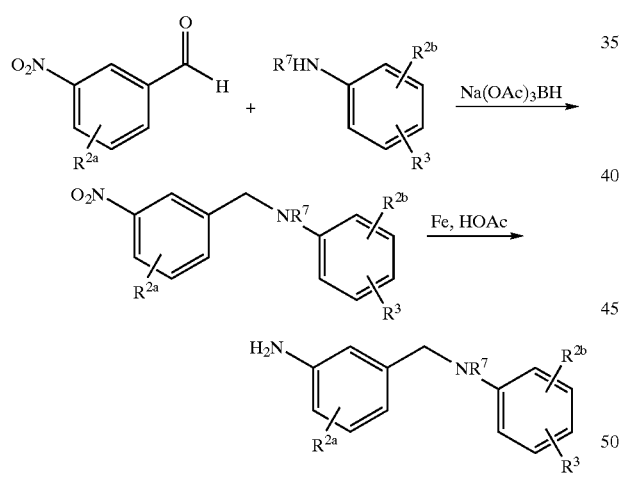
REACTION SCHEME H
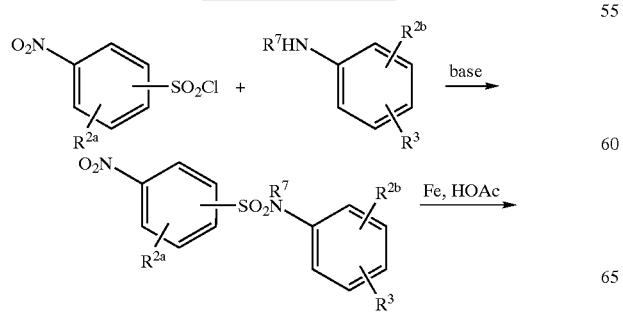
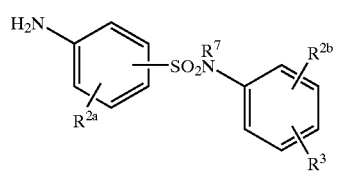
REACTION SCHEME I
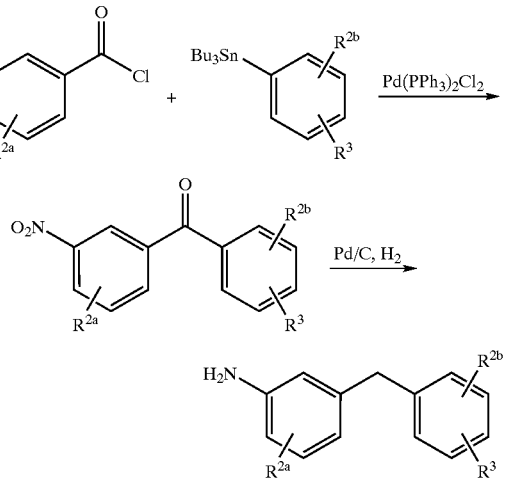
REACTION SCHEME J
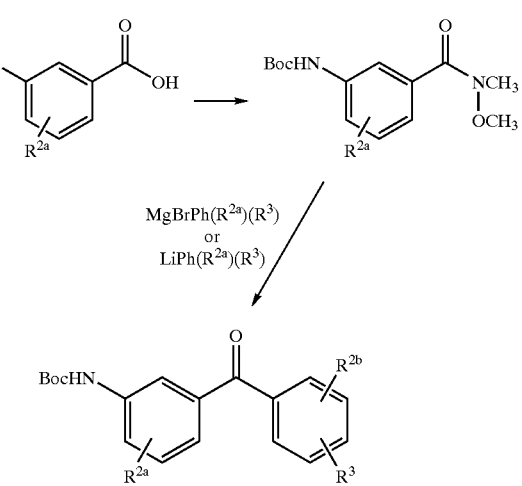
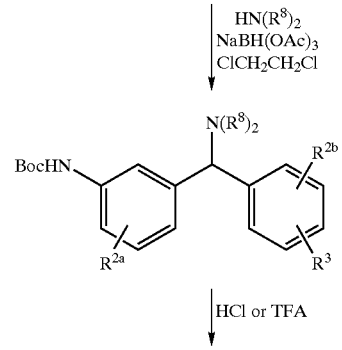

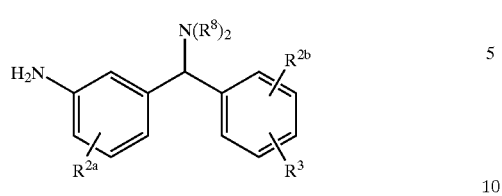
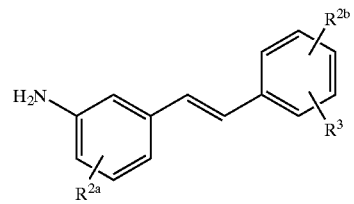
REACTION SCHEME K
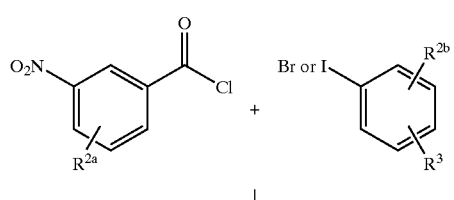
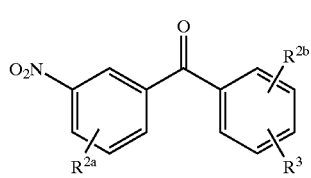
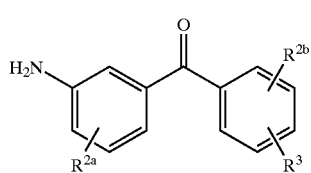
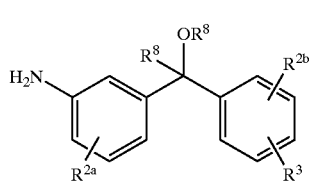
REACTION SCHEME L
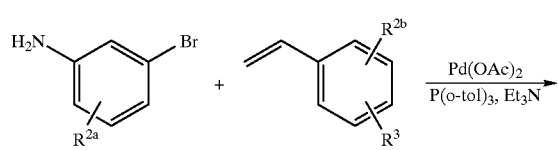
REACTION SCHEME M
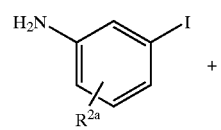
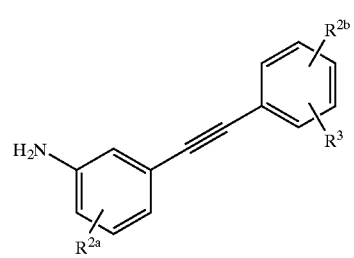
REACTION SCHEME N
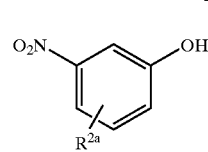
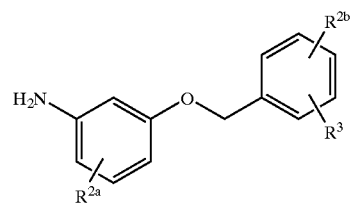

REACTION SCHEME P

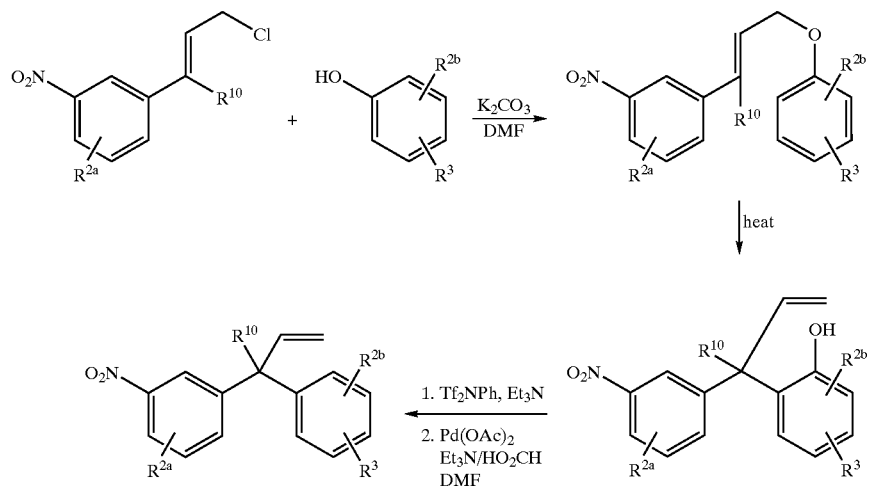

Reaction Schemes Q–S illustrate reactions wherein the non-sulfhydryl-containing moiety(ies) of the compounds of the instant invention is attached to the aminodiphenyl subunit to provide the instant compounds.

Thus, the aminodiphenyl subunit can be reductively alkylated with aldehydes such as 1-trityl4-carboxaldehyde or 1-trityl-4-imidazolylacetaldehyde, to give products such as VIII (Reaction Scheme Q). The trityl protecting group can be removed from VIII to give IX, or alternatively, VIII can first be treated with an alkyl halide then subsequently deprotected to give the alkylated imidazole X. Alternatively, the aminomethylbenzamide subunit can be acylated or sulfonylated by standard techniques.

The imidazole acetic acid XI can be converted to the acetate XIII by standard procedures, and XIII can be first reacted with an alkyl halide, then treated with refluxing methanol to provide the regiospecifically alkylated imidazole acetic acid ester XIV. Hydrolysis and reaction with the aminodiphenyl subunit in the presence of condensing reagents such as 1-(3-dimethylaminopropyl)-3-ethylcarbodiimide (EDC) leads to acylated products such as XV. Coupling reactions with other suitably substituted aldehydes may be performed as illustrated in Schemes 3 and 6–9 hereinabove.

Reaction Scheme S illustrates a one pot synthesis of an instant compound wherein the N-terminus nitrogen is substituted with two different non-sulfhydryl-containing moieties. Thus, the aminodiphenyl subunit is treated with one equivalent of an appropriate aldehyde and, after the reductive adduct has been formed, the in situ intermediate is treated with an equivalent of a different aldehyde.

REACTION SCHEME Q

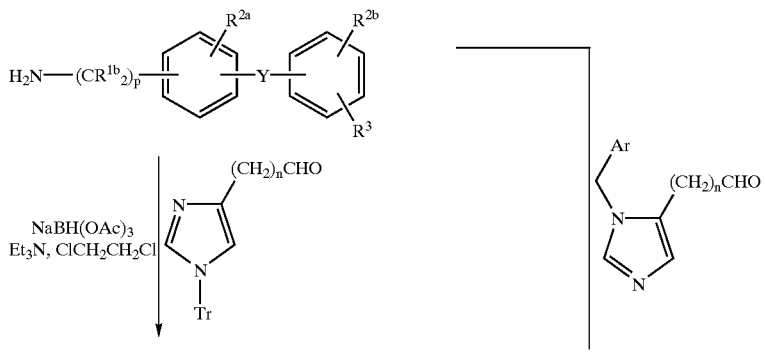

-continued

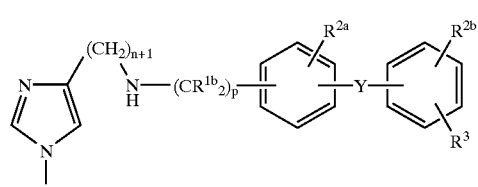

VIII

CF$_3$CO$_2$H, CH$_2$Cl$_2$
(C$_2$H$_5$)$_3$SiH ↓

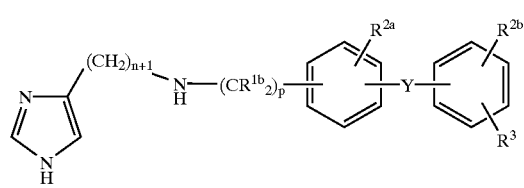

IX

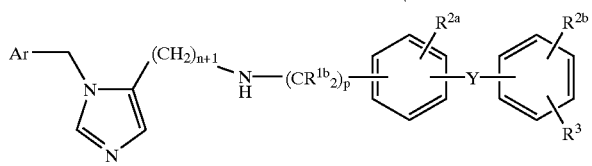

X

NaBH(OAc)$_3$
Et$_3$N, ClCH$_2$CH$_2$Cl

REACTION SCHEME R

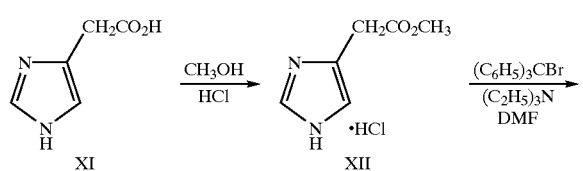

XI        XII

CH$_3$OH / HCl → ; (C$_6$H$_5$)$_3$CBr / (C$_2$H$_5$)$_3$N / DMF →

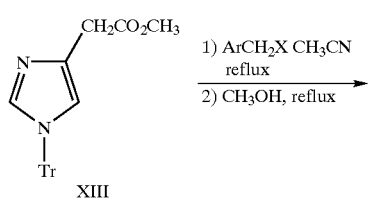

XIII

1) ArCH$_2$X CH$_3$CN reflux
2) CH$_3$OH, reflux

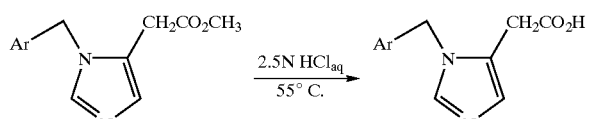

XIV 2.5N HCl$_{aq}$ / 55° C. →

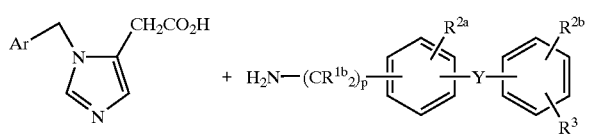

+ H$_2$N—(CR$^{1b}_2$)$_p$—Ar—Y—Ar—R$^3$

↓ EDC·HCl
  HOBt

-continued

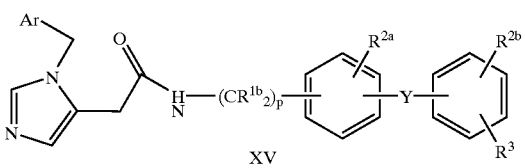

XV

REACTION SCHEME S

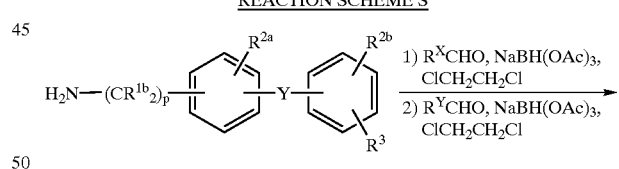

1) R$^X$CHO, NaBH(OAc)$_3$, ClCH$_2$CH$_2$Cl
2) R$^Y$CHO, NaBH(OAc)$_3$, ClCH$_2$CH$_2$Cl

NaOH
H$_2$O, CH$_3$OH;
H$^+$ wherein, in the above Reaction Schemes, R' is R$^{1a}$; R" is (R$^6$)$_r$—V—A$^1$—(CR$^{1a}$)$_n$—; R'" is selected such that R'''CH$_2$—is R$^8$; and R$^x$ and RY are selected such that R$^x$CH$_2$— and RYCH$_2$—are either R$^4$ or R$^5$.

EXAMPLES

Examples provided are intended to assist in a further understanding of the invention. Particular materials employed, species and conditions are intended to be further illustrative of the invention and not limitative of the reasonable scope thereof.

The standard workup referred to in the examples refers to solvent extraction and washing the organic solution with 10% citric acid, 10% sodium bicarbonate and brine as appropriate. Solutions were dried over sodium sulfate and evaporated in vacuo on a rotary evaporator.

Example 1

(S)-1-(3-chlorophenyl)-4-[1-(4cyanobenzyl)-imidazolylmethyl]-5-[2-(methanesulfonyl)ethyl]-2-piperazinone dihydrochloride

Step A: 1-triphenylmethyl-4-(hydroxymethyl)-imidazole

To a solution of 4-(hydroxymethyl)imidazole hydrochloride (35.0 g, 260 mmol) in 250 mL of dry DMF at room temperature was added triethylamine (90.6 mL, 650 mmol). A white solid precipitated from the solution. Chlorotriphenylmethane (76.1 g, 273 mmol) in 500 mL of DMF was added dropwise. The reaction mixture was stirred for 20 hours, poured over ice, filtered, and washed with ice water. The resulting product was slurried with cold dioxane, filtered, and dried in vacuo to provide the titled product as a white solid which was sufficiently pure for use in the next step.

Step B: 1-triphenylmethyl-4-(acetoxymethyl)-imidazole

Alcohol from Step A (260 mmol, prepared above) was suspended in 500 mL of pyridine. Acetic anhydride (74 mL, 780 mmol) was added dropwise, and the reaction was stirred for 48 hours during which it became homogeneous. The solution was poured into 2 L of EtOAc, washed with water (3×1 L), 5% aq. HCl soln. (2×1 L), sat. aq. NaHCO$_3$, and brine, then dried (Na$_2$SO$_4$), filtered, and concentrated in vacuo to provide the crude product. The acetate was isolated as a white powder which was sufficiently pure for use in the next reaction.

Step C: 1-(4-cyanobenzyl)-5-(acetoxymethyl)-imidazole hydrobromide

A solution of the product from Step B (85.8 g, 225 mmol) and α-bromo-p-tolunitrile (50.1 g, 232 mmol) in 500 mL of EtOAc was stirred at 60° C. for 20 hours, during which a pale yellow precipitate formed. The reaction was cooled to room temperature and filtered to provide the solid imidazolium bromide salt. The filtrate was concentrated in vacuo to a volume 200 mL, reheated at 60° C. for two hours, cooled to room temperature, and filtered again. The filtrate was concentrated in vacuo to a volume 100 mL, reheated at 60° C. for another two hours, cooled to room temperature, and concentrated in vacuo to provide a pale yellow solid. All of the solid material was combined, dissolved in 500 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid which was used in the next step without further purification.

Step D: 1-(4-cyanobenzyl)-5-(hydroxymethyl)-imidazole

To a solution of the acetate from Step C (50.4 g, 150 mmol) in 1.5 L of 3:1 THF/water at 0° C. was added lithium hydroxide monohydrate (18.9 g, 450 mmol). After one hour, the reaction was concentrated in vacuo, diluted with EtOAc (3 L), and washed with water, sat. aq. NaHCO$_3$ and brine. The solution was then dried (Na$_2$SO$_4$), filtered, and concentrated in vacuo to provide the crude product as a pale yellow fluffy solid which was sufficiently pure for use in the next step without further purification.

Step E: 1-(4-cyanobenzyl)-5-imidazolecarboxaldehyde

To a solution of the alcohol from Step D (21.5 g, 101 mmol) in 500 mL of DMSO at room temperature was added triethylamine (56 mL, 402 mmol), then SO$_3$-pyridine complex (40.5 g, 254 mmol). After 45 minutes, the reaction was poured into 2.5 L of EtOAc, washed with water (4×1 L) and brine, dried (Na$_2$SO4), filtered, and concentrated in vacuo to provide the aldehyde as a white powder which was sufficiently pure for use in the next step without further purification.

Step F: (S)-2-(tert-butoxycarbonylamino)-N-methoxy-N-methyl-4-(methylthio)butanamide L-N-Boc-methionine (30.0 g, 0.120 mol), N,O-dimethylhydroxylamine hydrochloride (14.1 g, 0.144 mol), EDC hydrochloride (27.7 g, 0.144 mol) and HOBT (19.5 g, 0.144 mol) were stirred in dry DMF (300 mL) at 20° C. under nitrogen. More N,O-dimethylhydroxylamine hydrochloride (2.3 g, 23 mmol) was added to obtain pH 7–8. The reaction was stirred overnight, the DMF distilled to half the original volume under high vacuum, and the residue partitioned between ethyl acetate and sat. NaHCO$_3$ soln. The organic phase was washed with saturated sodium bicarbonate, water, 10% citric acid, and brine, and dried with sodium sulfate. The solvent was removed in vacuo to give the title compound.

Step G: (S)-2-(tert-butoxycarbonylamino)-4-(methylthio)butanal

A suspension of lithium aluminum hydride (5.02 g, 0.132 mol) in ether (500 mL) was stirred at room temperature for one hour. The solution was cooled to −50° C. under nitrogen, and a solution of the product from Step F (39.8 g, ca. 0.120 mol) in ether (200 mL) was added over 30 min, maintaining the temperature below −40° C. When the addition was complete, the reaction was warmed to 5° C., then recooled to −45° C. Analysis by tlc revealed incomplete reaction. The solution was rewarmed to 5 ° C., stirred for 30 minutes, then cooled to −50° C. A solution of potassium hydrogen sulfate (72 g, 0.529 mol) in 200 mL water was slowly added, maintaining the temperature below −20° C. The mixture was warmed to 5° C., filtered through Celite, and concentrated in vacuo to provide the title aldehyde.

Step H: (S)-2-(tert-butoxycarbonylamino)-N-(3-chlorophenyl)-4-(methylthio)butanamine To a solution of 3-chloroaniline (10.3 mL, 97.4 mmol), the product from Step G (23.9 g, 97.4 mmol), and acetic acid (27.8 mL, 487 mmol) in dichloroethane (250 mL) under nitrogen was added sodium triacetoxyborohydride (41.3 g, 195 mmol). The reaction was stirred overnight, then quenched with saturated sodium bicarbonate solution. The solution was diluted with CHCl$_3$, and the organic phase was washed with water, 10% citric acid and brine. The solution was dried over sodium sulfate and concentrated in vacuo to provide the crude product (34.8 g) which was chromatographed on silica gel with 20% ethyl acetate in hexane to obtain the title compound.

Step I: (S)-4-(tert-butoxycarbonyl)-1-(3-chlorophenyl)-5-[2-(methylthio)ethyl]piperazin-2-one A solution of the product from Step H (22.0 g, 63.8 mmol) in ethyl acetate (150 mL) was vigorously stirred at 0° C. with saturated sodium bicarbonate (150 mL). Chloroacetyl chloride (5.6 mL, 70.2 mmol) was added dropwise, and the reaction stirred at 0° C. for 2h. The layers were separated, and the ethyl acetate phase was washed with 10% citric acid and saturated brine, and dried over sodium sulfate. After concentration in vacuo, the resulting crude product (27.6 g) was dissolved in DMF (300 mL) and cooled to 0° C. under argon. Cesium carbonate (63.9 g, 196 mmol) was added, and the reaction was stirred for two days, allowing it to warm to room temperature. Another portion of cesium carbonate (10 g, 30 mmol) was added, and the reaction was stirred for 16 hours. The DMF was distilled in vacuo, and the residue partitioned between ethyl acetate and water. The organic phase was washed with saturated brine, and dried over sodium sulfate. The crude product was chromatographed on silica gel with 20–25% ethyl acetate in hexane to obtain the title compound.

Step J: (S)4-(tert-butoxycarbonyl)-1-(3-chlorophenyl)-5-[2-(methanesulfonyl)ethyl]piperazin-2-one A solution of the product from Step I (14.2 g, 37 mmol) in methanol (300 mL) was cooled to 0° C., and a solution of magnesium monoperoxyphthalate (54.9 g, 111 mmol) in 210 mL MeOH was added over 20 minutes. The ice bath was removed, and the solution was allowed to warm to room temperature. After 45 minutes, the reaction was concentrated in vacuo to half the original volume, then quenched by the addition of 2N Na$_2$S$_2$O$_3$ soln. The solution was poured into EtOAc and sat NaHCO$_3$ solution, and the organic layer was washed with brine, dried (Na$_2$SO$_4$), filtered, and concentrated in vacuo to provide the crude sulfone. This material was chromatographed on silica gel with 60–100% ethyl acetate in hexane to obtain the titled compound.

Step K: (S)-1-(3-chlorophenyl)-5-[2-(methanesulfonyl)ethyl]piperazin-2-one

Through a solution of Boc-protected piperazinone from Step J (1.39 g, 3.33 mmol) in 30 mL of EtOAc at 0° C. was bubbled anhydrous HCl gas. The saturated solution was stirred for 35 minutes, then concentrated in vacuo to provide the hydrochloride salt as a white powder. This material was suspended in EtOAc and treated with dilute aqueous NaHCO$_3$ solution. The aqueous phase was extracted with EtOAc, and the combined organic mixture was washed with brine, dried (Na$_2$SO$_4$), filtered, and concentrated in vacuo. The resulting amine was reconcentrated from toluene to provide the titled material suitable for use in the next step.

Step L: (S)-1-(3-chlorophenyl)-4-[1-(4-cyanobenzyl)imidazolyl-methyl]-5-[2-(methanesulfonyl)-ethyl]-2-piperazinone dihydrochloride To a solution of the amine from Step K (898 mg, 2.83 mmol) and imidazole carboxaldehyde from Step E (897 mg, 4.25 mmol) in 15 mL of 1,2-dichloroethane was added sodium triacetoxyborohydride (1.21 g, 5.7 mmol). The reaction was stirred for 23 hours, then quenched at 0° C. with sat. NaHCO$_3$ solution. The solution was poured into CHCl$_3$, and the aqueous layer was back-extracted with CHCl$_3$. The combined organics were washed with brine, dried (Na$_2$SO$_4$), filtered, and concentrated in vacuo. The resulting product was purified by silica gel chromatography (95:5:0.5–90:10:0 EtOAc:MeOH:NH$_4$Cl), and the resultant product was taken up in EtOAc/methanol and treated with 2.1 equivalents of 1 M HCl/ether solution. After concentrated in vacuo, the product dihydrochloride was isolated as a white powder.

Example 2

1-(3-chlorophenyl)-4-[1-(4-cyanobenzyl)imidazolyl-methyl]-2-piperazinone dihydrochloride Step A: N-(3-chlorophenyl)ethylenediamine hydrochloride To a solution of 3-chloroaniline (30.0 mL, 284 mmol) in 500 mL of dichloromethane at 0° C. was added dropwise a solution of 4 N HCl in 1,4-dioxane (80 mL, 320 mmol HCl). The solution was warmed to room temperature, then concentrated to dryness in vacuo to provide a white powder. A mixture of this powder with 2-oxazolidinone (24.6 g, 282 mmol) was heated under nitrogen atmosphere at 160° C. for 10 hours, during which the solids melted, and gas evolution was observed. The reaction was allowed to cool, forming the crude diamine hydrochloride salt as a pale brown solid.

Step B: N-(tert-butoxycarbonyl)-N'-(3-chlorophenyl) ethylenediamine

The amine hydrochloride from Step A (ca. 282 mmol, crude material prepared above) was taken up in 500 mL of THF and 500 mL of sat. aq. NaHCO$_3$ soln., cooled to 0° C., and di-tert-butylpyrocarbonate (61.6 g, 282 mmol) was added. After 30 h, the reaction was poured into EtOAc, washed with water and brine, dried (Na$_2$SO$_4$), filtered, and concentrated in vacuo to provide the titled carbamate as a brown oil which was used in the next step without further purification.

Step C: N-[2-(tert-butoxycarbamoyl)ethyl]-N-(3-chlorophenyl)-2-chloroacetamide

A solution of the product from Step B (77 g, ca. 282 mmol) and triethylamine (67 mL, 480 mmol) in 500 mL of CH$_2$Cl$_2$ was cooled to 0° C. Chloroacetyl chloride (25.5 mL, 320 mmol) was added drop wise, and the reaction was maintained at 0° C. with stirring. After 3 h, another portion of chloroacetyl chloride (3.0 mL) was added dropwise. After 30 min, the reaction was poured into EtOAc (2 L) and washed with water, sat. aq. NH$_4$Cl soln, sat. aq. NaHCO$_3$ soln., and brine. The solution was dried (Na$_2$SO$_4$), filtered, and concentrated in vacuo to provide the chloroacetamide as a brown oil which was used in the next step without further purification.

Step D: 4(tert-butoxycarbonyl)-1-(3-chlorophenyl)-2-piperazinone

To a solution of the chloroacetamide from Step C (ca. 282 mmol) in 700 mL of dry DMF was added K$_2$CO$_3$ (88 g, 0.64 mol). The solution was heated in an oil bath at 70–75° C. for 20 hours, cooled to room temperature, and concentrated in vacuo to remove ca 500 mL of DMF. The remaining material was poured into 33% EtOAc/hexane, washed with water and brine, dried (Na$_2$SO$_4$), filtered, and concentrated in vacuo to provide the product as a brown oil. This material was purified by silica gel chromatography (25–50% EtOAc/hexane) to yield pure product, along with a sample of product (ca. 65% pure by HPLC) containing a less polar impurity.

Step E: 1-(3-chlorophenyl)-2-piperazinone

Through a solution of Boc-protected piperazinone from Step D (17.19 g, 55.4 mmol) in 500 mL of EtOAc at −78° C. was bubbled anhydrous HCl gas. The saturated solution was warmed to 0° C., and stirred for 12 hours. Nitrogen gas was bubbled through the reaction to remove excess HCl, and the mixture was warmed to room temperature. The solution was concentrated in vacuo to provide the hydrochloride as a white powder. This material was taken up in 300 mL of CH$_2$Cl$_2$ and treated with dilute aqueous NaHCO$_3$ solution. The aqueous phase was extracted with CH2Cl2 (8×300 mL) until tlc analysis indicated complete extraction. The combined organic mixture was dried (Na$_2$SO$_4$), filtered, and concentrated in vacuo to provide the titled free amine as a pale brown oil.

Step F: 1-(3-chlorophenyl)4-[1-(4-cyanobenzyl) imidazolylmethyl]-2-piperazinone dihydrochloride To a solution of the amine from Step E (55.4 mmol, prepared above) in 200 mL of 1,2-dichloroethane at 0° C. was added 4 Å powdered molecular sieves (10 g), followed by sodium triacetoxyborohydride (17.7 g, 83.3 mmol). The imidazole carboxaldehyde from Step E of Example 4 (11.9 g, 56.4 mmol) was added, and the reaction was stirred at 0° C. After 26 hours, the reaction was poured into EtOAc, washed with dilute aq. NaHCO$_3$, and the aqueous layer was back-extracted with EtOAc. The combined organics were washed with brine, dried (Na$_2$SO$_4$), filtered, and concentrated in vacuo. The resulting product was taken up in 500 mL of 5:1 benzene:CH$_2$Cl$_2$, and propyl-amine (20 mL) was added. The mixture was stirred for 12 hours, then concentrated in vacuo to afford a pale yellow foam. This material was -purified by silica gel chromatography (2–7% MeOH/CH$_2$Cl$_2$), and the resultant. white foam was taken up in CH$_2$Cl$_2$ and treated with 2.1 equivalents of 1 M HCl/ether solution. After concentrated in vacuo, the product dihydrochloride was isolated as a white powder.

Example 3

Preparation of N-(2(R)-amino-3-mercaptopropyl)-valyl-isoleucyl-leucine methyl ester (Compound 3-1)

Step A. Preparation of N-(2(R)-t-butoxycarbonyl-amino-3-triphenyl-methylmercaptopropyl)-valyl-isoleucyl-leucine methyl ester The tripeptide ester valyl-isoleucyl-leucine methyl ester was synthesized using conventional solution phase peptide synthesis methods. The trifluoroacetate salt of this tripeptide (360 mg, 0.77 mmol) was dissolved in 5 mL of methanol with 147 mg (1.5 mmol) of potassium acetate and 670 mg (1.5 mmol) of N-Boc-S-tritylcysteinal (prepared using the procedure of Goel, Krolls, Stier, and Kesten Org. Syn. 67: 69–74 (1988) for the preparation of N-Boc-leucinal) was added. Sodium cyanoborohydride (47 mg, 0.75 mmol) was added and the mixture was stirred overnight. The mixture was diluted with ether and washed with water, 5% ammonium hydroxide and brine. The solution was dried (sodium sulfate) and evaporated to give a white foam which was purified by chromatography (1–15% acetone in methylene chloride). The title compound was obtained as an oily material.

Step B. Preparation of N-(2(R)-amino-3-mercaptopropyl)-valyl-isoleucyl-leucine methyl ester A sample of the protected pseudopeptide prepared as described in Step A (728 mg, 0.92 mmol) was dissolved in 100 ML of methylene chloride, 50 mL of TFA was added and the resulting yellow solution was treated immediately with 0.80 mL (5 mmol) of triethylsilane. After 45 min, the solvents were evaporated and the residue was partitioned between hexane and 0.1% aqueous TFA. The aqueous solution was lyophilized. This material was further purified by reverse phase HPLC (5–95% acetonitrile/0.1% TFA/water) to afford the title compound. $^1$H NMR (CD$_3$OD) δ 8.65 (1H, d), 4.45 (1H, m), 4.3 (1H, d), 3.7 (3H, s), 3.4 (1H, m), 3.15 (1H, d), 2.75–2.95 (m), 0.8–1.05 (18 H, m). FAB mass spectrum, ml/z=447 (M+1). Anal. Calcd for C$_{21}$H$_{42}$N$_4$O$_4$S. 1.8 TFA: C, 45.24; H, 6.75; N, 8.56. Found: C, 45.26; H, 6.77; N. 8.50.

Example 4

N-(2(R)-amino-3-mercaptopropyl)-valyl-isoleucyl-leucine (Compound 7-2)

Step A. Preparation of N-(2(R)-t-butoxycarbonylamino-3-triphenylmethylmercaptopropyl)-valyl-isoleucyl-leucine The product of Example 3, Step A (60 mg, 0.076 mmol) was dissolved in 1 mL of methanol and 150 μL of IN NaOH was added. After stirring overnight, the solution was acidified with 150 μL of 10% citric acid and the product was extracted with ether. The ether solution was washed with water and brine and dried (sodium sulfate). Evaporation provided the title compound as a solid.

Step B. Preparation of N-(2(R)-amino-3-mercaptopropyl)-valyl-isoleucyl-leucine

Using the method of Example 3, Step B, the protecting groups were removed with TFA and triethylsilane to provide the title compound. FAB mass spectrum, m/z=433 (M+1).

Anal. Calcd for C$_{20}$H$_{40}$N$_4$O$_4$S. 2 TFA: C, 43.63; H, 6.41; N, 8.48. Found: C, 43.26; H, 6.60; N. 8.49.

Example 5

Preparation of 2(S)-[2(S)-[2(R)-Amino-3-mercapto]-propylamino-3(S)-methyl]pentyloxy-3-phenylpropionyl-homoserine lactone (Compound 5-1) and 2(S)-[2(S)-[2(R)-Amino-3-mercapto]-propylamino-3(S)-methyl]pentyloxy-3-phenyl-propionyl-homoserine (Compound 5-2)

Step A: Preparation of N-(α-chloroacetyl)-L-isoleucinol

To a stirred solution of L-isoleucinol (20 g, 0.17 mol) and triethylamine (28.56 ml, 0.204 mol) in CH$_2$Cl$_2$ (500 ml) at −78° C. was added chloroacetyl chloride (16.3 ml, 0.204 mol) over 5 minutes. The cooling bath was removed and the solution allowed to warm to −20° C. _The mixture was diluted with EtOAc and washed sequentially with 1 M HCl, and brine and dried (Na$_2$SO$_4$). Evaporation in vacuo afforded the amide title compound (35 g, 100%).

Rf=0.3 CH$_2$Cl$_2$: MeOH (95:5); $^1$H NMR (CDCl$_3$) δ 6.80 (1H, brd, J=5 Hz), 4.10 (2H, s), 3.84 (1H, m), 3.79 (2H, m), 2.5 (1H, brs), 1.72 (1H, m), 1.55 (1H, m), 1.17 (1H, m), 0.96 (3H, d, J=6 Hz) 0.90 (3H, t, J=6 Hz).

Step B: Preparation of 5(S)-[1(S)-methyl]propyl-2,3,5,6-tetra-hydro-4H-1,4-oxazin-3-one To a stirred solution of N-(a-chloroacetyl)-L-isoleucinol (7.4 g, 0.038 mol) in THF (125 ml) under argon at 0° C. was slowly added sodium hydride (2.2 g of a 60% dispersion in mineral oil, 0.055 mol) with concomitant gas evolution. After completing the addition, the mixture was warmed to room temperature (R. T.) and stirred for 16 hr. Water (2.8 ml) was added and the solvents evaporated in vacuo. The residue was dissolved in CHCl$_3$ (70 ml) and washed with water saturated NaCl solution. The organic layer was dried (Na$_2$SO$_4$) and evaporated in vacuo. The residue was chromatographed using silica gel eluting with CH$_2$Cl$_2$:MeOH (96:4) to afford the lactam title compound (4.35 g, 72%) as a white solid. Rf=0.35 CH$_2$Cl$_2$:MeOH (95:5); $^1$H NMR δ(CDCl$_3$) 6.72 (1H, brs), 4.20 (1H, d, J=14.5 Hz), 4.10 (1H, d, J=14.5 Hz), 3.88 (1H, dd, J=9 and 3.5 Hz), 3.58(1H, dd, J=9 and 6.5 Hz), 3.45 (1H, brqt, J=3.5 Hz), 1.70–1.45 (2H, m), 1.34–1.15 ($^1$H, m), 0.96 (3H, t, J=6.5 Hz), 0.94 (3H, d, J=6.5 Hz).

Step C: Preparation of N-(tert-butoxycarbonyl)-5(S)-[1(S)-methyl]propyl-2,3,5,6-tetrahydro-4H- 1,4-oxazin-3-one 5(S)-[1(S)-Methyl]propyl-2,3,5,6-tetrahydro 4H-1,4-oxazin-3-one (12.2 g, 0.0776 mol) and DMAP (18.9 g, 0.155 mol) were dissolved in methylene chloride (120 ml) under argon at R. T. Boc anhydride (33.9 g, 0.155 mol) was added to the stirred solution in one portion, with concomitant gas evolution and the mixture was stirred at R. T. for 16 hr. The solvent was evaporated in vacuo and the residue was taken up in ethyl acetate and washed sequentially with 10% citric acid, 50% NaHCO$_3$ and finally brine. The organic extract was dried (Na$_2$SO$_4$) and evaporated in vacuo. Chromatography of the residue over silica gel eluting with 20% EtOAc in hexanes afforded the title compound (14.1 g, 71%) as a white solid.

Rf=0.75 EtOAc:hexanes (20:80); mp 59–60° C. Anal. Calc'd. for C$_{13}$H$_{23}$O$_4$N: C, 60.68; H,9.01; N, 5.44. Found: C, 60.75; H, 9.01; N, 5.58. $^1$H NMR (CDCl$_3$) δ 4.25 (1H, d, J=15 Hz), 4.15 (1H, d, J=15 Hz), 4.15–4.00 (2H, m), 3.73 (1H, dd, J=10 and 2 Hz), 1.88 (1H, qt, J=6 Hz), 1.55 (9H, s), 1.50–1.36 (1H, m), 1.35–1.19 (1H, m) 1.00 (3H, d, J=6 Hz) 0.95 (3H, d, J=6.5 Hz).

Step D: Preparation of N-(tert-Butoxycarbonyl)-2(S)-benzyl-5(S)-[1(S)-methyl]propyl-2,3,5,6-tetrahydro-4H-1,4-oxazin-3-one A solution of N-(tert-butoxycarbonyl)-5(S)-[1(S)-methyl] propyl-2,3,5,6-tetrahydro4H-1,4oxazin-3-one (5.75 g, 22.34 mmol) in DME (100 ml) under argon was cooled to −60° C. The cold solution was transferred via canula to a second flask containing sodium bis(trimethylsilyl)amide (24.58 ml of a 1M solution in THF, 24.58 mmol) at −78° C. under argon. After stirring for 10 minutes, benzyl bromide (2.25 ml, 18.99 mmol) was added over 5 minutes and the resulting mixture was stirred at −78° C. for 3 hours. After this time, the reaction mixture was transferred via cannula to another flask containing sodium bis(trimethylsilyl)amide (24.58 ml of a 1M solution in THF, 24.58 mmol) at −78° C., under argon. After stirring for a further 5 minutes, the reaction was quenched by the addition of saturated aqueous ammonium chloride solution (24.6 ml) and allowed to warm to room temperature. This mixture was diluted with brine (50 ml) and water (20 ml) and then extracted with ethyl acetate (2×100 ml). The organic extracts were washed with brine (50 ml) and evaporated in vacuo to afford an oil. Chromatography of the residue over silica gel (230–400 mesh, 300 g) eluting with 10–20% ethyl acetate in hexanes afforded the title compound (5.12 g, 67%) as a clear oil. Rf=0.25 EtOAc:Hexanes (20:80); $^1$H NMR (CDCl$_3$)δ7.35–7.15 (5H, m), 4.31 (1H, dd, J=6 and 2 Hz), 4.03 (1H, d, J=12 Hz), 3.88 (1H, dd, J=6 and 1 Hz), 3.66 (1H, dd, J=12 and 2 Hz), 3.29 (1H, dd, J=12 and 3 Hz), 1.54 (9H, s), 3.12 (1H, dd, J=12 and 7 Hz), 1.47 (1H, m), 1.25 (1H, m), 1.10 (1H, m), 0.83 (3H, d, J=6Hz), 0.80 (3H, t, J=6Hz).

Step E: Preparation of N-(tert-butoxycarbonyl)-2(S)-[2(S)-amino-3(S)-methyl]pentyloxy-3-phenyl-propionic acid To a stirred solution of N-(tert-butoxycarbonyl)-2(S)-benzyl-5(S)-[1(S)-methyl]-propyl-2,3,5,6-tetrahydro-4H-1,4-oxazin-3-one (5.1 g, 14.7 mmol) in THF (150 ml) and water (50 ml) at 0° C. was added hydrogen peroxide (15 ml of a 30% aqueous solution, 132 mmol) and lithium hydroxide (3.0 g, 63.9 mmol). After stirring for 30 minutes, the reaction was quenched with a solution of sodium sulfite (28.25 g, 0.224 mol) in water (70 ml). The THF was evaporated in vacuo and the aqueous phase was acidified to pH 3–4 by addition of 10% citric acid solution and extracted with EtOAc. The organic extracts were dried (Na$_2$SO$_4$), evaporated in vacuo and the residue purified by chromatography over silica gel eluting with 4% MeOH in CH$_2$Cl$_2$ to give the lactam 2(S)-benzyl-5(S)-[1(S)-methyl]propyl-2,3,5,6-tetrahydro-4H-1,4-oxazin-3-one (0.82 g 22%) and then with 20% MeOH in CH$_2$Cl$_2$ to afford the title compound (4.03 g, 75%) as a viscous oil.

Rf=0.4 MeOH:CH$_2$Cl$_2$ (5:95)+0.3% AcOH; $^1$H NMR (d$_6$ DMSO) δ 7.35–7.10 (5H, m), 6.68 (1H, br, s), 3.75 (1H, dd, J=7.5 and 2.5 Hz) 3.54 (1H, m), 3.5–3.2 (2H, m) 2.99 (1H, dd, J=12.5 and 2.5 Hz), 2.75 (1H, dd, J=12.5 and 7.5 Hz), 1.50–1.35 (11H, m), 0.98 (1H, sept, J=6 Hz), 0.78 (3H, t, J=6 Hz), 0.65 (3H, d, J=6 Hz); FAB MS 366 (MH$^+$) 266 (MH$_2^+$-CO$_2^t$Bu).

Step F: Preparation of N-(tert-butoxycarbonyl)-2(S)-[2(S)-amino-3(S)-methyl]-pentyloxy-3-phenyl-propionyl-homoserine lactone To a stirred solution of N-(tert-butoxycarbonyl)-2(S)-[2(S)-amino-3(S)-methyl]-pentyloxy-3-phenylpropionic acid (0.53 g, 1.45 mmol) and 3-hydroxy-1,2,3,-benzotriazin-4(3H)-one (HOOBT) (0.26 g, 1.6 mmol) in DMF (15 ml) at room temperature was added EDC (0.307 g, 1.6 mmol) and L-homoserine lactone hydrochloride (0.219 g, 6.0 mmol). The pH was adjusted to pH=6.5 by addition of NEt$_3$ (the pH was monitored by application of an aliquot of the reaction mixture to a moist strip of pH paper). After stirring at room temperature for 16 hr, the reaction was diluted with EtOAc and washed with saturated NaHCO$_3$ and then brine and dried (NaSO$_4$). Evaporation in vacuo (sufficient to remove DMF) and chromatography over silica gel eluting with 5% acetone in CH$_2$Cl$_2$ afforded the title compound (520 mg, 80%) as a white solid, mp 115–117° C.

Rf=0.3 Acetone: CH$_2$Cl$_2$ (5:95). $^1$H NMR (CDCl$_3$) δ 7.73 (1H, brd, J=5 Hz), 7.40–7.15 (5H, m), 4.68 (1H, dt, J=9 and 7.5 Hz), 4.65–4.35 (2H, m), 4.33–4.18 (1H, m), 4.20 (1H, dd, J=7 and 3 Hz), 3.78 (1H, m), 3.49 (1H, dd, J=7.5 and 4.0

Hz), 3.37 (1H, dd, J=7.5 and 6.5 Hz), 3.15 (1H, dd, 3==11.5 and 2 Hz), 2.86 (1H, dd, J=11.5 and 7.5 Hz), 2.68 (1H, m) 2.11 (1H, q, J=9 Hz), 1.55–1.30 (11H, m), 1.07 (1H, m), 0.87 (3H, t, J=6.3 Hz), 0.79 (3H, d, J=6 Hz).

Step G: Preparation of 2(S)-[2(S)-amino-3(S)-methyl)-pentyloxy-3-phenylpropionyl-homoserine lactone hydrochloride Anhydrous HCl gas was bubbled through a cold (0° C.) solution of N-(tert-butoxycarbonyl)-2(S)-[2(S)-amino-3(S)-methyl]pentyloxy-3-phenylpropionyl-homoserine lactone (3.0 g, 6.7 mmol) in ethyl acetate (120 ml) until a saturated solution was obtained. The resulting mixture was stirred at 0° C. for 1 hr. The solution was purged with nitrogen and the mixture concentrated in vacuo to afford the title compound as a sticky foam which was used without further purification.
$^1$H NMR (d$_6$ DMSO) δ 8.60 (1H, d, J=7 Hz), 8.08 (3H, brs), 7.35–7.15 (5H, m), 4.60 (1H, qt, J=8 Hz), 4.36 (1H, t J=7.5 Hz), 4.22 (1H, q, J=7.5 Hz), 4.15–3.95 (2H, m), 3.64 (1H, dd, J=9 and 2.5 Hz), 3.15–3.00 (2H, m), 2.92 (1H, dd, J=12.5 and 5.0 Hz), 2.40–2.15 (2H, m), 1.65 (1H, m), 1.43 (1H, m), 1.07 (1H, m), 0.82 (3H, t, J=6 Hz), 0.72 (3H, d, J=6.0 Hz).

Step H: Preparation of 2(S)-[2(S)-[2(R)-(tert-butoxycarbonyl)-amino-3-triphenylmethylmercapto]propylamino-3(S)-methyl]-pentyloxy-3-phenylpropionyl-homoserine lactone 2(S)-[2(S)-Amino-3(S)methyl]pentyloxy-3-phenylpropionyl-homoserine hydrochloride (6.7 mmol) and N-(tert-butoxy-carbonyl)-S-triphenylmethylcysteine aldehyde (0.74 g, 7.5 mmol) (prepared from N-(tert-butoxycarbonyl)-S-triphenylmethylcysteine by the procedure of Goel, O. P.; Krolls, U.; Stier, M.; Keston, S. *Org. Syn.* 1988, 67, 69.) and potassium acetate (3.66 g, 8.2 mmol) were dissolved in methanol (48 ml). Activated 4A molecular sieves (6g) and then Na(CN)BH$_3$ (0.70 g, 10.7 mmol) were added and the resulting slurry was stirred under argon at room temperature for 16 hr. The solids were removed by filtration and the filtrate evaporated in vacuo. The residue was dissolved in EtOAc and washed sequentially with saturated aqueous NaHCO$_3$ and brine and then dried (Na$_2$SO$_4$). Evaporation in vacuo afforded an oil which was purified by chromatography over silica gel eluting with a gradient of 30–50% EtOAc in hexane to afford the title compound (2.34 g, 45%) contaminated with a small amount of the corresponding methyl ester.

$^1$H NMR (CD$_3$OD) δ 7.60–7.05(20H, m), 4.64 (1H, d, J=9.0 Hz), 4.39 (1H, br t, J=9Hz), 4.25(1H, m), 3.93 (1H, m), 3.75–3.60(1H, m), 3.55 (1H, dd, J=9.0 and 2Hz), 3.20 (1H, dd, J=9.0 and 6.0 Hz), 3.04 (1H, dd, J=15.0 and 5.0 Hz), 2.85 (1H, dd, J=15.0 and 9.0 Hz), 2.60 (1H, dd, J=12.0 and 5.0 Hz), 2.50–2.15 (7H, m), 1.45 (9H, s), 1.40–1.20 (1H, m), 1.07 (1H, m), 0.87 (3H, t, J=6 Hz), 0.67 (3H, d, J=6.0 Hz).

Step I: Preparation of 2(S)-[2(S)-[2(R)-Amino-3-mercapto]-propylamino-3(S)-methyl]pentyloxy-3-phenylpropionyl-homoserine lactone To a stirred solution of 2(S)-[2(S)-[2(R)-(tert-butoxycarbonyl)amino-3-triphenylmethylmercapto]-propylamino-3(S)-methyl]pentyloxy-3-phenylpropionyl-homoserine lactone (2.72 g, 3.49 mmol) in CH$_2$Cl$_2$ (90 ml) was added HSiEt3 (2.16 ml, 13.5 mmol) and TFA (43.2 ml, 0.56 mol) and the solution was stirred at R. T. under argon for 2 hrs. The solvent was evaporated in vacuo and the residue partitioned between 0.1% aqueous TFA (200 ml) and hexanes (100 ml). The aqueous layer was separated and washed with hexanes (20 ml) and then lyophilised. The resulting white lyophilate was chromatographed in 5 equal portions over a Waters Prepak cartridge (C-18, 15–20 mM 100 A) eluting with a gradient of 95:5 to 5:95 0.1% TFA in H20: 0.1% TFA in CH$_3$CN at 100 ml/min over 60 min. The desired compound eluted after 19 min. The CH$_3$CN was evaporated in vacuo and the aqueous solution lyophilised to afford the title compound (1.95 g, 77%) as the TFA salt.

The salt is hygroscopic and is prone to disulphide formation if left in solution and exposed to air. $^1$H NMR δ (CD$_3$OD) 7.40–7.15 (5H,m), 4.55–5.40 (2H, m), 4.33 (1H, m), 4.18 (1H, m), 3.90–3.62 (3H, m), 3.53 (1H, dd, J=10.5 and 4.0 Hz), 3.37 (1H, dd, J=10.5 and 6.0 Hz), 3.23 (1H, m), 3.15–2.95 (2H, m), 2.88 (1H, dd, J=12.5 and 5.0 Hz), 2.55–2.25 (2H, m), 1.92 (1H, m), 1.49 (1H, m), 1.23 (1H, m), 0.94 (3H, t, J=6 Hz), 0.90 (3H, d, J=6Hz). FAB MS 873 (2M–H$^+$) 438 (MH$^+$) 361 (MH±Ph)

Anal. calc'd for C$_{22}$H$_{36}$O$_4$N$_3$S 2.6 TFA: C, 43.58; H, 5.25; N, 5,82. Found: C, 43.62; H, 5.07; N, 5.80.

Step J: Preparation of 2(S)-[2(S)-[2(R)-Amino-3-mercapto]-propylamino-3(S)-methyl)pentyloxy-3-phenylpropionyl-homoserine 2(S)-[2(S)-[2(R)-Amino-3-mercapto]propyl-amino-3(S)-methyl]pentyloxy-3-phenylpropionyl-homoserine lactone (0.00326 mmol) was dissolved in methanol (0.0506 ml) and IN sodium hydroxide (0.0134 ml) was added followed by methanol (0.262 ml). The conversion of the lactone to the hydroxy-acid was confirmed by HPLC analysis and NMR.

Example 6

Preparation of 2(S)-[2(S)-[2(R)-Amino-3-mercapto]-propylamino-3(S)-methyl]pentyloxy-3-phenylpropionyl-methionine Step A: Preparation of 2(S)-[2(S)-12(R)-(tert-butoxy-carbonyl)-amino-3-triphenyl-methylmercapto]-propylamino-3(S)-methyl]pentyloxy-3-phenyl-propionyl-methionine To a solution of 2(S)-[2(S)-[2(R)-(tert-butoxycarbonyl)-amino-3-triphenylmethylmercapto]-propylamino-3(S)-methyl]-pentyloxy-3-phenylpropionyl-methionine methyl ester (120 mg, 0.143 mmol) in methanol (4 ml) was added sodium hydroxide (1N, 0.57 ml, 0.57 mmol) and the resulting mixture was stirred at room temperature for 3 hours. Another portion of sodium hydroxide (1N, 0.25 ml) was added and stirring continued for 0.5 hours. The reaction mixture was concentrated and the residue was dissolved in a minimum amount of water and neutralized with hydrochloric acid (1N, 0.87 ml). The aqueous solution was extracted with ethyl acetate three times. The combined extracts were dried (Na$_2$SO$_4$) and concentrated to yield the title compound (110 mg, 0.133 mmol, 93%). NMR (CD$_3$OD) δ 0.70 (3H, d, J=6 Hz), 0.80 (3H, t, J=6Hz), 1.05 (H, m), 1.34 (9H, s), 1.60 (H, m), 1.95 (3H, S), 2.7~2.9 (3H, m), 2.95~3.1 (2H, m), 3.95 (H, d of d, J=8, 4 Hz), 4.27 (H, d of d, J=8.6 Hz), 7.1~7.4 (20H, m).

Step B: Preparation of 2(S)-[2(S)-[2(R)-Amino-3-mercapto]-propylamino-3(S)-methyl]pentyloxy-3-phenylpropionyl-methionine The title compound was prepared in the same manner as that described in Example 5, Step I, but using 2(S)-[2(S)-[2(R)-(tert-butoxycarbonyl)-amino-3- triphenylmethylmercapto]-propylamino-3(S)-methyl]-pentyloxy-3-phenylpropionyl-methionine in place of 2(S)-[2(S)-[2(R)-(tert-butoxycarbonyl)-amino-3-triphenylmethylmercapto]-propylamino-3(S)-methyl)-pentyloxy-3-phenylpropionyl-homoserine lactone. NMR (CD$_3$OD) δ 0.82 (3H, d, J=6Hz), 0.95 (3H, t, J=6 Hz), 1.20 (H, m), 1.40 (H, m), 1.85 (H, m), 2.10 (3H, s), 2.4~2.6 (2H, m), 3.1~3.2 (2H, m), 3.35 (H, d of d, J=14, 6 Hz), 3.55 (H, d of d, J=14, 5Hz), 4.20 (H, d of d, J=10, 5 Hz), 4.63 (H, d of d, J=10.6 Hz), 7.27 (5H, m).

Anal. Calcd for $C_{23}H_{39}N_3O_4S \cdot 2CF_3CO_2H \cdot 2H_2O$: C, 43.25; H, 6.05; N, 5.60. Found: C, 43.09; H, 6.01; N, 5.46.

Example 7

Preparation of 2(S)-[2(S)-[2(R)-Amino-3-mercapto]-propylamino-3(S)-methyl]pentyloxy-3-phenylpropionyl-methionine sulfone methyl ester (Compound 7-1)

Step A: Preparation of Methionine sulfone methyl ester

Thionyl chloride (2.63 ml, 36 mmol) was added dropwise to a stirred solution of N-Boc-Met sulfone (5 g, 18 mmol) in methanol (40 ml) cooled at 0° C. After the completion of the addition, the resulting mixture was warmed to room temperature and stirred overnight. The reaction mixture was recooled to 0° C. and slowly treated with solid sodium bicarbonate to adjust the pH to 7. The mixture was concentrated in vacuo to remove methanol and the residue was dissolved in a minimum amount of water (solution pH ca. 10) and extracted with ethyl acetate four times. The combined extracts were dried (Na$_2$SO$_4$) and concentrated to give the title compound (1.5 g). NMR (CD3OD) δ 2.04 (H, m), 2.21 (H, m), 2.98 (3H, s), 3.23 (2H, t, J=7 Hz), 3.63 (H, d of d, J=8.6 Hz), 3.77 (3H, s).

Step B: Preparation of N-(tert-Butoxycarbonyl)-2 (S)-[2(S)-amino-3(S)-methyl]-pentyloxy-3-phenyl-propionyl-methionine sulfone methyl ester The title compound was prepared in the same fashion as that described in Example 8, Step F, but using methionine sulfone methyl ester in place of homoserine lactone hydrochloride. NMR (CD$_3$OD) δ 0.80 (3H, d, J=6 Hz), 0.88 (3H, t, J=6 Hz), 1.12 (H, m), 1.47 (9H, s), 2.10 (H, m), 2.32 (H, m), 2.93 (3H, s), 3.5~3.7 (2H, m), 3.74 (3H, s), 4.01 (H, d of d, J=7.4 Hz), 4.60 (H, d of d, J=9.5 Hz), 6.60 (H, d, J=8 Hz), 7.25 (5H, m).

Step C: Preparation of 2(S)-[2(S)-Amino-3(S)-methyl]-pentyloxy-3-phenylpropionyl-methionine sulfone methyl ester hydrochloride The title compound was prepared in the same fashion as that described in Example 5, Step G, but using N-(tert-butoxycarbonyl)-2(S)-[2(S)-amino-3(S)-methyl]pentyloxy-3-phenylpropionyl-methionine sulfone methyl ester in place of N-(tert-butoxycarbonyl)-2(S)-[2(S)-amino-3(S)-methyl]pentyloxy-3-phenylpropionyl-homoserine lactone. NMR (CD$_3$OD) δ 0.85 (3H, d, J=6 Hz), 0.94 (3H, t, J=6 Hz), 1.20 (H, m), 1.52 (H, m), 1.72 (H, m), 2.14 (H, m), 2.38 (H, m), 2.98 (3H, s), 3.57 (H, d of d, J=12, 6 Hz), 3.73 (H, d of d, J=12, 9 Hz), 3.78 (3H, s), 4.15 (H, d of d, J=8.6 Hz), 4.63 (H, d of d, J=8.5 Hz), 7.30 (5H, m).

Step D: Preparation of 2(S)-[2(S)-[2(R)-(tert-Butoxy-carbonyl)-amino-3-triphenylmethylmercapto]-propylamino-3(S)-methyl]pentyloxy-3-phenyl-propionyl-methionine sulfone methyl ester The title compound was prepared in a similar fashion as that described in Example 5, Step H, but using 2(S)-[2(S)- amino-3(S)-methyl]pentyloxy-3-phenyl-propionyl-methionine sulfone methyl ester hydrochloride in place of 2(S)-[2(S)-amino-3(S)-methyl]pentyloxy-3-phenylpropionyl-homoserine lactone hydrochloride. NMR (CD$_3$OD) δ 0.70 (3H, d, J=6 Hz), 0.88 (3H, t, J=6 Hz), 1.10 (H, m), 1.47 (9H, s), 2.15 (H, m), 2.67 (H, m), 2.92.(3H, s), 3.67 (H, m), 4.68 (H, d of d, J=10, 6 Hz), 7.15~7.45 (20H, m).

Step E: Preparation of 2(S)-[2(S)-[2(R)-Amino-3-mercapto]-propylamino-3(S)-methyl]pentyloxy-3-phenylpropionyl-methionine sulfone methyl ester The title compound was prepared in a similar fashion as that described in Example 5, Step I, but using 2(S)[2(S)-[2(R)-(tert-butoxycarbonyl)amino-3-triphenylmethylmercapto]propylamino-3(S)-methyl]pentyloxy-3-phenylpropionyl-methionine sulfone methyl ester in place of 2(S)-[2(S)-[2(R)-(tert-butoxy-carbonyl)-amino-3-triphenyl-methylmercapto]propylamino-3(S)-methyl]pentyloxy-3-phenyl-propionyl-homoserine lactone. NMR (CD$_3$OD) δ 0.83 (3H, d, J=6 Hz), 0.93 (3H, t, J=6 Hz), 1.20 (H, m), 1.51 (H, m), 1.80 (H, m), 2.22 (H, m), 2.43 (H, m), 3.00 (3H, s), 3.78 (3H, s), 4.20 (H, d of d, J=8.4 Hz), 4.72 (H, d of d, J=10, 6 Hz), 7.30 (5H, m).

FABMS m/z 532 (MH$^+$).

Example 8

Preparation of 2(S)-[2(S)-[2(R)-Amino-3-mercapto]-propylamino-3(S)-methyl]-pentyloxy-3-phenylpropionyl-methionine sulfone (Compound 8-1)

Step A: Preparation of 2(S)-[2(S)-[2(R)-(tert-Butoxy-carbonyl)-amino-3-triphenylmethylmercapto]-propylamino-3(S)-methyl]pentyloxy-3-phenyl-propionyl-methionine sulfone The title compound was prepared in a similar fashion as that described in Example 6, Step A, but using 2(S)-[2(S)-[2(R)-(tert-butoxycarbonyl)amino-3-triphenylmethylmercapto]-propylamino-3(S)-methyl]-pentyloxy-3-phenylpropionyl-methionine sulfone methyl ester in place of 2(S)-[2(S)-[2(R)-(tert-butoxycarbonyl) amino-3-triphenyl-methylmercapto]propylamino-3(S)-methyl]pentyloxy-methionine methyl ester. NMR (CD$_3$OD) δ 0.79 (3H, d, J=6 Hz), 0.90 (3H, t, J=6 Hz), 1.47 (9H, s), 2.92 (3H, s), 4.08 (H, m), 4.32 (H, m), 7.15~7.35 (20H, m).

Step B: Preparation of 2(S)-[2(S)-[2(R)-Amino-3-mercapto]-propylamino-3(S)-methyl]-pentyloxy-3-phenylpropionyl-methionine sulfone The title compound was prepared in a similar fashion as that described in Example 5, Step I, but using 2(S)-[2(S)-[2(R)-(tert-butoxycarbonyl)amino-triphenylmethylmercapto]propylamino-3(S)-methyl]-pentyloxy-3-phenylpropionyl-methionine sulfone in place of 2(S)-{2(S)-[2(R)-(tert-butoxycarbonyl)amino-3-triphenylmethyl-mercapto]propylamino-3(S)-methyl]-pentyloxy-3-phenylpropionyl-3(S)-methyl]pentyloxy-3-phenylpropionyl-homoserine lactone. NMR (CD$_3$OD) δ 0.84 (3H, d, J=6 Hz), 0.94 (3H, t, J=6 Hz), 1.21 (H, m), 1.50 (H, m), 1.82 (H, m), 2.24 (H. m), 2.47 (H. m), 2.98 (3H, s), 3.6~3.75 (3H, m), 4.20 (H, d of d, J=9.5 Hz), 4.64 (H, d of d, J=9.6 Hz), 7.30 (5H, m).

Anal. Calcd for $C_{23}H_{39}N_3O_6S_2 \cdot 3CF_3CO_2H$: C, 40.51; H, 4.92; N, 4.89. Found: C, 40.47; H, 5.11; N, 4.56.

Example 9

Preparation of 2(S)-[2(S)-[2(R)-Amino-3-mercapto]-propylamino-3(S)-methyl)-pentyloxy-3-phenylpropionyl-methionine sulfone isopropyl ester (Compound A)

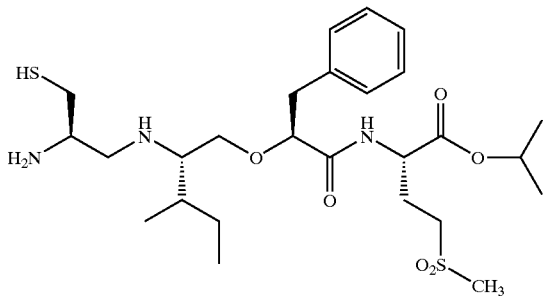

The title compound was prepared using methods A-E from Example 7, except for Method A. Methionine sulfone isopropyl ester was prepared by coupling t-butyloxycarbonyl-methionine sulfone with isopropyl alcohol using dicyclohexylcarbodiimide (DCC) and 4-dimethylaminopyridine (DMAP) followed by deprotection with HCl in EtOAc. NMR (CD$_3$OD) δ 0.83 (3H, d, J=6 Hz), 0.94 (3H, t, J=6 Hz), 1.11–1.56 (2H, m), 1.28 (6H, d, J=6 Hz), 1.8–1.96 (1H, m), 2.12–2.27 (1H, m), 2.89–3.0 (2H, m), 3.01 (3H, s), 3.06–3.3 (4H, m), 3.42 (1H, dd, J=6, 13 Hz), 3.65 (1H, dd, J=6,13 Hz), 3.68–3.91 (3H, m), 4.2–4.27 (1H, m), 4.61–4.7 (1H, m), 4.96–5.12 (2H, m), 7.19–7.44 (5H, m).

Anal. Calc'd. for C$_{26}$H$_{45}$N$_3$O$_6$S$_2$.2CF$_3$CO$_2$H: C, 44.07; H, 5.67; N, 4.97; Found: C, 44.35; H, 5.68; N, 5.23

Example 10

4-[1-(5-Chloro-2-oxo-2H-[1,2']bipyridinyl-5'-ylmethyl)-1H-pyrrol-2-ylmethyl]-benzonitrile

Step 1: 5-Chloro-5'-methyl-[1,2']bipyridinyl-2-one

5-Chloro-2-pyridinol (2.26 g, 17.4 mmol), 2-bromo-5-methylpyridine (3.00 g, 17.4 mmol), copper (0.022 g, 0.35 mmol) and K$_2$CO$_3$ (2.66 g, 19.2 mmol) were heated at 180° C. for 16 hrs. The brown reaction mixture was cooled, diluted with EtOAc and washed with saturated NaHCO$_3$. The aqueous layer was extracted with EtOAc (2×) and the combined organic extracts were washed with brine, dried (Na$_2$SO$_4$) and evaporated in vacuo. The residue was chromatographed (silica gel, EtOAc: CH$_2$Cl$_2$20:80 to 50:50 gradient elution) to afford the title compound as a white solid.

$^1$H NMR (400 MHz, CDCl$_3$) δ 8.37 (s, 1H), 7.96(d, J=3.0 Hz, 1H), 7.83 (d, J=8.4 Hz, 1H), 7.65(dd, J=2.4 and 8.2 Hz, 1H), 7.32(dd, J=2.9 and 9.7 Hz, 1H), 6.61(d, J=9.7 Hz, 1H) and 2.39(s,3H)ppm.

Step 2: 5'-Bromomethyl-5-chloro-1.2']bipyridinyl-2-one

A solution of the pyridine from Step 1(1.00 g, 4.53 mmol), N-bromosuccinimide (0.81 g, 4.53 mmol) and AIBN (0.030 g, 0.18 mmol) in CCl$_4$ (40mL) was heated at reflux for 2 hrs. The solids were filtered and the filtrate collected. The solvent was evaporated in vacuo and the residue chromatographed (silica gel, EtOAc: CH$_2$Cl$_2$25:75 to 50:50 gradient elution) to afford the title bromide.

$^1$H NMR (400 MHz, CDCl$_3$) δ 8.55 (s, 1H), 8.04( d, J=2.9 Hz, 1H), 8.01 (d, J=8.4 Hz, 1H), 7.88 (dd, J=2.4 and 8.6 Hz, 1H), 7.34(dd, J=2.9 and 9.8 Hz, 1H), 6.61(d, J=9.9 Hz, 1H) and 4.51 (s,2H) ppm.

Step 3: 4-[1-(5-Chloro-2-oxo-2H-[1,2']bipyridinyl-5'-ylmethyl)-1H-pyrrol-2-ylmethyl]-benzonitrile hydrochloride The bromide from Step 2 (0.750 g, 2.50 mmol) and the 4-(1-trityl-1H-imidazol-4-ylmethyl)-benzonitrile (1.06 g, 2.50 mmol) in CH$_3$CN (10 mL) were heated at 60° C. The reaction was cooled to room temperature and the solids collected by filtration and washed with EtOAc (10 mL). The solid was suspended in methanol (50 mL) and heated at reflux for 1 hr, cooled and the solvent evaporated in vacuo. The sticky residue was stirred in EtOAc (40 mL) for 4 hrs and the resulting solid hydrobromide salt collected by filtration and washed with EtOAc (40 mL) and dried in vacuo. The hydrobromide salt was partitioned between sat. NaHCO$_3$ and CH$_2$Cl$_2$ and extracted with CH$_2$Cl$_2$. The organic extracts were dried (Na$_2$SO$_4$) and evaporated in vacuo. The residue was chromatographed (silica gel, MeOH: CH$_2$Cl$_2$4:96 to 5:95 gradient elution) to afford the free base which was converted to the hydrochloride salt to afford the title compound as a white solid.

$^1$H NMR (400 MHz, CD$_3$OD) δ 9.11 (s, 1H), 8.35 (s, 1H), 8.03(d, J=2.9 Hz, 1H), 7.83 (d, J=8.4 Hz, 1H), 7.76 (dd, J=2.4 and 9.6 Hz, 1H), 7.68–7.58 (m, 3H), 7.48 (s, 1H), 7.31(d, J=8.6 Hz, 2H), 6.68 (d, J=9.3 Hz, 1H), 5.53 (s, 2H) and 4.24 (s, 2H) ppm. Analysis: Calc for C$_{22}$H$_{16}$N$_5$OCl: 1.75 HCl, 0.15 EtOAc C 56.69, H 3.99, N 14.62 Found: C 56.72, H 4.05, N 14.54

Example 11

Preparation of (R)-1-(3-chlorophenyl)-4-[1-(4-cyanobenzyl)-5-imidazolylmethyl]-5-[2-(ethanesulfonyl)methyl)-2-piperazinone dihydrochloride

Step A: Preparation of (R)-2-(tert-butoxycarbonylamino)-N-(3-chlorophenyl)-3-[(triphenylmethyl)thiol]-1-propanamine To a solution of 3-chloroaniline (0.709 mL. 6.70 mmol) in 30 mL of dichloromethane at room temperature was added 1.2 g of crushed 4 Å molecular sieves. Sodium triacetoxyborohydride (3.55 g, 16.7 mmol) was added, followed by dropwise addition of N-methylmorpholine to achieve a pH of 6.5. L-S-Trityl-N-Boc-cysteinal (3.15 g, 7.04 mmol) (prepared according to S. L. Graham et al. *J. Med. Chem*, (1994) Vol. 37, 725–732) was added, and the solution was stirred for 48 hours. The reaction was quenched with sat. aq. NaHCO$_3$, diluted with EtOAc, and the layers were separated. The organic material was washed with brine, dried (Na$_2$SO$_4$), filtered, and concentrated in vacuo to provide an oil which was purified by silica gel chromatography (15% EtOAc/hexane) to give the title amine.

Step B: Preparation of (R)-N-[2-(tert-butoxycarbonylamino)-3-((triphenylmethyl)thio) propyl]-2-chloro-N-(3-chlorophenyl)acetamide The aniline derivative from Step A (2.77 g, 4.95 mmol) was dissolved in 73 mL of EtOAc and 73 mL of sat. NaHCO$_3$ soln., then cooled to 0° C. With vigorous stirring, chloroacetyl chloride (0.533 mL. 6.69 mmol) was added dropwise. After 3 hours, the reaction was diluted with water and EtOAc, and the organic layer was washed with brine, dried (Na$_2$SO$_4$), filtered, and concentrated in vacuo to provide crude titled chloroacetamide which was used without further purification.

Step) C: Preparation of (R)-4-(tert-butoxycarbonyl)-1-(3-chlorophenyl)-5-[S-(triphenylmethyl)thiomethyl]piperazin-2-one To a solution of chloroacetamide from Step B (3.29 g crude, theoretically 4.95 mmol) in 53 mL of DMF at 0° C. was added cesium carbonate (4.84 g, 14.85 mmol). The solution was stirred for 48 hours, allowing it to warm to room temperature. The solution was poured into EtOAc, washed with water and brine, dried (Na$_2$SO$_4$), filtered, and concentrated in vacuo to provide the crude product as an oil. This material was purified by silica gel chromatography (20% EtOAc/hexane) to yield the product as a white solid.

Step D: Preparation of (R)-4-(tert-butoxycarbonyl)-1-(3-chlorophenyl)-5-(thiomethyl)piperazin-2-one A solution of piperazinone from Step C (625 mg, 1.04 mmol) in degassed EtOAc (38 mL) and EtOH (12 mL) was warmed to 30° C. A solution of AgNO$_3$ (177 mg, 1.04 mmol) and pyridine (0.084 mL, 1.04 mmol) in 8 mL of EtOH was added, and the solution was heated to reflux. After 45 minutes, the reaction was concentrated in vacuo, then redissolved in 26 mL of degassed EtOAc. Through this solution was bubbled H$_2$S gas for 2.5 minutes, then activated charcoal was added after 4 minutes. The material was filtered through celite and rinsed with degassed EtOAc, concentrated in vacuo, then reconcentrated from degassed CH$_2$Cl$_2$ to provide the crude product which was used without further purification.

Step E: Preparation of (R)-4-(tert-butoxycarbonyl)-1-(3-chlorophenyl)-5-[(ethylthio)methyl]piperazin-2-one A solution of the thiol from Step D (ca. 1.04 mmol) in 3 mL of THF was added via cannula to a suspension of NaH (51.4 mg, 60% disp. in mineral oil, 1.28 mmol) in 2 mL THF at 0° C. After 10 minutes, iodoethane was added (0.079 mL, 0.988 mmol), and the solution was stirred for 1.5 hours. The reaction was poured into EtOAc, washed with sat. NaHCO$_3$ and brine, dried (Na$_2$SO$_4$), filtered, and concentrated in vacuo to provide the crude product. This material was purified by silica gel chromatography (1% MeOH/CH$_2$Cl$_2$) to yield the titled product.

Step F: Preparation of (R)-4-(tert-butoxycarbonyl)-1-(3-chlorophenyl)-5-[(ethanesulfonyl)methyl]piperazin-2-one To a solution of the sulfide from Step E (217 mg, 0.563 mmol) in 3 mL of MeOH at 0° C. was added a solution of magnesium monoperoxyphthalate (835 mg, 1.69 mmol) in 2 mL MeOH. The reaction was stirred overnight, allowing it to warm to room temperature. The solution was cooled to 0° C., quenched by the addition of 4 mL 2N Na$_2$S$_2$O$_3$ soln., then concentrated in vacuo. The residue was partitioned between EtOAc and sat NaHCO$_3$ solution, and the organic layer was washed with brine, dried (Na$_2$SO$_4$), filtered, and concentrated in vacuo to provide the crude sulfone as a white waxy solid.

Step G: Preparation of (R)-1-(3-chlorophenyl)-4-[1-(4-cyanobenzyl)-5-imidazolylmethyl]-5-[2-(ethanesulfonyl)methyl]-2-piperazinone dihydrochloride To a solution of the Boc-protected piperazinone from Step F (224 mg, 0.538 mmol) in 5 mL of dichloromethane at 0° C. was added 2.5 mL of trifluoroacetic acid (TFA). After 45 minutes, the reaction was concentrated in vacuo, then azeotroped with benzene to remove the excess TFA. The residue was taken up in 4 mL of 1,2-dichloroethane and cooled to 0° C. To this solution was added 4 Å powdered molecular sieves (340 mg), followed by sodium triacetoxyborohydride (285 mg, 1.34 mmol) and several drops of triethylamine to achieve pH=6. The imidazole carboxaldehyde from Step E of Example 42 (125 mg, 0.592 mmol) was added, and the reaction was stirred at 0° C. After 2 days, the reaction was poured into EtOAc, washed with dilute aq. NaHCO$_3$, and brine, dried (Na$_2$SO$_4$), filtered, and concentrated in vacuo. The crude product was taken up in methanol and injected onto a preparative HPLC column and purified with a mixed gradient of 15%–50% acetonitrile/0.1% TFA; 85%–50% 0.1% aqueous TFA over 60 minutes. After concentration in vacuo, the resultant product was partitioned between dichloromethane and aq. NaHCO$_3$ soln., and the aqueous phase was extracted with CH$_2$Cl$_2$. The organic solution was washed with brine, dried (Na$_2$SO$_4$), filtered, and concentrated to dryness to provide the product free base, which was taken up in CH$_2$Cl$_2$ and treated with 2.1 equivalents of 1 M HCl/ether solution. After concentrated in vacuo, the product dihydrochloride was isolated as a white powder.

Biological Assays.

The ability of compounds of the present invention to inhibit cancer can be demonstrated using the following assays.

In Vitro Inhibition of Farnesyl-protein Transferase

Transferase Assays. Isoprenyl-protein transferase activity assays were carried out at 30° C. unless noted otherwise. A typical reaction contained (in a final volume of 50 µL): [$^3$H]farnesyl diphosphate or [$^3$H]geranylgeranyl diphosphate, Ras protein, 50 mM HEPES, pH 7.5, 5 mM MgCl$_2$, 5 mM dithiothreitol and isoprenyl-protein transferase. The FPTase employed in the assay was prepared by recombinant expression as described in Omer, C. A., Kral, A. M., Diehl, R. E., Prendergast, G. C., Powers, S., Allen, C. M., Gibbs, J. B. and Kohl, N. E. (1993) *Biochemistry* 32:5167–5176. The geranylgeranyl-protein transferase-type I employed in the assay was prepared as described in U.S. Pat. No. 5,470,832, incorporated by reference. After thermally pre-equilibrating the assay mixture in the absence of enzyme, reactions were initiated by the addition of isoprenyl-protein transferase and stopped at timed intervals (typically 15 min) by the addition of 1 M HCl in ethanol (1 mL). The quenched reactions were allowed to stand for 15 m (to complete the precipitation process). After adding 2 mL of 100% ethanol, the reactions were vacuum-filtered through Whatman GF/C filters. Filters were washed four times with 2 mL aliquots of 100% ethanol, mixed with scintillation fluid (10 mL) and then counted in a Beckman LS3801scintillation counter.

For inhibition studies, assays were run as described above, except inhibitors were prepared as concentrated solutions in 100% dimethyl sulfoxide and then diluted 20-fold into the enzyme assay mixture. IC$_{50}$ values were determined with both transferase substrates near KM concentrations. Nonsaturating substrate conditions for inhibitor IC$_{50}$ determinations were as follows: FTase, 650 nM Ras-CVLS, 100 nM farnesyl diphosphate; GGPTase-I, 500 nM Ras-CAIL, 100 nM geranylgeranyl diphosphate.

In vivo Ras Prenylation Assay

The cell lines used in this assay consist of either Rat1 or NIH3T3 cells transformed by either viral Ha-ras; an N-ras chimeric gene in which the C-terminal hypervariable region of v-Ha-ras was substituted with the corresponding region from the N-ras gene; or ras-CVLL, a v-Ha-ras mutant in which the C-terminal exon encodes leucine instead of serine, making the encoded protein a substrate for geranylgeranylation by GGPTase I. The assay can also be performed using cell lines transformed with human Ha-ras, N-ras or Ki4B-ras. The assay is performed essentially as described in DeClue, J. E. et al., Cancer Research 51:712–717, (1991). Cells in 10 cm dishes at 50–75% confluency are treated with the test compound(s) (final concentration of solvent, methanol or dimethyl sulfoxide, is 0.1%). After 4 hours at 37° C., the cells are labelled in 3 ml methionine-free DMEM supplemented with 10% regular DMEM, 2% fetal bovine serum, 400 $\mu$Ci[$^{35}$S]methionine (1000 Ci/mmol) and test compound(s). Cells treated with lovastatin, a compound that blocks Ras processing in cells by inhibiting the rate-limiting step in the isoprenoid biosynthetic pathway (Hancock, J. F. et al. Cell, 57:1167 (1989); DeClue, J. E. et al. *Cancer Res.,* 51:712 (1991); Sinensky, M. et al. *J. Biol. Chem.,* 265:19937 (1990)), serve as a positive control in this assay. After an additional 20 hours, the cells are lysed in 1 ml lysis buffer (1% NP40/20 mM HEPES, pH 7.5/5 mM MgCl2/1 mM DTT/10 mg/ml aprotinen/2 mg/ml leupeptin/2 mg/ml antipain/0.5 mM PMSF) and the lysates cleared by centrifugation at 100,000×g for 45 min. Alternatively, four hours after the addition of the labelling media, the media is removed, the cells washed, and 3 ml of media containing the same or a different test compound added. Following an additional 16 hour incubation, the lysis is carried out as above. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., J. Virol. 43:294–304, (1982)). Following a 2 hour antibody incubation at 4° C., 200 $\mu$l of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X- 100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to prenylated and nonprenylated Ras proteins are compared to determine the percent inhibition of prenyl transfer to protein.

In vivo Growth Inhibition of Ras Transformed Cells Assay

To determine the biological consequences of FPTase inhibition, the effect of the compounds of the instant invention on the anchorage-independent growth of Rat1 cells transformed with either a v-ras, v-raf, or v-mos oncogene is tested. Cell lines transformed with human Ha-ras, N-ras or Ki4B-ras can also be utilized. Cells transformed by v-Raf and v-Mos may be included in the analysis to evaluate the specificity of instant compounds for Ras-induced cell transformation.

Rat 1 cells transformed with either v-ras, v-raf, or v-mos are seeded at a density of 1×104 cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photo-micrographs are taken approximately 16 days after the cultures are seeded and comparisons are made.

In addition, the activity of the compounds of the present invention for treating cancer and/or inhibiting tumor growth is confirmed utilizing the nude mouse tumor xenograft assay described in Kohl et al., PNAS 91 (1994) 9141–45.

In vitro Growth Inhibition of Human Tumor Cells Assays

Cancer cells (MCF-7, MDA-468, T47D, MDA-231, SkOv3, A549, SkBr3,PC3, LNCaP or DU-145) are seeded in 6 well clusters at 10,000 or 20,000 cells per well. The growth media utilized in the cell assays is RPMI media [GIBCO], supplemented with 5 or 10% fetal calf serum, glutamine, penicillin and streptomycin. The cell are then treated under one of the following protocols:

Protocol A

After one day in growth media, the cells are exposed to various concentrations of an antineoplastic agent for a four (4) hour period. The cells are then washed twice and placed in a growth media containing a farnesyl-protein transferase inhibitor (FTI) and incubated for 7 to 10 days. At the end of the incubation the cells are harvested by tripsinization and counted in a Coulter counter.

Protocol B

The cells are placed in growth media containing a farnesyl-protein transferase inhibitor (FTI). After one day in the FTI containing growth media, the cells are exposed to various concentrations of a antineoplastic agent for a four (4) hour period. The cells are then washed twice and again placed in a growth media containing a farnesyl-protein transferase inhibitor (FTI) and incubated for 7 to 10 days. At the end of the incubation the cells are harvested by tripsinization and counted in a Coulter counter.

Protocol C

The cells are placed in growth media containing a farnesyl-protein transferase inhibitor (FTI) and various concentrations of a antineoplastic agent. The cells are incubated for 7 to 10 days. At the end of the incubation the cells are harvested by tripsinization and counted in a Coulter counter.

Protocol D-1

The cells are placed in growth media containing a antineoplastic agent at various concentrations for four (4) hours. The monolayer of cells is then separated from the media and washed 4 times with PBS. The cells are trypsinized and counted with a Coulter counter. 20,000 cells are replated on 6 well plates in 0.35% agar over a 0.7% agar layer, both layers which contain vehicle only, 0.2 $\mu$M, 2 $\mu$M or 20 $\mu$M of a farnesyl-protein transferase inhibitor. The cells are fed and treated with the FTI, or vehicle only, twice weekly. At the end of twelve days incubation the cells are scored manually from duplicate wells.

Protocol D-2

The cells are placed in growth media containing a antineoplastic agent for four (4) hours. The monolayer of cells is then separated from the media and washed 4 times with PBS. The cells are trypsinized and counted with a Coulter counter. 10,000 cells are replated on 12 well plates in the standard RPMI media described above which contain vehicle only, 0.2 $\mu$M or 2 $\mu$M of a farnesyl-protein transferase inhibitor. The cells are fed and treated with the FTI, or vehicle only, twice weekly and at those times the colonies are scored manually from duplicate wells. At the end of seven days incubation the cells are scored manually from duplicate wells.

Protocol E-1

Protocol is similar to Protocol A except that the cells are plated at 4,000 to 10,000 cells per well. At the end of 5 days incubation with the FTI, 1 $\mu$L of a 5 mg/ml atock of MTT ( ) was added and the cells were incubated an additional 4 hours. The media was then removed and the cells were solubilized with 1 ml isopropanol for 2–3 minutes. The optical density of the cells was then read at 570 nm wavelength.

Protocol E-2

Protocol is similar to Protocol B except that the cells are plated at 4,000 to 10,000 cells per well. At the end of 5 days incubation with the FTI, 1, μL of a 5 mg/ml atock of MTT ( ) was added and the cells were incubated an additional 4 hours. The media was then removed and the cells were solubilized with 1 ml isopropanol for 2–3 minutes. The optical density of the cells was then read at 570 nm wavelength.

Protocol E-3

Protocol is similar to Protocol B except that the cells are plated at 4,000 to 10,000 cells per well. At the end of 5 days incubation with the FTI and the antineoplastic agent, 1 μL of a 5 mg/ml atock of MTT ( ) was added and the cells were incubated an additional 4 hours. The media was then removed and the cells were solubilized with 1 ml isopropanol for 2–3 minutes. The optical density of the cells was then read at 570 nm wavelength.

In vitro Cell Cycle Assay

Cancer cells (MCF-7, MDA468 or DU-145) are seeded in a 10 cm dish at 1,000,000 cells per dish. After one day in growth media, the cells are exposed to various concentrations of a antineoplastic agent along with vehicle (PBS) or 1 μM FTI in the vehicle. After 24 hours of exposure to the combination or antineoplastic agent, the cells are trypsinized and stained with ethidium bromide. The stained nucleii are analyzed by flow cytometry for evaluation of the DNA content.

In vivo Tumor Growth Inhibition Assay (Nude Mouse)

Rodent fibroblasts transformed with oncogenically mutated human Ha-ras or Ki-ras ($10^6$ cells/animal in 1 ml of DMEM salts) are injected subcutaneously into the left flank of 8–12 week old female nude mice (Harlan) on day 0. The mice in each oncogene group are randomly assigned to a vehicle, compound or combination treatment group. Animals are dosed subcutaneously starting on day 1 and daily for the duration of the experiment. Alternatively, the farnesyl-protein transferase inhibitor may be administered by a continuous infusion pump. Compound, compound combination or vehicle is delivered in a total volume of 0.1 ml. Tumors are excised and weighed when all of the vehicle-treated animals exhibited lesions of 0.5–1.0 cm in diameter, typically 11–15 days after the cells were injected. The average weight of the tumors in each treatment group for each cell line is calculated.

The following dosage groups are utilized to determine the efficacy of the combination of the farnesyl-protein transferase inhibitor (FTI) and antineoplastic agent (agent):

| Group | O  | Vehicle controls |
|-------|----|------------------|
| Group | A: | FTI at maximum no effect dose |
| Group | B: | FTI at minimal efficacy dose |
| Group | C: | agent at maximal no effect dose |
| Group | D: | agent at minimal efficacy dose |
| Group | E: | A + C |
| Group | F: | A + D |
| Group | G: | B + C |
| Group | H: | B + D |

Additional doses of FTI and agent can be selected as needed.

What is claimed is:

1. A method for achieving a synergistic therapeutic effect in a mammal in need thereof which comprises administering to said mammal amounts of at least two therapeutic agents selected from a group consisting of:

a) a prenyl-protein transferase inhibitor and b) an antineoplastic agent selected from paclitaxel, epothilone A, epothilone B, desoxyepothilone A or desoxyepothilone B, wherein the synergistic therapeutic effect is the treatment of cancers of the brain, breast, colon, genitourinary tract, lymphatic system, pancreas, rectum, stomach, larynx, liver, lung, prostate, stet histiocytic lymphoma lung adenocarcinoma, pancreatic carcinoma, colo-rectal carcinoma, small cell lung cancers or neurological tumor cancer whose growth is inhibited by the administration of the prenyl-protein transferase inhibitor and the antineoplastic agent.

2. The method according to claim 1 wherein the prenyl-protein transferase inhibitor is selected from:

2(S)-Butyl-1-(2,3-diaminoprop-1-yl)-1-(1-naphthoyl)piperazine;

1-(3-Amino-2-(2-naphthylmethylamino)prop-1-yl)-2(S)-butyl-4-(1-naphthoyl)piperazine;

2(S)-Butyl-1-{5-[1-(2-naphthylmethyl)]-4,5-dihydroimidazol}methyl-4-(1-naphthoyl)piperazine;

1-[5-(1-Benzylimidazol)methyl]-2(S)-butyl-4-(2-naphthoyl)piperazine;

1-{5-[1-(4-nitrobenzyl)]imidazolylmethyl}-2(S)-butyl-4-(1-naphthoyl)piperazine;

1-(3-Acetamidomethylthio-2(R)-aminoprop-1-yl)-2(S)-butyl-4-(1-naphthoyl)piperazine;

2(S)-Butyl-1-[2-(1-imidazolyl)ethyl]sulfonyl-4-(1-naphthoyl)piperazine;

2(R)-Butyl-1-imidazolyl-4-methyl-4-(1-naphthoyl)piperazine;

2(S)-Butyl-4-(1-naphthoyl)-1-(3-pyridylmethyl)piperazine;

1-2(S)-butyl-(2(R)-(4-nitrobenzyl)amino-3-hydroxypropyl)-4-(1-naphthoyl)piperazine;

1-(2(R)-Amino-3-hydroxyheptadecyl)-2(S)-butyl-4-(1-naphthoyl)-piperazine;

2(S)-Benzyl-1-imidazolyl-4-methyl-4-(1-naphthoyl)piperazine;

1-(2(R)-Amino-3-(3-benzylthio)propyl)-2(S)-butyl-4-(1-naphthoyl)piperazine;

1-(2(R)-Amino-3-[3-(4-nitrobenzylthio)propyl])-2(S)-butyl-4-(1-naphthoyl)piperazine;

2(S)-Butyl-1-[(4-imidazolyl)ethyl]-4-(1-naphthoyl)piperazine;

2(S)-Butyl-1-[(4-imidazolyl)methyl]-4-(1-naphthoyl)piperazine;

2(S)-Butyl-1-[(1-naphth-2-ylmethyl)-1H-imidazol-5-yl)acetyl]-4-(1-naphthoyl)piperazine;

2(S)-Butyl-1-[(1-naphth-2-ylmethyl)-1H -imidazol-5-yl)ethyl]-4-(1-naphthoyl)piperazine;

1-(2(R)-Amino-3-hydroypropyl)-2(S)-butyl-4-(1-naphthoyl)piperazine;

1-(2(R)-Amino-4-hydroxybutyl)-2(S)-butyl-4-(1-naphthoyl)piperazine;

1-(2-Amino-3-(2-benzyloxyphenyl)propyl)-2(S)-butyl-4-(1-naphthoyl)piperazine;

1-(2-Amino-3-(2-hydroxyphenyl)propyl)-2(S)-butyl-4-(1-naphthoyl)piperazine;

1-[3-(4-imidazolyl)propyl]-2(S)-butyl-4-(1-naphthoyl)-piperazine;

2(S)-n-Butyl-4-(2,3-dimethylphenyl)-1-(4-imidazolylmethyl)-piperazin-5-one;

2(S)-n-Butyl-1-[1-(4-cyanobenzyl)imidazol-5-ylmethyl]-4-(2,3-dimethylphenyl)piperazin-5-one;

1-[1-(4-Cyanobenzyl)imidazol-5-ylmethyl]-4-(2,3-dimethylphenyl)-2(S)-(2-methoxyethyl)piperazin-5-one;

2(S)-n-Butyl-4-(1-naphthoyl)-1-[1-(1-naphthylmethyl)imidazol-5-ylmethyl]-piperazine;

2(S)-n-Butyl-4-(1-naphthoyl)-1-[1-(2-naphthylmethyl)imidazol-5-ylmethyl]-piperazine;

2(S)-n-Butyl-1-[1-(4-cyanobenzyl)imidazol-5-ylmethyl]-4-(1-naphthoyl)piperazine;

2(S)-n-Butyl-1-[1-(4-methoxybenzyl)imidazol-5-ylmethyl]-4-(1-naphthoyl)piperazine;

2(S)-n-Butyl-1-[1-(3-methyl-2-butenyl)imidazol-5-ylmethyl]-4-(1-naphthoyl)piperazine;

2(S)-n-Butyl-1-[1-(4-fluorobenzyl)imidazol-5-ylmethyl]-4-(1-naphthoyl)piperazine;

2(S)-n-Butyl-1-[1-(4-chlorobenzyl)imidazol-5-ylmethyl]-4-(1-naphthoyl)piperazine;

1-[1-(4-Bromobenzyl)imidazol-5-ylmethyl]-2(S)-n-butyl-4-(1-naphthoyl)piperazine;

2(S)-n-Butyl-4-(1-naphthoyl)-1-[1-(4-trifluoromethylbenzyl)imidazol-5-ylmethyl]-piperazine;

2(S)-n-Butyl-1-[1-(4-methylbenzyl)imidazol-5-ylmethyl]-4-(1-naphthoyl)-piperazine;

2(S)-n-Butyl-1-[1-(3-methylbenzyl)imidazol-5-ylmethyl]-4-(1-naphthoyl)-piperazine;

1-[1-(4-Phenylbenzyl)imidazol-5-ylmethyl]-2(S)-n-butyl-4-(1-naphthoyl)-piperazine;

2(S)-n-Butyl-4-(1-naphthoyl)-1-[1-(2-phenylethyl)imidazol-5-ylmethyl]-piperazine;

2(S)-n-Butyl-4-(1-naphthoyl)-1-[1-(4-trifluoromethoxy)imidazol-5-ylmethyl]piperazine;

1-{[1-(4-cyanobenzyl)-1H-imidazol-5-yl]acetyl}-2(S)-n-butyl-4-(1-naphthoyl)piperazine;

(S)-1-(3-Chlorophenyl)-4-[1-(4-cyanobenzyl)-5-imidazolylmethyl]-5-[2-(methanesulfonyl)ethyl]-2-piperazinone;

(S)-1-(3-Chlorophenyl)-4-[1-(4-cyanobenzyl)-5-imidazolylmethyl]-5-[2-(ethanesulfonyl)ethyl]-2-piperazinone;

(R)-1-(3-Chlorophenyl)-4-[1-(4-cyanobenzyl)-5-imidazolylmethyl]-5-[2-ethanesulfonyl)methyl]-2-piperazinone;

(S)-1-(3-Chlorophenyl)-4-[1-(4-cyanobenzyl)-5-imidazolylmethyl]-5-[N-ethyl-2-acetamido]-2-piperazinone;

(±)-5-(2-Butynyl)-1-(3-chlorophenyl)-4-[1-(4-cyanobenzyl)-5-imidazolylmethyl]-2-piperazinone;

1-(3-Chlorophenyl)-4-[1-(4-cyanobenzyl)-5-imidazolylmethyl]-2-piperazinone;

5(S)-Butyl-4-[1-(4-cyanobenzyl-2-methyl)-5-imidazolylmethyl]-1-(2,3-dimethylphenyl)-piperazin-2-one;

4-[1-(2-(4-Cyanophenyl)-2-propyl)-5-imidazolylmethyl]-1-(3-chlorophenyl)-5(S)-(2-methylsulfonylethyl)piperazin-2-one;

5(S)-n-Butyl-4-[1-(4-cyanobenzyl)-5-imidazolylmethyl]-1-(2-methylphenyl)piperazin-2-one;

4-[1-(4-Cyanobenzyl)-5-imidazolylmethyl]-5(S)-(2-fluoroethyl)-1-(3-chlorophenyl)piperazin-2-one;

4-[3-(4-Cyanobenzyl)pyridin-4-yl]-1-(3-chlorophenyl)-5(S)-(2-methylsulfonylethyl)-piperazin-2-one;

4-[5-(4-Cyanobenzyl)-1-imidazolylethyl]-1-(3-chlorophenyl)piperazin-2-one;

2(S)-[2(S)-[2(R)-Amino-3-mercapto]propylamino-3(S)-methyl]-pentyloxy-3-phenylpropionyl-homoserine lactone, 2(S)-[2(S)-[2(R)-Amino-3-mercapto]propylamino-3(S)-methyl]pentyloxy-3-phenylpropionyl-homoserine, 2(S)-[2(S)-[2(R)-Amino-3-mercapto]propylamino-3(S)-methyl]pentyloxy-2-methyl-3-phenylpropionyl-homoserine lactone, 2(S)-[2(S)-[2(R)-Amino-3-mercapto]propylamino-3(S)-methyl]pentyloxy-2-methyl-3-phenylpropionyl-homoserine, 2(S)-[2(S)-[2(R)-Amino-3-mercapto]propylamino-3(S)-methyl]pentyloxy-4-pentenoyl-homoserine lactone, 2(S)-[2(S)-[2(R)-Amino-3-mercapto]propylamino-3(S)-methyl]-pentyloxy-4-pentenoyl-homoserine, 2(S)-[2(S)-[2(R)-Amino-3-mercapto]propylamino-3(S)-methyl]pentyloxypentanoyl-homoserine lactone, 2(S)-[2(S)-[2(R)-Amino-3-mercapto]propylaniino-3(S)-methyl]pentyloxypentanoyl-homoserine, 2(S)-[2(S)-[2(R)-Amino-3-mercapto]propylamino-3(S)-methyl]5-pentyloxy-4-methylpentanoyl-homoserine lactone, 2(S)-[2(S)-[2(R)-Amino-3-mercapto]propylamino-3(S)-methyl]pentyloxy-4-methylpentanoyl-homoserine, 2(S)-[2(S)-[2(R)-Amino-3-mercapto]Propylamino-3(S)-methyl]pentyloxy-3-methylbutanoyl-homoserine lactone, 2(S)-[2(S)-[2(R)-Amino-3-mercapto]propylamino-3(S)-methyl]pentyloxy-3-methylbutanoyl-homoserine, 2(S)-[2(S)-[2(R)-Amino-3-mercapto]propylamino-3(S)-methyl]pentyloxy-3-phenylbutanoyl-homoserine lactone, 2(S)-[2(S)-[2(R)-Amino-3-mercapto]propylamino-3(S)-methyl]-pentyloxy-3-phenylbutanoyl-homoserine, 2(S)-[2(S)-[2(R)-Amino-3-mercapto]propylamino-3(S)-methyl]pentylthio-2-methyl-3-phenylpropionyl-homoserine lactone, 2(S)-[2(S)-[2(R)-Amino-3-mercapto]propylamino-3(S)-methyl]pentylthio-2-methyl-3-phenylpropionyl-homoserine, 2(S)-[2(S)-[2(R)-Amino-3-mercapto]propylamino-3(S)-methyl]pentylsulfonyl-2-methyl-3-phenylpropionyl-homoserine lactone, 2(S)-[2(S)-[2(R)-Amino-3-mercapto]propylamino-3(S)-methyl]-pentylsulfonyl-2-methyl-3-phenylpropionyl-homoserine, 2(S)-[2(S)-[2(R)-Amino-3-mercapto]propylaniino-3(S)-methyl]-pentyloxy-3-phenylpropionyl-methionine methyl ester, 2(S)-[2(S)-[2(R)-Amino-3-mercapto]propylamino-3(S)-methyl]pentyloxy-3-phenylpropionyl-methionine, 2(S)-[2(S)-[2(R)-Amino-3-mercapto]propylamino-3(S)-methyl]pentyloxy-3-phenylpropionyl-methionine sulfone methyl ester, 2(S)-[2(S)-[2(R)-Amino-3-mercapto]propylamino-3(S)-methyl]pentyloxy-3-phenylpropionyl-methionine sulfone (Compound A), 2(S)-[2(S)-[2(R)-Amino-3-mercapto]propylamino-3(S)-methyl]-pentyloxy-3-phenylpropionyl-methionine sulfone isopropyl ester, 2-(S)-[2(S)-[2(R)-Amino-3-mercapto]propylamino-3(S)-methyl]-pentyloxy-3-naphth-2-yl-propionyt-methionine sulfone methyl ester, 2-(S)-[2(S)-[2(R)-Amino-3-mercapto]propylamino-3(S)-methyl]-pentyloxy-3-naphth-2-yl-propionyl-methionine sulfone, 2-(S)-[2(S)-[2(R)-Amino-3-mercapto]propylamino-3(S)-methyl]pentyloxy-3-naphth-1-yl-propionyl-methionine sulfone methyl ester, 2-(S)-[2(S)-[2(R)-Amino-3-mercapto]propylamino-3(S)-methyl]pentyloxy-3-naphth-1-yl-propionyl-methionine sulfone, 2-(S)-[2(S)-[2(R)-Amino-3-mercapto]propylamino-3(S)-methyl1pentyloxy-3-methybutanoyl-methionine methyl ester, 2-(S)-[2(S)-[2(R)-Amino-3-mercapto]propylamino-3(S)-methyl]pentyloxy-3-methybutanoyl-methionine, Disulphide of 2(S)-[2(S)-[2(R)-Amino-3-mercapto]propylamino-3(S) methyl]pentyloxy-3-phenylpropionyl-homoserine lactone, Disulphide of 2(S)-[2(S)-[2(R)-Amino-3-mercapto]propylamino-3(S)-methyl]pentyloxy-3-phenylpropionyl-homoserine, Disulphide of 2(S)-[2(S)-[2(R)-Amino-3-mercapto]propylamino-3(S)methyl]pentyloxy-3-methylbutanoyl-methionine methyl ester 1-(4-Biphenylmethyl)-5-(4-cyanobenzyl)imidazole 1-(4-Cyanobenzyl)-5(4'-phenylbenzamido)ethyl-imidazole 1-(2'-Trifluoromethyl-4-biphenylmethyl)-5-(4-cyanobenzyl)imidazole 1-(4-Biphenylethyl)-5-(4-cyanobenzyl)imidazole 1-(2'-Bromo-4-biphenylmethyl)-5-(4-cyanobenzyl) imidazole 1-(2'-Methyl-4-biphenylmethyl)-5-(4-cyanobenzyl) imidazole 1-(2'-Trifluoromethoxy-4-biphenylmethyl)-5-(4-cyanobenzyl)imidazole 1-(4-(3', 5'-dichloro)-biphenylmethyl)-5-(4-cyanobenzyl) imidazole 1-(2'-Methoxy-4-biphenylmethyl)-5-(4-cyanobenzyl) imidazole 1-(2'-Chloro-4-biphenylmethyl)-5-(4-cyanobenzyl) imidazole 1-(2-Chloro-4-biphenylmethyl)-5-(4-cyanobenzyl) imidazole 1-(3-Chloro-4-biphenylmethyl)-5-(4-cyanobenzyl) imidazole 1-(4-(3', 5'-Bis-trifluoromethyl)-biphenylmethyl)-5-(4-cyanobenzyl) imidazole 1-(2'-Trifluoromethyl-4-biphenylmethyl)-5-(4-cyanobenzyl)-4-methylimidazole 1-(4-Biphenylmethyl)-5-(4-cyanophenyloxy-imidazole 5-(4-Cyanophenyloxy)-1-(2'-methyl-4-biphenylmethyl)-imidazole 5-(4-Biphenyloxy)-1-(4-cyanobenzyl)-imidazole 5-(2'-Methyl-4-biphenoxy)-1-(4-cyanobenzyl)-imidazole 5-(4-(3', 5'-dichloro)biphenylmethyl)-1-(4-cyanobenzyl) imidazole 1-(4-biphenylmethyl)-5-(1-(R,S)-acetoxy-1-(4-cyanophenyl)methylimidazole 1-(4-Biphenylmethyl)-5-(1-(R,S)-hydroxy-1-(4-cyanophenyl) methylimidazole 1-(4-Biphenylmethyl)-5-(1-(R,S)-amino-1-(4-cyanophenyl) methylimidazole 1-(4-biphenylmethyl)-5-(1-(R,S)-methoxy-1-(4-cyanophenyl)-methylimidazole 1-(4-Cyanobenzyl)-5-(1-hydroxy-1-(4-biphenyl)-methyl imidazole 1-(4-Cyanobenzyl)-5-(1-oxo-1-(4-biphenyl)-methyl imidazole 1-(4-Cyanobenzyl)-5-(1-hydroxy-1-(3-fluoro-4-biphenyl)-methyl)-imidazole 1-(4-Cyanobenzyl)-5-(1-hydroxy-1-(3-biphenyl)methyl-imidazole 5-(2-[1,1'-Biphenyl]vinylene)-1-(4-cyanobenzyl) imidazole 1-[N-(1-(4-cyanobenzyl)-5-imidazolylmethyl)amino]-3-methoxy-4-phenylbenzene 1-(4-Biphenylmethyl)-5-(4-bromophenyloxy)-imidazole 1-(3'-Methyl-4-biphenylmethyl)-5-(4-cyanobenzyl) imidazole 1-(4'-Methyl-4-biphenylmethyl)-5-(4-cyanobenzyl) imidazole 1-(3'-Trifluoromethyl-4-biphenylmethyl)-5-(4-cyanobenzyl) imidazole 1-(4'-Trifluoromethyl-4-biphenylmethyl)-5-(4-cyanobenzyl) imidazole 1-(3'-Chloro-4-biphenylmethyl)-5-(4-cyanobenzyl) imidazole 1-(4'-Chloro-4-biphenylmethyl)-5-(4-cyanobenzyl) imidazole 1-(2'3'-Dichloro-4-biphenylmethyl)-5-(4-cyanobenzyl) imidazole 1-(2'4'-Dichloro-4-biphenylmethyl)-5-(4-cyanobenzyl) imidazole 1-(2'5'-Dichloro-4-biphenylmethyl)-5-(4-cyanobenzyl) imidazole 1-(3'-Trifluoromethoxy-4-biphenylmethyl)-5-(4-cyanobenzyl) imidazole 1-(2'-Fluoro-4-biphenylmethyl)-5-(4-cyanobenzyl) imidazole 1-(4-(2'-Trifluoromethylphenyl)-2-Chlorophenylmethyl)-5-(4-cyanobenzyl) imidazole 1-{1-(4-(2'-trifluoromethylphenyl)phenyl)ethyl}-5-(4-cyanobenzyl) imidazole 1-(2'-Trifluoromethyl-4-biphenylpropyl)-5-(4-cyanobenzyl) imidazole 1-(2'-N-t-Butoxycarbonylamino-4-biphenylmethyl)-5-(4-cyanobenzyl) imidazole 1-(2'-Aminomethyl-4-biphenylmethyl)-5-(4-cyanobenzyl) imidazole 1-(2'-Acetylaminomethyl-4-biphenylmethyl)-5-(4-cyanobenzyl) imidazole 1-(2'-Methylsulfonylaminomethyl-4-biphenylmethyl)-5-(4-cyanobenzyl) imidazole 1-(2'-Ethylaminomethyl-4-biphenylmethyl)-5-(4-cyanobenzyl) imidazole 1-(2'-Phenylaminomethyl-4-biphenylmethyl)-5-(4-cyanobenzyl) imidazole 1-(2'-Glycinylaminomethyl-4-biphenylmethyl)-5-(4-cyanobenzyl) imidazole 1-(2'-Methyl-4-biphenylmethyl)-2-chloro-5-(4-cyanobenzyl) imidazole 1-(2'-Methyl-4-biphenylmethyl)-4-chloro 5-(4-cyanobenzyl) imidazole 1-(3'-chloro-2-methyl-4-biphenylmethyl)-4-(4-cyanobenzyl)imidazole 1-(3'-Chloro-2-methyl-4-biphenylmethyl)-5-(4-cyanobenzyl)imidazole 1-(3'-Trifluoromethyl-2-methyl-4-biphenylmethyl)-4-(4-cyanobenzyl) imidazole 1-(3'-Trifluoromethyl-2-methyl-4-biphenylmethyl)-5-(4-cyanobenzyl)imidazole 1-(3'-Methoxy-2-methyl-4-biphenylmethyl)-5-(4-cyanobenzyl)imidazole 1-(2'-Chloro-4'-fluoro-4-biphenylmethyl)-5-(4-cyanobenzyl)imidazole 1-(2'-Ethyl-4-biphenylmethyl)-5-(4-cyanobenzyl) imidazole 1-(2'-(2-propyl)-4-biphenylmethyl)-5-(4-cyanobenzyl) imidazole 1-(2'-(2-Methyl-2-propyl)-4-biphenylmethyl)-5-(4-cyanobenzyl)imidazole 1-(2'-Ethyl-4-biphenylmethyl)-5-(4-(1H-tetrazol-5-yl)(benzyl)imidazole 1-[1-(4-Cyanobenzyl)imidazol-5-ylmethoxy]-4-(2'-methylphenyl)-2-(3-N-phthalimido-1-propyl)benzene 1-(3', 5'-Ditrifluoromethyl-2-methyl-4-biphenylmethyl)-5-(4-cyanobenzyl)imidazole 1-(3', 5'-Chloro-2-methyl-4-biphenylmethyl)-5-(4-cyanobenzyl)imidazole 1-(3', 5'-Dimethyl-2-methyl-4-biphenylmethyl)-5-(4-cyanobenzyl)imidazole 1-(3-(N-Boc-aminomethyl)-4-biphenylmethyl)-5-(4-cyanobenzyl)-imidazole 1-(3-Aminomethyl-4-biphenylmethyl)-5-(4-cyanobenzyl)imidazole 1-(4-Cyanobenzyl)-2-methyl-5-(2'-methylbiphenyl-4-yloxy)imidazole 5-(4-Cyanobenzyl)-1-(3-cyano-2'-trifluoromethylbiphenyl-4-ylmethyl)-imidazole 2-Amino-5-(biphenyl-4-ylmethyl)-1-(4-cyanobenzyl) imidazole 2-Amino-1-(biphenyl-4-ylmethyl)-5-(4-cyanobenzyl) imidazole 1-(3-Butylbiphenyl-4-ylmethyl-5-(4-cyanobenzyl)-imidazole 1-(3-Propylbiphenyl-4-ylmethyl)-5-(4-cyanobenzyl)-imidazole 1-(4-Biphenylmethyl)-4-(4-cyanobenzyl-2-methylimidazole 1-(4-cyanobenzyl)-5-[(3-fluoro-4-biphenyl)methyl] imidazole 1-(4-Cyanobenzyl)-5-[1-(4-biphenyl)-1-hydroxy]ethyl-2-methylimidazole 1-(4-Cyanobenzyl)-5-(4-biphenylmethyl)-2-methylimidazole 1-(4-Cyanobenzyl)-5-[1-(4-biphenyl)]ethyl-2-methyl imidazole 1-(4-Cyanobenzyl-5-[1-(4-biphenyl)]vinylidene-2-methylimidazole and 1-(4-Cyanobenzyl)-5-[2-(4-biphenyl)]vinylene-2-methylimidazole 1-(4-[Pyrid-2-yl]phenylmethyl)-5-(4-cyanobenzyl) imidazole 1-(4-[3-Methylpyrazin-2-yl]phenylmethyl)-5-(4-cyanobenzyl)imidazole 1-(4-(Pyrimidinyl-5-yl)phenylmethyl)-5-(4-cyanobenzyl) imidazole 1-(2-Phenylpyrid-5-ylmethyl)-5-(4-cyanobenzyl) imidazole 1-(2-Phenyl-N-Oxopyrid-5-ylmethyl)-5-(4-cyanobenzyl) imidazole 1-(3-Phenylpyrid-6-ylmethyl)-5-(4-cyanobenzyl) imidazole 1-(3-Phenyl-N-Oxopyrid-6-ylmethyl)-5-(4-cyanobenzyl) imidazole 1-(2-(3-Trifluoromethoxyphenyl)-pyrid-5-ylmethyl)-5-(4-cyanobenzyl)imidazole 1-(2-(2-Trifluoromethylphenyl)-pyrid-5-ylmethyl)-5-(4-cyanobenzyl)imidazole 1-(3-Phenyl-2-Chloropyrid-6-ylmethyl)-5-(4-cyanobenzyl)imidazole 1-(3-Phenyl-4-chloropyrid-6-ylmethyl)-5-(4-cyanobenzyl)imidazole 1-(2-Amino-3-phenylpyrid-6-ylmethyl)-5-(4-cyanobenzyl)imidazole 1-(2-[Pyrid-2-yl]pyrid-5-ylmethyl)-5-(4-cyanobenzyl) imidazole N-[(1-{4-Cyanobenzyl)-1H-imidazol-5-yl)methyl}-5-(pyrid-2-yl)-2-amino-pyrimidine N,N-bis(4-Imidazolemethyl)amino-3-[(3carboxyphenyl) oxy]benzene N,N-bis(4-Imidazolemethyl)amino-4-[(3carboxyphenyl) oxy]benzene N,N-bis(4-Imidazolemethyl)amino-3-[(3-carbomethoxyphenyl)-oxy]benzene N,N-bis(4-Imidazolemethyl)amino-4-[(3-carbomethoxyphenyl)-oxy]benzene N-(4-Imidazolemethyl)-N-(4-nitrobenzyl)aminomethyl-3-[(3-carboxyphenyl)oxy]benzene N-(4-Imidazolemethyl)-N-(4-nitrobenzyl)aminomethyl-3-[(3-carbomethoxyphenyl)oxy]benzene N-(4-Imidazolemethyl)-N-(4-nitrobenzyl)amino-3-(phenoxy)benzene N-(4-Imidazolemethyl)-N-(4-nitrobenzyl)amino-4-(phenoxy)benzene N-(4-Imidazolemethyl)-N-(4-nitrobenzyl)amino-4-(phenylthio)benzene N-Butyl-N-[1-(4-cyanobenzyl)-5-imidazolemethyl] amino-4-(phenoxy)benzene N-[1-(4-Cyanobenzyl)-5-imidazolemethyl]amino-4-(phenoxy)benzene N-(4-Imidazolemethyl)amino-3-[(3-carboxyphenyl)oxy] benzene 1-[N-(1-(4-cyanobenzyl)-5-imidazolylmethyl)-N-(4-cyanobenzyl)amino]-4-(phenoxy)benzene (±)-4-[(4-imidazolylmethyl)amino]pentyl-1-(phenoxy) benzene 1-[(N-(1-(4-cyanobenzyl)-5-imidazolylmethyl)-N-(n-butyl)amino)methyl]-4-(phenoxy)benzene 4-[N-(1-(4-cyanobenzyl)-5-imidazolylmethyl)-N-(n-butyl)amino]-1-(phenylthio)benzene (±)-4-[N-(1-(4-cyanobenzyl)-4-imidazolylmethyl)-N-(n-butyl)amino]-1-(phenylsulfinyl)benzene 3-[N-(4-imidazolylmethyl)-N-(n-butyl)amino]-N-(phenyl)benzenesulfonamide and 1-[N-(1-(4-cyanobenzyl)-5-imidazolylmethyl)amino]-3-methoxy-4-phenylbenzene 4-{3-[4-(-2-Oxo-2-H-pyridin-1-yl)benzyl]-3-H-imidazol-4-ylmethyl]benzonitrile 4-{3-[4-3-Methyl-2-oxo-2-H-pyridin-1-yl)benzyl]-3-H-imidazol-4-ylmethyl]benzonitrile 4-{3-[4-(-2-Oxo-piperidin-1-yl)benzyl]-3-H-imidazol-4-ylmethyl]-benzonitrile 4-{3-[3-Methyl-4-(2-oxopiperidin-1-yl)-benzyl]-3-H-imidizol-4-ylmethyl}-benzonitrile (4-{3-[4-(2-Oxo-pyrrolidin-1-yl)-benzyl]-3H-imidizol-4-ylmethyl}-benzonitrile 4-{3-[4-(3-Methyl-2-oxo-2-H-pyrazin-1-yl}-benzyl-3-H-imidizol-4-ylmethyl)-benzonitrile 4-{3-[2-Methoxy-4-(2-oxo-2-H-pyridin-1-yl)-benzyl]-3-H-imidizol-4-ylmethyl}-benzonitrile 4-{1-[4-(5-chloro-2-oxo-2H-pyridin-1-yl)-benzyl]-1H-pyrrol-2-ylmethyl}-benzonitrile 4-[1-(2-Oxo-2H-[1,2']bipyridinyl-5'-ylmethyl)-1H-pyrrol-2-ylmethyl]-benzonitrile 4-[1-(5-Chloro-2-oxo-2H-[1,2']bipyridinyl-5'-ylmethyl)-1H-pyrrol-2-ylmethyl]-benzonitrile 4-[3-(2-Oxo-1-phenyl-1,2-dihydropyridin-4-ylmethyl)-3H-imidazol-4-ylmethyl]benzonitrile 4-{3-[1-(3-Chloro-phenyl)-2-oxo-1,2-dihydropyridin-4-ylmethyl]-3H-imidazol-4-ylmethyl)benzonitrile or a pharmaceutically acceptable salt, disulfide or optical isomer thereof.

3. The method according to claim 1 wherein an amount of a prenyl-protein transferase inhibitor and an amount of a microtubule-stabilizing agent selected from paclitaxel. epothilone A, epothilone B, desoxyepothilone A or desoxyepothilone B are administered simultaneously.

4. The method according to claim 1 wherein an amount of a microtubule-stabilizing agent selected from paclitaxel, epothilone A, epothilone B, desoxyepothilone A or desoxyepothilone B and an amount of a prenyl-protein transferase inhibitor are administered consecutively.

5. The method according to claim 1 wherein the prenyl-protein transferase inhibitor is selected from:

2(S)-[2(S)-[2(R)-Amino-3-mercapto]-propylamino-3(S)-methyl]-pentyloxy-3-phenylpropionyl-methionine sulfone isopropyl ester

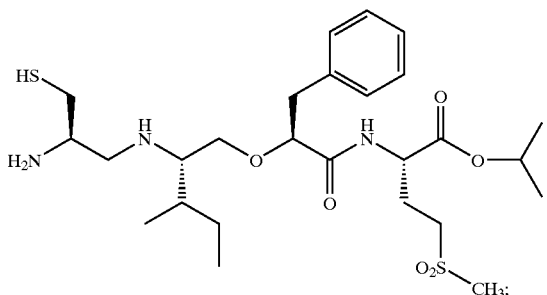

1-(3-Chlorophenyl)-4-[1-(4-cyanobenzyl)-5-imidazolylmethyl]-2-piperazinone;

(R)-1-(3-Chlorophenyl)-4-[1-(4-cyanobenzyl)-5-imidazolylmethyl]-5-(2-(ethanesulfonyl)methyl]-2-piperazinone;

4-[1-{5-Chloro-2-oxo-2H-[1,2']bipyridinyl-5'-ylmethyl)-1H-pyrrol-2-ylmethyl]-benzonitrile and 1-[N-(1-(4-cyanobenzyl)-5-imidazolylmethyl]-N-(4-cyanobenzyl)amino]-4-(phenoxy)benzene or a pharmaceutically acceptable salt, disulfide or optical isomer thereof.

6. A pharmaceutical composition comprising an amount of a prenyl-protein transferase inhibitor and an amount of an antineoplastic agent selected from paclitaxel, epothilone A, epothilone B, desoxyepothilone A or desoxyepothilone B which is a microtubule-stabilizing agent, wherein said composition achieves a synergistic effect for treating cancer in a mammal; in need thereof.

7. A method of preparing a pharmaceutical composition which comprises mixing an amount of a prenyl-protein transferase inhibitor and an amount of an antineoplastic agent which is a microtubule-stabilizing agent selected from paclitaxel, epothilone A, epothilone B, desoxyepothilone A or desoxyepothilone B, wherein said composition achieves a synergistic effect for treating cancer in a mammal.

8. A method for achieving a synergistic therapeutic effect in a mammal in need thereof which comprises administering to said mammal amounts of at least two therapeutic agents selected from a group consisting of:

a) a prenyl-protein transferase inhibitor and b) an antineoplastic agent which is a microtubule-stabilizing agent selected from paclitaxel, docetaxel epothilone A, epothilone B, desoxyepothilone A or descyepothilone B; the synergistic therapeutic effect is the treatment of cancers of the brain, breast, colon, genitourinary tract, lymphatic system, pancreas, rectum, stomach, larynx, liver, lung, prostate, stet histiocytic lymphoma lung adenocarcinoma, pancreatic carcinoma, colorectal carcinoma, small cell lung cancers or neurological tumor cancer whose growth is inhibited by the administration of the prenyl-protein transferase inhibitor and the antineoplastic agent.

9. The method according to claim 8 wherein the prenyl-protein transferase inhibitor is selected from;

2(S)-Butyl-1-(2,3-diaminoprop-1-yl)-1-(1-naphthoyl)piperazine;

1-(3-Amino-2-(2-naphthylmethylamino)prop-1-yl)-2(S)-butyl-4-(1-naphthoyl)piperazine;

2(S)-Butyl-1-{5-[1-(2-naphthylmethyl)]-4,5-dihydroimidazol)methyl-4-(1-naphthoyl)piperazine;

1-[5-(1-Benzylimidazol)methyl]-2(S)-butyl-4-(1-naphthoyl)piperazine;

1-{5-{1-(4-nitrobenzyl)]imidazolylmethyl}-2(S)-butyl-4-(1-naphthoyl)piperazine;

1-(3-Acetamidomethylthio-2(R)-aminoprop-1-yl)-2(S)-butyl-4-{1-naphthoyl)piperazine;

2(S)-Butyl-1-[2-(1-imidazolyl)ethyl]sulfonyl-4-(1-naphthoyl)piperazine;

2(R)-Butyl-1-imidazolyl-4-methyl-4-(1-naphthoyl)piperazine;

2(S)-Butyl-4-(1-naphthoyl)-1-(3-pyridylmethyl)piperazine;

1-2(S)-butyl-(2(R)-(4-nitrobenzyl)amino-3-hydroxypropyl)-4-(1-naphthoyl)piperazine;

1-(2(R)-Amino-3-hydroxyheptadecyl)-2(S)-butyl-4-(1-naphthoyl)-piperazine;

2(S)-Benzyl-1-imidazolyl-4-methyl-4-(1-naphthoyl)piperazine;

1-(2(R)-Amino-3-[3-benzylthio)propyl)-2(S)-butyl-4-(1-naphthoyl)piperazine;

1-(2(R)-Amino-3-[3-(4-nitrobenzylthio)propyl])-2(S)-butyl-4-(1-naphthoyl)piperazine;
2(S)-Butyl-1-[(4-imidazolyl)ethyl]-4-(1-naphthoyl)piperazine;
2(S)-Butyl-1-[(4-imidazolyl)methyl]-4-(1-naphthoyl)piperazine;
2(S)-Butyl-1-[(1-naphth-2-ylmethyl)-1H-imidazol-5-yl)acetyl]-4-(1-naphthoyl)piperazine;
2(S)-Butyl-1-[(1-naphth-2-ylmethyl)-1H-imidazol-5-yl)ethyl]-4-(1-naphthoyl)piperazine;
1-(2(R)-Amino-3-hydroypropyl)-2(S)-butyl-4-(1-naphthoyl)piperazine;
1-(2(R)-Amino-4-hydroxybutyl)-2(S)-butyl-4-(1-naphthoyl)piperazine;
1-(2-Amino-3-(2-benzyloxyphenyl)propyl)-2(S)-butyl-4-(1-naphthoyl)piperazine;
1-(2-Amino-3-(2-hydroxyphenyl)propyl)-2(S)-butyl-4-(1-naphthoyl)piperazine;
1-[3-(4-imidazolyl)propyl]-2(S)-butyl-4-(1-naphthoyl)-piperazine;
2(S)-n-Butyl-4-(2,3-dimethylphenyl)-1-(4-imidazolylmethyl)-piperazin-5-one;
2(S)-n-Butyl-1-[1-(4-cyanobenzyl)imidazol-5-ylmethyl]-4-(2,3-dimethylphenyl)piperazin-5-one;
1-[1-(4-Cyanobenzyl)imidazol-5-ylmethyl]-4-(2,3-dimethylphenyl)-2(S)-(2-methoxyethyl)piperazin-5-one;
2(S)-n-Butyl-4-(1-naphthoyl)-1-[1-(1-naphthylmethyl)imidazol-5-ylmethyl]-piperazine;
2(S)-n-Butyl-4-(1-naphthoyl)-1-[1-(2-naphthylmethyl)imidazol-5-ylmethyl]-piperazine;
2(S)-n-Butyl-1-[1-(4-cyanobenzyl)imidazol-5-ylmethyl]-4-(1-naphthoyl)piperazine;
2(S)-n-Butyl-1-[1-(4-methoxybenzyl)imidazol-5-ylmethyl]-4-(1-naphthoyl)piperazine;
2(S)-n-Butyl-1-[1-(3-methyl-2-butenyl)imidazol-5-ylmethyl]-4-(1-naphthoyl)piperazine;
2(S)-n-Butyl-1-[1-(4-fluorobenzyl)imidazol-5-ylmethyl]-4-(1-naphthoyl)piperazine;
2(S)-n-Butyl-1-[1-(4-chlorobenzyl)imidazol-5-ylmethyl]-4-(1-naphthoyl)piperazine;
1-[1-(4-Bromobenzyl)imidazol-5-ylmethyl]-2(S)-n-butyl-4-(1-naphthoyl)piperazine;
2(S)-n-Butyl-4-(1-naphthoyl)-1-[1-(4-trifluoromethylbenzyl)imidazol-5-ylmethyl]-piperazine;
2(S)-n-Butyl-1-[1-(4-methylbenzyl)imidazol-5-ylmethyl]-4-(1-naphthoyl)-piperazine;
2(S)-n-Butyl-1-[1-(3-methylbenzyl)imidazol-5-ylmethyl]-4-(1-naphthoyl)-piperazine;
1-[1-{4-Phenylbenzyl}imidazol-5-ylmethyl]-2(S)-n-butyl-4-(1-naphthoyl]-piperazine;
2(S)-n-Butyl-4-(1-naphthoyl)-1-[1-(2-phenylethyl)imidazol-5-ylmethyl]-piperazine;
2(S)-n-Butyl-4-(1-naphthoyl)-1-[1-(4-trifluoromethoxy)imidazol-5-ylmethyl]piperazine;
1-{[1-(4-cyanobenzyl)-1H-imidazol-5-yl]acetyl}-2(S)-n-butyl-4-(1-naphthoyl)piperazine;
(S)-1-(3-Chlorophenyl)-4-[1-(4-cyanobenzyl)-5-imidazolylmethyl]-5-[2-(methanesulfonyl)ethyl]-2-piperazinone;
(S)-1-(3-Chlorophenyl}-4-[1-{4-cyanobenzyl)-5-imidazolylmethyl]-5-[2-(ethanesulfonyl)ethyl]-2-piperazinone;
(R)-1-(3-Chlorophenyl)-4-[1-(4-cyanobenzyl)-5-imidazolylmethyl]-5-[2-(ethanesulfonyl)methyl]-2-piperazinone;
(S)-1-(3-Chlorophenyl)-4-[1-(4-cyanobenzyl)-5-imidazolylmethyl]-5-[N-ethyl-2-acetamido]-2-piperazinone;
(±)-5-(2-Butynyl}-1-(3-chlorophenyl)-4-[1-(4-cyanobenzyl)-5-imidazolylmethyl]-2-piperazinone;
1-(3-Chlorophenyl)-4-[1-(4-cyanobenzyl)-5-imidazolylmethyl]-2-piperazinone;
5(S)-Butyl-4-[1-(4-cyanobenzyl-2-methyl)-5-imidazolylmethyl]-1-(2,3-dimethylphenyl)-piperazin-2-one;
4-[1-(2-(4-Cyanophenyl)-2-propyl)-5-imidazolylmethyl]-1-(3-chlorophenyl)-5(S)-(2-methylsulfonylethyl)piperazin-2-one;
5(S)-n-Butyl-4-[1-(4-cyanobenzyl)-5-imidazolylmethyl]-1-(2-methylphenyl)piperazin-2-one;
4-[1-(4-Cyanobenzyl)-5-imidazolylmethyl]-5(S)-(2-fluoroethyl)-1-(3-chlorophenyl)piperazin-2-one;
4-[3-(4-Cyanobenzyl)pyridin-4-yl]-1-(3-chlorophenyl)-5(S)-(2-methylsulfonylethyl)-piperazin-2-one;
4-[5-(4-Cyanobenzyl)-1-imidazolylethyl]-1-(3-chlorophenyl)piperazin-2-one;
2(S)-[2(S)-[2(R)-Amino-3-mercapto]propylamino-3(S)-methyl]-pentyloxy-3-phenylpropionyl-homoserine lactone,
2(S)-[2(S)-[2(R)-Amino-3-mercapto]propylamino-3(S)-methyl]pentyloxy-3-phenylpropionyl-homoserine,
2(S)-[2(S)-[2(R)-Amino-3-mercapto]propylamino-3(S)-methyl]pentyloxy-2-methyl-3-phenylpropionyl-homoserine lactone,
2(S)-[2(S)-[2(R)-Amino-3-mercapto]propylamino-3(S)-methyl]pentyloxy-2-methyl-3-phenylpropionyl-homoserine,
2(S)-[2(S)-[2(R)-Amino-3-mercapto]propylamino-3(S)-methyl]pentyloxy-4-pentenoyl-homoserine lactone,
2(S)-[2(S)-[2(R)-Amino-3-mercapto]propylamino-3(S)-methyl]-pentyloxy-4-pentenoyl-homoserine,
2(S)-[2(S)-[2(R)-Amino-3-mercapto]propylamino-3(S)-methyl]pentyloxypentanoyl-homoserine lactone,
2(S)-[2(S)-[2(R)-Amino-3-mercapto]propylaniino-3(S)-methyl]pentyloxypentanoyl-homoserine,
2(S)-[2(S)-[2(R)-Amino-3-mercapto]propylamino-3(S)-methyl]5-pentyloxy-4-methylpentanoyl-homoserine lactone,
2(S)-[2(S)-[2(R)-Amino-3-mercapto]propylamino-3(S)-methyl]pentyloxy-4-methylpentanoyl-homoserine,
2(S)-[2(S)-[2(R)-Amino-3-mercapto]propylamino-3(S)-methyl]pentyloxy-3-methylbutanoyl-homoserine lactone,
2(S)-[2(S)-[2(R)-Amino-3-mercapto]propylamino-3(S)-methyl]pentyloxy-3-methylbutanoyl-homoserine,
2(S)-[2(S)-[2(R)-Amino-3-mercapto]propylamino-3(S)-methyl]pentyloxy-3-phenylbutanoyl-homoserine lactone,
2(S)-[2(S)-[2(R)-Amino-3-mercapto]propylamino-3(S)-methyl]-pentyloxy-3-phenylbutanoyl-homoserine,
2(S)-[2(S)-[(2(R)-Amino-3-mercapto]propylamino-3(S)-methyl]pentylthio-2-methyl-3-phenylpropionyl-homoserine lactone,
2(S)-[2(S)-[2(R)-Amino-3-mercapto]propylamino-3(S)-methyl]pentylthio-2-methyl-3-phenylpropionyl-homoserine, 2(S)-[2(S)-[2(R)-Amino-3-mercapto]propylamino-3(S)-methyl]pentylsulfonyl-2-methyl-3-phenylpropionyl-homoserine lactone, 2(S)-[2(S)-[2(R)-Amino-3-mercapto]propylamino-3(S)-methyl]-pentylsulfonyl-2-methyl-3-phenylpropionyl-homoserine, 2(S)-[2(S)-[2(R)-Amino-3-mercapto]propylaniino-3(S)-methyl]-pentyloxy-3-phenylpropionyl-methionine methyl ester, 2(S)-[2(S)-[2(R)-Amino-3-mercapto]propylamino-3(S)-methyl]pentyloxy-3-phenylpropionyl-methionine, 2(S)-[2(S)-[2(R)-Amino-3-mercapto]propylamino-3(S)-methyl]pentyloxy-3-phenylpropionyl-methionine sulfone methyl ester, 2(S)-[2(S)-[2(R)-Amino-3-mercapto]propylamino-3(S)-methyl]pentyloxy-3-phenylpropionyl-methionine sulfone (Compound A), 2(S)-[2(S)-[2(R)-Amino-3-mercapto]propylamino-3(S)-methyl]-pentyloxy-3-phenylpropionyl-methionine sulfone isopropyl ester, 2-(S)-[2(S)-[2(R)-Amino-3-mercapto]propylamino-3(S)-methyl]-pentyloxy-3-naphth-2-yl-propionyt-methionine sulfone methyl ester, 2-(S)-[2(S)-[2(R)-Amino-3-mercapto]propylamino-3(S)-methyl]-pentyloxy-3-naphth-2-yl-propionyl-methionine sulfone, 2-(S)-[2(S)-[2(R)-Amino-3-mercapto]propylamino-3(S)-methyl]pentyloxy-3-naphth-1-yl-propionyl-methionine sulfone methyl ester, 2-(S)-[2(S)-[2(R)-Amino-3-mercapto]propylamino-3(S)-methyl]pentyloxy-3-naphth-1-yl-propionyl-methionine sulfone, 2-(S)-[2(S)-[2(R)-Amino-3-mercapto]propylamino-3(S)-methyl]pentyloxy-3-methybutanoyl-methionine methyl ester, 2-(S)-[2(S)-[2(R)-Amino-3-mercapto]propylamino-3(S)-methyl]pentyloxy-3-methybutanoyl-methionine, Disulphide of 2(S)-[2(S)-[2(R)-Amino-3-mercapto]propylamino-3(S)methyl]pentyloxy-3-phenylpropionyl-homoserine lactone, Disulphide of 2(S)-[2(S)-[2(R)-Amino-3-mercapto]propylamino-3(S)-methyl]pentyloxy-3-phenylpropionyl-homoserine, Disulphide of 2(S)-[2(S)-[2(R)-Amino-3-mercapto]propylamino-3(S)methyl]pentyloxy-3-methylbutanoyl-methionine methyl ester 1-(4-Biphenylmethyl)-5-(4-cyanobenzyl)imidazole 1-(4-Cyanobenzyl)-5-(4'-phenylbenzamido)ethyl-imidazole 1-(2'-Trifluoromethyl-4-biphenylmethyl)-5-(4-cyanobenzyl)imidazole 1-(4-Biphenylethyl)-5-(4-cyanobenzyl) imidazole 1-(2'-Bromo-4-biphenylmethyl)-5-(4-cyanobenzyl) imidazole 1-(2'-Methyl-4-biphenylmethyl)-5-(4-cyanobenzyl) imidazole 1-(2'-Trifluoromethoxy-4-biphenylmethyl)-5-(4-cyanobenzyl)imidazole 1-(4-(3', 5'-dichloro)-biphenylmethyl)-5-(4-cyanobenzyl) imidazole 1-(2'-Methoxy-4-biphenylmethyl)-5-(4-cyanobenzyl) imidazole 1-(2'-Chloro-4-biphenylmethyl)-5-(4-cyanobenzyl) imidazole 1-(2-Chloro-4-biphenylmethyl)-5-(4-cyanobenzyl) imidazole 1-(3-Chloro-4-biphenylmethyl)-5-(4-cyanobenzyl) imidazole 1-(4-(3', 5'-Bis-trifluoromethyl)-biphenylmethyl)-5-(4-cyanobenzyl) imidazole 1-(2'-Trifluoromethyl-4-biphenylmethyl)-5-(4-cyanobenzyl)-4-methylimidazole 1-(4-Biphenylmethyl)-5-(4-cyanophenyloxy)-imidazole 5-(4-Cyanophenyloxy)-1-(2'-methyl-4-biphenylmethyl)-imidazole 5-(4-Biphenyloxy)-1-(4-cyanobenzyl)-imidazole 5-(2'-Methyl-4-biphenoxy)-1-(4-cyanobenzyl)-imidazole 5-(4-(3', 5'-dichloro)biphenylmethyl)-1-(4-cyanobenzyl) imidazole 1-(4-biphenylmethyl)-5-(1-(R,S)-acetoxy-1-(4-cyanophenyl)methylimidazole 1-(4-Biphenylmethyl)-5-(1-(R,S)-hydroxy-1-(4-cyanophenyl) methylimidazole 1-(4-Biphenylmethyl)-5-(1-(R,S)-amino-1-(4-cyanophenyl) methylimidazole 1-(4-biphenylmethyl)-5-(1-(R,S)-methoxy-1-(4-cyanophenyl)-methylimidazole 1-(4-Cyanobenzyl)-5-(1-hydroxy-1-(4-biphenyl)-methyl imidazole 1-(4-Cyanobenzyl)-5-(1-oxo-1-(4-biphenyl)-methyl imidazole 1-(4-Cyanobenzyl)-5-(1-hydroxy-1-(3-fluoro-4-biphenyl)-methyl)-imidazole 1-(4-Cyanobenzyl)-5-(1-hydroxy-1-(3-biphenyl)methyl-imidazole 5-(2-[1,1'-Biphenyl]vinylene)-1-(4-cyanobenzyl) imidazole 1-[N-(1-(4-cyanobenzyl)-5-imidazolylmethyl)amino]-3-methoxy-4-phenylbenzene 1-(4-Biphenylmethyl)-5-(4-bromophenyloxy)-imidazole 1-(3'-Methyl-4-biphenylmethyl)-5-(4-cyanobenzyl) imidazole 1-(4'-Methyl-4-biphenylmethyl)-5-(4-cyanobenzyl) imidazole 1-(3'-Trifluoromethyl-4-biphenylmethyl)-5-(4-cyanobenzyl) imidazole 1-(4'-Trifluoromethyl-4-biphenylmethyl)-5-(4-cyanobenzyl) imidazole 1-(3'-Chloro-4-biphenylmethyl)-5-(4-cyanobenzyl) imidazole 1-(4'-Chloro-4-biphenylmethyl)-5-(4-cyanobenzyl) imidazole 1-(2'3'-Dichloro-4-biphenylmethyl)-5-(4-cyanobenzyl) imidazole 1-(2'4'-Dichloro-4-biphenylmethyl)-5-(4-cyanobenzyl) imidazole 1-(2'5'-Dichloro-4-biphenylmethyl)-5-(4-cyanobenzyl) imidazole 1-(3'-Trifluoromethoxy-4-biphenylmethyl)-5-(4-cyanobenzyl) imidazole 1-(2'-Fluoro-4-biphenylmethyl)-5-(4-cyanobenzyl) imidazole 1-(4-(2'-Trifluoromethylphenyl)-2-Chlorophenylmethyl)-5-(4-cyanobenzyl) imidazole 1-{1-(4-(2'-trifluoromethylphenyl)phenyl)ethyl}-5-(4-cyanobenzyl) imidazole 1-(2'-Trifluoromethyl-4-biphenylpropyl)-5-(4-cyanobenzyl) imidazole
1-(2'-N-t-Butoxycarbonylamino-4-biphenylmethyl)-5-(4-cyanobenzyl) imidazole
1-(2'-Aminomethyl-4-biphenylmethyl)-5-(4-cyanobenzyl) imidazole
1-(2'-Acetylaminomethyl-4-biphenylmethyl)-5-(4-cyanobenzyl) imidazole
1-(2'-Methylsulfonylaminomethyl-4-biphenylmethyl)-5-(4-cyanobenzyl) imidazole
1-(2'-Ethylaminomethyl-4-biphenylmethyl)-5-(4-cyanobenzyl) imidazole
1-(2'-Phenylaminomethyl-4-biphenylmethyl)-5-(4-cyanobenzyl) imidazole
1-(2'-Glycinylaminomethyl-4-biphenylmethyl)-5-(4-cyanobenzyl) imidazole
1(2'-Methyl-4-biphenylmethyl)-2-chloro-5-(4-cyanobenzyl) imidazole
1-(2'-Methyl-4-biphenylmethyl)-4-chloro 5-(4-cyanobenzyl) imidazole
1-(3'-Chloro-2-methyl-4-biphenylmethyl)-4-(4-cyanobenzyl)imidazole
1-(3'-Chloro-2-methyl-4-biphenylmethyl)-5-(4-cyanobenzyl)imidazole
1-(3'-Trifluoromethyl-2-methyl-4-biphenylmethyl)-4-(4-cyanobenzyl) imidazole
1-(3'-Trifluoromethyl-2-methyl-4-biphenylmethyl)-5-(4-cyanobenzyl) imidazole
1-(3'-Methoxy-2-methyl-4-biphenylmethyl)-5-(4-cyanobenzyl)imidazole
1-(2'-Chloro-4'-fluoro-4-biphenylmethyl)-5-(4-cyanobenzyl)imidazole
1-(2'-Ethyl-4-biphenylmethyl)-5-(4-cyanobenzyl) imidazole
1-(2'-(2-Propyl)-4-biphenylmethyl)-5-(4-cyanobenzyl) imidazole
1-(2'-(2-Methyl-2-propyl)-4-biphenylmethyl)-5-(4-cyanobenzyl)imidazole
1-(2'-Ethyl-4-biphenylmethyl)-5-(4-(1H-tetrazol-5-yl))benzyl)imidazole
1-[1-(4-Cyanobenzyl)imidazol-5-ylmethoxy]-4-(2'-methylphenyl)-2-(3-N-phthalimido-1-propyl)benzene
1-(3', 5'-Ditrifluoromethyl-2-methyl-4-biphenylmethyl)-5,(4-cyanobenzyl)imidazole
1-(3', 5'-Chloro-2-methyl-4-biphenylmethyl)-5-(4-cyanobenzyl)imidazole
1-(3', 5'-Dimethyl-2-methyl-4-biphenylmethyl)-5-(4-cyanobenzyl)imidazole
1-(3-(N-Boc-aminomethyl)-4-biphenylmethyl)-5-(4-cyanobenzyl)-imidazole
1-(3-Aminomethyl-4-biphenylmethyl)-5-(4-cyanobenzyl)imidazole
1-(4-Cyanobenzyl)-2-methyl-5-(2'-methylbiphenyl-4-yloxy)imidazole
5-(4-Cyanobenzyl)-1-(3-cyano-2'-trifluoromethylbiphenyl-4-ylmethyl)-imidazole
2-Amino-5-(biphenyl-4-ylmethyl)-1-(4-cyanobenzyl) imidazole
2-Amino-1-(biphenyl-4-ylmethyl)-5-(4-cyanobenzyl) imidazole
1-(3-Butylbiphenyl-4-ylmethyl)-5-(4-cyanobenzyl)-imidazole
1-(3-Propylbiphenyl-4-ylmethyl)-5-(4-cyanobenzyl)-imidazole
1-(4-Biphenylmethyl)-4-(4-cyanobenzyl-2-methylimidazole
1-(4-Cyanobenzyl)-5-[(3-fluoro-4-biphenyl)methyl] imidazole
1-(4-Cyanobenzyl)-5-[1-(4-biphenyl)-1-hydroxy]ethyl-2-methylimidazole
1-(4-Cyanobenzyl)-5-(4-biphenylmethyl)-2-methylimidazole
1-(4-Cyanobenzyl)-5-[1-(4-biphenyl)]ethyl-2-methyl imidazole
1-(4-Cyanobenzyl-5-[1-(4-biphenyl]vinylidene-2-methylimidazole and
1-(4-Cyanobenzyl)-5-[2-(4-biphenyl)]vinylene-2-methylimidazole
1(4-[Pyrid-2-yl]phenylmethyl)-5-(4-cyanobenzyl) imidazole
1-(4-[3-Methylpyrazin-2-yl]phenylmethyl)-5-(4-cyanobenzyl)imidazole
1-(4-(Pyrimidinyl-5-yl)phenylmethyl)-5-(4-cyanobenzyl) imidazole
1-(2-Phenylpyrid-5-ylmethyl)-5-(4-cyanobenzyl) imidazole
1-(2-Phenyl-N-Oxopyrid-5-ylmethyl)-5-(4-cyanobenzyl) imidazole
1-(3-Phenylpyrid-6-ylmethyl)-5-(4-cyanobenzyl) imidazole
1-(3-Phenyl-N-Oxopyrid-6-ylmethyl)-5-(4-cyanobenzyl) imidazole
1-(2-(3-Trifluoromethoxyphenyl)-pyrid-5-ylmethyl)-5-(4-cyanobenzyl)imidazole
1-(2-(2-Trifluoromethylphenyl)-pyrid-5-ylmethyl)-5-(4-cyanobenzyl)imidazole
1-(3-Phenyl-2-Chloropyrid-6-ylmethyl)-5-(4-cyanobenzyl)imidazole
1-(3-Phenyl-4-chloropyrid-6-ylmethyl)-5-(4-cyanobenzyl)imidazole
1-(2-Amino-3-phenylpyrid-6-ylmethyl)-5-(4-cyanobenzyl)imidazole
1-(2-[Pyrid-2-yl]pyrid-5-ylmethyl)-5-(4-cyanobenzyl) imidazole
N-}1-(4-Cyanobenzyl)-1H-imidazol-5-yl)methyl}-5-(pyrid-2-yl)-2-amino-pyrimidine
N,N-bis(4-Imidazolemethyl)amino-3-[(3carboxyphenyl)oxy]benzene
N,N-bis (4-Imidazolemethyl)amino-4-[(3carboxyphenyl)oxy]benzene
N,N-bis(4-Imidazolemethyl)amino-3-[(3-carbomethoxyphenyl)-oxy]benzene
N,N-bis(4-Imidazolemethyl)amino-4-[(3-carbomethoxyphenyl)-oxy]benzene
N-(4-Imidazolemethyl)-N-(4-nitrobenzyl)aminomethyl-3-[(3-carboxyphenyl)oxy]benzene
N-(4-Imidazolemethyl)-N-(4-nitrobenzyl)aminomethyl-3-[(3-carbomethoxyphenyl)oxy]benzene
N-(4-Imidazolemethyl)-N-(4-nitrobenzyl)amino-3-(phenoxy)benzene
N-(4-Imidazolemethyl)-N-(4-nitrobenzyl)amino-4-(phenoxy)benzene
N-(4-Imidazolemethyl)-N-(4-nitrobenzyl)amino-4-(phenylthio)benzene N-Butyl-N-[1-(4-cyanobenzyl)-5-imidazolemethyl]amino-4-(phenoxy)benzene N-[1-(4-Cyanobenzyl)-5-imidazolemethyl]amino-4-(phenoxy)benzene N-(4-Imidazolemethyl)amino-3-[(3-carboxyphenyl)oxy]benzene 1-[N-(1-(4-cyanobenzyl)-5-imidazolylmethyl)-N-(4-cyanobenzyl)amino]-4-(phenoxy)benzene (±)-4-[(4-imidazolylmethyl)amino]pentyl-1-(phenoxy)benzene 1-[(N-(1-(4-cyanobenzyl)-5-imidazolylmethyl)-N-(n-butyl)amino)methyl]-4-(phenoxy)benzene 4-[N-(1-(4-cyanobenzyl)-5-imidazolylmethyl)-N-(n-butyl)amino]-1-(phenylthio)benzene (±)-4-[N-(1-(4-cyanobenzyl)-4-imidazolylmethyl)-N-(n-butyl)amino]-1-(phenylsulfinyl)benzene 3-[N-(4-imidazolylmethyl)-N-(n-butyl)amino]-N-(phenyl)benzenesulfonamide and 1-[N-(1-(4-cyanobenzyl)-5-imidazolylmethyl)amino]-3-methoxy-4-phenylbenzene 4-[3-[4-(2-Oxo-2-H-pyridin-1-yl)benzyl]-3-H-imidazol-4-ylmethyl]benzonitrile 4-{3-[4-3-Methyl-2-oxo-2-H-pyridin-1-yl)benzyl]-3-H-imidazol-4-ylmethyl}benzonitrile 4-[3-[4-{-2-Oxo-piperidin-1-yl)benzyl]-3-H-imidazol-4-ylmethyl]benzonitrile 4-{3-[3-Methyl-4-(2-oxopiperidin-1-yl)-benzyl]-3-H-imidizol-4-ylmethyl}-benzonitrile {4-{3-[4-(2-Oxo-pyrrolidin-1-yl)-benzyl]-3H-imidazol-4-ylmethyl}-benzonitrile 4-{3-[4-(3-Methyl-2-oxo-2-H-pyrazin-1-yl)-benzyl]-3-H-imidizol-4-ylmethyl}-benzonitrile 4-{3-[2-Methoxy-4-(2-oxo-2-H-pyridin-1-yl)-benzyl]-3-H-imidizol-4-ylmethyl}-benzonitrile 4-{1-[4-(5-Chloro-2-oxo-2H-pyridin-1-yl)-benzyl]-1H-pyrrol-2-ylmethyl}-benzonitrile 4-[1-(2-Oxo-2H-[1,2']bipyridinyl-5'-ylmethyl)-1H-pyrrol-2-ylmethyl]-benzonitrile 4-[1-(5-Chloro-2-oxo-2H-[1,2']bipyridinyl-5'-ylmethyl)-1H-pyrrol-2-ylmethyl]-benzonitrile 4-[3-(2-Oxo-1-phenyl-1,2-dihydropyridin-4-ylmethyl)-3H-imidazol-4-ylmethyl]benzonitrile 4-{3-[1-(3-Chloro-phenyl)-2-oxo-1,2-dihydropyridin-4-ylmethyl]-3H-imidazol-4-ylmethyl}benzonitrile or a pharmaceutically acceptable salt, disulfide or optical isomer thereof.

10. The method according to claim 8 wherein an amount of a prenyl-protein transferase inhibitor and an amount of a microtubule-stabilizing agent comprising paclitaxel, docetaxel epothilone A, epothilone B, desoxyepothilone A or desoxyepothilone B are administered simultaneously.

11. The method according to claim 8 wherein an amount of a microtubule-stabilizing agent comprising paclitaxel, docetaxel epothilone A, epothilone B, desoxyepothilone A or desoxyepothilone B and an amount of a prenyl-protein transferase inhibitor are administered consecutively.

12. The method according to claim 8 wherein the prenyl-protein transferase inhibitor is selected from:

2(S)-[2(S)-[2(R)-Amino-3-mercapto]-propylamino-3(S)-methyl]-pentyloxy-3-phenylpropionyl-methionine sulfone isopropyl ester

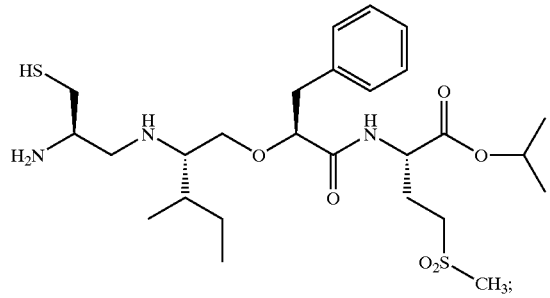

1-(3-Chlorophenyl)-4-[1-(4-cyanobenzyl)-5-imidazolylmethyl]-2-piperazinone;

(R)-1-(3-Chlorophenyl)-4-[1-(4-cyanobenzyl)-5-imidazolylmethyl]-5-[2-(ethanesulfonyl)methyl]-2-piperazinone;

4-[1-(5-Chloro-2-oxo-2H-[1,2']bipyridinyl-5'-ylmethyl)-1H-pyrrol-2-ylmethyl]-benzonitrile and 1-[N-(1-(4-cyanobenzyl)-5-imidazolylmethyl)-N-(4-cyanobenzyl)amino]-4-(phenoxy)benzene or a pharmaceutically acceptable salt, disulfide or optical isomer thereof.

13. A pharmaceutical composition comprising an amount of a prenyl-protein transferase inhibitor and an amount of an antineoplastic agent which is a microtubule-stabilizing agent selected from paclitaxel, docetaxel epothilone A, epothilone B, desoxyepothilone A or desoxyepothilone B, wherein said composition achieves a synergistic effect for treating cancer in a mammal in need thereof.

14. A method of preparing a pharmaceutical composition which comprises mixing an amount of a prenyl-protein transferase inhibitor and an amount of an antineoplastic agent which is a microtubule-stabilizing agent selected from paclitaxel, docetaxel epothilone A, epothilone B, desoxyepothilone A or desoxyepothilone B, wherein said composition achieves a synergistic effect for treating cancer in a mammal.

* * * * *